United States Patent
Goldstein

(10) Patent No.: US 11,274,130 B2
(45) Date of Patent: Mar. 15, 2022

(54) HV1 MODULATORS AND USES

(71) Applicant: The Regents of the University of California, Oakland, CA (US)

(72) Inventor: Steven Alan Goldstein, Chicago, IL (US)

(73) Assignee: The Regents of the University of California, Oakland, CA (US)

( * ) Notice: Subject to any disclaimer, the term of this patent is extended or adjusted under 35 U.S.C. 154(b) by 53 days.

(21) Appl. No.: 16/474,906

(22) PCT Filed: Dec. 29, 2017

(86) PCT No.: PCT/US2017/068896
§ 371 (c)(1),
(2) Date: Jun. 28, 2019

(87) PCT Pub. No.: WO2018/126111
PCT Pub. Date: Jul. 5, 2018

(65) Prior Publication Data
US 2019/0330285 A1    Oct. 31, 2019

Related U.S. Application Data

(60) Provisional application No. 62/441,097, filed on Dec. 30, 2016, provisional application No. 62/447,433, filed on Jan. 17, 2017.

(51) Int. Cl.
*C07K 14/435* (2006.01)
*C07K 14/705* (2006.01)

(52) U.S. Cl.
CPC .. *C07K 14/43518* (2013.01); *C07K 14/43522* (2013.01); *C07K 14/705* (2013.01); *C07K 2319/02* (2013.01); *C07K 2319/41* (2013.01)

(58) Field of Classification Search
CPC ............................................... C07K 14/43518
See application file for complete search history.

(56) References Cited

U.S. PATENT DOCUMENTS

| 7,132,505 B1 | 11/2006 | Lazdunski et al. |
| 2012/0270236 A1 | 10/2012 | Ramsey et al. |
| 2015/0087552 A1 | 3/2015 | Jensen et al. |
| 2015/0203812 A1 | 7/2015 | Tombola |

OTHER PUBLICATIONS

International Search Report and Written Opinion for PCT/US2017/068896, dated Apr. 23, 2018.
Lishko et al., "Acid Extrusion from Human Spermatozoa Is Mediated by Flagellar Voltage-Gated Proton Channel" Cell, 2010, v 140, p. 327-337.
Sokolov et al., "Inhibition of Sodium Channel Gating by Trapping the Domain II Voltage Sensor with Protoxin II" Molecular Pharmacology, 2008, v 73, p. 1020-1028.
Kennedy et al., "A Designer Peptide Toxin Isolated by Phage Display that Inhibits the Human Voltage-Gated Proton Channel, hHv1" BioPhysical Journal, 2017, v 112, n 3, Supplement 1, p. 415a.

*Primary Examiner* — Prema M Mertz
(74) *Attorney, Agent, or Firm* — Greer, Burns & Crain, Ltd.; Gregory P. Einhorn

(57) ABSTRACT

The present invention provides novel agents for modulation of Hv1 channels. The present invention provides agents for activating and/or inhibiting Hv1 channel function and/or activity, and reagents and methods relating thereto.

2 Claims, 10 Drawing Sheets
Specification includes a Sequence Listing.

FIG. 2

```
              Sequence Element A      Sequence Element B         Sequence Element C
                          10                20              30              40
C6/1-41     S S T C I P S G Q P C A D S D D C C E T F H C K W V F F T S K F M C R R V W G K D - - -
C5/1-39     - - G C K W Y L G D C A D S D D C C E T F H C K W V F F T S K F M C R R V W G K D - - -
HaTx/1-35   - - E C R Y L F G G C K T T S D C C K H L G C K - - - F R D K Y - C - - A W D F T F S -
              NT                                                                              CT
```

FIG. 3

FIG. 3A   MSALLILALVGAAVASSTCIPSGQPCADSDDCCETFHCKWVFFTSKFMCRRVWGKDGEQKLISEEDLGALC
NGAGFATPVTLALVPALLATFWSLL

FIG. 3B   MSALLILALVGAAVAECRYLFGGCKTTSDCCKHLGCKFRDKYCAWDFTFSGNGNGNGSSTCIPSGQPCADS
DDCCETFHCKWVFFTSKFMCRRVWGKDGEQKLISEEDLGALCNGAGFATPVTLALVPALLATFWSLL

FIG. 3C   MSALLILALVGAAVASSTCIPSGQPCADSDDCCETFHCKWVFFTSKFMCRRVWGKDDSSEQKLISEEDSSTCI
PSGQPCADSDDCCETFHCKWVFFTSKFMCRRVWGKDGEQKLISEEDLGALCNGAGFATPVTLALVPALLAT
FWSLL

FIG. 3D   MSALLILALVGAAVASSTCIPSGQPCADSDDCCETFHCKWVFFTSKFMCRRVWGKDDSSGNGNGNGSSTCI
PSGQPCADSDDCCETFHCKWVFFTSKFMCRRVWGKDGEQKLISEEDLGALCNGAGFATPVTLALVPALLAT
FWSLL

FIG. 3E   MSALLILALVGAAVASSTCIPSGQPCADSDDCCETFHCKWVFFTSKFMCRRVWGKDDSSGGNGNGNGNG
NGNGAAAGGNGNGNGNGNGNGNGSSTCIPSGQPCADSDDCCETFHCKWVFFTSKFMCRRVWGKDGEQKLIS
EEDLGALCNGAGFATPVTLALVPALLATFWSLL

KEY:
Gray = Signal peptide for T-toxin expression
Dark Gray = rigid linker from natural spider toxin DkTx
Dash with dots = c-Myc epitope
Underline = C6 Sequence
Double Underline = HaTx1 sequence
Boxed = hydrophobic sequence
Dashed = flexible linker

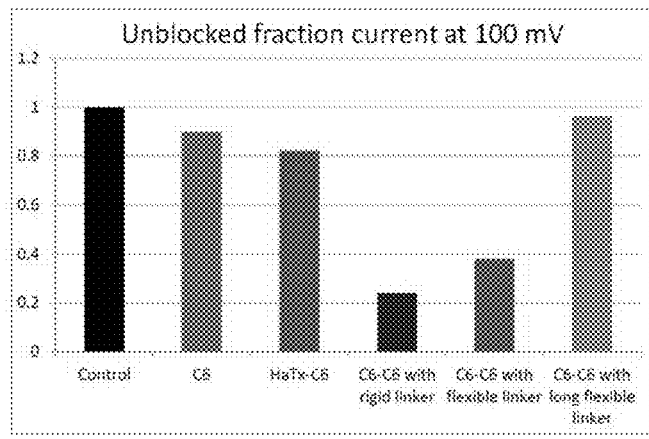

FIG. 3F

FIG. 6
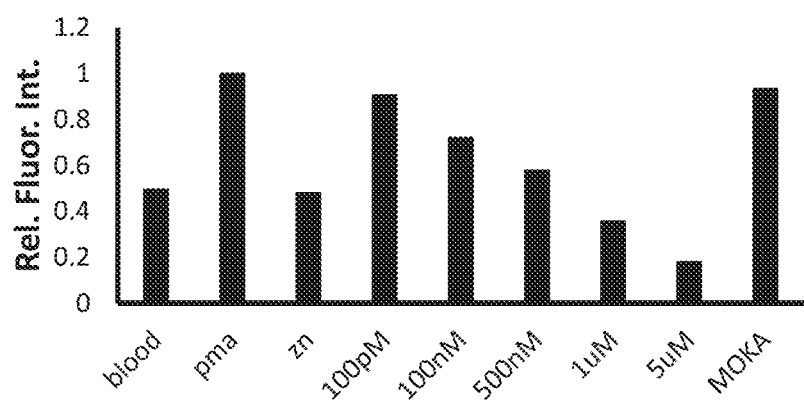
FIG. 6A
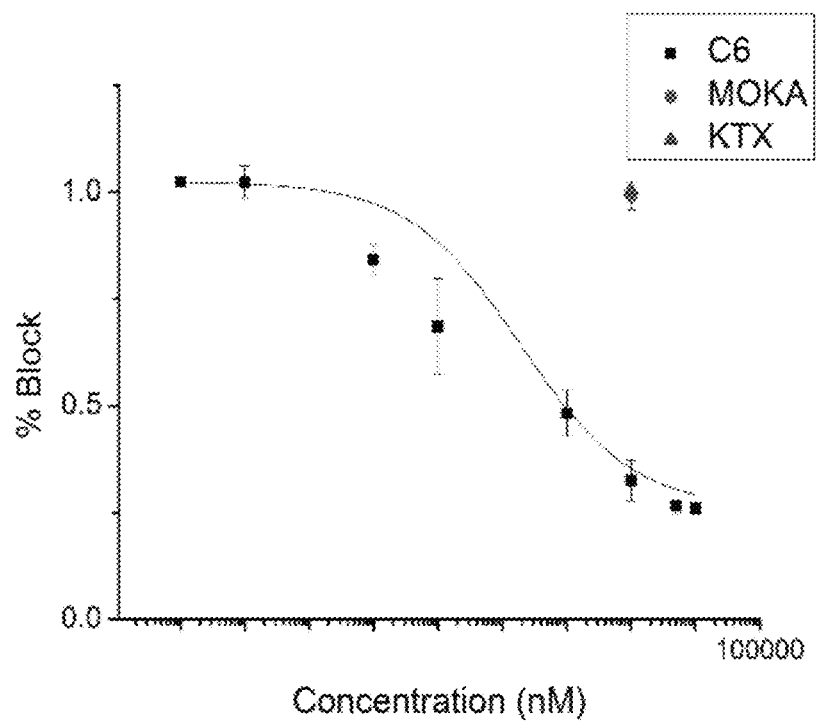
FIG. 6B

FIG. 7

FIG. 7A (SEQ ID NO: 807)

ATGTCTGCACTTCTGATCCTAGCTCTTGTTGGAGCTGCAatgAGCAGCACCTGCATTCCGAGCGGCCAGCCGTGTGCGGATAGCGATGATTGCTGCGAAACCTTTCATTGCAAATGGGTGTTTTTTACCAGCAAATTTATGTGCCGCCGCGTGTGGGGCAAAGATaccggtGTTGCTATCG*ATTACAAAGACGATGACGACAAG*CTTGCGGCCGCTggtaacggaaatggcaacgggaatggcaacggtaacggaaacgggGATGGTACTCGagtTGCTGTGGGCCAGGACACGCAGGAGGTCATCGTGGTGCCACACTCCTTGCCCTTTAAGGTGGTGGTGATCTCAGCCATCCTGGCCCTGGTGGTGCTCACCATCATCTCCCTTATCATCCTCATCATGCTTTGGCAGAAGAAACCACGTAGGATCCACCGGCCGGTCGCCACCatggtgagcaagggcgaggagctgttcaccggggtggtgcccatcctggtcgagctggacggcgacgtaaacggccacaagttcagcgtgtccggcgagggcgagggcgatgccacctacggcaagctgaccctgaagctgatctgcaccaccggcaagctgcccgtgccctggcccaccctcgtgaccaccctgggctacggccttcagtgcttcgcccgctaccccgaccacatgaagcagcacgacttcttcaagtccgccatgcccgaaggctacgtccaggagcgcaccatcttcttcaaggacgacggcaactacaagacccgcgccgaggtgaagttcgagggcgacaccctggtgaaccgcatcgagctgaagggcatcgacttcaaggaggacggcaacatcctggggcacaagctggagtacaactacaacagccacaacgtctatatcaccgccgacaagcagaagaacggcatcaaggccaacttcaagatccgccacaacatcgaggacggcggcgtgcagctcgccgaccactaccagcagaacacccccatcggcgacggccccgtgctgctgccgacaaccactacctgagctaccagtccaaactgagcaaagaccccaacgagaagcgcgatcacatggtcctgctggagttcgtgaccgccgccgggatcactctcggcatggacgagctgtacaagTAA

FIG. 7B (SEQ ID NO: 808)

MSALLILALVGAAMSSTCIPSGQPCADSDDCCETFHCKWVFFTSKFMCRRVWGKDTGVAIDYKDDDDKLAAAGNGNGNGNGNGNGNGDGTRVAVGQDTQEVIVVPHSLPFKVVVISAILALVVLTIISLIILMLWQKKPRRHRPVATMVSKGEELFTGVVPILVELDGDVNGHKFSVSGEGEGDATYGKLTLKLICTTGKLPVPWPTLVTTLGYGLQCFARYPDHMKQHDFFKSAMPEGYVQERTIFFKDDGNYKTRAEVKFEGDTLVNRIELKGIDFKEDGNILGHKLEYNYNSHNVYITADKQKNGIKANFKIRHNIEDGGVQLADHYQQNTPIGDGPVLLPDNHYLSYQSKLSKDPNEKRDHMVLLEFVTAAGITLGMDELYK

KEY:

| Secretory Sequence |

C6 sequence
Linker sequences
PDGFR transmembrane helix
*Flag epitope*
mVenus FIG. 8
FIG. 8A
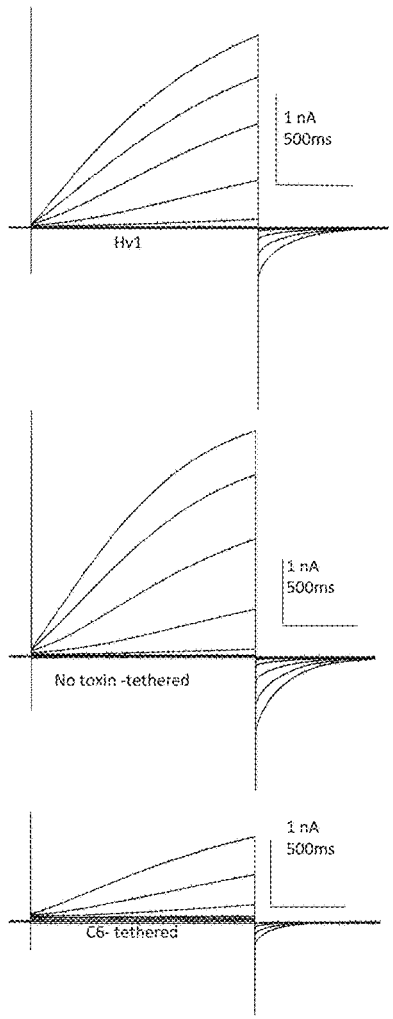
FIG. 8B
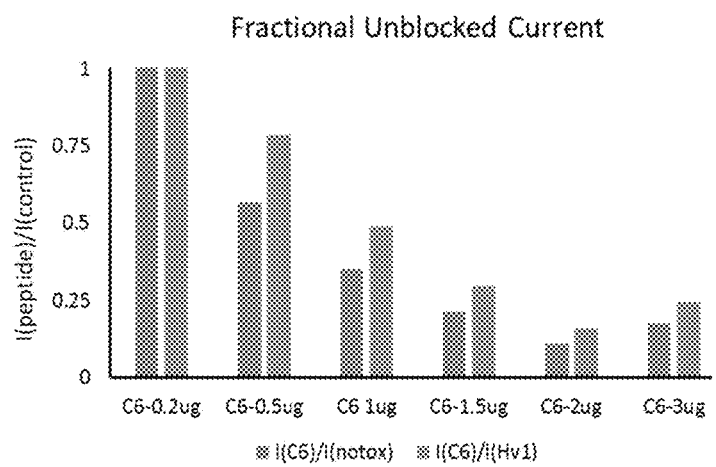
FIG. 8C
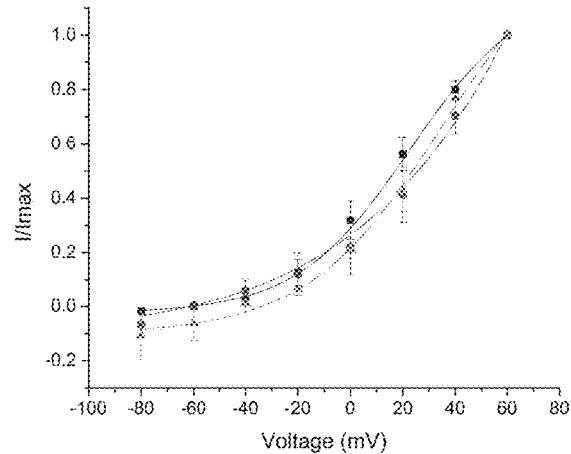

FIG. 9
FIG. 9A
| Name | SEQ ID NO: | Sequence | Blocks |
|---|---|---|---|
| CiHv1 | 113 | VVVISPGVDIALIFVGESEALAAIGLLVILRLWRVFR | NO |
| hHv1 | 114 | | YES |
| hS3S4CiHv1 | 811 | | YES |
| ciS3S4hHv1 | 816 | | |
| shortN | 817 | | |
| shortNC | 818 | | |
| shortC | 819 | | |
| ciS3S4hHv1-2 | 812 | | NO |
| shortN-2 | 813 | | X |
| shortNC-2 | 814 | | |
| shortC-2 | 815 | | |
| shortNC-3 | 820 | | X |
| shortC-3 | 821 | | |
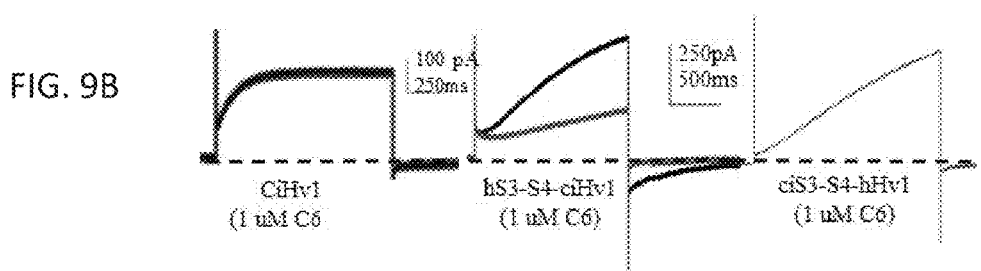
FIG. 9B
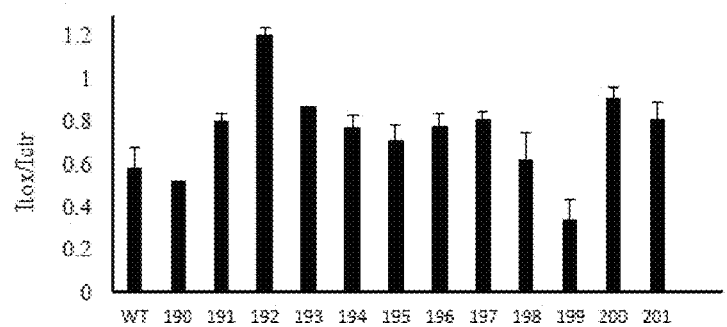
FIG. 9C

SEQUENCE LISTING

```
<160> NUMBER OF SEQ ID NOS: 821

<210> SEQ ID NO 1
<211> LENGTH: 35
<212> TYPE: PRT
<213> ORGANISM: Haplopelma schmidti

<400> SEQUENCE: 1

Glu Cys Leu Glu Ile Phe Lys Ala Cys Asn Pro Ser Asn Asp Gln Cys
1               5                   10                  15

Cys Lys Ser Ser Lys Leu Val Cys Ser Arg Lys Thr Arg Trp Cys Lys
            20                  25                  30

Tyr Gln Ile
        35

<210> SEQ ID NO 2
<211> LENGTH: 35
<212> TYPE: PRT
<213> ORGANISM: Haplopelma hainanum

<400> SEQUENCE: 2

Glu Cys Leu Gly Phe Gly Lys Gly Cys Asn Pro Ser Asn Asp Gln Cys
1               5                   10                  15

Cys Lys Ser Ser Asn Leu Val Cys Ser Arg Lys His Arg Trp Cys Lys
            20                  25                  30

Tyr Glu Ile
        35

<210> SEQ ID NO 3
<211> LENGTH: 35
<212> TYPE: PRT
<213> ORGANISM: Haplopelma hainanum

<400> SEQUENCE: 3

Glu Cys Leu Gly Phe Gly Lys Gly Cys Asn Pro Ser Asn Asp Gln Cys
1               5                   10                  15
```

Cys Lys Ser Ala Asn Leu Val Cys Ser Arg Lys His Arg Trp Cys Lys
            20                  25                  30

Tyr Glu Ile
        35

<210> SEQ ID NO 4
<211> LENGTH: 34
<212> TYPE: PRT
<213> ORGANISM: Paraphysa scrofa

<400> SEQUENCE: 4

Asp Cys Leu Gly Phe Leu Trp Lys Cys Asn Pro Ser Asn Asp Lys Cys
1               5                   10                  15

Cys Arg Pro Asn Leu Val Cys Ser Arg Lys Asp Lys Trp Cys Lys Tyr
            20                  25                  30

Gln Ile

<210> SEQ ID NO 5
<211> LENGTH: 33
<212> TYPE: PRT
<213> ORGANISM: Ceratogyrus marshalli

<400> SEQUENCE: 5

Asp Cys Leu Gly Trp Phe Lys Ser Cys Asp Pro Lys Asn Asp Lys Cys
1               5                   10                  15

Cys Lys Asn Tyr Thr Cys Ser Arg Arg Asp Arg Trp Cys Lys Tyr Asp
            20                  25                  30

Leu

<210> SEQ ID NO 6
<211> LENGTH: 33
<212> TYPE: PRT
<213> ORGANISM: Ceratogyrus marshalli

<400> SEQUENCE: 6

Asp Cys Leu Gly Trp Phe Lys Ser Cys Asp Pro Lys Asn Asp Lys Cys
1               5                   10                  15

Cys Lys Asn Tyr Thr Cys Ser Arg Arg Asp Arg Trp Cys Lys Tyr Tyr
            20                  25                  30

Leu

<210> SEQ ID NO 7
<211> LENGTH: 34
<212> TYPE: PRT
<213> ORGANISM: Grammostola rosea

<400> SEQUENCE: 7

Asp Cys Leu Gly Trp Phe Lys Gly Cys Asp Pro Asp Asn Asp Lys Cys
1               5                   10                  15

Cys Glu Gly Tyr Lys Cys Asn Arg Arg Asp Lys Trp Cys Lys Tyr Lys
            20                  25                  30

Leu Trp

<210> SEQ ID NO 8
<211> LENGTH: 35
<212> TYPE: PRT
<213> ORGANISM: Theraphosa blondi

<400> SEQUENCE: 8

Ala Ala Cys Leu Gly Met Phe Glu Ser Cys Asp Pro Asn Asn Asp Lys

```
                1               5                  10                  15
Cys Cys Pro Asn Arg Glu Cys Asn Arg Lys His Lys Trp Cys Lys Tyr
                20                  25                  30

Lys Leu Trp
        35

<210> SEQ ID NO 9
<211> LENGTH: 35
<212> TYPE: PRT
<213> ORGANISM: Chilobrachys guangxiensis

<400> SEQUENCE: 9

Asp Asp Cys Leu Gly Met Phe Ser Ser Cys Asn Pro Asp Asn Asp Lys
1               5                   10                  15

Cys Cys Glu Gly Arg Lys Cys Asp Arg Arg Asp Gln Trp Cys Lys Trp
                20                  25                  30

Asn Pro Trp
        35

<210> SEQ ID NO 10
<211> LENGTH: 33
<212> TYPE: PRT
<213> ORGANISM: Chilobrachys guangxiensis

<400> SEQUENCE: 10

Asp Cys Leu Gly Leu Phe Trp Ile Cys Asn Tyr Met Asp Lys Cys
1               5                   10                  15

Cys Pro Gly Tyr Lys Cys Glu Arg Ser Ser Pro Trp Cys Lys Ile Asp
                20                  25                  30

Ile

<210> SEQ ID NO 11
<211> LENGTH: 35
<212> TYPE: PRT
<213> ORGANISM: Theraphosa blondi

<400> SEQUENCE: 11

Asp Asp Cys Leu Gly Met Phe Ser Ser Cys Asp Pro Asn Asn Asp Lys
1               5                   10                  15

Cys Cys Pro Asn Arg Val Cys Arg Val Arg Asp Gln Trp Cys Lys Tyr
                20                  25                  30

Lys Leu Trp
        35

<210> SEQ ID NO 12
<211> LENGTH: 35
<212> TYPE: PRT
<213> ORGANISM: Theraphosa blondi

<400> SEQUENCE: 12

Asp Asp Cys Leu Gly Met Phe Ser Ser Cys Asp Pro Lys Asn Asp Lys
1               5                   10                  15

Cys Cys Pro Asn Arg Val Cys Arg Ser Arg Asp Gln Trp Cys Lys Tyr
                20                  25                  30

Lys Leu Trp
        35

<210> SEQ ID NO 13
<211> LENGTH: 33
<212> TYPE: PRT
```

<213> ORGANISM: Haplopelma schmidti

<400> SEQUENCE: 13

Ala Cys Lys Gly Val Phe Asp Ala Cys Thr Pro Gly Lys Asn Glu Cys
1               5                   10                  15

Cys Pro Asn Arg Val Cys Ser Asp Lys His Lys Trp Cys Lys Trp Lys
            20                  25                  30

Leu

<210> SEQ ID NO 14
<211> LENGTH: 36
<212> TYPE: PRT
<213> ORGANISM: Grammostola rosea

<400> SEQUENCE: 14

Gly Cys Leu Glu Phe Trp Trp Lys Cys Asn Pro Asn Asp Asp Lys Cys
1               5                   10                  15

Cys Arg Pro Lys Leu Lys Cys Ser Lys Leu Phe Lys Leu Cys Asn Phe
            20                  25                  30

Ser Phe Gly Lys
        35

<210> SEQ ID NO 15
<211> LENGTH: 36
<212> TYPE: PRT
<213> ORGANISM: Hadronyche versuta

<400> SEQUENCE: 15

Ala Asp Cys Gly Trp Leu Phe His Ser Cys Ser Asn Ala Asp Cys
1               5                   10                  15

Cys Glu Asn Trp Ala Cys Ala Thr Thr Gly Arg Phe Arg Tyr Leu Cys
            20                  25                  30

Lys Tyr Gln Ile
        35

<210> SEQ ID NO 16
<211> LENGTH: 33
<212> TYPE: PRT
<213> ORGANISM: Pandinus imperator

<400> SEQUENCE: 16

Gly Asp Cys Leu Pro His Leu Lys Arg Cys Lys Ala Asp Asn Asp Cys
1               5                   10                  15

Cys Gly Lys Lys Cys Lys Arg Arg Gly Thr Asn Ala Glu Lys Arg Cys
            20                  25                  30

Arg

<210> SEQ ID NO 17
<211> LENGTH: 34
<212> TYPE: PRT
<213> ORGANISM: Grammostola rosea

<400> SEQUENCE: 17

Glu Cys Gly Lys Phe Met Trp Lys Cys Lys Asn Ser Asn Asp Cys Cys
1               5                   10                  15

Lys Asp Leu Val Cys Ser Ser Arg Trp Lys Trp Cys Val Leu Ala Ser
            20                  25                  30

Pro Phe

<210> SEQ ID NO 18
<211> LENGTH: 33
<212> TYPE: PRT
<213> ORGANISM: Haplopelma hainanum

<400> SEQUENCE: 18

Glu Cys Lys Gly Phe Gly Lys Ser Cys Val Pro Gly Lys Asn Glu Cys
1               5                   10                  15

Cys Ser Gly Tyr Ala Cys Asn Ser Arg Asp Lys Trp Cys Lys Val Leu
            20                  25                  30

Leu

<210> SEQ ID NO 19
<211> LENGTH: 33
<212> TYPE: PRT
<213> ORGANISM: Scorpio maurus palmatus

<400> SEQUENCE: 19

Gly Asp Cys Leu Pro His Leu Lys Leu Cys Lys Glu Asn Lys Asp Cys
1               5                   10                  15

Cys Ser Lys Lys Cys Lys Arg Arg Gly Thr Asn Ile Glu Lys Arg Cys
            20                  25                  30

Arg

<210> SEQ ID NO 20
<211> LENGTH: 31
<212> TYPE: PRT
<213> ORGANISM: Heteropoda venatoria

<400> SEQUENCE: 20

Glu Cys Gly Thr Leu Phe Ser Gly Cys Ser Thr His Ala Asp Cys Cys
1               5                   10                  15

Glu Gly Phe Ile Cys Lys Leu Trp Cys Arg Tyr Glu Arg Thr Trp
            20                  25                  30

<210> SEQ ID NO 21
<211> LENGTH: 36
<212> TYPE: PRT
<213> ORGANISM: Haplopelma hainanum

<400> SEQUENCE: 21

Glu Cys Arg Tyr Trp Leu Gly Thr Cys Ser Lys Thr Gly Asp Cys Cys
1               5                   10                  15

Ser His Leu Ser Cys Ser Pro Lys His Gly Trp Cys Val Trp Asp Trp
            20                  25                  30

Thr Phe Arg Lys
        35

<210> SEQ ID NO 22
<211> LENGTH: 32
<212> TYPE: PRT
<213> ORGANISM: Chilobrachys guangxiensis

<400> SEQUENCE: 22

Gly Cys Gln Lys Phe Phe Trp Thr Cys His Pro Gly Gln Pro Pro Cys
1               5                   10                  15

Cys Ser Gly Leu Ala Cys Thr Trp Pro Thr Glu Ile Cys Ile Asp Gly
            20                  25                  30

<210> SEQ ID NO 23
<211> LENGTH: 33

```
<212> TYPE: PRT
<213> ORGANISM: Haplopelma hainanum

<400> SEQUENCE: 23

Gly Cys Lys Gly Phe Gly Asp Ser Cys Thr Pro Gly Lys Asn Glu Cys
1               5                   10                  15

Cys Pro Asn Tyr Ala Cys Ser Ser Lys His Lys Trp Cys Lys Val Tyr
                20                  25                  30

Leu

<210> SEQ ID NO 24
<211> LENGTH: 29
<212> TYPE: PRT
<213> ORGANISM: Heteropoda venatoria

<400> SEQUENCE: 24

Asp Asp Cys Gly Thr Leu Phe Ser Gly Cys Asp Thr Ser Lys Asp Cys
1               5                   10                  15

Cys Glu Gly Tyr Val Cys His Leu Trp Cys Lys Tyr Lys
                20                  25

<210> SEQ ID NO 25
<211> LENGTH: 34
<212> TYPE: PRT
<213> ORGANISM: Stromatopelma calceatum

<400> SEQUENCE: 25

Asp Cys Thr Arg Met Phe Gly Ala Cys Arg Arg Asp Ser Asp Cys Cys
1               5                   10                  15

Pro His Leu Gly Cys Lys Pro Thr Ser Lys Tyr Cys Ala Trp Asp Gly
                20                  25                  30

Thr Ile

<210> SEQ ID NO 26
<211> LENGTH: 34
<212> TYPE: PRT
<213> ORGANISM: Chilobrachys guangxiensis

<400> SEQUENCE: 26

Arg Cys Ile Glu Glu Gly Lys Trp Cys Pro Lys Lys Ala Pro Cys Cys
1               5                   10                  15

Gly Arg Leu Glu Cys Lys Gly Pro Ser Pro Lys Gln Lys Lys Cys Thr
                20                  25                  30

Arg Pro

<210> SEQ ID NO 27
<211> LENGTH: 35
<212> TYPE: PRT
<213> ORGANISM: Thrixopelma pruriens

<400> SEQUENCE: 27

Glu Cys Arg Tyr Trp Leu Gly Gly Cys Ser Ala Gly Gln Thr Cys Cys
1               5                   10                  15

Lys His Leu Val Cys Ser Arg Arg His Gly Trp Cys Val Trp Asp Gly
                20                  25                  30

Thr Phe Ser
        35

<210> SEQ ID NO 28
<211> LENGTH: 35
```

```
<212> TYPE: PRT
<213> ORGANISM: Heteroscodra maculata

<400> SEQUENCE: 28

Glu Cys Arg Tyr Leu Phe Gly Gly Cys Ser Ser Thr Ser Asp Cys Cys
1               5                   10                  15

Lys His Leu Ser Cys Arg Ser Asp Trp Lys Tyr Cys Ala Trp Asp Gly
            20                  25                  30

Thr Phe Ser
        35

<210> SEQ ID NO 29
<211> LENGTH: 36
<212> TYPE: PRT
<213> ORGANISM: Chilobrachys guangxiensis

<400> SEQUENCE: 29

Glu Gly Glu Cys Gly Gly Phe Trp Trp Lys Cys Gly Ser Gly Lys Pro
1               5                   10                  15

Ala Cys Cys Pro Lys Tyr Val Cys Ser Pro Lys Trp Gly Leu Cys Asn
            20                  25                  30

Phe Pro Met Pro
        35

<210> SEQ ID NO 30
<211> LENGTH: 36
<212> TYPE: PRT
<213> ORGANISM: Chilobrachys guangxiensis

<400> SEQUENCE: 30

Asp Gly Glu Cys Gly Gly Phe Trp Trp Lys Cys Gly Ser Gly Lys Pro
1               5                   10                  15

Ala Cys Cys Pro Lys Tyr Val Cys Ser Pro Lys Trp Gly Leu Cys Asn
            20                  25                  30

Phe Pro Met Pro
        35

<210> SEQ ID NO 31
<211> LENGTH: 37
<212> TYPE: PRT
<213> ORGANISM: Hadronyche versuta

<400> SEQUENCE: 31

Asp Asp Asp Cys Gly Trp Ile Met Asp Asp Cys Thr Ser Asp Ser Asp
1               5                   10                  15

Cys Cys Pro Asn Trp Val Cys Ser Lys Thr Gly Phe Val Lys Asn Ile
            20                  25                  30

Cys Lys Tyr Glu Met
        35

<210> SEQ ID NO 32
<211> LENGTH: 31
<212> TYPE: PRT
<213> ORGANISM: Chilobrachys guangxiensis

<400> SEQUENCE: 32

Leu Cys Ser Arg Glu Gly Glu Phe Cys Tyr Lys Leu Arg Lys Cys Cys
1               5                   10                  15

Ala Gly Phe Tyr Cys Lys Ala Phe Val Leu His Cys Tyr Arg Asn
            20                  25                  30
```

```
<210> SEQ ID NO 33
<211> LENGTH: 32
<212> TYPE: PRT
<213> ORGANISM: Brachypelma smithii

<400> SEQUENCE: 33
```

Ser Phe Cys Ile Pro Phe Lys Pro Cys Lys Ser Asp Glu Asn Cys Cys
1               5                   10                  15
Lys Lys Phe Lys Cys Lys Thr Thr Gly Ile Val Lys Leu Cys Arg Trp
            20                  25                  30

```
<210> SEQ ID NO 34
<211> LENGTH: 33
<212> TYPE: PRT
<213> ORGANISM: Chilobrachys guangxiensis

<400> SEQUENCE: 34
```

Glu Cys Arg Lys Met Phe Gly Gly Cys Ser Val Asp Ser Asp Cys Cys
1               5                   10                  15
Ala His Leu Gly Cys Lys Pro Thr Leu Lys Tyr Cys Ala Trp Asp Gly
            20                  25                  30
Thr

```
<210> SEQ ID NO 35
<211> LENGTH: 33
<212> TYPE: PRT
<213> ORGANISM: Heteropoda venatoria

<400> SEQUENCE: 35
```

Asp Cys Gly Thr Ile Trp His Tyr Cys Gly Thr Asp Gln Ser Glu Cys
1               5                   10                  15
Cys Glu Gly Trp Lys Cys Ser Arg Gln Leu Cys Lys Tyr Val Ile Asp
            20                  25                  30
Trp

```
<210> SEQ ID NO 36
<211> LENGTH: 34
<212> TYPE: PRT
<213> ORGANISM: Haplopelma schmidti

<400> SEQUENCE: 36
```

Gly Cys Leu Gly Asp Lys Cys Asp Tyr Asn Asn Gly Cys Cys Ser Gly
1               5                   10                  15
Tyr Val Cys Ser Arg Thr Trp Lys Trp Cys Val Leu Ala Gly Pro Trp
            20                  25                  30
Arg Arg

```
<210> SEQ ID NO 37
<211> LENGTH: 34
<212> TYPE: PRT
<213> ORGANISM: Chilobrachys guangxiensis

<400> SEQUENCE: 37
```

Gly Cys Gly Gly Leu Met Ala Gly Cys Asp Gly Lys Ser Thr Phe Cys
1               5                   10                  15
Cys Ser Gly Tyr Asn Cys Ser Pro Thr Trp Lys Trp Cys Val Tyr Ala
            20                  25                  30
Arg Pro

<210> SEQ ID NO 38
<211> LENGTH: 34
<212> TYPE: PRT
<213> ORGANISM: Chilobrachys guangxiensis

<400> SEQUENCE: 38

Glu Cys Arg Lys Met Phe Gly Gly Cys Ser Val His Ser Asp Cys Cys
1               5                   10                  15

Ala His Leu Gly Cys Lys Pro Thr Leu Lys Tyr Cys Ala Trp Asp Gly
            20                  25                  30

Thr Phe

<210> SEQ ID NO 39
<211> LENGTH: 34
<212> TYPE: PRT
<213> ORGANISM: Chilobrachys guangxiensis

<400> SEQUENCE: 39

Gly Cys Gly Gly Leu Met Asp Gly Cys Asp Gly Lys Ser Thr Phe Cys
1               5                   10                  15

Cys Ser Gly Phe Asn Cys Ser Pro Thr Trp Lys Trp Cys Val Tyr Ala
            20                  25                  30

Arg Pro

<210> SEQ ID NO 40
<211> LENGTH: 30
<212> TYPE: PRT
<213> ORGANISM: Heteropoda venatoria

<400> SEQUENCE: 40

Asp Asp Cys Gly Gly Leu Phe Ser Gly Cys Asp Ser Asn Ala Asp Cys
1               5                   10                  15

Cys Glu Gly Tyr Val Cys Arg Leu Trp Cys Lys Tyr Lys Leu
            20                  25                  30

<210> SEQ ID NO 41
<211> LENGTH: 35
<212> TYPE: PRT
<213> ORGANISM: Grammostola rosea

<400> SEQUENCE: 41

Glu Cys Arg Tyr Leu Phe Gly Gly Cys Lys Thr Thr Ser Asp Cys Cys
1               5                   10                  15

Lys His Leu Gly Cys Lys Phe Arg Asp Lys Tyr Cys Ala Trp Asp Phe
            20                  25                  30

Thr Phe Ser
        35

<210> SEQ ID NO 42
<211> LENGTH: 35
<212> TYPE: PRT
<213> ORGANISM: Grammostola rosea

<400> SEQUENCE: 42

Glu Cys Arg Tyr Leu Phe Gly Gly Cys Lys Thr Thr Ala Asp Cys Cys
1               5                   10                  15

Lys His Leu Gly Cys Lys Phe Arg Asp Lys Tyr Cys Ala Trp Asp Phe
            20                  25                  30

Thr Phe Ser
        35

<210> SEQ ID NO 43
<211> LENGTH: 35
<212> TYPE: PRT
<213> ORGANISM: Psalmopoeus cambridgei

<400> SEQUENCE: 43

Ser Glu Cys Arg Trp Phe Met Gly Gly Cys Asp Ser Thr Leu Asp Cys
1               5                   10                  15

Cys Lys His Leu Ser Cys Lys Met Gly Leu Tyr Tyr Cys Ala Trp Asp
            20                  25                  30

Gly Thr Phe
        35

<210> SEQ ID NO 44
<211> LENGTH: 36
<212> TYPE: PRT
<213> ORGANISM: Chilobrachys guangxiensis

<400> SEQUENCE: 44

Glu Cys Arg Lys Met Phe Gly Gly Cys Ser Val Asp Ser Asp Cys Cys
1               5                   10                  15

Ala His Leu Gly Cys Lys Pro Thr Leu Lys Tyr Cys Ala Trp Asp Gly
            20                  25                  30

Thr Phe Gly Lys
        35

<210> SEQ ID NO 45
<211> LENGTH: 38
<212> TYPE: PRT
<213> ORGANISM: Heteroscodra maculata

<400> SEQUENCE: 45

Glu Cys Arg Tyr Phe Trp Gly Glu Cys Asn Asp Glu Met Val Cys Cys
1               5                   10                  15

Glu His Leu Val Cys Lys Glu Lys Trp Pro Ile Thr Tyr Lys Ile Cys
            20                  25                  30

Val Trp Asp Arg Thr Phe
        35

<210> SEQ ID NO 46
<211> LENGTH: 36
<212> TYPE: PRT
<213> ORGANISM: Chilobrachys guangxiensis

<400> SEQUENCE: 46

Asp Gly Glu Cys Gly Gly Phe Trp Trp Lys Cys Gly Arg Gly Lys Pro
1               5                   10                  15

Pro Cys Cys Lys Gly Tyr Ala Cys Ser Lys Thr Trp Gly Trp Cys Ala
            20                  25                  30

Val Glu Ala Pro
        35

<210> SEQ ID NO 47
<211> LENGTH: 40
<212> TYPE: PRT
<213> ORGANISM: Psalmopoeus cambridgei

<400> SEQUENCE: 47

Glu Asp Cys Ile Pro Lys Trp Lys Gly Cys Val Asn Arg His Gly Asp
1               5                   10                  15

Cys Cys Glu Gly Leu Glu Cys Trp Lys Arg Arg Arg Ser Phe Glu Val
            20                  25                  30

Cys Val Pro Lys Thr Pro Lys Thr
            35                  40

<210> SEQ ID NO 48
<211> LENGTH: 35
<212> TYPE: PRT
<213> ORGANISM: Allagelena opulenta

<400> SEQUENCE: 48

Gly Gly Cys Leu Pro His Asn Arg Phe Cys Asn Ala Leu Ser Gly Pro
1               5                   10                  15

Arg Cys Cys Ser Gly Leu Lys Cys Lys Glu Leu Ser Ile Trp Asp Ser
            20                  25                  30

Arg Cys Leu
            35

<210> SEQ ID NO 49
<211> LENGTH: 37
<212> TYPE: PRT
<213> ORGANISM: Chilobrachys guangxiensis

<400> SEQUENCE: 49

Gln Cys Gly Glu Phe Met Trp Lys Cys Gly Ala Gly Lys Pro Thr Cys
1               5                   10                  15

Cys Ser Gly Tyr Asp Cys Ser Pro Thr Trp Lys Trp Cys Val Leu Lys
            20                  25                  30

Ser Pro Gly Arg Arg
            35

<210> SEQ ID NO 50
<211> LENGTH: 36
<212> TYPE: PRT
<213> ORGANISM: Chilobrachys guangxiensis

<400> SEQUENCE: 50

Thr Cys Tyr Asp Ile Gly Glu Leu Cys Ser Ser Asp Lys Pro Cys Cys
1               5                   10                  15

Ser Gly Tyr Tyr Cys Ser Pro Arg Trp Gly Trp Cys Ile Tyr Ser Thr
            20                  25                  30

Arg Gly Gly Arg
            35

<210> SEQ ID NO 51
<211> LENGTH: 37
<212> TYPE: PRT
<213> ORGANISM: Hadronyche versuta

<400> SEQUENCE: 51

Ser Ala Val Cys Ile Pro Ser Gly Gln Pro Cys Pro Tyr Ser Lys Tyr
1               5                   10                  15

Cys Cys Ser Gly Ser Cys Thr Tyr Lys Thr Asn Glu Asn Gly Asn Ser
            20                  25                  30

Val Gln Arg Cys Asp
            35

<210> SEQ ID NO 52
<211> LENGTH: 42
<212> TYPE: PRT
<213> ORGANISM: Haplopelma hainanum

```
<400> SEQUENCE: 52

Cys Ala Ala Glu Gly Ile Pro Cys Asp Pro Asn Pro Val Lys Asp Leu
1               5                   10                  15

Pro Cys Cys Ser Gly Leu Ala Cys Leu Lys Pro Thr Leu His Gly Ile
            20                  25                  30

Trp Tyr Lys His His Tyr Cys Tyr Thr Gln
        35                  40

<210> SEQ ID NO 53
<211> LENGTH: 37
<212> TYPE: PRT
<213> ORGANISM: Mesobuthus eupeus

<400> SEQUENCE: 53

Gly Cys Asn Arg Lys Asn Lys Cys Asn Ser Asp Ala Asp Cys Cys
1               5                   10                  15

Arg Tyr Gly Glu Arg Cys Ile Ser Thr Lys Val Asn Tyr Tyr Cys Arg
            20                  25                  30

Pro Asp Arg Gly Pro
            35

<210> SEQ ID NO 54
<211> LENGTH: 32
<212> TYPE: PRT
<213> ORGANISM: Chilobrachys guangxiensis

<400> SEQUENCE: 54

Val Cys Arg Gly Tyr Gly Leu Pro Cys Thr Pro Glu Lys Asn Asp Cys
1               5                   10                  15

Cys Gln Arg Leu Tyr Cys Ser Gln His Arg Leu Cys Ser Val Lys Ala
            20                  25                  30

<210> SEQ ID NO 55
<211> LENGTH: 28
<212> TYPE: PRT
<213> ORGANISM: Haplopelma schmidti

<400> SEQUENCE: 55

Lys Cys Leu Pro Pro Gly Lys Pro Cys Tyr Gly Ala Thr Gln Lys Ile
1               5                   10                  15

Pro Cys Cys Gly Val Cys Ser His Asn Lys Cys Thr
            20                  25

<210> SEQ ID NO 56
<211> LENGTH: 28
<212> TYPE: PRT
<213> ORGANISM: Chilobrachys guangxiensis

<400> SEQUENCE: 56

Cys Gly Gly Trp Met Ala Lys Cys Ala Asp Ser Asp Cys Cys Glu
1               5                   10                  15

Thr Phe His Cys Thr Arg Phe Asn Val Cys Gly Lys
            20                  25

<210> SEQ ID NO 57
<211> LENGTH: 28
<212> TYPE: PRT
<213> ORGANISM: Macrothele gigas

<400> SEQUENCE: 57
```

-continued

Ser Cys Lys Leu Thr Phe Trp Arg Cys Lys Lys Asp Lys Glu Cys Cys
1               5                   10                  15

Gly Trp Asn Ile Cys Thr Gly Leu Cys Ile Pro Pro
            20                  25

<210> SEQ ID NO 58
<211> LENGTH: 34
<212> TYPE: PRT
<213> ORGANISM: Stromatopelma calceatum griseipes

<400> SEQUENCE: 58

Thr Cys Arg Tyr Leu Phe Gly Gly Cys Lys Thr Thr Ala Asp Cys Cys
1               5                   10                  15

Lys His Leu Ala Cys Arg Ser Asp Gly Lys Tyr Cys Ala Trp Asp Gly
            20                  25                  30

Thr Phe

<210> SEQ ID NO 59
<211> LENGTH: 34
<212> TYPE: PRT
<213> ORGANISM: Chilobrachys guangxiensis

<400> SEQUENCE: 59

Glu Cys Lys Trp Tyr Leu Gly Asp Cys Lys Ala His Glu Asp Cys Cys
1               5                   10                  15

Glu His Leu Arg Cys His Ser Arg Trp Asp Trp Cys Ile Trp Asp Gly
            20                  25                  30

Thr Phe

<210> SEQ ID NO 60
<211> LENGTH: 34
<212> TYPE: PRT
<213> ORGANISM: Haplopelma hainanum

<400> SEQUENCE: 60

Glu Cys Lys Tyr Leu Trp Gly Thr Cys Glu Lys Asp Glu His Cys Cys
1               5                   10                  15

Glu His Leu Gly Cys Asn Lys Lys His Gly Trp Cys Gly Trp Asp Gly
            20                  25                  30

Thr Phe

<210> SEQ ID NO 61
<211> LENGTH: 29
<212> TYPE: PRT
<213> ORGANISM: Grammostola rosea

<400> SEQUENCE: 61

Tyr Cys Gln Lys Trp Leu Trp Thr Cys Asp Ser Glu Arg Lys Cys Cys
1               5                   10                  15

Glu Asp Met Val Cys Arg Leu Trp Cys Lys Lys Arg Leu
            20                  25

<210> SEQ ID NO 62
<211> LENGTH: 29
<212> TYPE: PRT
<213> ORGANISM: Grammostola rosea

<400> SEQUENCE: 62

Tyr Cys Gln Lys Trp Met Trp Thr Cys Asp Ser Lys Arg Lys Cys Cys
1               5                   10                  15

Glu Asp Met Val Cys Gln Leu Trp Cys Lys Lys Arg Leu
            20                  25

<210> SEQ ID NO 63
<211> LENGTH: 29
<212> TYPE: PRT
<213> ORGANISM: Paraphysa scrofa

<400> SEQUENCE: 63

Tyr Cys Gln Lys Trp Met Trp Thr Cys Asp Ser Ala Arg Lys Cys Cys
1               5                   10                  15

Glu Gly Leu Val Cys Arg Leu Trp Cys Lys Lys Ile Ile
            20                  25

<210> SEQ ID NO 64
<211> LENGTH: 29
<212> TYPE: PRT
<213> ORGANISM: Macrothele gigas

<400> SEQUENCE: 64

Gly Cys Lys Leu Thr Phe Trp Lys Cys Lys Asn Lys Lys Glu Cys Cys
1               5                   10                  15

Gly Trp Asn Ala Cys Ala Leu Gly Ile Cys Met Pro Arg
            20                  25

<210> SEQ ID NO 65
<211> LENGTH: 36
<212> TYPE: PRT
<213> ORGANISM: Haplopelma schmidti

<400> SEQUENCE: 65

Glu Cys Arg Trp Tyr Leu Gly Gly Cys Ser Gln Asp Gly Asp Cys Cys
1               5                   10                  15

Lys His Leu Gln Cys His Ser Asn Tyr Glu Trp Cys Val Trp Asp Gly
            20                  25                  30

Thr Phe Ser Lys
        35

<210> SEQ ID NO 66
<211> LENGTH: 35
<212> TYPE: PRT
<213> ORGANISM: Psalmopoeus cambridgei

<400> SEQUENCE: 66

Gly Ala Cys Arg Trp Phe Leu Gly Gly Cys Lys Ser Thr Ser Asp Cys
1               5                   10                  15

Cys Glu His Leu Ser Cys Lys Met Gly Leu Asp Tyr Cys Ala Trp Asp
            20                  25                  30

Gly Thr Phe
        35

<210> SEQ ID NO 67
<211> LENGTH: 41
<212> TYPE: PRT
<213> ORGANISM: Hysterocrates gigas

<400> SEQUENCE: 67

Gly Val Asp Lys Ala Gly Cys Arg Tyr Met Phe Gly Gly Cys Ser Val
1               5                   10                  15

Asn Asp Asp Cys Cys Pro Arg Leu Gly Cys His Ser Leu Phe Ser Tyr
            20                  25                  30

-continued

```
Cys Ala Trp Asp Leu Thr Phe Ser Asp
        35                  40
```

<210> SEQ ID NO 68
<211> LENGTH: 35
<212> TYPE: PRT
<213> ORGANISM: Conus pennaceus

<400> SEQUENCE: 68

```
Asp Cys Thr Ser Trp Phe Gly Arg Cys Thr Val Asn Ser Glu Cys Cys
1               5                   10                  15

Ser Asn Ser Cys Asp Gln Thr Tyr Cys Glu Leu Tyr Ala Phe Pro Ser
            20                  25                  30

Phe Gly Ala
        35
```

<210> SEQ ID NO 69
<211> LENGTH: 36
<212> TYPE: PRT
<213> ORGANISM: Phoneutria nigriventer

<400> SEQUENCE: 69

```
Ile Ala Cys Ala Pro Arg Phe Ser Leu Cys Asn Ser Asp Lys Glu Cys
1               5                   10                  15

Cys Lys Gly Leu Arg Cys Gln Ser Arg Ile Ala Asn Met Trp Pro Thr
            20                  25                  30

Phe Cys Ser Gln
        35
```

<210> SEQ ID NO 70
<211> LENGTH: 36
<212> TYPE: PRT
<213> ORGANISM: Phoneutria reidyi

<400> SEQUENCE: 70

```
Ile Ala Cys Ala Pro Arg Gly Leu Leu Cys Phe Arg Asp Lys Glu Cys
1               5                   10                  15

Cys Lys Gly Leu Thr Cys Lys Gly Arg Phe Val Asn Thr Trp Pro Thr
            20                  25                  30

Phe Cys Leu Val
        35
```

<210> SEQ ID NO 71
<211> LENGTH: 36
<212> TYPE: PRT
<213> ORGANISM: Chilobrachys guangxiensis

<400> SEQUENCE: 71

```
Asp Cys Arg Lys Met Phe Gly Gly Cys Ser Lys His Glu Asp Cys Cys
1               5                   10                  15

Ala His Leu Ala Cys Lys Arg Thr Phe Asn Tyr Cys Ala Trp Asp Gly
            20                  25                  30

Ser Phe Ser Lys
        35
```

<210> SEQ ID NO 72
<211> LENGTH: 35
<212> TYPE: PRT
<213> ORGANISM: Chilobrachys guangxiensis

<400> SEQUENCE: 72

```
Glu Cys Arg Trp Leu Phe Gly Gly Cys Glu Lys Asp Ser Asp Cys Cys
1               5                   10                  15

Glu His Leu Gly Cys Arg Arg Ala Lys Pro Ser Trp Cys Gly Trp Asp
                20                  25                  30

Phe Thr Val
        35

<210> SEQ ID NO 73
<211> LENGTH: 35
<212> TYPE: PRT
<213> ORGANISM: Chilobrachys guangxiensis

<400> SEQUENCE: 73

Glu Cys Arg Trp Leu Phe Gly Gly Cys Glu Lys Asp Ser Asp Cys Cys
1               5                   10                  15

Glu His Leu Gly Cys Arg Arg Ala Lys Pro Ser Trp Cys Gly Trp Asp
                20                  25                  30

Phe Thr Phe
        35

<210> SEQ ID NO 74
<211> LENGTH: 36
<212> TYPE: PRT
<213> ORGANISM: Phoneutria nigriventer

<400> SEQUENCE: 74

Ile Ala Cys Ala Pro Arg Phe Ser Ile Cys Asn Ser Asp Lys Glu Cys
1               5                   10                  15

Cys Lys Gly Leu Arg Cys Gln Ser Arg Ile Ala Asn Met Trp Pro Thr
                20                  25                  30

Phe Cys Leu Val
        35

<210> SEQ ID NO 75
<211> LENGTH: 39
<212> TYPE: PRT
<213> ORGANISM: Haplopelma hainanum

<400> SEQUENCE: 75

Cys Ile Gly Glu Gly Val Pro Cys Asp Glu Asn Asp Pro Arg Cys Cys
1               5                   10                  15

Ser Gly Leu Val Cys Leu Lys Pro Thr Leu His Gly Ile Trp Tyr Lys
                20                  25                  30

Ser Tyr Tyr Cys Tyr Lys Lys
        35

<210> SEQ ID NO 76
<211> LENGTH: 35
<212> TYPE: PRT
<213> ORGANISM: Haplopelma hainanum

<400> SEQUENCE: 76

Asp Cys Ala Gly Tyr Met Arg Glu Cys Lys Glu Lys Leu Cys Cys Ser
1               5                   10                  15

Gly Tyr Val Cys Ser Ser Arg Trp Lys Trp Cys Val Leu Pro Ala Pro
                20                  25                  30

Trp Arg Arg
        35

<210> SEQ ID NO 77
```

```
<211> LENGTH: 36
<212> TYPE: PRT
<213> ORGANISM: Haplopelma hainanum

<400> SEQUENCE: 77

Glu Cys Arg Trp Tyr Leu Gly Gly Cys Ser Gln Asp Gly Asp Cys Cys
1               5                   10                  15

Lys His Leu Gln Cys His Ser Asn Tyr Glu Trp Cys Ile Trp Asp Gly
            20                  25                  30

Thr Phe Ser Lys
            35

<210> SEQ ID NO 78
<211> LENGTH: 35
<212> TYPE: PRT
<213> ORGANISM: Chilobrachys guangxiensis

<400> SEQUENCE: 78

Glu Cys Lys Lys Leu Phe Gly Gly Cys Thr Thr Ser Ser Glu Cys Cys
1               5                   10                  15

Ala His Leu Gly Cys Lys Gln Lys Trp Pro Phe Tyr Cys Ala Trp Asp
            20                  25                  30

Trp Ser Phe
            35

<210> SEQ ID NO 79
<211> LENGTH: 40
<212> TYPE: PRT
<213> ORGANISM: Heriaeus melloteei

<400> SEQUENCE: 79

Gly Cys Ile Pro Ser Phe Gly Glu Cys Ala Trp Phe Ser Gly Glu Ser
1               5                   10                  15

Cys Cys Thr Gly Ile Cys Lys Trp Val Phe Phe Thr Ser Lys Phe Met
            20                  25                  30

Cys Arg Arg Val Trp Gly Lys Asp
            35                  40

<210> SEQ ID NO 80
<211> LENGTH: 35
<212> TYPE: PRT
<213> ORGANISM: Hadrurus gertschi

<400> SEQUENCE: 80

Ser Glu Lys Asp Cys Ile Lys His Leu Gln Arg Cys Arg Glu Asn Lys
1               5                   10                  15

Asp Cys Cys Ser Lys Lys Cys Ser Arg Arg Gly Thr Asn Pro Glu Lys
            20                  25                  30

Arg Cys Arg
            35

<210> SEQ ID NO 81
<211> LENGTH: 30
<212> TYPE: PRT
<213> ORGANISM: Thrixopelma pruriens

<400> SEQUENCE: 81

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Trp
            20                  25                  30
```

<210> SEQ ID NO 82
<211> LENGTH: 30
<212> TYPE: PRT
<213> ORGANISM: Chilobrachys guangxiensis

<400> SEQUENCE: 82

Tyr Cys Gln Lys Trp Met Trp Thr Cys Asp Ser Lys Arg Ala Cys Cys
1               5                   10                  15

Glu Gly Leu Arg Cys Lys Leu Trp Cys Arg Lys Ile Ile Gly
            20                  25                  30

<210> SEQ ID NO 83
<211> LENGTH: 30
<212> TYPE: PRT
<213> ORGANISM: Heteropoda venatoria

<400> SEQUENCE: 83

Asp Asp Cys Gly Lys Leu Phe Ser Gly Cys Asp Thr Asn Ala Asp Cys
1               5                   10                  15

Cys Glu Gly Tyr Val Cys Arg Leu Trp Cys Lys Leu Asp Trp
            20                  25                  30

<210> SEQ ID NO 84
<211> LENGTH: 31
<212> TYPE: PRT
<213> ORGANISM: Grammostola rosea

<400> SEQUENCE: 84

Tyr Cys Gln Lys Trp Met Trp Thr Cys Asp Glu Glu Arg Lys Cys Cys
1               5                   10                  15

Glu Gly Leu Val Cys Arg Leu Trp Cys Lys Lys Lys Ile Glu Trp
            20                  25                  30

<210> SEQ ID NO 85
<211> LENGTH: 31
<212> TYPE: PRT
<213> ORGANISM: Conus marmoreus

<400> SEQUENCE: 85

Ala Cys Ser Lys Lys Trp Glu Tyr Cys Ile Val Pro Ile Leu Gly Phe
1               5                   10                  15

Val Tyr Cys Cys Pro Gly Leu Ile Cys Gly Pro Phe Val Cys Val
            20                  25                  30

<210> SEQ ID NO 86
<211> LENGTH: 31
<212> TYPE: PRT
<213> ORGANISM: Grammostola rosea

<400> SEQUENCE: 86

Tyr Cys Gln Lys Trp Met Trp Thr Cys Asp Glu Glu Arg Lys Cys Cys
1               5                   10                  15

Glu Gly Leu Val Cys Arg Leu Trp Cys Lys Arg Ile Ile Asn Met
            20                  25                  30

<210> SEQ ID NO 87
<211> LENGTH: 32
<212> TYPE: PRT
<213> ORGANISM: Grammostola rosea

<400> SEQUENCE: 87

```
Tyr Cys Gln Lys Trp Met Trp Thr Cys Asp Glu Glu Arg Lys Cys Cys
1               5                   10                  15

Glu Gly Leu Val Cys Arg Leu Trp Cys Lys Lys Ile Glu Glu Gly
            20                  25                  30
```

<210> SEQ ID NO 88
<211> LENGTH: 32
<212> TYPE: PRT
<213> ORGANISM: Chilobrachys guangxiensis

<400> SEQUENCE: 88

```
Gly Cys Gly Thr Met Trp Ser Pro Cys Ser Thr Glu Lys Pro Cys Cys
1               5                   10                  15

Asp Asn Phe Ser Cys Gln Pro Ala Ile Lys Trp Cys Ile Trp Ser Pro
            20                  25                  30
```

<210> SEQ ID NO 89
<211> LENGTH: 34
<212> TYPE: PRT
<213> ORGANISM: Psalmopoeus cambridgei

<400> SEQUENCE: 89

```
Glu Cys Arg Trp Tyr Leu Gly Gly Cys Lys Glu Asp Ser Glu Cys Cys
1               5                   10                  15

Glu His Leu Gln Cys His Ser Tyr Trp Glu Trp Cys Leu Trp Asp Gly
            20                  25                  30

Ser Phe
```

<210> SEQ ID NO 90
<211> LENGTH: 39
<212> TYPE: PRT
<213> ORGANISM: Ceratogyrus marshalli

<400> SEQUENCE: 90

```
Gly Val Asp Lys Glu Gly Cys Arg Lys Leu Leu Gly Gly Cys Thr Ile
1               5                   10                  15

Asp Asp Asp Cys Cys Pro His Leu Gly Cys Asn Lys Lys Tyr Trp His
            20                  25                  30

Cys Gly Trp Asp Gly Thr Phe
            35
```

<210> SEQ ID NO 91
<211> LENGTH: 36
<212> TYPE: PRT
<213> ORGANISM: Chilobrachys guangxiensis

<400> SEQUENCE: 91

```
Glu Cys Thr Lys Phe Leu Gly Gly Cys Ser Glu Asp Ser Glu Cys Cys
1               5                   10                  15

Pro His Leu Gly Cys Lys Asp Val Leu Tyr Tyr Cys Ala Trp Asp Gly
            20                  25                  30

Thr Phe Gly Lys
            35
```

<210> SEQ ID NO 92
<211> LENGTH: 35
<212> TYPE: PRT
<213> ORGANISM: Chilobrachys guangxiensis

<400> SEQUENCE: 92

```
Glu Cys Thr Lys Leu Leu Gly Gly Cys Thr Lys Asp Ser Glu Cys Cys
```

-continued

```
              1               5              10              15

Pro His Leu Gly Cys Arg Lys Lys Trp Pro Tyr His Cys Gly Trp Asp
                             20              25              30

Gly Thr Phe
                      35

<210> SEQ ID NO 93
<211> LENGTH: 37
<212> TYPE: PRT
<213> ORGANISM: Hadronyche versuta

<400> SEQUENCE: 93

Ser Pro Thr Cys Ile Pro Ser Gly Gln Pro Cys Pro Tyr Asn Glu Asn
1               5                  10                  15

Cys Cys Ser Gln Ser Cys Thr Phe Lys Glu Asn Glu Asn Gly Asn Thr
            20                  25                  30

Val Lys Arg Cys Asp
        35

<210> SEQ ID NO 94
<211> LENGTH: 35
<212> TYPE: PRT
<213> ORGANISM: Chilobrachys guangxiensis

<400> SEQUENCE: 94

Ala Cys Arg Glu Trp Leu Gly Gly Cys Ser Lys Asp Ala Asp Cys Cys
1               5                  10                  15

Ala His Leu Glu Cys Arg Lys Lys Trp Pro Tyr His Cys Val Trp Asp
            20                  25                  30

Trp Thr Val
        35

<210> SEQ ID NO 95
<211> LENGTH: 36
<212> TYPE: PRT
<213> ORGANISM: Atrax robustus

<400> SEQUENCE: 95

Ser Val Cys Ile Pro Ser Gly Gln Pro Cys Pro Tyr Asn Glu His Cys
1               5                  10                  15

Cys Ser Gly Ser Cys Thr Tyr Lys Glu Asn Glu Asn Gly Asn Thr Val
            20                  25                  30

Gln Arg Cys Asp
        35

<210> SEQ ID NO 96
<211> LENGTH: 37
<212> TYPE: PRT
<213> ORGANISM: Hadronyche versuta

<400> SEQUENCE: 96

Ser Ser Thr Cys Ile Pro Ser Gly Gln Pro Cys Pro Tyr Asn Glu Asn
1               5                  10                  15

Cys Cys Ser Gln Ser Cys Thr Tyr Lys Glu Asn Glu Asn Gly Asn Thr
            20                  25                  30

Val Lys Arg Cys Asp
        35

<210> SEQ ID NO 97
<211> LENGTH: 36
```

```
<212> TYPE: PRT
<213> ORGANISM: Hadronyche formidabilis

<400> SEQUENCE: 97

Ser Thr Cys Thr Pro Thr Asp Gln Pro Cys Pro Tyr His Glu Ser Cys
1               5                   10                  15

Cys Ser Gly Ser Cys Thr Tyr Lys Ala Asn Glu Asn Gly Asn Gln Val
            20                  25                  30

Lys Arg Cys Asp
        35

<210> SEQ ID NO 98
<211> LENGTH: 37
<212> TYPE: PRT
<213> ORGANISM: Hadronyche formidabilis

<400> SEQUENCE: 98

Ser Pro Thr Cys Ile Arg Ser Gly Gln Pro Cys Pro Tyr Asn Glu Asn
1               5                   10                  15

Cys Cys Ser Gln Ser Cys Thr Phe Lys Thr Asn Glu Asn Gly Asn Thr
            20                  25                  30

Val Lys Arg Cys Asp
        35

<210> SEQ ID NO 99
<211> LENGTH: 37
<212> TYPE: PRT
<213> ORGANISM: Hadronyche infensa

<400> SEQUENCE: 99

Ser Pro Thr Cys Ile Pro Thr Gly Gln Pro Cys Pro Tyr Asn Glu Asn
1               5                   10                  15

Cys Cys Ser Gln Ser Cys Thr Tyr Lys Ala Asn Glu Asn Gly Asn Gln
            20                  25                  30

Val Lys Arg Cys Asp
        35

<210> SEQ ID NO 100
<211> LENGTH: 37
<212> TYPE: PRT
<213> ORGANISM: Hadronyche infensa

<400> SEQUENCE: 100

Ser Ser Thr Cys Ile Arg Thr Asp Gln Pro Cys Pro Tyr Asn Glu Ser
1               5                   10                  15

Cys Cys Ser Gly Ser Cys Thr Tyr Lys Ala Asn Glu Asn Gly Asn Gln
            20                  25                  30

Val Lys Arg Cys Asp
        35

<210> SEQ ID NO 101
<211> LENGTH: 37
<212> TYPE: PRT
<213> ORGANISM: Hadronyche versuta

<400> SEQUENCE: 101

Ser Ser Thr Cys Ile Pro Ser Gly Gln Pro Cys Pro Tyr Asn Glu Asn
1               5                   10                  15

Cys Cys Ser Gln Ser Cys Thr Phe Lys Glu Asn Glu Asn Gly Asn Thr
            20                  25                  30
```

```
Val Lys Arg Cys Asp
        35

<210> SEQ ID NO 102
<211> LENGTH: 37
<212> TYPE: PRT
<213> ORGANISM: Hadronyche versuta

<400> SEQUENCE: 102

Ser Pro Thr Cys Ile Pro Ser Gly Gln Pro Cys Pro Tyr Asn Glu Asn
1               5                   10                  15

Cys Cys Ser Lys Ser Cys Thr Tyr Lys Glu Asn Glu Asn Gly Asn Thr
            20                  25                  30

Val Gln Arg Cys Asp
        35

<210> SEQ ID NO 103
<211> LENGTH: 37
<212> TYPE: PRT
<213> ORGANISM: Hadronyche versuta

<400> SEQUENCE: 103

Ser Pro Thr Cys Ile Pro Ser Gly Gln Pro Cys Pro Tyr Asn Glu Asn
1               5                   10                  15

Cys Cys Ser Gln Ser Cys Thr Tyr Lys Glu Asn Glu Asn Gly Asn Thr
            20                  25                  30

Val Lys Arg Cys Asp
        35

<210> SEQ ID NO 104
<211> LENGTH: 38
<212> TYPE: PRT
<213> ORGANISM: Macrothele gigas

<400> SEQUENCE: 104

Cys Met Gly Tyr Asp Ile His Cys Thr Asp Arg Leu Pro Cys Cys Phe
1               5                   10                  15

Gly Leu Glu Cys Val Lys Thr Ser Gly Tyr Trp Trp Tyr Lys Lys Thr
            20                  25                  30

Tyr Cys Arg Arg Lys Ser
        35

<210> SEQ ID NO 105
<211> LENGTH: 39
<212> TYPE: PRT
<213> ORGANISM: Missulena bradleyi

<400> SEQUENCE: 105

Ser Pro Val Cys Thr Pro Ser Gly Gln Pro Cys Gln Pro Asn Thr Gln
1               5                   10                  15

Pro Cys Cys Asn Asn Ala Glu Glu Glu Gln Thr Ile Asn Cys Asn Gly
            20                  25                  30

Asn Thr Val Tyr Arg Cys Ala
        35

<210> SEQ ID NO 106
<211> LENGTH: 39
<212> TYPE: PRT
<213> ORGANISM: Haplopelma hainanum

<400> SEQUENCE: 106
```

```
Ser Pro Val Cys Thr Pro Ser Gly Gln Pro Cys Gln Pro Asn Thr Gln
1               5                   10                  15

Pro Cys Cys Asn Asn Ala Glu Glu Glu Gln Thr Ile Asn Cys Asn Gly
            20                  25                  30

Asn Thr Val Tyr Arg Cys Ala
            35
```

<210> SEQ ID NO 107
<211> LENGTH: 29
<212> TYPE: PRT
<213> ORGANISM: Chilobrachys guangxiensis

<400> SEQUENCE: 107

```
Tyr Cys Gln Lys Trp Met Trp Thr Cys Asp Ser Glu Arg Lys Cys Cys
1               5                   10                  15

Glu Gly Tyr Val Cys Glu Leu Trp Cys Lys Tyr Asn Leu
            20                  25
```

<210> SEQ ID NO 108
<211> LENGTH: 33
<212> TYPE: PRT
<213> ORGANISM: Chilobrachys guangxiensis

<400> SEQUENCE: 108

```
Ala Cys Gly Gln Phe Trp Trp Lys Cys Gly Glu Gly Lys Pro Pro Cys
1               5                   10                  15

Cys Ala Asn Phe Ala Cys Lys Ile Gly Leu Tyr Leu Cys Ile Trp Ser
            20                  25                  30

Pro
```

<210> SEQ ID NO 109
<211> LENGTH: 36
<212> TYPE: PRT
<213> ORGANISM: Grammostola rosea

<400> SEQUENCE: 109

```
Asp Cys Val Arg Phe Trp Gly Lys Cys Ser Gln Thr Ser Asp Cys Cys
1               5                   10                  15

Pro His Leu Ala Cys Lys Ser Lys Trp Pro Arg Asn Ile Cys Val Trp
            20                  25                  30

Asp Gly Ser Val
            35
```

<210> SEQ ID NO 110
<211> LENGTH: 36
<212> TYPE: PRT
<213> ORGANISM: Chilobrachys guangxiensis

<400> SEQUENCE: 110

```
Asp Cys Arg Ala Leu Tyr Gly Gly Cys Thr Lys Asp Glu Asp Cys Cys
1               5                   10                  15

Lys His Leu Ala Cys Arg Arg Thr Leu Pro Thr Tyr Cys Ala Trp Asp
            20                  25                  30

Leu Thr Phe Pro
            35
```

<210> SEQ ID NO 111
<211> LENGTH: 22
<212> TYPE: PRT
<213> ORGANISM: Homo sapiens

```
<400> SEQUENCE: 111

Ile Leu Asp Ile Val Leu Leu Phe Gln Glu His Gln Phe Glu Ala Leu
1               5                   10                  15

Gly Leu Leu Ile Leu Leu
            20

<210> SEQ ID NO 112
<211> LENGTH: 13
<212> TYPE: PRT
<213> ORGANISM: Homo sapiens

<400> SEQUENCE: 112

Ile Leu Asp Ile Val Leu Leu Phe Gln Glu His Gln Phe
1               5                   10

<210> SEQ ID NO 113
<211> LENGTH: 38
<212> TYPE: PRT
<213> ORGANISM: Ciona intestinalis

<400> SEQUENCE: 113

Val Val Val Val Ile Ser Phe Gly Val Asp Ile Ala Leu Ile Phe Val
1               5                   10                  15

Gly Glu Ser Glu Ala Leu Ala Ala Ile Gly Leu Leu Val Ile Leu Arg
            20                  25                  30

Leu Trp Arg Val Phe Arg
            35

<210> SEQ ID NO 114
<211> LENGTH: 36
<212> TYPE: PRT
<213> ORGANISM: Homo sapiens

<400> SEQUENCE: 114

Val Val Val Val Val Ser Phe Ile Leu Asp Ile Val Leu Leu Phe Gln
1               5                   10                  15

Glu His Gln Phe Glu Ala Leu Gly Leu Leu Ile Leu Leu Arg Leu Trp
            20                  25                  30

Arg Val Ala Arg
            35

<210> SEQ ID NO 115
<211> LENGTH: 33
<212> TYPE: PRT
<213> ORGANISM: Artificial Sequence
<220> FEATURE:
<223> OTHER INFORMATION: toxin sequence element

<400> SEQUENCE: 115

Asp Cys Ala Gly Tyr Met Arg Glu Cys Lys Lys Asp Lys Glu Cys Cys
1               5                   10                  15

Gly Trp Asn Ile Cys Asn Arg Lys His Lys Trp Cys Lys Tyr Lys Leu
            20                  25                  30

Trp

<210> SEQ ID NO 116
<211> LENGTH: 35
<212> TYPE: PRT
<213> ORGANISM: Artificial Sequence
<220> FEATURE:
<223> OTHER INFORMATION: toxin sequence element
```

```
<400> SEQUENCE: 116

Gly Cys Gln Met Thr Phe Trp Lys Cys Asn Ala Leu Asp His Asn Cys
1               5                   10                  15

Cys His Gly Tyr Ala Ala Cys Gly Cys Lys Lys Ile Ile Val Ser Ala
            20                  25                  30

Arg Ile Ala
        35

<210> SEQ ID NO 117
<211> LENGTH: 37
<212> TYPE: PRT
<213> ORGANISM: Artificial Sequence
<220> FEATURE:
<223> OTHER INFORMATION: toxin sequence element

<400> SEQUENCE: 117

Gly Gly Cys Leu Pro His Asn Arg Phe Cys Asn Pro Ser Asn Asp Gln
1               5                   10                  15

Cys Cys Lys Ser Ala Asn Leu Val Cys Arg Leu Trp Cys Lys Lys Lys
            20                  25                  30

Ile Glu Gly Asp Pro
        35

<210> SEQ ID NO 118
<211> LENGTH: 39
<212> TYPE: PRT
<213> ORGANISM: Artificial Sequence
<220> FEATURE:
<223> OTHER INFORMATION: toxin sequence element

<400> SEQUENCE: 118

Gly Cys Lys Gly Phe Gly Asp Ser Cys Ala Asp Ser Asp Cys Cys
1               5                   10                  15

Glu Thr Phe His Cys Lys Trp Val Phe Phe Thr Ser Lys Phe Met Cys
            20                  25                  30

Arg Arg Val Trp Gly Lys Asp
        35

<210> SEQ ID NO 119
<211> LENGTH: 37
<212> TYPE: PRT
<213> ORGANISM: Artificial Sequence
<220> FEATURE:
<223> OTHER INFORMATION: toxin sequence element

<400> SEQUENCE: 119

Gly Cys Leu Gly Asp Lys Cys Ala Asp Ser Asp Cys Cys Glu Thr
1               5                   10                  15

Phe His Cys Lys Trp Val Phe Phe Thr Ser Lys Phe Met Cys Arg Arg
            20                  25                  30

Val Trp Gly Lys Asp
        35

<210> SEQ ID NO 120
<211> LENGTH: 41
<212> TYPE: PRT
<213> ORGANISM: Artificial Sequence
<220> FEATURE:
<223> OTHER INFORMATION: toxin sequence element

<400> SEQUENCE: 120

Ser Pro Thr Cys Ile Pro Ser Gly Gln Pro Cys Ala Asp Ser Asp
```

```
                1               5                  10                 15
Cys Cys Glu Thr Phe His Cys Lys Trp Val Phe Phe Thr Ser Lys Phe
                20                 25                 30

Met Cys Arg Arg Val Trp Gly Lys Asp
            35                  40

<210> SEQ ID NO 121
<211> LENGTH: 38
<212> TYPE: PRT
<213> ORGANISM: Artificial Sequence
<220> FEATURE:
<223> OTHER INFORMATION: toxin sequence element
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid

<400> SEQUENCE: 121

Asp Glu Asp Cys Gln Pro Pro Gly Asn Phe Cys Xaa Asn Thr Ser Asp
1               5                   10                  15

Cys Cys Glu His Leu Xaa Cys Pro Thr Thr Pro Arg Phe Pro Tyr Leu
                20                  25                  30

Cys Gln Tyr Xaa Met Gly
            35

<210> SEQ ID NO 122
<211> LENGTH: 29
<212> TYPE: PRT
<213> ORGANISM: Artificial Sequence
<220> FEATURE:
<223> OTHER INFORMATION: toxin sequence element

<400> SEQUENCE: 122

Gly Ala Cys Arg Trp Phe Leu Gly Gly Cys Thr Pro Glu Lys Asn Asp
1               5                   10                  15

Cys Cys Gln Arg Leu Tyr Cys Gly Pro Phe Val Cys Val
                20                  25

<210> SEQ ID NO 123
<211> LENGTH: 33
<212> TYPE: PRT
<213> ORGANISM: Artificial Sequence
<220> FEATURE:
<223> OTHER INFORMATION: toxin sequence element

<400> SEQUENCE: 123

Ser Pro Val Cys Thr Pro Ser Gly Gln Pro Cys Arg Glu Asn Lys Asp
1               5                   10                  15

Cys Cys Ser Lys Lys Cys Lys Thr Thr Gly Ile Val Lys Leu Cys Arg
                20                  25                  30

Trp

<210> SEQ ID NO 124
<211> LENGTH: 38
<212> TYPE: PRT
<213> ORGANISM: Artificial Sequence
<220> FEATURE:
```

<223> OTHER INFORMATION: toxin sequence element

<400> SEQUENCE: 124

```
Ala Cys Ser Lys Lys Trp Glu Tyr Cys Thr Lys Asp Ser Glu Cys Cys
1               5                   10                  15

Pro His Leu Gly Cys Trp Lys Arg Arg Arg Ser Phe Glu Val Cys Val
            20                  25                  30

Pro Lys Thr Pro Lys Thr
        35
```

<210> SEQ ID NO 125
<211> LENGTH: 33
<212> TYPE: PRT
<213> ORGANISM: Artificial Sequence
<220> FEATURE:
<223> OTHER INFORMATION: toxin sequence element

<400> SEQUENCE: 125

```
Arg Cys Ile Glu Glu Gly Lys Trp Cys Thr Lys Asp Glu Asp Cys Cys
1               5                   10                  15

Lys His Leu Ala Cys Asn Arg Lys His Lys Trp Cys Lys Tyr Lys Leu
            20                  25                  30

Trp
```

<210> SEQ ID NO 126
<211> LENGTH: 41
<212> TYPE: PRT
<213> ORGANISM: Artificial Sequence
<220> FEATURE:
<223> OTHER INFORMATION: toxin sequence element

<400> SEQUENCE: 126

```
Ser Pro Thr Cys Ile Arg Ser Gly Gln Pro Cys Ala Asp Ser Asp Asp
1               5                   10                  15

Cys Cys Glu Thr Phe His Cys Lys Trp Val Phe Phe Thr Ser Lys Phe
            20                  25                  30

Met Cys Arg Arg Val Trp Gly Lys Asp
        35                  40
```

<210> SEQ ID NO 127
<211> LENGTH: 40
<212> TYPE: PRT
<213> ORGANISM: Artificial Sequence
<220> FEATURE:
<223> OTHER INFORMATION: toxin sequence element

<400> SEQUENCE: 127

```
Ser Thr Cys Thr Pro Thr Asp Gln Pro Cys Ala Asp Ser Asp Asp Cys
1               5                   10                  15

Cys Glu Thr Phe His Cys Lys Trp Val Phe Phe Thr Ser Lys Phe Met
            20                  25                  30

Cys Arg Arg Val Trp Gly Lys Asp
        35                  40
```

<210> SEQ ID NO 128
<211> LENGTH: 39
<212> TYPE: PRT
<213> ORGANISM: Artificial Sequence
<220> FEATURE:
<223> OTHER INFORMATION: toxin sequence element

<400> SEQUENCE: 128

```
Gly Cys Lys Trp Tyr Leu Gly Asp Cys Ala Asp Ser Asp Asp Cys Cys
1               5                   10                  15
Glu Thr Phe His Cys Lys Trp Val Phe Phe Thr Ser Lys Phe Met Cys
                20                  25                  30
Arg Arg Val Trp Gly Lys Asp
            35
```

<210> SEQ ID NO 129
<211> LENGTH: 41
<212> TYPE: PRT
<213> ORGANISM: Artificial Sequence
<220> FEATURE:
<223> OTHER INFORMATION: toxin sequence element

<400> SEQUENCE: 129

```
Ser Ser Thr Cys Ile Pro Ser Gly Gln Pro Cys Ala Asp Ser Asp Asp
1               5                   10                  15
Cys Cys Glu Thr Phe His Cys Lys Trp Val Phe Phe Thr Ser Lys Phe
                20                  25                  30
Met Cys Arg Arg Val Trp Gly Lys Asp
            35                  40
```

<210> SEQ ID NO 130
<211> LENGTH: 33
<212> TYPE: PRT
<213> ORGANISM: Artificial Sequence
<220> FEATURE:
<223> OTHER INFORMATION: toxin sequence element

<400> SEQUENCE: 130

```
Ala Cys Ser Lys Lys Trp Glu Tyr Cys Lys Glu Lys Leu Cys Cys Ser
1               5                   10                  15
Gly Tyr Val Cys Lys Arg Arg Gly Thr Asn Ile Glu Lys Arg Cys Arg
                20                  25                  30
Gly
```

<210> SEQ ID NO 131
<211> LENGTH: 29
<212> TYPE: PRT
<213> ORGANISM: Artificial Sequence
<220> FEATURE:
<223> OTHER INFORMATION: toxin sequence element

<400> SEQUENCE: 131

```
Ala Cys Gly Gln Phe Trp Trp Lys Cys Thr Ser Asp Ser Asp Cys Cys
1               5                   10                  15
Pro Asn Trp Val Cys Arg Leu Trp Cys Lys Tyr Lys Leu
                20                  25
```

<210> SEQ ID NO 132
<211> LENGTH: 35
<212> TYPE: PRT
<213> ORGANISM: Artificial Sequence
<220> FEATURE:
<223> OTHER INFORMATION: toxin sequence element

<400> SEQUENCE: 132

```
Cys Arg Tyr Trp Leu Gly Gly Cys Ser Gln Asp Gly Asp Cys Cys Lys
1               5                   10                  15
His Leu Gln Cys Ser Pro Arg Trp Gly Trp Cys Ile Tyr Ser Thr Arg
                20                  25                  30
Gly Gly Arg
```

<210> SEQ ID NO 133
<211> LENGTH: 31
<212> TYPE: PRT
<213> ORGANISM: Artificial Sequence
<220> FEATURE:
<223> OTHER INFORMATION: toxin sequence element

<400> SEQUENCE: 133

Asp Cys Gly Thr Ile Trp His Tyr Cys Thr Pro Glu Lys Asn Asp Cys
1               5                   10                  15

Cys Gln Arg Leu Tyr Cys Ser Pro Arg Trp Arg Leu Val His Leu
            20                  25                  30

<210> SEQ ID NO 134
<211> LENGTH: 34
<212> TYPE: PRT
<213> ORGANISM: Artificial Sequence
<220> FEATURE:
<223> OTHER INFORMATION: toxin sequence element

<400> SEQUENCE: 134

Ile Ala Cys Ala Pro Arg Phe Ser Ile Cys Asp Pro Lys Asn Asp Lys
1               5                   10                  15

Cys Cys Pro Asn Arg Val Cys Ser Asp Lys His Lys Trp Cys Lys Trp
            20                  25                  30

Lys Leu

<210> SEQ ID NO 135
<211> LENGTH: 34
<212> TYPE: PRT
<213> ORGANISM: Artificial Sequence
<220> FEATURE:
<223> OTHER INFORMATION: toxin sequence element

<400> SEQUENCE: 135

Ser Ser Thr Cys Ile Pro Ser Gly Gln Pro Cys Arg Glu Asn Lys Asp
1               5                   10                  15

Cys Cys Ser Lys Lys Cys Ser Asp Lys His Lys Trp Cys Lys Trp Lys
            20                  25                  30

Leu Gly

<210> SEQ ID NO 136
<211> LENGTH: 40
<212> TYPE: PRT
<213> ORGANISM: Artificial Sequence
<220> FEATURE:
<223> OTHER INFORMATION: toxin sequence element

<400> SEQUENCE: 136

Asp Gly Glu Cys Gly Gly Phe Trp Trp Lys Cys Lys Asn Ser Asn Asp
1               5                   10                  15

Cys Cys Lys Asp Leu Val Cys Lys Glu Lys Trp Pro Ile Thr Tyr Lys
            20                  25                  30

Ile Cys Val Trp Asp Arg Thr Phe
        35                  40

<210> SEQ ID NO 137
<211> LENGTH: 34
<212> TYPE: PRT
<213> ORGANISM: Artificial Sequence
<220> FEATURE:

<223> OTHER INFORMATION: toxin sequence element

<400> SEQUENCE: 137

Ile Ala Cys Ala Pro Arg Phe Ser Leu Cys Asp Thr Ser Lys Asp Cys
1               5                   10                  15

Cys Glu Gly Tyr Val Cys Asn Arg Lys His Lys Trp Cys Lys Tyr Lys
            20                  25                  30

Leu Trp

<210> SEQ ID NO 138
<211> LENGTH: 39
<212> TYPE: PRT
<213> ORGANISM: Artificial Sequence
<220> FEATURE:
<223> OTHER INFORMATION: toxin sequence element

<400> SEQUENCE: 138

Glu Cys Lys Gly Phe Gly Lys Ser Cys Ala Asp Ser Asp Asp Cys Cys
1 5 10 15

Glu Thr Phe His Cys Lys Trp Val Phe Phe Thr Ser Lys Phe Met Cys
20 25 30

Arg Arg Val Trp Gly Lys Asp
35

<210> SEQ ID NO 139
<211> LENGTH: 41
<212> TYPE: PRT
<213> ORGANISM: Artificial Sequence
<220> FEATURE:
<223> OTHER INFORMATION: toxin sequence element

<400> SEQUENCE: 139

Ser Pro Val Cys Thr Pro Ser Gly Gln Pro Cys Ala Asp Ser Asp Asp
1 5 10 15

Cys Cys Glu Thr Phe His Cys Lys Trp Val Phe Phe Thr Ser Lys Phe
20 25 30

Met Cys Arg Arg Val Trp Gly Lys Asp
35 40

<210> SEQ ID NO 140
<211> LENGTH: 33
<212> TYPE: PRT
<213> ORGANISM: Artificial Sequence
<220> FEATURE:
<223> OTHER INFORMATION: toxin sequence element

<400> SEQUENCE: 140

Asp Asp Cys Gly Gly Leu Phe Ser Gly Cys Thr Pro Gly Lys Asn Glu
1 5 10 15

Cys Cys Pro Asn Arg Val Cys Lys Ile Gly Leu Tyr Leu Cys Ile Trp
20 25 30

Ser

<210> SEQ ID NO 141
<211> LENGTH: 37
<212> TYPE: PRT
<213> ORGANISM: Artificial Sequence
<220> FEATURE:
<223> OTHER INFORMATION: toxin sequence element

<400> SEQUENCE: 141

Gly Cys Leu Gly Asp Lys Cys Ala Asp Ser Asp Asp Cys Cys Glu Thr

```
                 1               5                  10                  15
Phe His Cys Lys Trp Val Phe Phe Thr Ser Lys Phe Met Cys Arg Arg
                20                  25                  30

Val Trp Gly Lys Asp
        35

<210> SEQ ID NO 142
<211> LENGTH: 36
<212> TYPE: PRT
<213> ORGANISM: Artificial Sequence
<220> FEATURE:
<223> OTHER INFORMATION: toxin sequence element

<400> SEQUENCE: 142

Cys Arg Tyr Leu Phe Gly Gly Cys Ala Trp Phe Ser Gly Glu Ser Cys
1               5                  10                  15

Cys Thr Gly Ile Cys Ser Pro Arg Trp Gly Trp Cys Ile Tyr Ser Thr
                20                  25                  30

Arg Gly Gly Arg
        35

<210> SEQ ID NO 143
<211> LENGTH: 36
<212> TYPE: PRT
<213> ORGANISM: Artificial Sequence
<220> FEATURE:
<223> OTHER INFORMATION: toxin sequence element

<400> SEQUENCE: 143

Gly Asp Cys Leu Pro His Leu Lys Leu Cys Asn Pro Asn Asp Asp Lys
1               5                  10                  15

Cys Cys Arg Pro Lys Leu Lys Cys Ser Arg Arg Gly Thr Asn Pro Glu
                20                  25                  30

Lys Arg Cys Arg
        35

<210> SEQ ID NO 144
<211> LENGTH: 33
<212> TYPE: PRT
<213> ORGANISM: Artificial Sequence
<220> FEATURE:
<223> OTHER INFORMATION: toxin sequence element

<400> SEQUENCE: 144

Asp Asp Cys Gly Thr Leu Phe Ser Gly Cys Pro Tyr Ser Lys Tyr Cys
1               5                  10                  15

Cys Ser Gly Ser Cys Lys Arg Arg Gly Thr Asn Ile Glu Lys Arg Cys
                20                  25                  30

Arg

<210> SEQ ID NO 145
<211> LENGTH: 29
<212> TYPE: PRT
<213> ORGANISM: Artificial Sequence
<220> FEATURE:
<223> OTHER INFORMATION: toxin sequence element
<220> FEATURE:
<221> NAME/KEY: misc_feature
<222> LOCATION: (11)..(11)
<223> OTHER INFORMATION: Xaa can be any naturally occurring amino acid

<400> SEQUENCE: 145

Ala Ala Glu Gly Cys Leu Cys Asp Arg Cys Xaa His Ser Gly Asp Cys
```

```
1               5                   10                  15
Cys Glu Asp Phe His Cys Thr Cys Glu Phe Phe Asn Met
                20                  25
```

<210> SEQ ID NO 146
<211> LENGTH: 99
<212> TYPE: DNA
<213> ORGANISM: Artificial Sequence
<220> FEATURE:
<223> OTHER INFORMATION: toxin sequence element

<400> SEQUENCE: 146
gattgcgcgg gctatatgcg cgaatgtaaa aaagataaag aatgctgcgg ctggaacatt      60
tgcaaccgca aacataaatg gtgcaaatat aaactgtgg                             99

<210> SEQ ID NO 147
<211> LENGTH: 105
<212> TYPE: DNA
<213> ORGANISM: Artificial Sequence
<220> FEATURE:
<223> OTHER INFORMATION: toxin sequence element

<400> SEQUENCE: 147
ggctgccaaa tgacctttg gaaatgtaac gcgctggatc acaactgctg ccatggctat       60
gccgcctgtg gatgcaaaaa aattattgta ccgcgagaa tcgcg                      105

<210> SEQ ID NO 148
<211> LENGTH: 111
<212> TYPE: DNA
<213> ORGANISM: Artificial Sequence
<220> FEATURE:
<223> OTHER INFORMATION: toxin sequence element

<400> SEQUENCE: 148
ggcggctgcc tgccgcataa ccgcttttgt aacccgagca acgatcagtg ctgcaaaagc      60
gcgaacctgg tgtgccgcct gtggtgcaaa aaaaaaattg aagggatcc g               111

<210> SEQ ID NO 149
<211> LENGTH: 117
<212> TYPE: DNA
<213> ORGANISM: Artificial Sequence
<220> FEATURE:
<223> OTHER INFORMATION: toxin sequence element

<400> SEQUENCE: 149
ggctgcaaag gctttggcga tagctgtgcg gatagcgatg attgctgcga aacctttcat      60
tgcaaatggg tgttttttac cagcaaattt atgtgccgcc gcgtgtgggg caaagat        117

<210> SEQ ID NO 150
<211> LENGTH: 111
<212> TYPE: DNA
<213> ORGANISM: Artificial Sequence
<220> FEATURE:
<223> OTHER INFORMATION: toxin sequence element

<400> SEQUENCE: 150
ggctgcctgg gcgataaatg tgcggatagc gatgattgct gcgaaaccttt tcattgcaaa     60 tgggtgtttt ttaccagcaa atttatgtgc cgccgcgtgt ggggcaaaga t              111

<210> SEQ ID NO 151
<211> LENGTH: 127
<212> TYPE: DNA

```
<213> ORGANISM: Artificial Sequence
<220> FEATURE:
<223> OTHER INFORMATION: toxin sequence element

<400> SEQUENCE: 151
agcccgacct gcattccgag cggccagccg tgtgcggata gcgatgattg ctgcgaaacc    60
tttcattgca aatgggtgtt ttttaccagc aaatttatgt gccgccgcgt gtggggcaaa   120
gatggat                                                            127

<210> SEQ ID NO 152
<211> LENGTH: 114
<212> TYPE: DNA
<213> ORGANISM: Artificial Sequence
<220> FEATURE:
<223> OTHER INFORMATION: toxin sequence element
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (64)..(65)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t

<400> SEQUENCE: 152
gacgaagatt gccaaccgcc gggcaacttt tgtancaaca ccagcgattg ctgcgaacat    60
ctgnnctgcc cgaccacccc ccgctttccc tatctgtgcc ataccncat ggga          114

<210> SEQ ID NO 153
<211> LENGTH: 88
<212> TYPE: DNA
<213> ORGANISM: Artificial Sequence
<220> FEATURE:
<223> OTHER INFORMATION: toxin sequence element

<400> SEQUENCE: 153
aggcgcgtgc cgctggtttc tgggcggctg taccccggaa aaaacgatt gctgccagcg    60 cctgtattgc ggcccgtttg tgtgcgtg                                      88

<210> SEQ ID NO 154
<211> LENGTH: 99
<212> TYPE: DNA
<213> ORGANISM: Artificial Sequence
<220> FEATURE:
<223> OTHER INFORMATION: toxin sequence element

<400> SEQUENCE: 154
agcccggtgt gcaccccgag cggccagccg tgtcgcgaaa acaaagattg ctgcagcaaa    60
aaatgcaaaa ccaccggcat tgtgaaactg tgccgctgg                          99

<210> SEQ ID NO 155
<211> LENGTH: 114
<212> TYPE: DNA
<213> ORGANISM: Artificial Sequence
<220> FEATURE:
<223> OTHER INFORMATION: toxin sequence element

<400> SEQUENCE: 155
gcgtgcagca aaaatggga atattgtacc aaagatagcg aatgctgccc gcatctgggc    60
tgctggaaac gccgccgcag ctttgaagtg tgcgtgccga aaccccgaa aacc          114
```

<210> SEQ ID NO 156
<211> LENGTH: 99
<212> TYPE: DNA
<213> ORGANISM: Artificial Sequence
<220> FEATURE:
<223> OTHER INFORMATION: toxin sequence element

<400> SEQUENCE: 156
cgctgcattg aagaaggcaa atggtgtacc aaagatgaag attgctgcaa acatctggcg    60
tgcaaccgca aacataaatg gtgcaaatat aaactgtgg                          99

<210> SEQ ID NO 157
<211> LENGTH: 123
<212> TYPE: DNA
<213> ORGANISM: Artificial Sequence
<220> FEATURE:
<223> OTHER INFORMATION: toxin sequence element

<400> SEQUENCE: 157
agcccgacct gcattcgcag cggccagccg tgtgcggata gcgatgattg ctgcgaaacc    60
tttcattgca aatgggtgtt ttttaccagc aaatttatgt gccgccgcgt gtggggcaaa   120
gat                                                                 123

<210> SEQ ID NO 158
<211> LENGTH: 120
<212> TYPE: DNA
<213> ORGANISM: Artificial Sequence
<220> FEATURE:
<223> OTHER INFORMATION: toxin sequence element

<400> SEQUENCE: 158
agcacctgca ccccgaccga tcagccgtgt gcggatagcg atgattgctg cgaaaccttt    60
cattgcaaat gggtgttttt taccagcaaa tttatgtgcc gccgcgtgtg ggcaaagat   120

<210> SEQ ID NO 159
<211> LENGTH: 111
<212> TYPE: DNA
<213> ORGANISM: Artificial Sequence
<220> FEATURE:
<223> OTHER INFORMATION: toxin sequence element

<400> SEQUENCE: 159
aaatgccgct ggctgtttgg cggggtaccc cgggcaaaaa cgaatgctgg ccgaactatg    60
cgtgccatag ctattgggaa tggggcctgt gggatggcag ctttggatcc g           111

<210> SEQ ID NO 160
<211> LENGTH: 117
<212> TYPE: DNA
<213> ORGANISM: Artificial Sequence
<220> FEATURE:
<223> OTHER INFORMATION: toxin sequence element

<400> SEQUENCE: 160
ggctgcaaat ggtatctggg cgattgtgcg gatagcgatg attgctgcga aacctttcat    60
tgcaaatggg tgttttttac cagcaaattt atgtgccgcc gcgtgtgggg caaagat     117

<210> SEQ ID NO 161
<211> LENGTH: 123
<212> TYPE: DNA
<213> ORGANISM: Artificial Sequence
<220> FEATURE:

<223> OTHER INFORMATION: toxin sequence element

<400> SEQUENCE: 161
agcagcacct gcattccgag cggccagccg tgtgcggata gcgatgattg ctgcgaaacc     60
tttcattgca aatgggtgtt ttttaccagc aaatttatgt gccgccgcgt gtggggcaaa    120
gat                                                                  123

<210> SEQ ID NO 162
<211> LENGTH: 99
<212> TYPE: DNA
<213> ORGANISM: Artificial Sequence
<220> FEATURE:
<223> OTHER INFORMATION: toxin sequence element

<400> SEQUENCE: 162
gcgtgcagca aaaatgggga atattgtaaa gaaaaactgt gctgcagcgg ctatgtgtgc     60
aaacgccgcg gcaccaacat tgaaaaacgc tgccgcgga                            99

<210> SEQ ID NO 163
<211> LENGTH: 87
<212> TYPE: DNA
<213> ORGANISM: Artificial Sequence
<220> FEATURE:
<223> OTHER INFORMATION: toxin sequence element

<400> SEQUENCE: 163
gcgtgcggcc agttttggtg gaaatgtacc agcgatagcg attgctgccc gaactgggtg     60
tgccgcctgt ggtgcaaata taaactg                                         87

<210> SEQ ID NO 164
<211> LENGTH: 105
<212> TYPE: DNA
<213> ORGANISM: Artificial Sequence
<220> FEATURE:
<223> OTHER INFORMATION: toxin sequence element

<400> SEQUENCE: 164
tgccgctatt ggctgggcgg ctgtagccag gatggcgatt gctgcaaaca tctgcagtgc     60
agcccgcgct ggggctggtg catttatagc acccgcggcg gccgc                    105

<210> SEQ ID NO 165
<211> LENGTH: 93
<212> TYPE: DNA
<213> ORGANISM: Artificial Sequence
<220> FEATURE:
<223> OTHER INFORMATION: toxin sequence element

<400> SEQUENCE: 165
gattgcggca ccatttggca ttattgtacc ccggaaaaaa acgattgctg ccagcgcctg     60
tattgcagcc cgcgctggag gctggtgcat tta                                  93

<210> SEQ ID NO 166
<211> LENGTH: 102
<212> TYPE: DNA
<213> ORGANISM: Artificial Sequence
<220> FEATURE:
<223> OTHER INFORMATION: toxin sequence element

<400> SEQUENCE: 166
attgcgtgcg cgccgcgctt tagcatttgt gatccgaaaa acgataaatg ctgcccgaac     60
cgcgtgtgca gcgataaaca taaatggtgc aaatggaaac tg                       102

<210> SEQ ID NO 167
<211> LENGTH: 102
<212> TYPE: DNA
<213> ORGANISM: Artificial Sequence
<220> FEATURE:
<223> OTHER INFORMATION: toxin sequence element

<400> SEQUENCE: 167
agcagcacct gcattccgag cggccagccg tgtcgcgaaa acaaagattg ctgcagcaaa    60
aaatgcagcg ataaacataa atggtgcaaa tggaaactgg ga                     102

<210> SEQ ID NO 168
<211> LENGTH: 120
<212> TYPE: DNA
<213> ORGANISM: Artificial Sequence
<220> FEATURE:
<223> OTHER INFORMATION: toxin sequence element

<400> SEQUENCE: 168
gatggcgaat gcggcggctt ttggtggaaa tgtaaaaaca gcaacgattg ctgcaaagat    60
ctggtgtgca agaaaaatg gccgattacc tataaaattt gcgtgtggga tcgcaccttt   120

<210> SEQ ID NO 169
<211> LENGTH: 102
<212> TYPE: DNA
<213> ORGANISM: Artificial Sequence
<220> FEATURE:
<223> OTHER INFORMATION: toxin sequence element

<400> SEQUENCE: 169
attgcgtgcg cgccgcgctt tagcctgtgt gataccagca agattgctg cgaaggctat    60 gtgtgcaacc gcaaacataa atggtgcaaa tataaactgt gg                     102

<210> SEQ ID NO 170
<211> LENGTH: 117
<212> TYPE: DNA
<213> ORGANISM: Artificial Sequence
<220> FEATURE:
<223> OTHER INFORMATION: toxin sequence element

<400> SEQUENCE: 170
gaatgcaaag ctttggcaa aagctgtgcg gatagcgatg attgctgcga aacctttcat    60
tgcaaatggg tgttttttac cagcaaattt atgtgccgcc gcgtgtgggg caaagat     117

<210> SEQ ID NO 171
<211> LENGTH: 123
<212> TYPE: DNA
<213> ORGANISM: Artificial Sequence
<220> FEATURE:
<223> OTHER INFORMATION: toxin sequence element

<400> SEQUENCE: 171
agcccggtgt gcaccccgag cggccagccg tgtgcggata gcgatgattg ctgcgaaacc    60
tttcattgca aatgggtgtt ttttaccagc aaatttatgt gccgccgcgt gtggggcaaa   120
gat                                                                123

<210> SEQ ID NO 172
<211> LENGTH: 102
<212> TYPE: DNA
<213> ORGANISM: Artificial Sequence
<220> FEATURE:

<223> OTHER INFORMATION: toxin sequence element

<400> SEQUENCE: 172
gatgattgcg gcggcctgtt tagcggctgt accccgggca aaaacgaatg ctgcccgaac     60
cgcgtgtgca aaattggcct gtatctgtgc atttggagcc cg     102

<210> SEQ ID NO 173
<211> LENGTH: 111
<212> TYPE: DNA
<213> ORGANISM: Artificial Sequence
<220> FEATURE:
<223> OTHER INFORMATION: toxin sequence element

<400> SEQUENCE: 173
ggctgcctgg gcgataaatg tgcggatagc gatgattgct gcgaaacctt tcattgcaaa     60
tgggtgtttt ttaccagcaa atttatgtgc cgccgcgtgt ggggcaaaga t     111

<210> SEQ ID NO 174
<211> LENGTH: 108
<212> TYPE: DNA
<213> ORGANISM: Artificial Sequence
<220> FEATURE:
<223> OTHER INFORMATION: toxin sequence element

<400> SEQUENCE: 174
tgccgctatc tgtttggcgg ctgtgcgtgg tttagcggcg aaagctgctg caccggcatt     60
tgcagcccgc gctggggctg gtgcatttat agcacccgcg gcggccgc     108

<210> SEQ ID NO 175
<211> LENGTH: 108
<212> TYPE: DNA
<213> ORGANISM: Artificial Sequence
<220> FEATURE:
<223> OTHER INFORMATION: toxin sequence element

<400> SEQUENCE: 175
ggcgattgcc tgccgcatct gaaactgtgt aacccgaacg atgataaatg ctgccgcccg     60
aaactgaaat gcagccgccg cggcaccaac ccggaaaaac gctgccgc     108

<210> SEQ ID NO 176
<211> LENGTH: 99
<212> TYPE: DNA
<213> ORGANISM: Artificial Sequence
<220> FEATURE:
<223> OTHER INFORMATION: toxin sequence element

<400> SEQUENCE: 176
gatgattgcg gcaccctgtt tagcggctgt ccgtatagca atattgctg cagcggcagc     60 tgcaaacgcc gcggcaccaa cattgaaaaa cgctgccgc     99

<210> SEQ ID NO 177
<211> LENGTH: 86
<212> TYPE: DNA
<213> ORGANISM: Artificial Sequence
<220> FEATURE:
<223> OTHER INFORMATION: toxin sequence element
<220> FEATURE:
<221> NAME/KEY: misc_feature
<222> LOCATION: (23)..(23)
<223> OTHER INFORMATION: n is a, c, g, or t

<400> SEQUENCE: 177
gctgcctgtg cgatagatgt gtncatagcg gtgattgttg cgaagacttt cattgcacct     60
gcgagttttt taacatgtaa tttatg       86

<210> SEQ ID NO 178
<211> LENGTH: 10
<212> TYPE: PRT
<213> ORGANISM: Artificial Sequence
<220> FEATURE:
<223> OTHER INFORMATION: toxin sequence element

<400> SEQUENCE: 178

Ala Ala Cys Leu Gly Met Phe Glu Ser Cys
1               5                   10

<210> SEQ ID NO 179
<211> LENGTH: 9
<212> TYPE: PRT
<213> ORGANISM: Artificial Sequence
<220> FEATURE:
<223> OTHER INFORMATION: toxin sequence element

<400> SEQUENCE: 179

Ala Cys Gly Gln Phe Trp Trp Lys Cys
1               5

<210> SEQ ID NO 180
<211> LENGTH: 9
<212> TYPE: PRT
<213> ORGANISM: Artificial Sequence
<220> FEATURE:
<223> OTHER INFORMATION: toxin sequence element

<400> SEQUENCE: 180

Ala Cys Lys Gly Val Phe Asp Ala Cys
1               5

<210> SEQ ID NO 181
<211> LENGTH: 9
<212> TYPE: PRT
<213> ORGANISM: Artificial Sequence
<220> FEATURE:
<223> OTHER INFORMATION: toxin sequence element

<400> SEQUENCE: 181

Ala Cys Arg Glu Trp Leu Gly Gly Cys
1               5

<210> SEQ ID NO 182
<211> LENGTH: 10
<212> TYPE: PRT
<213> ORGANISM: Artificial Sequence
<220> FEATURE:
<223> OTHER INFORMATION: toxin sequence element

<400> SEQUENCE: 182

Ala Asp Cys Gly Trp Leu Phe His Ser Cys
1               5                   10

<210> SEQ ID NO 183
<211> LENGTH: 8
<212> TYPE: PRT
<213> ORGANISM: Artificial Sequence
<220> FEATURE:
<223> OTHER INFORMATION: toxin sequence element

<400> SEQUENCE: 183

Cys Ala Ala Glu Gly Ile Pro Cys

```
1               5

<210> SEQ ID NO 184
<211> LENGTH: 8
<212> TYPE: PRT
<213> ORGANISM: Artificial Sequence
<220> FEATURE:
<223> OTHER INFORMATION: toxin sequence element

<400> SEQUENCE: 184

Cys Gly Gly Trp Met Ala Lys Cys
1               5

<210> SEQ ID NO 185
<211> LENGTH: 8
<212> TYPE: PRT
<213> ORGANISM: Artificial Sequence
<220> FEATURE:
<223> OTHER INFORMATION: toxin sequence element

<400> SEQUENCE: 185

Cys Ile Gly Glu Gly Val Pro Cys
1               5

<210> SEQ ID NO 186
<211> LENGTH: 8
<212> TYPE: PRT
<213> ORGANISM: Artificial Sequence
<220> FEATURE:
<223> OTHER INFORMATION: toxin sequence element

<400> SEQUENCE: 186

Cys Met Gly Tyr Asp Ile His Cys
1               5

<210> SEQ ID NO 187
<211> LENGTH: 9
<212> TYPE: PRT
<213> ORGANISM: Artificial Sequence
<220> FEATURE:
<223> OTHER INFORMATION: toxin sequence element

<400> SEQUENCE: 187

Asp Cys Ala Gly Tyr Met Arg Glu Cys
1               5

<210> SEQ ID NO 188
<211> LENGTH: 9
<212> TYPE: PRT
<213> ORGANISM: Artificial Sequence
<220> FEATURE:
<223> OTHER INFORMATION: toxin sequence element

<400> SEQUENCE: 188

Asp Cys Gly Thr Ile Trp His Tyr Cys
1               5

<210> SEQ ID NO 189
<211> LENGTH: 9
<212> TYPE: PRT
<213> ORGANISM: Artificial Sequence
<220> FEATURE:
<223> OTHER INFORMATION: toxin sequence element

<400> SEQUENCE: 189

Asp Cys Leu Gly Phe Leu Trp Lys Cys
1               5
```

```
<210> SEQ ID NO 190
<211> LENGTH: 9
<212> TYPE: PRT
<213> ORGANISM: Artificial Sequence
<220> FEATURE:
<223> OTHER INFORMATION: toxin sequence element

<400> SEQUENCE: 190

Asp Cys Leu Gly Leu Phe Trp Ile Cys
1               5

<210> SEQ ID NO 191
<211> LENGTH: 9
<212> TYPE: PRT
<213> ORGANISM: Artificial Sequence
<220> FEATURE:
<223> OTHER INFORMATION: toxin sequence element

<400> SEQUENCE: 191

Asp Cys Leu Gly Trp Phe Lys Gly Cys
1               5

<210> SEQ ID NO 192
<211> LENGTH: 9
<212> TYPE: PRT
<213> ORGANISM: Artificial Sequence
<220> FEATURE:
<223> OTHER INFORMATION: toxin sequence element

<400> SEQUENCE: 192

Asp Cys Leu Gly Trp Phe Lys Ser Cys
1               5

<210> SEQ ID NO 193
<211> LENGTH: 9
<212> TYPE: PRT
<213> ORGANISM: Artificial Sequence
<220> FEATURE:
<223> OTHER INFORMATION: toxin sequence element

<400> SEQUENCE: 193

Asp Cys Arg Ala Leu Tyr Gly Gly Cys
1               5

<210> SEQ ID NO 194
<211> LENGTH: 9
<212> TYPE: PRT
<213> ORGANISM: Artificial Sequence
<220> FEATURE:
<223> OTHER INFORMATION: toxin sequence element

<400> SEQUENCE: 194

Asp Cys Arg Lys Met Phe Gly Gly Cys
1               5

<210> SEQ ID NO 195
<211> LENGTH: 9
<212> TYPE: PRT
<213> ORGANISM: Artificial Sequence
<220> FEATURE:
<223> OTHER INFORMATION: toxin sequence element

<400> SEQUENCE: 195

Asp Cys Thr Arg Met Phe Gly Ala Cys
1               5
```

<210> SEQ ID NO 196
<211> LENGTH: 9
<212> TYPE: PRT
<213> ORGANISM: Artificial Sequence
<220> FEATURE:
<223> OTHER INFORMATION: toxin sequence element

<400> SEQUENCE: 196

Asp Cys Val Arg Phe Trp Gly Lys Cys
1               5

<210> SEQ ID NO 197
<211> LENGTH: 10
<212> TYPE: PRT
<213> ORGANISM: Artificial Sequence
<220> FEATURE:
<223> OTHER INFORMATION: toxin sequence element

<400> SEQUENCE: 197

Asp Asp Cys Gly Gly Leu Phe Ser Gly Cys
1               5                   10

<210> SEQ ID NO 198
<211> LENGTH: 10
<212> TYPE: PRT
<213> ORGANISM: Artificial Sequence
<220> FEATURE:
<223> OTHER INFORMATION: toxin sequence element

<400> SEQUENCE: 198

Asp Asp Cys Gly Lys Leu Phe Ser Gly Cys
1               5                   10

<210> SEQ ID NO 199
<211> LENGTH: 10
<212> TYPE: PRT
<213> ORGANISM: Artificial Sequence
<220> FEATURE:
<223> OTHER INFORMATION: toxin sequence element

<400> SEQUENCE: 199

Asp Asp Cys Gly Thr Leu Phe Ser Gly Cys
1               5                   10

<210> SEQ ID NO 200
<211> LENGTH: 10
<212> TYPE: PRT
<213> ORGANISM: Artificial Sequence
<220> FEATURE:
<223> OTHER INFORMATION: toxin sequence element

<400> SEQUENCE: 200

Asp Asp Cys Leu Gly Met Phe Ser Ser Cys
1               5                   10

<210> SEQ ID NO 201
<211> LENGTH: 11
<212> TYPE: PRT
<213> ORGANISM: Artificial Sequence
<220> FEATURE:
<223> OTHER INFORMATION: toxin sequence element

<400> SEQUENCE: 201

Asp Asp Asp Cys Gly Trp Ile Met Asp Cys
1               5                   10

```
<210> SEQ ID NO 202
<211> LENGTH: 11
<212> TYPE: PRT
<213> ORGANISM: Artificial Sequence
<220> FEATURE:
<223> OTHER INFOR
<211> LENGTH: 9
<212> TYPE: PRT
<213> ORGANISM: Artificial Sequence
<220> FEATURE:
<223> OTHER INFORMATION: toxin sequence element

<400> SEQUENCE: 208

Glu Cys Lys Tyr Leu Trp Gly Thr Cys
1               5

<210> SEQ ID NO 209
<211> LENGTH: 9
<212> TYPE: PRT
<213> ORGANISM: Artificial Sequence
<220> FEATURE:
<223> OTHER INFORMATION: toxin sequence element

<400> SEQUENCE: 209

Glu Cys Leu Glu Ile Phe Lys Ala Cys
1               5

<210> SEQ ID NO 210
<211> LENGTH: 9
<212> TYPE: PRT
<213> ORGANISM: Artificial Sequence
<220> FEATURE:
<223> OTHER INFORMATION: toxin sequence element

<400> SEQUENCE: 210

Glu Cys Leu Gly Phe Gly Lys Gly Cys
1               5

<210> SEQ ID NO 211
<211> LENGTH: 9
<212> TYPE: PRT
<213> ORGANISM: Artificial Sequence
<220> FEATURE:
<223> OTHER INFORMATION: toxin sequence element

<400> SEQUENCE: 211

Glu Cys Arg Lys Met Phe Gly Gly Cys
1               5

<210> SEQ ID NO 212
<211> LENGTH: 9
<212> TYPE: PRT
<213> ORGANISM: Artificial Sequence
<220> FEATURE:
<223> OTHER INFORMATION: toxin sequence element

<400> SEQUENCE: 212

Glu Cys Arg Trp Leu Phe Gly Gly Cys
1               5

<210> SEQ ID NO 213
<211> LENGTH: 9
<212> TYPE: PRT
<213> ORGANISM: Artificial Sequence
<220> FEATURE:
<223> OTHER INFORMATION: toxin sequence element

<400> SEQUENCE: 213

Glu Cys Arg Trp Tyr Leu Gly Gly Cys
1               5

<210> SEQ ID NO 214
<211> LENGTH: 9

```
<212> TYPE: PRT
<213> ORGANISM: Artificial Sequence
<220> FEATURE:
<223> OTHER INFORMATION: toxin sequence element

<400> SEQUENCE: 214

Glu Cys Arg Tyr Phe Trp Gly Glu Cys
1               5

<210> SEQ ID NO 215
<211> LENGTH: 9
<212> TYPE: PRT
<213> ORGANISM: Artificial Sequence
<220> FEATURE:
<223> OTHER INFORMATION: toxin sequence element

<400> SEQUENCE: 215

Glu Cys Arg Tyr Leu Phe Gly Gly Cys
1               5

<210> SEQ ID NO 216
<211> LENGTH: 9
<212> TYPE: PRT
<213> ORGANISM: Artificial Sequence
<220> FEATURE:
<223> OTHER INFORMATION: toxin sequence element

<400> SEQUENCE: 216

Glu Cys Arg Tyr Trp Leu Gly Gly Cys
1               5

<210> SEQ ID NO 217
<211> LENGTH: 9
<212> TYPE: PRT
<213> ORGANISM: Artificial Sequence
<220> FEATURE:
<223> OTHER INFORMATION: toxin sequence element

<400> SEQUENCE: 217

Glu Cys Arg Tyr Trp Leu Gly Thr Cys
1               5

<210> SEQ ID NO 218
<211> LENGTH: 9
<212> TYPE: PRT
<213> ORGANISM: Artificial Sequence
<220> FEATURE:
<223> OTHER INFORMATION: toxin sequence element

<400> SEQUENCE: 218

Glu Cys Thr Lys Phe Leu Gly Gly Cys
1               5

<210> SEQ ID NO 219
<211> LENGTH: 9
<212> TYPE: PRT
<213> ORGANISM: Artificial Sequence
<220> FEATURE:
<223> OTHER INFORMATION: toxin sequence element

<400> SEQUENCE: 219

Glu Cys Thr Lys Leu Leu Gly Gly Cys
1               5

<210> SEQ ID NO 220
<211> LENGTH: 10
<212> TYPE: PRT
```

```
<213> ORGANISM: Artificial Sequence
<220> FEATURE:
<223> OTHER INFORMATION: toxin sequence element

<400> SEQUENCE: 220

Glu Asp Cys Ile Pro Lys Trp Lys Gly Cys
1               5                   10

<210> SEQ ID NO 221
<211> LENGTH: 11
<212> TYPE: PRT
<213> ORGANISM: Artificial Sequence
<220> FEATURE:
<223> OTHER INFORMATION: toxin sequence element

<400> SEQUENCE: 221

Glu Gly Glu Cys Gly Gly Phe Trp Trp Lys Cys
1               5                   10

<210> SEQ ID NO 222
<211> LENGTH: 10
<212> TYPE: PRT
<213> ORGANISM: Artificial Sequence
<220> FEATURE:
<223> OTHER INFORMATION: toxin sequence element

<400> SEQUENCE: 222

Gly Ala Cys Arg Trp Phe Leu Gly Gly Cys
1               5                   10

<210> SEQ ID NO 223
<211> LENGTH: 9
<212> TYPE: PRT
<213> ORGANISM: Artificial Sequence
<220> FEATURE:
<223> OTHER INFORMATION: toxin sequence element

<400> SEQUENCE: 223

Gly Cys Ala Asn Ala Tyr Lys Ser Cys
1               5

<210> SEQ ID NO 224
<211> LENGTH: 9
<212> TYPE: PRT
<213> ORGANISM: Artificial Sequence
<220> FEATURE:
<223> OTHER INFORMATION: toxin sequence element

<400> SEQUENCE: 224

Gly Cys Gly Gly Leu Met Ala Gly Cys
1               5

<210> SEQ ID NO 225
<211> LENGTH: 9
<212> TYPE: PRT
<213> ORGANISM: Artificial Sequence
<220> FEATURE:
<223> OTHER INFORMATION: toxin sequence element

<400> SEQUENCE: 225

Gly Cys Gly Gly Leu Met Asp Gly Cys
1               5

<210> SEQ ID NO 226
<211> LENGTH: 9
<212> TYPE: PRT
<213> ORGANISM: Artificial Sequence
```

-continued

```
<220> FEATURE:
<223> OTHER INFORMATION: toxin sequence element

<400> SEQUENCE: 226

Gly Cys Gly Thr Met Trp Ser Pro Cys
1               5

<210> SEQ ID NO 227
<211> LENGTH: 9
<212> TYPE: PRT
<213> ORGANISM: Artificial Sequence
<220> FEATURE:
<223> OTHER INFORMATION: toxin sequence element

<400> SEQUENCE: 227

Gly Cys Ile Pro Ser Phe Gly Glu Cys
1               5

<210> SEQ ID NO 228
<211> LENGTH: 9
<212> TYPE: PRT
<213> ORGANISM: Artificial Sequence
<220> FEATURE:
<223> OTHER INFORMATION: toxin sequence element

<400> SEQUENCE: 228

Gly Cys Lys Gly Phe Gly Asp Ser Cys
1               5

<210> SEQ ID NO 229
<211> LENGTH: 9
<212> TYPE: PRT
<213> ORGANISM: Artificial Sequence
<220> FEATURE:
<223> OTHER INFORMATION: toxin sequence element

<400> SEQUENCE: 229

Gly Cys Lys Leu Thr Phe Trp Lys Cys
1               5

<210> SEQ ID NO 230
<211> LENGTH: 9
<212> TYPE: PRT
<213> ORGANISM: Artificial Sequence
<220> FEATURE:
<223> OTHER INFORMATION: toxin sequence element

<400> SEQUENCE: 230

Gly Cys Leu Glu Phe Trp Trp Lys Cys
1               5

<210> SEQ ID NO 231
<211> LENGTH: 7
<212> TYPE: PRT
<213> ORGANISM: Artificial Sequence
<220> FEATURE:
<223> OTHER INFORMATION: toxin sequence element

<400> SEQUENCE: 231

Gly Cys Leu Gly Asp Lys Cys
1               5

<210> SEQ ID NO 232
<211> LENGTH: 9
<212> TYPE: PRT
<213> ORGANISM: Artificial Sequence
<220> FEATURE:
```

```
<223> OTHER INFORMATION: toxin sequence element

<400> SEQUENCE: 232

Gly Cys Asn Arg Lys Asn Lys Lys Cys
1               5

<210> SEQ ID NO 233
<211> LENGTH: 9
<212> TYPE: PRT
<213> ORGANISM: Artificial Sequence
<220> FEATURE:
<223> OTHER INFORMATION: toxin sequence element

<400> SEQUENCE: 233

Gly Cys Gln Lys Phe Phe Trp Thr Cys
1               5

<210> SEQ ID NO 234
<211> LENGTH: 10
<212> TYPE: PRT
<213> ORGANISM: Artificial Sequence
<220> FEATURE:
<223> OTHER INFORMATION: toxin sequence element

<400> SEQUENCE: 234

Gly Asp Cys Leu Pro His Leu Lys Leu Cys
1               5                   10

<210> SEQ ID NO 235
<211> LENGTH: 10
<212> TYPE: PRT
<213> ORGANISM: Artificial Sequence
<220> FEATURE:
<223> OTHER INFORMATION: toxin sequence element

<400> SEQUENCE: 235

Gly Asp Cys Leu Pro His Leu Lys Arg Cys
1               5                   10

<210> SEQ ID NO 236
<211> LENGTH: 10
<212> TYPE: PRT
<213> ORGANISM: Artificial Sequence
<220> FEATURE:
<223> OTHER INFORMATION: toxin sequence element

<400> SEQUENCE: 236

Gly Gly Cys Leu Pro His Asn Arg Phe Cys
1               5                   10

<210> SEQ ID NO 237
<211> LENGTH: 14
<212> TYPE: PRT
<213> ORGANISM: Artificial Sequence
<220> FEATURE:
<223> OTHER INFORMATION: toxin sequence element

<400> SEQUENCE: 237

Gly Val Asp Lys Ala Gly Cys Arg Tyr Met Phe Gly Gly Cys
1               5                   10

<210> SEQ ID NO 238
<211> LENGTH: 14
<212> TYPE: PRT
<213> ORGANISM: Artificial Sequence
<220> FEATURE:
<223> OTHER INFORMATION: toxin sequence element
```

<400> SEQUENCE: 238

Gly Val Asp Lys Glu Gly Cys Arg Lys Leu Leu Gly Gly Cys
1               5                   10

<210> SEQ ID NO 239
<211> LENGTH: 10
<212> TYPE: PRT
<213> ORGANISM: Artificial Sequence
<220> FEATURE:
<223> OTHER INFORMATION: toxin sequence element

<400> SEQUENCE: 239

Ile Ala Cys Ala Pro Arg Phe Ser Ile Cys
1               5                   10

<210> SEQ ID NO 240
<211> LENGTH: 10
<212> TYPE: PRT
<213> ORGANISM: Artificial Sequence
<220> FEATURE:
<223> OTHER INFORMATION: toxin sequence element

<400> SEQUENCE: 240

Ile Ala Cys Ala Pro Arg Phe Ser Leu Cys
1               5                   10

<210> SEQ ID NO 241
<211> LENGTH: 10
<212> TYPE: PRT
<213> ORGANISM: Artificial Sequence
<220> FEATURE:
<223> OTHER INFORMATION: toxin sequence element

<400> SEQUENCE: 241

Ile Ala Cys Ala Pro Arg Gly Leu Leu Cys
1               5                   10

<210> SEQ ID NO 242
<211> LENGTH: 9
<212> TYPE: PRT
<213> ORGANISM: Artificial Sequence
<220> FEATURE:
<223> OTHER INFORMATION: toxin sequence element

<400> SEQUENCE: 242

Lys Cys Leu Pro Pro Gly Lys Pro Cys
1               5

<210> SEQ ID NO 243
<211> LENGTH: 9
<212> TYPE: PRT
<213> ORGANISM: Artificial Sequence
<220> FEATURE:
<223> OTHER INFORMATION: toxin sequence element

<400> SEQUENCE: 243

Leu Cys Ser Arg Glu Gly Glu Phe Cys
1               5

<210> SEQ ID NO 244
<211> LENGTH: 9
<212> TYPE: PRT
<213> ORGANISM: Artificial Sequence
<220> FEATURE:
<223> OTHER INFORMATION: toxin sequence element

```
<400> SEQUENCE: 244

Gln Cys Gly Glu Phe Met Trp Lys Cys
1               5

<210> SEQ ID NO 245
<211> LENGTH: 9
<212> TYPE: PRT
<213> ORGANISM: Artificial Sequence
<220> FEATURE:
<223> OTHER INFORMATION: toxin sequence element

<400> SEQUENCE: 245

Arg Cys Ile Glu Glu Gly Lys Trp Cys
1               5

<210> SEQ ID NO 246
<211> LENGTH: 11
<212> TYPE: PRT
<213> ORGANISM: Artificial Sequence
<220> FEATURE:
<223> OTHER INFORMATION: toxin sequence element

<400> SEQUENCE: 246

Ser Ala Val Cys Ile Pro Ser Gly Gln Pro Cys
1               5                   10

<210> SEQ ID NO 247
<211> LENGTH: 9
<212> TYPE: PRT
<213> ORGANISM: Artificial Sequence
<220> FEATURE:
<223> OTHER INFORMATION: toxin sequence element

<400> SEQUENCE: 247

Ser Cys Lys Leu Thr Phe Trp Arg Cys
1               5

<210> SEQ ID NO 248
<211> LENGTH: 10
<212> TYPE: PRT
<213> ORGANISM: Artificial Sequence
<220> FEATURE:
<223> OTHER INFORMATION: toxin sequence element

<400> SEQUENCE: 248

Ser Glu Cys Arg Trp Phe Met Gly Gly Cys
1               5                   10

<210> SEQ ID NO 249
<211> LENGTH: 12
<212> TYPE: PRT
<213> ORGANISM: Artificial Sequence
<220> FEATURE:
<223> OTHER INFORMATION: toxin sequence element

<400> SEQUENCE: 249

Ser Glu Lys Asp Cys Ile Lys His Leu Gln Arg Cys
1               5                   10

<210> SEQ ID NO 250
<211> LENGTH: 9
<212> TYPE: PRT
<213> ORGANISM: Artificial Sequence
<220> FEATURE:
<223> OTHER INFORMATION: toxin sequence element

<400> SEQUENCE: 250
```

```
Ser Phe Cys Ile Pro Phe Lys Pro Cys
1               5

<210> SEQ ID NO 251
<211> LENGTH: 11
<212> TYPE: PRT
<213> ORGANISM: Artificial Sequence
<220> FEATURE:
<223> OTHER INFORMATION: toxin sequence element

<400> SEQUENCE: 251

Ser Pro Thr Cys Ile Pro Ser Gly Gln Pro Cys
1               5                   10

<210> SEQ ID NO 252
<211> LENGTH: 11
<212> TYPE: PRT
<213> ORGANISM: Artificial Sequence
<220> FEATURE:
<223> OTHER INFORMATION: toxin sequence element

<400> SEQUENCE: 252

Ser Pro Thr Cys Ile Pro Thr Gly Gln Pro Cys
1               5                   10

<210> SEQ ID NO 253
<211> LENGTH: 11
<212> TYPE: PRT
<213> ORGANISM: Artificial Sequence
<220> FEATURE:
<223> OTHER INFORMATION: toxin sequence element

<400> SEQUENCE: 253

Ser Pro Thr Cys Ile Arg Ser Gly Gln Pro Cys
1               5                   10

<210> SEQ ID NO 254
<211> LENGTH: 11
<212> TYPE: PRT
<213> ORGANISM: Artificial Sequence
<220> FEATURE:
<223> OTHER INFORMATION: toxin sequence element

<400> SEQUENCE: 254

Ser Pro Val Cys Thr Pro Ser Gly Gln Pro Cys
1               5                   10

<210> SEQ ID NO 255
<211> LENGTH: 11
<212> TYPE: PRT
<213> ORGANISM: Artificial Sequence
<220> FEATURE:
<223> OTHER INFORMATION: toxin sequence element

<400> SEQUENCE: 255

Ser Ser Thr Cys Ile Pro Ser Gly Gln Pro Cys
1               5                   10

<210> SEQ ID NO 256
<211> LENGTH: 11
<212> TYPE: PRT
<213> ORGANISM: Artificial Sequence
<220> FEATURE:
<223> OTHER INFORMATION: toxin sequence element

<400> SEQUENCE: 256
```

Ser Ser Thr Cys Ile Arg Thr Asp Gln Pro Cys
1               5                   10

<210> SEQ ID NO 257
<211> LENGTH: 10
<212> TYPE: PRT
<213> ORGANISM: Artificial Sequence
<220> FEATURE:
<223> OTHER INFORMATION: toxin sequence element

<400> SEQUENCE: 257

Ser Thr Cys Thr Pro Thr Asp Gln Pro Cys
1               5                   10

<210> SEQ ID NO 258
<211> LENGTH: 10
<212> TYPE: PRT
<213> ORGANISM: Artificial Sequence
<220> FEATURE:
<223> OTHER INFORMATION: toxin sequence element

<400> SEQUENCE: 258

Ser Val Cys Ile Pro Ser Gly Gln Pro Cys
1               5                   10

<210> SEQ ID NO 259
<211> LENGTH: 9
<212> TYPE: PRT
<213> ORGANISM: Artificial Sequence
<220> FEATURE:
<223> OTHER INFORMATION: toxin sequence element

<400> SEQUENCE: 259

Thr Cys Arg Tyr Leu Phe Gly Gly Cys
1               5

<210> SEQ ID NO 260
<211> LENGTH: 9
<212> TYPE: PRT
<213> ORGANISM: Artificial Sequence
<220> FEATURE:
<223> OTHER INFORMATION: toxin sequence element

<400> SEQUENCE: 260

Thr Cys Tyr Asp Ile Gly Glu Leu Cys
1               5

<210> SEQ ID NO 261
<211> LENGTH: 9
<212> TYPE: PRT
<213> ORGANISM: Artificial Sequence
<220> FEATURE:
<223> OTHER INFORMATION: toxin sequence element

<400> SEQUENCE: 261

Val Cys Arg Gly Tyr Gly Leu Pro Cys
1               5

<210> SEQ ID NO 262
<211> LENGTH: 9
<212> TYPE: PRT
<213> ORGANISM: Artificial Sequence
<220> FEATURE:
<223> OTHER INFORMATION: toxin sequence element

<400> SEQUENCE: 262

Tyr Cys Gln Lys Trp Leu Trp Thr Cys

```
<210> SEQ ID NO 263
<211> LENGTH: 9
<212> TYPE: PRT
<213> ORGANISM: Artificial Sequence
<220> FEATURE:
<223> OTHER INFORMATION: toxin sequence element

<400> SEQUENCE: 263

Tyr Cys Gln Lys Trp Met Trp Thr Cys
1               5

<210> SEQ ID NO 264
<211> LENGTH: 8
<212> TYPE: PRT
<213> ORGANISM: Artificial Sequence
<220> FEATURE:
<223> OTHER INFORMATION: toxin sequence element

<400> SEQUENCE: 264

Cys Lys Gln Ala Asp Glu Pro Cys
1               5

<210> SEQ ID NO 265
<211> LENGTH: 9
<212> TYPE: PRT
<213> ORGANISM: Artificial Sequence
<220> FEATURE:
<223> OTHER INFORMATION: toxin sequence element

<400> SEQUENCE: 265

Ala Cys Arg Lys Lys Trp Glu Tyr Cys
1               5

<210> SEQ ID NO 266
<211> LENGTH: 11
<212> TYPE: PRT
<213> ORGANISM: Artificial Sequence
<220> FEATURE:
<223> OTHER INFORMATION: toxin sequence element

<400> SEQUENCE: 266

Asp Asp Asp Cys Glu Pro Pro Gly Asn Phe Cys
1               5                   10

<210> SEQ ID NO 267
<211> LENGTH: 11
<212> TYPE: PRT
<213> ORGANISM: Artificial Sequence
<220> FEATURE:
<223> OTHER INFORMATION: toxin sequence element

<400> SEQUENCE: 267

Val Lys Pro Cys Arg Lys Glu Gly Gln Leu Cys
1               5                   10

<210> SEQ ID NO 268
<211> LENGTH: 9
<212> TYPE: PRT
<213> ORGANISM: Artificial Sequence
<220> FEATURE:
<223> OTHER INFORMATION: toxin sequence element

<400> SEQUENCE: 268

Trp Cys Lys Gln Ser Gly Glu Met Cys
1               5
```

```
<210> SEQ ID NO 269
<211> LENGTH: 8
<212> TYPE: PRT
<213> ORGANISM: Artificial Sequence
<220> FEATURE:
<223> OTHER INFORMATION: toxin sequence element

<400> SEQUENCE: 269

Cys Leu Ser Gly Gly Glu Val Cys
1               5

<210> SEQ ID NO 270
<211> LENGTH: 11
<212> TYPE: PRT
<213> ORGANISM: Artificial Sequence
<220> FEATURE:
<223> OTHER INFORMATION: toxin sequence element

<400> SEQUENCE: 270

Gly Lys Pro Cys His Glu Glu Gly Cys Gln Leu
1               5                   10

<210> SEQ ID NO 271
<211> LENGTH: 8
<212> TYPE: PRT
<213> ORGANISM: Artificial Sequence
<220> FEATURE:
<223> OTHER INFORMATION: toxin sequence element

<400> SEQUENCE: 271

Cys Ile Pro Phe Leu His Pro Cys
1               5

<210> SEQ ID NO 272
<211> LENGTH: 9
<212> TYPE: PRT
<213> ORGANISM: Artificial Sequence
<220> FEATURE:
<223> OTHER INFORMATION: toxin sequence element

<400> SEQUENCE: 272

Ala Cys Ser Lys Lys Trp Glu Tyr Cys
1               5

<210> SEQ ID NO 273
<211> LENGTH: 12
<212> TYPE: PRT
<213> ORGANISM: Artificial Sequence
<220> FEATURE:
<223> OTHER INFORMATION: toxin sequence element

<400> SEQUENCE: 273

Ala Asp Ser Asp Asp Cys Cys Glu Thr Phe His Cys
1               5                   10

<210> SEQ ID NO 274
<211> LENGTH: 13
<212> TYPE: PRT
<213> ORGANISM: Artificial Sequence
<220> FEATURE:
<223> OTHER INFORMATION: toxin sequence element

<400> SEQUENCE: 274

Ala Trp Phe Ser Gly Glu Ser Cys Cys Thr Gly Ile Cys
1               5                   10
```

<210> SEQ ID NO 275
<211> LENGTH: 12
<212> TYPE: PRT
<213> ORGANISM: Artificial Sequence
<220> FEATURE:
<223> OTHER INFORMATION: toxin sequence element

<400> SEQUENCE: 275

Asp Glu Glu Arg Lys Cys Cys Glu Gly Leu Val Cys
1               5                   10

<210> SEQ ID NO 276
<211> LENGTH: 13
<212> TYPE: PRT
<213> ORGANISM: Artificial Sequence
<220> FEATURE:
<223> OTHER INFORMATION: toxin sequence element

<400> SEQUENCE: 276

Asp Glu Asn Asp Pro Arg Cys Cys Ser Gly Leu Val Cys
1               5                   10

<210> SEQ ID NO 277
<211> LENGTH: 13
<212> TYPE: PRT
<213> ORGANISM: Artificial Sequence
<220> FEATURE:
<223> OTHER INFORMATION: toxin sequence element

<400> SEQUENCE: 277

Asp Gly Lys Ser Thr Phe Cys Cys Ser Gly Phe Asn Cys
1               5                   10

<210> SEQ ID NO 278
<211> LENGTH: 13
<212> TYPE: PRT
<213> ORGANISM: Artificial Sequence
<220> FEATURE:
<223> OTHER INFORMATION: toxin sequence element

<400> SEQUENCE: 278

Asp Gly Lys Ser Thr Phe Cys Cys Ser Gly Tyr Asn Cys
1               5                   10

<210> SEQ ID NO 279
<211> LENGTH: 13
<212> TYPE: PRT
<213> ORGANISM: Artificial Sequence
<220> FEATURE:
<223> OTHER INFORMATION: toxin sequence element

<400> SEQUENCE: 279

Asp Pro Asp Asn Asp Lys Cys Cys Glu Gly Tyr Lys Cys
1               5                   10

<210> SEQ ID NO 280
<211> LENGTH: 13
<212> TYPE: PRT
<213> ORGANISM: Artificial Sequence
<220> FEATURE:
<223> OTHER INFORMATION: toxin sequence element

<400> SEQUENCE: 280

Asp Pro Lys Asn Asp Lys Cys Cys Lys Asn Tyr Thr Cys
1               5                   10

```
<210> SEQ ID NO 281
<211> LENGTH: 13
<212> TYPE: PRT
<213> ORGANISM: Artificial Sequence
<220> FEATURE:
<223> OTHER INFORMATION: toxin sequence element

<400> SEQUENCE: 281

Asp Pro Lys Asn Asp Lys Cys Cys Pro Asn Arg Val Cys
1               5                   10

<210> SEQ ID NO 282
<211> LENGTH: 13
<212> TYPE: PRT
<213> ORGANISM: Artificial Sequence
<220> FEATURE:
<223> OTHER INFORMATION: toxin sequence element

<400> SEQUENCE: 282

Asp Pro Asn Asn Asp Lys Cys Cys Pro Asn Arg Glu Cys
1               5                   10

<210> SEQ ID NO 283
<211> LENGTH: 13
<212> TYPE: PRT
<213> ORGANISM: Artificial Sequence
<220> FEATURE:
<223> OTHER INFORMATION: toxin sequence element

<400> SEQUENCE: 283

Asp Pro Asn Asn Asp Lys Cys Cys Pro Asn Arg Val Cys
1               5                   10

<210> SEQ ID NO 284
<211> LENGTH: 16
<212> TYPE: PRT
<213> ORGANISM: Artificial Sequence
<220> FEATURE:
<223> OTHER INFORMATION: toxin sequence element

<400> SEQUENCE: 284

Asp Pro Asn Pro Val Lys Asp Leu Pro Cys Cys Ser Gly Leu Ala Cys
1               5                   10                  15

<210> SEQ ID NO 285
<211> LENGTH: 12
<212> TYPE: PRT
<213> ORGANISM: Artificial Sequence
<220> FEATURE:
<223> OTHER INFORMATION: toxin sequence element

<400> SEQUENCE: 285

Asp Ser Ala Arg Lys Cys Cys Glu Gly Leu Val Cys
1               5                   10

<210> SEQ ID NO 286
<211> LENGTH: 12
<212> TYPE: PRT
<213> ORGANISM: Artificial Sequence
<220> FEATURE:
<223> OTHER INFORMATION: toxin sequence element

<400> SEQUENCE: 286

Asp Ser Glu Arg Lys Cys Cys Glu Asp Met Val Cys
1               5                   10

<210> SEQ ID NO 287
```

<211> LENGTH: 12
<212> TYPE: PRT
<213> ORGANISM: Artificial Sequence
<220> FEATURE:
<223> OTHER INFORMATION: toxin sequence element

<400> SEQUENCE: 287

Asp Ser Glu Arg Lys Cys Cys Glu Gly Met Val Cys
1               5                   10

<210> SEQ ID NO 288
<211> LENGTH: 12
<212> TYPE: PRT
<213> ORGANISM: Artificial Sequence
<220> FEATURE:
<223> OTHER INFORMATION: toxin sequence element

<400> SEQUENCE: 288

Asp Ser Glu Arg Lys Cys Cys Glu Gly Tyr Val Cys
1               5                   10

<210> SEQ ID NO 289
<211> LENGTH: 12
<212> TYPE: PRT
<213> ORGANISM: Artificial Sequence
<220> FEATURE:
<223> OTHER INFORMATION: toxin sequence element

<400> SEQUENCE: 289

Asp Ser Lys Arg Ala Cys Cys Glu Gly Leu Arg Cys
1               5                   10

<210> SEQ ID NO 290
<211> LENGTH: 12
<212> TYPE: PRT
<213> ORGANISM: Artificial Sequence
<220> FEATURE:
<223> OTHER INFORMATION: toxin sequence element

<400> SEQUENCE: 290

Asp Ser Lys Arg Lys Cys Cys Glu Asp Met Val Cys
1               5                   10

<210> SEQ ID NO 291
<211> LENGTH: 12
<212> TYPE: PRT
<213> ORGANISM: Artificial Sequence
<220> FEATURE:
<223> OTHER INFORMATION: toxin sequence element

<400> SEQUENCE: 291

Asp Ser Asn Ala Asp Cys Cys Glu Gly Tyr Val Cys
1               5                   10

<210> SEQ ID NO 292
<211> LENGTH: 12
<212> TYPE: PRT
<213> ORGANISM: Artificial Sequence
<220> FEATURE:
<223> OTHER INFORMATION: toxin sequence element

<400> SEQUENCE: 292

Asp Ser Thr Leu Asp Cys Cys Lys His Leu Ser Cys
1               5                   10

<210> SEQ ID NO 293
<211> LENGTH: 12

<212> TYPE: PRT
<213> ORGANISM: Artificial Sequence
<220> FEATURE:
<223> OTHER INFORMATION: toxin sequence element

<400> SEQUENCE: 293

Asp Thr Asn Ala Asp Cys Cys Glu Gly Tyr Val Cys
1               5                   10

<210> SEQ ID NO 294
<211> LENGTH: 12
<212> TYPE: PRT
<213> ORGANISM: Artificial Sequence
<220> FEATURE:
<223> OTHER INFORMATION: toxin sequence element

<400> SEQUENCE: 294

Asp Thr Ser Lys Asp Cys Cys Glu Gly Tyr Val Cys
1               5                   10

<210> SEQ ID NO 295
<211> LENGTH: 12
<212> TYPE: PRT
<213> ORGANISM: Artificial Sequence
<220> FEATURE:
<223> OTHER INFORMATION: toxin sequence element

<400> SEQUENCE: 295

Asp Tyr Asn Asn Gly Cys Cys Ser Gly Tyr Val Cys
1               5                   10

<210> SEQ ID NO 296
<211> LENGTH: 12
<212> TYPE: PRT
<213> ORGANISM: Artificial Sequence
<220> FEATURE:
<223> OTHER INFORMATION: toxin sequence element

<400> SEQUENCE: 296

Glu Lys Asp Glu His Cys Cys Glu His Leu Gly Cys
1               5                   10

<210> SEQ ID NO 297
<211> LENGTH: 12
<212> TYPE: PRT
<213> ORGANISM: Artificial Sequence
<220> FEATURE:
<223> OTHER INFORMATION: toxin sequence element

<400> SEQUENCE: 297

Glu Lys Asp Ser Asp Cys Cys Glu His Leu Gly Cys
1               5                   10

<210> SEQ ID NO 298
<211> LENGTH: 12
<212> TYPE: PRT
<213> ORGANISM: Artificial Sequence
<220> FEATURE:
<223> OTHER INFORMATION: toxin sequence element

<400> SEQUENCE: 298

Glu Ser Asn Ala Asp Cys Cys Glu Asn Trp Ala Cys
1               5                   10

<210> SEQ ID NO 299
<211> LENGTH: 12
<212> TYPE: PRT

```
<213> ORGANISM: Artificial Sequence
<220> FEATURE:
<223> OTHER INFORMATION: toxin sequence element

<400> SEQUENCE: 299

Phe Arg Asp Lys Glu Cys Cys Lys Gly Leu Thr Cys
1               5                   10

<210> SEQ ID NO 300
<211> LENGTH: 13
<212> TYPE: PRT
<213> ORGANISM: Artificial Sequence
<220> FEATURE:
<223> OTHER INFORMATION: toxin sequence element

<400> SEQUENCE: 300

Gly Ala Gly Lys Pro Thr Cys Cys Ser Gly Tyr Asp Cys
1               5                   10

<210> SEQ ID NO 301
<211> LENGTH: 13
<212> TYPE: PRT
<213> ORGANISM: Artificial Sequence
<220> FEATURE:
<223> OTHER INFORMATION: toxin sequence element

<400> SEQUENCE: 301

Gly Glu Gly Lys Pro Pro Cys Cys Ala Asn Phe Ala Cys
1               5                   10

<210> SEQ ID NO 302
<211> LENGTH: 13
<212> TYPE: PRT
<213> ORGANISM: Artificial Sequence
<220> FEATURE:
<223> OTHER INFORMATION: toxin sequence element

<400> SEQUENCE: 302

Gly Arg Gly Lys Pro Pro Cys Cys Lys Gly Tyr Ala Cys
1               5                   10

<210> SEQ ID NO 303
<211> LENGTH: 13
<212> TYPE: PRT
<213> ORGANISM: Artificial Sequence
<220> FEATURE:
<223> OTHER INFORMATION: toxin sequence element

<400> SEQUENCE: 303

Gly Ser Gly Lys Pro Ala Cys Cys Pro Lys Tyr Val Cys
1               5                   10

<210> SEQ ID NO 304
<211> LENGTH: 13
<212> TYPE: PRT
<213> ORGANISM: Artificial Sequence
<220> FEATURE:
<223> OTHER INFORMATION: toxin sequence element

<400> SEQUENCE: 304

Gly Thr Asp Gln Ser Glu Cys Cys Glu Gly Trp Lys Cys
1               5                   10

<210> SEQ ID NO 305
<211> LENGTH: 13
<212> TYPE: PRT
<213> ORGANISM: Artificial Sequence
```

```
<220> FEATURE:
<223> OTHER INFORMATION: toxin sequence element

<400> SEQUENCE: 305

His Pro Gly Gln Pro Pro Cys Cys Ser Gly Leu Ala Cys
1               5                   10

<210> SEQ ID NO 306
<211> LENGTH: 11
<212> TYPE: PRT
<213> ORGANISM: Artificial Sequence
<220> FEATURE:
<223> OTHER INFORMATION: toxin sequence element

<400> SEQUENCE: 306

Lys Ala Asp Asn Asp Cys Cys Gly Lys Lys Cys
1               5                   10

<210> SEQ ID NO 307
<211> LENGTH: 12
<212> TYPE: PRT
<213> ORGANISM: Artificial Sequence
<220> FEATURE:
<223> OTHER INFORMATION: toxin sequence element

<400> SEQUENCE: 307

Lys Ala His Glu Asp Cys Cys Glu His Leu Arg Cys
1               5                   10

<210> SEQ ID NO 308
<211> LENGTH: 12
<212> TYPE: PRT
<213> ORGANISM: Artificial Sequence
<220> FEATURE:
<223> OTHER INFORMATION: toxin sequence element

<400> SEQUENCE: 308

Lys Glu Asp Ser Glu Cys Cys Glu His Leu Gln Cys
1               5                   10

<210> SEQ ID NO 309
<211> LENGTH: 11
<212> TYPE: PRT
<213> ORGANISM: Artificial Sequence
<220> FEATURE:
<223> OTHER INFORMATION: toxin sequence element

<400> SEQUENCE: 309

Lys Glu Lys Leu Cys Cys Ser Gly Tyr Val Cys
1               5                   10

<210> SEQ ID NO 310
<211> LENGTH: 11
<212> TYPE: PRT
<213> ORGANISM: Artificial Sequence
<220> FEATURE:
<223> OTHER INFORMATION: toxin sequence element

<400> SEQUENCE: 310

Lys Glu Asn Lys Asp Cys Cys Ser Lys Lys Cys
1               5                   10

<210> SEQ ID NO 311
<211> LENGTH: 12
<212> TYPE: PRT
<213> ORGANISM: Artificial Sequence
<220> FEATURE:
```

```
<223> OTHER INFORMATION: toxin sequence element

<400> SEQUENCE: 311

Lys Lys Asp Lys Glu Cys Cys Gly Trp Asn Ile Cys
1               5                   10

<210> SEQ ID NO 312
<211> LENGTH: 12
<212> TYPE: PRT
<213> ORGANISM: Artificial Sequence
<220> FEATURE:
<223> OTHER INFORMATION: toxin sequence element

<400> SEQUENCE: 312

Lys Asn Lys Lys Glu Cys Cys Gly Trp Asn Ala Cys
1               5                   10

<210> SEQ ID NO 313
<211> LENGTH: 12
<212> TYPE: PRT
<213> ORGANISM: Artificial Sequence
<220> FEATURE:
<223> OTHER INFORMATION: toxin sequence element

<400> SEQUENCE: 313

Lys Asn Ser Asn Asp Cys Cys Lys Asp Leu Val Cys
1               5                   10

<210> SEQ ID NO 314
<211> LENGTH: 12
<212> TYPE: PRT
<213> ORGANISM: Artificial Sequence
<220> FEATURE:
<223> OTHER INFORMATION: toxin sequence element

<400> SEQUENCE: 314

Lys Ser Asp Glu Asn Cys Cys Lys Lys Phe Lys Cys
1               5                   10

<210> SEQ ID NO 315
<211> LENGTH: 12
<212> TYPE: PRT
<213> ORGANISM: Artificial Sequence
<220> FEATURE:
<223> OTHER INFORMATION: toxin sequence element

<400> SEQUENCE: 315

Lys Ser Thr Ser Asp Cys Cys Glu His Leu Ser Cys
1               5                   10

<210> SEQ ID NO 316
<211> LENGTH: 12
<212> TYPE: PRT
<213> ORGANISM: Artificial Sequence
<220> FEATURE:
<223> OTHER INFORMATION: toxin sequence element

<400> SEQUENCE: 316

Lys Thr Thr Ala Asp Cys Cys Lys His Leu Ala Cys
1               5                   10

<210> SEQ ID NO 317
<211> LENGTH: 12
<212> TYPE: PRT
<213> ORGANISM: Artificial Sequence
<220> FEATURE:
<223> OTHER INFORMATION: toxin sequence element
```

```
<400> SEQUENCE: 317

Lys Thr Thr Ala Asp Cys Cys Lys His Leu Gly Cys
1               5                   10

<210> SEQ ID NO 318
<211> LENGTH: 12
<212> TYPE: PRT
<213> ORGANISM: Artificial Sequence
<220> FEATURE:
<223> OTHER INFORMATION: toxin sequence element

<400> SEQUENCE: 318

Lys Thr Thr Ser Asp Cys Cys Lys His Leu Gly Cys
1               5                   10

<210> SEQ ID NO 319
<211> LENGTH: 14
<212> TYPE: PRT
<213> ORGANISM: Artificial Sequence
<220> FEATURE:
<223> OTHER INFORMATION: toxin sequence element

<400> SEQUENCE: 319

Asn Ala Leu Ser Gly Pro Arg Cys Cys Ser Gly Leu Lys Cys
1               5                   10

<210> SEQ ID NO 320
<211> LENGTH: 12
<212> TYPE: PRT
<213> ORGANISM: Artificial Sequence
<220> FEATURE:
<223> OTHER INFORMATION: toxin sequence element

<400> SEQUENCE: 320

Asn Asp Glu Met Val Cys Cys Glu His Leu Val Cys
1               5                   10

<210> SEQ ID NO 321
<211> LENGTH: 17
<212> TYPE: PRT
<213> ORGANISM: Artificial Sequence
<220> FEATURE:
<223> OTHER INFORMATION: toxin sequence element

<400> SEQUENCE: 321

Asn Gly Pro His Thr Cys Cys Trp Gly Tyr Asn Gly Tyr Lys Lys Ala
1               5                   10                  15

Cys

<210> SEQ ID NO 322
<211> LENGTH: 13
<212> TYPE: PRT
<213> ORGANISM: Artificial Sequence
<220> FEATURE:
<223> OTHER INFORMATION: toxin sequence element

<400> SEQUENCE: 322

Asn Pro Asp Asn Asp Lys Cys Cys Glu Gly Arg Lys Cys
1               5                   10

<210> SEQ ID NO 323
<211> LENGTH: 14
<212> TYPE: PRT
<213> ORGANISM: Artificial Sequence
<220> FEATURE:
```

<223> OTHER INFORMATION: toxin sequence element

<400> SEQUENCE: 323

Asn Pro Asn Asp Asp Lys Cys Cys Arg Pro Lys Leu Lys Cys
1               5                   10

<210> SEQ ID NO 324
<211> LENGTH: 14
<212> TYPE: PRT
<213> ORGANISM: Artificial Sequence
<220> FEATURE:
<223> OTHER INFORMATION: toxin sequence element

<400> SEQUENCE: 324

Asn Pro Ser Asn Asp Lys Cys Cys Arg Pro Asn Leu Val Cys
1               5                   10

<210> SEQ ID NO 325
<211> LENGTH: 15
<212> TYPE: PRT
<213> ORGANISM: Artificial Sequence
<220> FEATURE:
<223> OTHER INFORMATION: toxin sequence element

<400> SEQUENCE: 325

Asn Pro Ser Asn Asp Gln Cys Cys Lys Ser Ala Asn Leu Val Cys
1               5                   10                  15

<210> SEQ ID NO 326
<211> LENGTH: 15
<212> TYPE: PRT
<213> ORGANISM: Artificial Sequence
<220> FEATURE:
<223> OTHER INFORMATION: toxin sequence element

<400> SEQUENCE: 326

Asn Pro Ser Asn Asp Gln Cys Cys Lys Ser Ser Lys Leu Val Cys
1               5                   10                  15

<210> SEQ ID NO 327
<211> LENGTH: 15
<212> TYPE: PRT
<213> ORGANISM: Artificial Sequence
<220> FEATURE:
<223> OTHER INFORMATION: toxin sequence element

<400> SEQUENCE: 327

Asn Pro Ser Asn Asp Gln Cys Cys Lys Ser Ser Asn Leu Val Cys
1               5                   10                  15

<210> SEQ ID NO 328
<211> LENGTH: 13
<212> TYPE: PRT
<213> ORGANISM: Artificial Sequence
<220> FEATURE:
<223> OTHER INFORMATION: toxin sequence element

<400> SEQUENCE: 328

Asn Ser Asp Ala Asp Cys Cys Arg Tyr Gly Glu Arg Cys
1               5                   10

<210> SEQ ID NO 329
<211> LENGTH: 12
<212> TYPE: PRT
<213> ORGANISM: Artificial Sequence
<220> FEATURE:
<223> OTHER INFORMATION: toxin sequence element

```
<400> SEQUENCE: 329

Asn Ser Asp Lys Glu Cys Cys Lys Gly Leu Arg Cys
1               5                   10

<210> SEQ ID NO 330
<211> LENGTH: 13
<212> TYPE: PRT
<213> ORGANISM: Artificial Sequence
<220> FEATURE:
<223> OTHER INFORMATION: toxin sequence element

<400> SEQUENCE: 330

Asn Tyr Met Asp Asp Lys Cys Cys Pro Gly Tyr Lys Cys
1               5                   10

<210> SEQ ID NO 331
<211> LENGTH: 12
<212> TYPE: PRT
<213> ORGANISM: Artificial Sequence
<220> FEATURE:
<223> OTHER INFORMATION: toxin sequence element

<400> SEQUENCE: 331

Pro Lys Lys Ala Pro Cys Cys Gly Arg Leu Glu Cys
1               5                   10

<210> SEQ ID NO 332
<211> LENGTH: 11
<212> TYPE: PRT
<213> ORGANISM: Artificial Sequence
<220> FEATURE:
<223> OTHER INFORMATION: toxin sequence element

<400> SEQUENCE: 332

Pro Tyr His Glu Ser Cys Cys Ser Gly Ser Cys
1               5                   10

<210> SEQ ID NO 333
<211> LENGTH: 11
<212> TYPE: PRT
<213> ORGANISM: Artificial Sequence
<220> FEATURE:
<223> OTHER INFORMATION: toxin sequence element

<400> SEQUENCE: 333

Pro Tyr Asn Glu His Cys Cys Ser Gly Ser Cys
1               5                   10

<210> SEQ ID NO 334
<211> LENGTH: 11
<212> TYPE: PRT
<213> ORGANISM: Artificial Sequence
<220> FEATURE:
<223> OTHER INFORMATION: toxin sequence element

<400> SEQUENCE: 334

Pro Tyr Asn Glu Asn Cys Cys Ser Lys Ser Cys
1               5                   10

<210> SEQ ID NO 335
<211> LENGTH: 11
<212> TYPE: PRT
<213> ORGANISM: Artificial Sequence
<220> FEATURE:
<223> OTHER INFORMATION: toxin sequence element
```

<400> SEQUENCE: 335

Pro Tyr Asn Glu Asn Cys Cys Ser Gln Ser Cys
1 5 10

<210> SEQ ID NO 336
<211> LENGTH: 11
<212> TYPE: PRT
<213> ORGANISM: Artificial Sequence
<220> FEATURE:
<223> OTHER INFORMATION: toxin sequence element

<400> SEQUENCE: 336

Pro Tyr Asn Glu Ser Cys Cys Ser Gly Ser Cys
1 5 10

<210> SEQ ID NO 337
<211> LENGTH: 11
<212> TYPE: PRT
<213> ORGANISM: Artificial Sequence
<220> FEATURE:
<223> OTHER INFORMATION: toxin sequence element

<400> SEQUENCE: 337

Pro Tyr Ser Lys Tyr Cys Cys Ser Gly Ser Cys
1 5 10

<210> SEQ ID NO 338
<211> LENGTH: 19
<212> TYPE: PRT
<213> ORGANISM: Artificial Sequence
<220> FEATURE:
<223> OTHER INFORMATION: toxin sequence element

<400> SEQUENCE: 338

Gln Pro Asn Thr Gln Pro Cys Cys Asn Asn Ala Glu Glu Glu Gln Thr
1 5 10 15

Ile Asn Cys

<210> SEQ ID NO 339
<211> LENGTH: 11
<212> TYPE: PRT
<213> ORGANISM: Artificial Sequence
<220> FEATURE:
<223> OTHER INFORMATION: toxin sequence element

<400> SEQUENCE: 339

Arg Glu Asn Lys Asp Cys Cys Ser Lys Lys Cys
1 5 10

<210> SEQ ID NO 340
<211> LENGTH: 12
<212> TYPE: PRT
<213> ORGANISM: Artificial Sequence
<220> FEATURE:
<223> OTHER INFORMATION: toxin sequence element

<400> SEQUENCE: 340

Arg Arg Asp Ser Asp Cys Cys Pro His Leu Gly Cys
1 5 10

<210> SEQ ID NO 341
<211> LENGTH: 12
<212> TYPE: PRT
<213> ORGANISM: Artificial Sequence
<220> FEATURE:
<223> OTHER INFORMATION: toxin sequence element

<400> SEQUENCE: 341

Ser Ala Gly Gln Thr Cys Cys Lys His Leu Val Cys
1               5                   10

<210> SEQ ID NO 342
<211> LENGTH: 12
<212> TYPE: PRT
<213> ORGANISM: Artificial Sequence
<220> FEATURE:
<223> OTHER INFORMATION: toxin sequence element

<400> SEQUENCE: 342

Ser Glu Asp Ser Glu Cys Cys Pro His Leu Gly Cys
1               5                   10

<210> SEQ ID NO 343
<211> LENGTH: 12
<212> TYPE: PRT
<213> ORGANISM: Artificial Sequence
<220> FEATURE:
<223> OTHER INFORMATION: toxin sequence element

<400> SEQUENCE: 343

Ser Lys Asp Ala Asp Cys Cys Ala His Leu Glu Cys
1               5                   10

<210> SEQ ID NO 344
<211> LENGTH: 12
<212> TYPE: PRT
<213> ORGANISM: Artificial Sequence
<220> FEATURE:
<223> OTHER INFORMATION: toxin sequence element

<400> SEQUENCE: 344

Ser Lys His Glu Asp Cys Cys Ala His Leu Ala Cys
1               5                   10

<210> SEQ ID NO 345
<211> LENGTH: 12
<212> TYPE: PRT
<213> ORGANISM: Artificial Sequence
<220> FEATURE:
<223> OTHER INFORMATION: toxin sequence element

<400> SEQUENCE: 345

Ser Lys Thr Gly Asp Cys Cys Ser His Leu Ser Cys
1               5                   10

<210> SEQ ID NO 346
<211> LENGTH: 12
<212> TYPE: PRT
<213> ORGANISM: Artificial Sequence
<220> FEATURE:
<223> OTHER INFORMATION: toxin sequence element

<400> SEQUENCE: 346

Ser Gln Asp Gly Asp Cys Cys Lys His Leu Gln Cys
1               5                   10

<210> SEQ ID NO 347
<211> LENGTH: 12
<212> TYPE: PRT
<213> ORGANISM: Artificial Sequence
<220> FEATURE:
<223> OTHER INFORMATION: toxin sequence element

<400> SEQUENCE: 347

Ser Gln Thr Ser Asp Cys Cys Pro His Leu Ala Cys
1               5                   10

<210> SEQ ID NO 348
<211> LENGTH: 12
<212> TYPE: PRT
<213> ORGANISM: Artificial Sequence
<220> FEATURE:
<223> OTHER INFORMATION: toxin sequence element

<400> SEQUENCE: 348

Ser Ser Asp Lys Pro Cys Cys Ser Gly Tyr Tyr Cys
1               5                   10

<210> SEQ ID NO 349
<211> LENGTH: 12
<212> TYPE: PRT
<213> ORGANISM: Artificial Sequence
<220> FEATURE:
<223> OTHER INFORMATION: toxin sequence element

<400> SEQUENCE: 349

Ser Ser Thr Ser Asp Cys Cys Lys His Leu Ser Cys
1               5                   10

<210> SEQ ID NO 350
<211> LENGTH: 12
<212> TYPE: PRT
<213> ORGANISM: Artificial Sequence
<220> FEATURE:
<223> OTHER INFORMATION: toxin sequence element

<400> SEQUENCE: 350

Ser Thr Glu Lys Pro Cys Cys Asp Asn Phe Ser Cys
1               5                   10

<210> SEQ ID NO 351
<211> LENGTH: 12
<212> TYPE: PRT
<213> ORGANISM: Artificial Sequence
<220> FEATURE:
<223> OTHER INFORMATION: toxin sequence element

<400> SEQUENCE: 351

Ser Thr His Ala Asp Cys Cys Glu Gly Phe Ile Cys
1               5                   10

<210> SEQ ID NO 352
<211> LENGTH: 12
<212> TYPE: PRT
<213> ORGANISM: Artificial Sequence
<220> FEATURE:
<223> OTHER INFORMATION: toxin sequence element

<400> SEQUENCE: 352

Ser Val Asp Ser Asp Cys Cys Ala His Leu Gly Cys
1               5                   10

<210> SEQ ID NO 353
<211> LENGTH: 12
<212> TYPE: PRT
<213> ORGANISM: Artificial Sequence
<220> FEATURE:
<223> OTHER INFORMATION: toxin sequence element

<400> SEQUENCE: 353

```
Ser Val His Ser Asp Cys Cys Ala His Leu Gly Cys
1               5                   10

<210> SEQ ID NO 354
<211> LENGTH: 12
<212> TYPE: PRT
<213> ORGANISM: Artificial Sequence
<220> FEATURE:
<223> OTHER INFORMATION: toxin sequence element

<400> SEQUENCE: 354

Ser Val Asn Asp Asp Cys Cys Pro Arg Leu Gly Cys
1               5                   10

<210> SEQ ID NO 355
<211> LENGTH: 12
<212> TYPE: PRT
<213> ORGANISM: Artificial Sequence
<220> FEATURE:
<223> OTHER INFORMATION: toxin sequence element

<400> SEQUENCE: 355

Thr Asp Arg Leu Pro Cys Cys Phe Gly Leu Glu Cys
1               5                   10

<210> SEQ ID NO 356
<211> LENGTH: 12
<212> TYPE: PRT
<213> ORGANISM: Artificial Sequence
<220> FEATURE:
<223> OTHER INFORMATION: toxin sequence element

<400> SEQUENCE: 356

Thr Ile Asp Asp Asp Cys Cys Pro His Leu Gly Cys
1               5                   10

<210> SEQ ID NO 357
<211> LENGTH: 12
<212> TYPE: PRT
<213> ORGANISM: Artificial Sequence
<220> FEATURE:
<223> OTHER INFORMATION: toxin sequence element

<400> SEQUENCE: 357

Thr Lys Asp Glu Asp Cys Cys Lys His Leu Ala Cys
1               5                   10

<210> SEQ ID NO 358
<211> LENGTH: 12
<212> TYPE: PRT
<213> ORGANISM: Artificial Sequence
<220> FEATURE:
<223> OTHER INFORMATION: toxin sequence element

<400> SEQUENCE: 358

Thr Lys Asp Ser Glu Cys Cys Pro His Leu Gly Cys
1               5                   10

<210> SEQ ID NO 359
<211> LENGTH: 13
<212> TYPE: PRT
<213> ORGANISM: Artificial Sequence
<220> FEATURE:
<223> OTHER INFORMATION: toxin sequence element

<400> SEQUENCE: 359
```

```
Thr Pro Glu Lys Asn Asp Cys Cys Gln Arg Leu Tyr Cys
1               5                   10
```

<210> SEQ ID NO 360
<211> LENGTH: 13
<212> TYPE: PRT
<213> ORGANISM: Artificial Sequence
<220> FEATURE:
<223> OTHER INFORMATION: toxin sequence element

<400> SEQUENCE: 360

Thr Pro Gly Lys Asn Glu Cys Cys Pro Asn Arg Val Cys
1 5 10

<210> SEQ ID NO 361
<211> LENGTH: 13
<212> TYPE: PRT
<213> ORGANISM: Artificial Sequence
<220> FEATURE:
<223> OTHER INFORMATION: toxin sequence element

<400> SEQUENCE: 361

Thr Pro Gly Lys Asn Glu Cys Cys Pro Asn Tyr Ala Cys
1 5 10

<210> SEQ ID NO 362
<211> LENGTH: 12
<212> TYPE: PRT
<213> ORGANISM: Artificial Sequence
<220> FEATURE:
<223> OTHER INFORMATION: toxin sequence element

<400> SEQUENCE: 362

Thr Ser Asp Ser Asp Cys Cys Pro Asn Trp Val Cys
1 5 10

<210> SEQ ID NO 363
<211> LENGTH: 12
<212> TYPE: PRT
<213> ORGANISM: Artificial Sequence
<220> FEATURE:
<223> OTHER INFORMATION: toxin sequence element

<400> SEQUENCE: 363

Thr Thr Ser Ser Glu Cys Cys Ala His Leu Gly Cys
1 5 10

<210> SEQ ID NO 364
<211> LENGTH: 13
<212> TYPE: PRT
<213> ORGANISM: Artificial Sequence
<220> FEATURE:
<223> OTHER INFORMATION: toxin sequence element

<400> SEQUENCE: 364

Val Asn Arg His Gly Asp Cys Cys Glu Gly Leu Glu Cys
1 5 10

<210> SEQ ID NO 365
<211> LENGTH: 13
<212> TYPE: PRT
<213> ORGANISM: Artificial Sequence
<220> FEATURE:
<223> OTHER INFORMATION: toxin sequence element

<400> SEQUENCE: 365

Val Pro Gly Lys Asn Glu Cys Cys Ser Gly Tyr Ala Cys

```
1               5                  10

<210> SEQ ID NO 366
<211> LENGTH: 13
<212> TYPE: PRT
<213> ORGANISM: Artificial Sequence
<220> FEATURE:
<223> OTHER INFORMATION: toxin sequence element

<400> SEQUENCE: 366

Tyr Gly Ala Thr Gln Lys Ile Pro Cys Cys Gly Val Cys
1               5                  10

<210> SEQ ID NO 367
<211> LENGTH: 12
<212> TYPE: PRT
<213> ORGANISM: Artificial Sequence
<220> FEATURE:
<223> OTHER INFORMATION: toxin sequence element

<400> SEQUENCE: 367

Tyr Lys Leu Arg Lys Cys Cys Ala Gly Phe Tyr Cys
1               5                  10

<210> SEQ ID NO 368
<211> LENGTH: 12
<212> TYPE: PRT
<213> ORGANISM: Artificial Sequence
<220> FEATURE:
<223> OTHER INFORMATION: toxin sequence element

<400> SEQUENCE: 368

Asp Val Phe Ser Leu Asp Cys Cys Thr Gly Ile Cys
1               5                  10

<210> SEQ ID NO 369
<211> LENGTH: 16
<212> TYPE: PRT
<213> ORGANISM: Artificial Sequence
<220> FEATURE:
<223> OTHER INFORMATION: toxin sequence element

<400> SEQUENCE: 369

Ile Val Pro Ile Ile Gly Phe Ile Tyr Cys Cys Pro Gly Leu Ile Cys
1               5                  10                 15

<210> SEQ ID NO 370
<211> LENGTH: 14
<212> TYPE: PRT
<213> ORGANISM: Artificial Sequence
<220> FEATURE:
<223> OTHER INFORMATION: toxin sequence element

<400> SEQUENCE: 370

Gly Met Ile Lys Ile Gly Pro Pro Cys Cys Ser Gly Trp Cys
1               5                  10

<210> SEQ ID NO 371
<211> LENGTH: 13
<212> TYPE: PRT
<213> ORGANISM: Artificial Sequence
<220> FEATURE:
<223> OTHER INFORMATION: toxin sequence element

<400> SEQUENCE: 371

Asp Pro Ile Phe Gln Asn Cys Cys Arg Gly Trp Asn Cys
1               5                  10
```

<210> SEQ ID NO 372
<211> LENGTH: 12
<212> TYPE: PRT
<213> ORGANISM: Artificial Sequence
<220> FEATURE:
<223> OTHER INFORMATION: toxin sequence element

<400> SEQUENCE: 372

Asn Val Leu Asp Gln Asn Cys Cys Asp Gly Tyr Cys
1               5                   10

<210> SEQ ID NO 373
<211> LENGTH: 11
<212> TYPE: PRT
<213> ORGANISM: Artificial Sequence
<220> FEATURE:
<223> OTHER INFORMATION: toxin sequence element

<400> SEQUENCE: 373

Asp Phe Leu Phe Pro Lys Cys Cys Asn Tyr Cys
1               5                   10

<210> SEQ ID NO 374
<211> LENGTH: 13
<212> TYPE: PRT
<213> ORGANISM: Artificial Sequence
<220> FEATURE:
<223> OTHER INFORMATION: toxin sequence element

<400> SEQUENCE: 374

Asp Pro Phe Leu Gln Asn Cys Cys Leu Gly Trp Asn Cys
1               5                   10

<210> SEQ ID NO 375
<211> LENGTH: 12
<212> TYPE: PRT
<213> ORGANISM: Artificial Sequence
<220> FEATURE:
<223> OTHER INFORMATION: toxin sequence element

<400> SEQUENCE: 375

Thr Phe Phe Phe Pro Asp Cys Cys Asn Ser Ile Cys
1               5                   10

<210> SEQ ID NO 376
<211> LENGTH: 16
<212> TYPE: PRT
<213> ORGANISM: Artificial Sequence
<220> FEATURE:
<223> OTHER INFORMATION: toxin sequence element

<400> SEQUENCE: 376

Ile Val Pro Ile Leu Gly Phe Val Tyr Cys Cys Pro Gly Leu Ile Cys
1               5                   10                  15

<210> SEQ ID NO 377
<211> LENGTH: 8
<212> TYPE: PRT
<213> ORGANISM: Artificial Sequence
<220> FEATURE:
<223> OTHER INFORMATION: toxin sequence element

<400> SEQUENCE: 377

Ala Leu Gly Ile Cys Met Pro Arg
1               5

```
<210> SEQ ID NO 378
<211> LENGTH: 14
<212> TYPE: PRT
<213> ORGANISM: Artificial Sequence
<220> FEATURE:
<223> OTHER INFORMATION: toxin sequence element

<400> SEQUENCE: 378

Ala Thr Thr Gly Arg Phe Arg Tyr Leu Cys Lys Tyr Gln Ile
1               5                   10

<210> SEQ ID NO 379
<211> LENGTH: 12
<212> TYPE: PRT
<213> ORGANISM: Artificial Sequence
<220> FEATURE:
<223> OTHER INFORMATION: toxin sequence element

<400> SEQUENCE: 379

Asp Arg Arg Asp Gln Trp Cys Lys Trp Asn Pro Trp
1               5                   10

<210> SEQ ID NO 380
<211> LENGTH: 8
<212> TYPE: PRT
<213> ORGANISM: Artificial Sequence
<220> FEATURE:
<223> OTHER INFORMATION: toxin sequence element

<400> SEQUENCE: 380

Glu Leu Trp Cys Lys Tyr Asn Leu
1               5

<210> SEQ ID NO 381
<211> LENGTH: 12
<212> TYPE: PRT
<213> ORGANISM: Artificial Sequence
<220> FEATURE:
<223> OTHER INFORMATION: toxin sequence element

<400> SEQUENCE: 381

Glu Arg Ser Ser Pro Trp Cys Lys Ile Asp Ile Trp
1               5                   10

<210> SEQ ID NO 382
<211> LENGTH: 7
<212> TYPE: PRT
<213> ORGANISM: Artificial Sequence
<220> FEATURE:
<223> OTHER INFORMATION: toxin sequence element

<400> SEQUENCE: 382

His Leu Trp Cys Lys Tyr Lys
1               5

<210> SEQ ID NO 383
<211> LENGTH: 15
<212> TYPE: PRT
<213> ORGANISM: Artificial Sequence
<220> FEATURE:
<223> OTHER INFORMATION: toxin sequence element

<400> SEQUENCE: 383

His Ser Leu Phe Ser Tyr Cys Ala Trp Asp Leu Thr Phe Ser Asp
1               5                   10                  15
```

-continued

```
<210> SEQ ID NO 384
<211> LENGTH: 15
<212> TYPE: PRT
<213> ORGANISM: Artificial Sequence
<220

<210> SEQ ID NO 390
<211> LENGTH: 10
<212> TYPE: PRT
<213> ORGANISM: Artificial Sequence
<220> FEATURE:
<223> OTHER INFORMATION: toxin sequence element

<400> SEQUENCE: 390

Lys Ala Phe Val Leu His Cys Tyr Arg Asn
1               5                   10

<210> SEQ ID NO 391
<211> LENGTH: 13
<212> TYPE: PRT
<213> ORGANISM: Artificial Sequence
<220> FEATURE:
<223> OTHER INFORMATION: toxin sequence element

<400> SEQUENCE: 391

Lys Asp Val Leu Tyr Tyr Cys Ala Trp Asp Gly Thr Phe
1               5                   10

<210> SEQ ID NO 392
<211> LENGTH: 17
<212> TYPE: PRT
<213> ORGANISM: Artificial Sequence
<220> FEATURE:
<223> OTHER INFORMATION: toxin sequence element

<400> SEQUENCE: 392

Lys Glu Lys Trp Pro Ile Thr Tyr Lys Ile Cys Val Trp Asp Arg Thr
1               5                   10                  15

Phe

<210> SEQ ID NO 393
<211> LENGTH: 11
<212> TYPE: PRT
<213> ORGANISM: Artificial Sequence
<220> FEATURE:
<223> OTHER INFORMATION: toxin sequence element

<400> SEQUENCE: 393

Lys Glu Leu Ser Ile Trp Asp Ser Arg Cys Leu
1               5                   10

<210> SEQ ID NO 394
<211> LENGTH: 14
<212> TYPE: PRT
<213> ORGANISM: Artificial Sequence
<220> FEATURE:
<223> OTHER INFORMATION: toxin sequence element

<400> SEQUENCE: 394

Lys Phe Arg Asp Lys Tyr Cys Ala Trp Asp Phe Thr Phe Ser
1               5                   10

<210> SEQ ID NO 395
<211> LENGTH: 13
<212> TYPE: PRT
<213> ORGANISM: Artificial Sequence
<220> FEATURE:
<223> OTHER INFORMATION: toxin sequence element

<400> SEQUENCE: 395

-continued

Lys Gly Pro Ser Pro Lys Gln Lys Lys Cys Thr Arg Pro
1               5                   10

<210> SEQ ID NO 396
<211> LENGTH: 14
<212> TYPE: PRT
<213> ORGANISM: Artificial Sequence
<220> FEATURE:
<223> OTHER INFORMATION: toxin sequence element

<400> SEQUENCE: 396

Lys Gly Arg Phe Val Asn Thr Trp Pro Thr Phe Cys Leu Val
1               5                   10

<210> SEQ ID NO 397
<211> LENGTH: 11
<212> TYPE: PRT
<213> ORGANISM: Artificial Sequence
<220> FEATURE:
<223> OTHER INFORMATION: toxin sequence element

<400> SEQUENCE: 397

Lys Ile Gly Leu Tyr Leu Cys Ile Trp Ser Pro
1               5                   10

<210> SEQ ID NO 398
<211> LENGTH: 9
<212> TYPE: PRT
<213> ORGANISM: Artificial Sequence
<220> FEATURE:
<223> OTHER INFORMATION: toxin sequence element

<400> SEQUENCE: 398

Lys Leu Trp Cys Arg Lys Ile Ile Gly
1               5

<210> SEQ ID NO 399
<211> LENGTH: 10
<212> TYPE: PRT
<213> ORGANISM: Artificial Sequence
<220> FEATURE:
<223> OTHER INFORMATION: toxin sequence element

<400> SEQUENCE: 399

Lys Leu Trp Cys Arg Tyr Glu Arg Thr Trp
1               5                   10

<210> SEQ ID NO 400
<211> LENGTH: 13
<212> TYPE: PRT
<213> ORGANISM: Artificial Sequence
<220> FEATURE:
<223> OTHER INFORMATION: toxin sequence element

<400> SEQUENCE: 400

Lys Met Gly Leu Asp Tyr Cys Ala Trp Asp Gly Thr Phe
1               5                   10

<210> SEQ ID NO 401
<211> LENGTH: 13
<212> TYPE: PRT
<213> ORGANISM: Artificial Sequence
<220> FEATURE:
<223> OTHER INFORMATION: toxin sequence element

<400> SEQUENCE: 401

Lys Met Gly Leu Tyr Tyr Cys Ala Trp Asp Gly Thr Phe

```
<210> SEQ ID NO 402
<211> LENGTH: 12
<212> TYPE: PRT
<213> ORGANISM: Artificial Sequence
<220> FEATURE:
<223> OTHER INFORMATION: toxin sequence element

<400> SEQUENCE: 402

Lys Pro Thr Leu Lys Tyr Cys Ala Trp Asp Gly Thr
1               5                   10

<210> SEQ ID NO 403
<211> LENGTH: 13
<212> TYPE: PRT
<213> ORGANISM: Artificial Sequence
<220> FEATURE:
<223> OTHER INFORMATION: toxin sequence element

<400> SEQUENCE: 403

Lys Pro Thr Leu Lys Tyr Cys Ala Trp Asp Gly Thr Phe
1               5                   10

<210> SEQ ID NO 404
<211> LENGTH: 13
<212> TYPE: PRT
<213> ORGANISM: Artificial Sequence
<220> FEATURE:
<223> OTHER INFORMATION: toxin sequence element

<400> SEQUENCE: 404

Lys Pro Thr Ser Lys Tyr Cys Ala Trp Asp Gly Thr Ile
1               5                   10

<210> SEQ ID NO 405
<211> LENGTH: 14
<212> TYPE: PRT
<213> ORGANISM: Artificial Sequence
<220> FEATURE:
<223> OTHER INFORMATION: toxin sequence element

<400> SEQUENCE: 405

Lys Gln Lys Trp Pro Phe Tyr Cys Ala Trp Asp Trp Ser Phe
1               5                   10

<210> SEQ ID NO 406
<211> LENGTH: 12
<212> TYPE: PRT
<213> ORGANISM: Artificial Sequence
<220> FEATURE:
<223> OTHER INFORMATION: toxin sequence element

<400> SEQUENCE: 406

Lys Arg Arg Gly Thr Asn Ala Glu Lys Arg Cys Arg
1               5                   10

<210> SEQ ID NO 407
<211> LENGTH: 12
<212> TYPE: PRT
<213> ORGANISM: Artificial Sequence
<220> FEATURE:
<223> OTHER INFORMATION: toxin sequence element

<400> SEQUENCE: 407

Lys Arg Arg Gly Thr Asn Ile Glu Lys Arg Cys Arg
1               5                   10
```

<210> SEQ ID NO 408
<211> LENGTH: 15
<212> TYPE: PRT
<213> ORGANISM: Artificial Sequence
<220> FEATURE:
<223> OTHER INFORMATION: toxin sequence element

<400> SEQUENCE: 408

Lys Arg Thr Phe Asn Tyr Cys Ala Trp Asp Gly Ser Phe Ser Lys
1               5                   10                  15

<210> SEQ ID NO 409
<211> LENGTH: 15
<212> TYPE: PRT
<213> ORGANISM: Artificial Sequence
<220> FEATURE:
<223> OTHER INFORMATION: toxin sequence element

<400> SEQUENCE: 409

Lys Ser Lys Trp Pro Arg Asn Ile Cys Val Trp Asp Gly Ser Val
1               5                   10                  15

<210> SEQ ID NO 410
<211> LENGTH: 11
<212> TYPE: PRT
<213> ORGANISM: Artificial Sequence
<220> FEATURE:
<223> OTHER INFORMATION: toxin sequence element

<400> SEQUENCE: 410

Lys Thr Thr Gly Ile Val Lys Leu Cys Arg Trp
1               5                   10

<210> SEQ ID NO 411
<211> LENGTH: 18
<212> TYPE: PRT
<213> ORGANISM: Artificial Sequence
<220> FEATURE:
<223> OTHER INFORMATION: toxin sequence element

<400> SEQUENCE: 411

Lys Trp Val Phe Phe Thr Ser Lys Phe Met Cys Arg Arg Val Trp Gly
1               5                   10                  15

Lys Asp

<210> SEQ ID NO 412
<211> LENGTH: 18
<212> TYPE: PRT
<213> ORGANISM: Artificial Sequence
<220> FEATURE:
<223> OTHER INFORMATION: toxin sequence element

<400> SEQUENCE: 412

Leu Lys Pro Thr Leu His Gly Ile Trp Tyr Lys His His Tyr Cys Tyr
1               5                   10                  15

Thr Gln

<210> SEQ ID NO 413
<211> LENGTH: 18
<212> TYPE: PRT
<213> ORGANISM: Artificial Sequence
<220> FEATURE:
<223> OTHER INFORMATION: toxin sequence element

<400> SEQUENCE: 413

```
Leu Lys Pro Thr Leu His Gly Ile Trp Tyr Lys Ser Tyr Tyr Cys Tyr
1               5                   10                  15

Lys Lys

<210> SEQ ID NO 414
<211> LENGTH: 9
<212> TYPE: PRT
<213> ORGANISM: Artificial Sequence
<220> FEATURE:
<223> OTHER INFORMATION: toxin sequence element

<400> SEQUENCE: 414

Asn Gly Asn Thr Val Tyr Arg Cys Ala
1               5

<210> SEQ ID NO 415
<211> LENGTH: 13
<212> TYPE: PRT
<213> ORGANISM: Artificial Sequence
<220> FEATURE:
<223> OTHER INFORMATION: toxin sequence element

<400> SEQUENCE: 415

Asn Lys Lys His Gly Trp Cys Gly Trp Asp Gly Thr Phe
1               5                   10

<210> SEQ ID NO 416
<211> LENGTH: 13
<212> TYPE: PRT
<213> ORGANISM: Artificial Sequence
<220> FEATURE:
<223> OTHER INFORMATION: toxin sequence element

<400> SEQUENCE: 416

Asn Lys Lys Tyr Trp His Cys Gly Trp Asp Gly Thr Phe
1               5                   10

<210> SEQ ID NO 417
<211> LENGTH: 12
<212> TYPE: PRT
<213> ORGANISM: Artificial Sequence
<220> FEATURE:
<223> OTHER INFORMATION: toxin sequence element

<400> SEQUENCE: 417

Asn Arg Lys His Lys Trp Cys Lys Tyr Lys Leu Trp
1               5                   10

<210> SEQ ID NO 418
<211> LENGTH: 12
<212> TYPE: PRT
<213> ORGANISM: Artificial Sequence
<220> FEATURE:
<223> OTHER INFORMATION: toxin sequence element

<400> SEQUENCE: 418

Asn Arg Arg Asp Lys Trp Cys Lys Tyr Lys Leu Trp
1               5                   10

<210> SEQ ID NO 419
<211> LENGTH: 11
<212> TYPE: PRT
<213> ORGANISM: Artificial Sequence
<220> FEATURE:
<223> OTHER INFORMATION: toxin sequence element
```

<400> SEQUENCE: 419

Asn Ser Arg Asp Lys Trp Cys Lys Val Leu Leu
1               5                   10

<210> SEQ ID NO 420
<211> LENGTH: 8
<212> TYPE: PRT
<213> ORGANISM: Artificial Sequence
<220> FEATURE:
<223> OTHER INFORMATION: toxin sequence element

<400> SEQUENCE: 420

Gln Leu Trp Cys Lys Lys Arg Leu
1               5

<210> SEQ ID NO 421
<211> LENGTH: 11
<212> TYPE: PRT
<213> ORGANISM: Artificial Sequence
<220> FEATURE:
<223> OTHER INFORMATION: toxin sequence element

<400> SEQUENCE: 421

Gln Pro Ala Ile Lys Trp Cys Ile Trp Ser Pro
1               5                   10

<210> SEQ ID NO 422
<211> LENGTH: 14
<212> TYPE: PRT
<213> ORGANISM: Artificial Sequence
<220> FEATURE:
<223> OTHER INFORMATION: toxin sequence element

<400> SEQUENCE: 422

Gln Ser Arg Ile Ala Asn Met Trp Pro Thr Phe Cys Leu Val
1               5                   10

<210> SEQ ID NO 423
<211> LENGTH: 14
<212> TYPE: PRT
<213> ORGANISM: Artificial Sequence
<220> FEATURE:
<223> OTHER INFORMATION: toxin sequence element

<400> SEQUENCE: 423

Gln Ser Arg Ile Ala Asn Met Trp Pro Thr Phe Cys Ser Gln
1               5                   10

<210> SEQ ID NO 424
<211> LENGTH: 14
<212> TYPE: PRT
<213> ORGANISM: Artificial Sequence
<220> FEATURE:
<223> OTHER INFORMATION: toxin sequence element

<400> SEQUENCE: 424

Arg Lys Lys Trp Pro Tyr His Cys Gly Trp Asp Gly Thr Phe
1               5                   10

<210> SEQ ID NO 425
<211> LENGTH: 14
<212> TYPE: PRT
<213> ORGANISM: Artificial Sequence
<220> FEATURE:
<223> OTHER INFORMATION: toxin sequence element

<400> SEQUENCE: 425

```
Arg Lys Lys Trp Pro Tyr His Cys Val Trp Asp Trp Thr Val
1               5                   10
```

<210> SEQ ID NO 426
<211> LENGTH: 8
<212> TYPE: PRT
<213> ORGANISM: Artificial Sequence
<220> FEATURE:
<223> OTHER INFORMATION: toxin sequence element

<400> SEQUENCE: 426

```
Arg Leu Trp Cys Lys Lys Ile Ile
1               5
```

<210> SEQ ID NO 427
<211> LENGTH: 11
<212> TYPE: PRT
<213> ORGANISM: Artificial Sequence
<220> FEATURE:
<223> OTHER INFORMATION: toxin sequence element

<400> SEQUENCE: 427

```
Arg Leu Trp Cys Lys Lys Lys Ile Glu Glu Gly
1               5                   10
```

<210> SEQ ID NO 428
<211> LENGTH: 10
<212> TYPE: PRT
<213> ORGANISM: Artificial Sequence
<220> FEATURE:
<223> OTHER INFORMATION: toxin sequence element

<400> SEQUENCE: 428

```
Arg Leu Trp Cys Lys Lys Lys Ile Glu Trp
1               5                   10
```

<210> SEQ ID NO 429
<211> LENGTH: 9
<212> TYPE: PRT
<213> ORGANISM: Artificial Sequence
<220> FEATURE:
<223> OTHER INFORMATION: toxin sequence element

<400> SEQUENCE: 429

```
Arg Leu Trp Cys Lys Lys Lys Leu Trp
1               5
```

<210> SEQ ID NO 430
<211> LENGTH: 8
<212> TYPE: PRT
<213> ORGANISM: Artificial Sequence
<220> FEATURE:
<223> OTHER INFORMATION: toxin sequence element

<400> SEQUENCE: 430

```
Arg Leu Trp Cys Lys Lys Arg Leu
1               5
```

<210> SEQ ID NO 431
<211> LENGTH: 8
<212> TYPE: PRT
<213> ORGANISM: Artificial Sequence
<220> FEATURE:
<223> OTHER INFORMATION: toxin sequence element

<400> SEQUENCE: 431

Arg Leu Trp Cys Lys Leu Asp Trp
1               5

<210> SEQ ID NO 432
<211> LENGTH: 10
<212> TYPE: PRT
<213> ORGANISM: Artificial Sequence
<220> FEATURE:
<223> OTHER INFORMATION: toxin sequence element

<400> SEQUENCE: 432

Arg Leu Trp Cys Lys Arg Ile Ile Asn Met
1               5                   10

<210> SEQ ID NO 433
<211> LENGTH: 8
<212> TYPE: PRT
<213> ORGANISM: Artificial Sequence
<220> FEATURE:
<223> OTHER INFORMATION: toxin sequence element

<400> SEQUENCE: 433

Arg Leu Trp Cys Lys Tyr Lys Leu
1               5

<210> SEQ ID NO 434
<211> LENGTH: 14
<212> TYPE: PRT
<213> ORGANISM: Artificial Sequence
<220> FEATURE:
<223> OTHER INFORMATION: toxin sequence element

<400> SEQUENCE: 434

Arg Arg Ala Lys Pro Ser Trp Cys Gly Trp Asp Phe Thr Phe
1               5                   10

<210> SEQ ID NO 435
<211> LENGTH: 14
<212> TYPE: PRT
<213> ORGANISM: Artificial Sequence
<220> FEATURE:
<223> OTHER INFORMATION: toxin sequence element

<400> SEQUENCE: 435

Arg Arg Ala Lys Pro Ser Trp Cys Gly Trp Asp Phe Thr Val
1               5                   10

<210> SEQ ID NO 436
<211> LENGTH: 15
<212> TYPE: PRT
<213> ORGANISM: Artificial Sequence
<220> FEATURE:
<223> OTHER INFORMATION: toxin sequence element

<400> SEQUENCE: 436

Arg Arg Thr Leu Pro Thr Tyr Cys Ala Trp Asp Leu Thr Phe Pro
1               5                   10                  15

<210> SEQ ID NO 437
<211> LENGTH: 13
<212> TYPE: PRT
<213> ORGANISM: Artificial Sequence
<220> FEATURE:
<223> OTHER INFORMATION: toxin sequence element

<400> SEQUENCE: 437

Arg Ser Asp Gly Lys Tyr Cys Ala Trp Asp Gly Thr Phe

```
1               5                   10
```

<210> SEQ ID NO 438
<211> LENGTH: 14
<212> TYPE: PRT
<213> ORGANISM: Artificial Sequence
<220> FEATURE:
<223> OTHER INFORMATION: toxin sequence element

<400> SEQUENCE: 438

```
Arg Ser Asp Trp Lys Tyr Cys Ala Trp Asp Gly Thr Phe Ser
1               5                   10
```

<210> SEQ ID NO 439
<211> LENGTH: 12
<212> TYPE: PRT
<213> ORGANISM: Artificial Sequence
<220> FEATURE:
<223> OTHER INFORMATION: toxin sequence element

<400> SEQUENCE: 439

```
Arg Ser Arg Asp Gln Trp Cys Lys Tyr Lys Leu Trp
1               5                   10
```

<210> SEQ ID NO 440
<211> LENGTH: 12
<212> TYPE: PRT
<213> ORGANISM: Artificial Sequence
<220> FEATURE:
<223> OTHER INFORMATION: toxin sequence element

<400> SEQUENCE: 440

```
Arg Val Arg Asp Gln Trp Cys Lys Tyr Lys Leu Trp
1               5                   10
```

<210> SEQ ID NO 441
<211> LENGTH: 11
<212> TYPE: PRT
<213> ORGANISM: Artificial Sequence
<220> FEATURE:
<223> OTHER INFORMATION: toxin sequence element

<400> SEQUENCE: 441

```
Ser Asp Lys His Lys Trp Cys Lys Trp Lys Leu
1               5                   10
```

<210> SEQ ID NO 442
<211> LENGTH: 6
<212> TYPE: PRT
<213> ORGANISM: Artificial Sequence
<220> FEATURE:
<223> OTHER INFORMATION: toxin sequence element

<400> SEQUENCE: 442

```
Ser His Asn Lys Cys Thr
1               5
```

<210> SEQ ID NO 443
<211> LENGTH: 11
<212> TYPE: PRT
<213> ORGANISM: Artificial Sequence
<220> FEATURE:
<223> OTHER INFORMATION: toxin sequence element

<400> SEQUENCE: 443

```
Ser Lys Leu Phe Lys Leu Cys Asn Phe Ser Phe
1               5                   10
```

<210> SEQ ID NO 444
<211> LENGTH: 14
<212> TYPE: PRT
<213> ORGANISM: Artificial Sequence
<220> FEATURE:
<223> OTHER INFORMATION: toxin sequence element

<400> SEQUENCE: 444

Ser Lys Thr Gly Phe Val Lys Asn Ile Cys Lys Tyr Glu Met
1               5                   10

<210> SEQ ID NO 445
<211> LENGTH: 12
<212> TYPE: PRT
<213> ORGANISM: Artificial Sequence
<220> FEATURE:
<223> OTHER INFORMATION: toxin sequence element

<400> SEQUENCE: 445

Ser Lys Thr Trp Gly Trp Cys Ala Val Glu Ala Pro
1               5                   10

<210> SEQ ID NO 446
<211> LENGTH: 15
<212> TYPE: PRT
<213> ORGANISM: Artificial Sequence
<220> FEATURE:
<223> OTHER INFORMATION: toxin sequence element

<400> SEQUENCE: 446

Ser Pro Lys His Gly Trp Cys Val Trp Asp Trp Thr Phe Arg Lys
1               5                   10                  15

<210> SEQ ID NO 447
<211> LENGTH: 12
<212> TYPE: PRT
<213> ORGANISM: Artificial Sequence
<220> FEATURE:
<223> OTHER INFORMATION: toxin sequence element

<400> SEQUENCE: 447

Ser Pro Lys Trp Gly Leu Cys Asn Phe Pro Met Pro
1               5                   10

<210> SEQ ID NO 448
<211> LENGTH: 15
<212> TYPE: PRT
<213> ORGANISM: Artificial Sequence
<220> FEATURE:
<223> OTHER INFORMATION: toxin sequence element

<400> SEQUENCE: 448

Ser Pro Arg Trp Gly Trp Cys Ile Tyr Ser Thr Arg Gly Gly Arg
1               5                   10                  15

<210> SEQ ID NO 449
<211> LENGTH: 15
<212> TYPE: PRT
<213> ORGANISM: Artificial Sequence
<220> FEATURE:
<223> OTHER INFORMATION: toxin sequence element

<400> SEQUENCE: 449

Ser Pro Thr Trp Lys Trp Cys Val Leu Lys Ser Pro Gly Arg Arg
1               5                   10                  15

<210> SEQ ID NO 450
<211> LENGTH: 12
<212> TYPE: PRT
<213> ORGANISM: Artificial Sequence
<220> FEATURE:
<223> OTHER INFORMATION: toxin sequence element

<400> SEQUENCE: 450

Ser Pro Thr Trp Lys Trp Cys Val Tyr Ala Arg Pro
1               5                   10

<210> SEQ ID NO 451
<211> LENGTH: 10
<212> TYPE: PRT
<213> ORGANISM: Artificial Sequence
<220> FEATURE:
<223> OTHER INFORMATION: toxin sequence element

<400> SEQUENCE: 451

Ser Gln His Arg Leu Cys Ser Val Lys Ala
1               5                   10

<210> SEQ ID NO 452
<211> LENGTH: 11
<212> TYPE: PRT
<213> ORGANISM: Artificial Sequence
<220> FEATURE:
<223> OTHER INFORMATION: toxin sequence element

<400> SEQUENCE: 452

Ser Arg Lys Asp Lys Trp Cys Lys Tyr Gln Ile
1               5                   10

<210> SEQ ID NO 453
<211> LENGTH: 11
<212> TYPE: PRT
<213> ORGANISM: Artificial Sequence
<220> FEATURE:
<223> OTHER INFORMATION: toxin sequence element

<400> SEQUENCE: 453

Ser Arg Lys His Arg Trp Cys Lys Tyr Glu Ile
1               5                   10

<210> SEQ ID NO 454
<211> LENGTH: 11
<212> TYPE: PRT
<213> ORGANISM: Artificial Sequence
<220> FEATURE:
<223> OTHER INFORMATION: toxin sequence element

<400> SEQUENCE: 454

Ser Arg Lys Thr Arg Trp Cys Lys Tyr Gln Ile
1               5                   10

<210> SEQ ID NO 455
<211> LENGTH: 11
<212> TYPE: PRT
<213> ORGANISM: Artificial Sequence
<220> FEATURE:
<223> OTHER INFORMATION: toxin sequence element

<400> SEQUENCE: 455

Ser Arg Gln Leu Cys Lys Tyr Val Ile Asp Trp
1               5                   10

```
<210> SEQ ID NO 456
<211> LENGTH: 11
<212> TYPE: PRT
<213> ORGANISM: Artificial Sequence
<220> FEATURE:
<223> OTHER INFORMATION: toxin sequence element

<400> SEQUENCE: 456

Ser Arg Arg Asp Arg Trp Cys Lys Tyr Asp Leu
1               5                   10

<210> SEQ ID NO 457
<211> LENGTH: 11
<212> TYPE: PRT
<213> ORGANISM: Artificial Sequence
<220> FEATURE:
<223> OTHER INFORMATION: toxin sequence element

<400> SEQUENCE: 457

Ser Arg Arg Asp Arg Trp Cys Lys Tyr Tyr Leu
1               5                   10

<210> SEQ ID NO 458
<211> LENGTH: 12
<212> TYPE: PRT
<213> ORGANISM: Artificial Sequence
<220> FEATURE:
<223> OTHER INFORMATION: toxin sequence element

<400> SEQUENCE: 458

Ser Arg Arg Gly Thr Asn Pro Glu Lys Arg Cys Arg
1               5                   10

<210> SEQ ID NO 459
<211> LENGTH: 14
<212> TYPE: PRT
<213> ORGANISM: Artificial Sequence
<220> FEATURE:
<223> OTHER INFORMATION: toxin sequence element

<400> SEQUENCE: 459

Ser Arg Arg His Gly Trp Cys Val Trp Asp Gly Thr Phe Ser
1               5                   10

<210> SEQ ID NO 460
<211> LENGTH: 13
<212> TYPE: PRT
<213> ORGANISM: Artificial Sequence
<220> FEATURE:
<223> OTHER INFORMATION: toxin sequence element

<400> SEQUENCE: 460

Ser Arg Thr Trp Lys Trp Cys Val Leu Ala Gly Pro Trp
1               5                   10

<210> SEQ ID NO 461
<211> LENGTH: 11
<212> TYPE: PRT
<213> ORGANISM: Artificial Sequence
<220> FEATURE:
<223> OTHER INFORMATION: toxin sequence element

<400> SEQUENCE: 461

Ser Ser Lys His Lys Trp Cys Lys Val Tyr Leu
1               5                   10

<210> SEQ ID NO 462
```

```
<211> LENGTH: 13
<212> TYPE: PRT
<213> ORGANISM: Artificial Sequence
<220> FEATURE:
<223> OTHER INFORMATION: toxin sequence element

<400> SEQUENCE: 462

Ser Ser Arg Trp Lys Trp Cys Val Leu Ala Ser Pro Phe
1               5                   10

<210> SEQ ID NO 463
<211> LENGTH: 13
<212> TYPE: PRT
<213> ORGANISM: Artificial Sequence
<220> FEATURE:
<223> OTHER INFORMATION: toxin sequence element

<400> SEQUENCE: 463

Ser Ser Arg Trp Lys Trp Cys Val Leu Pro Ala Pro Trp
1               5                   10

<210> SEQ ID NO 464
<211> LENGTH: 15
<212> TYPE: PRT
<213> ORGANISM: Artificial Sequence
<220> FEATURE:
<223> OTHER INFORMATION: toxin sequence element

<400> SEQUENCE: 464

Thr Phe Lys Glu Asn Glu Asn Gly Asn Thr Val Lys Arg Cys Asp
1               5                   10                  15

<210> SEQ ID NO 465
<211> LENGTH: 15
<212> TYPE: PRT
<213> ORGANISM: Artificial Sequence
<220> FEATURE:
<223> OTHER INFORMATION: toxin sequence element

<400> SEQUENCE: 465

Thr Phe Lys Thr Asn Glu Asn Gly Asn Thr Val Lys Arg Cys Asp
1               5                   10                  15

<210> SEQ ID NO 466
<211> LENGTH: 7
<212> TYPE: PRT
<213> ORGANISM: Artificial Sequence
<220> FEATURE:
<223> OTHER INFORMATION: toxin sequence element

<400> SEQUENCE: 466

Thr Gly Leu Cys Ile Pro Pro
1               5

<210> SEQ ID NO 467
<211> LENGTH: 8
<212> TYPE: PRT
<213> ORGANISM: Artificial Sequence
<220> FEATURE:
<223> OTHER INFORMATION: toxin sequence element

<400> SEQUENCE: 467

Thr Arg Phe Asn Val Cys Gly Lys
1               5

<210> SEQ ID NO 468
<211> LENGTH: 9
```

```
<212> TYPE: PRT
<213> ORGANISM: Artificial Sequence
<220> FEATURE:
<223> OTHER INFORMATION: toxin sequence element

<400> SEQUENCE: 468

Thr Trp Pro Thr Glu Ile Cys Ile Asp
1               5

<210> SEQ ID NO 469
<211> LENGTH: 15
<212> TYPE: PRT
<213> ORGANISM: Artificial Sequence
<220> FEATURE:
<223> OTHER INFORMATION: toxin sequence element

<400> SEQUENCE: 469

Thr Tyr Lys Ala Asn Glu Asn Gly Asn Gln Val Lys Arg Cys Asp
1               5                   10                  15

<210> SEQ ID NO 470
<211> LENGTH: 15
<212> TYPE: PRT
<213> ORGANISM: Artificial Sequence
<220> FEATURE:
<223> OTHER INFORMATION: toxin sequence element

<400> SEQUENCE: 470

Thr Tyr Lys Glu Asn Glu Asn Gly Asn Thr Val Lys Arg Cys Asp
1               5                   10                  15

<210> SEQ ID NO 471
<211> LENGTH: 15
<212> TYPE: PRT
<213> ORGANISM: Artificial Sequence
<220> FEATURE:
<223> OTHER INFORMATION: toxin sequence element

<400> SEQUENCE: 471

Thr Tyr Lys Glu Asn Glu Asn Gly Asn Thr Val Gln Arg Cys Asp
1               5                   10                  15

<210> SEQ ID NO 472
<211> LENGTH: 15
<212> TYPE: PRT
<213> ORGANISM: Artificial Sequence
<220> FEATURE:
<223> OTHER INFORMATION: toxin sequence element

<400> SEQUENCE: 472

Thr Tyr Lys Thr Asn Glu Asn Gly Asn Ser Val Gln Arg Cys Asp
1               5                   10                  15

<210> SEQ ID NO 473
<211> LENGTH: 18
<212> TYPE: PRT
<213> ORGANISM: Artificial Sequence
<220> FEATURE:
<223> OTHER INFORMATION: toxin sequence element

<400> SEQUENCE: 473

Val Lys Thr Ser Gly Tyr Trp Trp Tyr Lys Lys Thr Tyr Cys Arg Arg
1               5                   10                  15

Lys Ser

<210> SEQ ID NO 474
```

<211> LENGTH: 17
<212> TYPE: PRT
<213> ORGANISM: Artificial Sequence
<220> FEATURE:
<223> OTHER INFORMATION: toxin sequence element

<400> SEQUENCE: 474

Trp Lys Arg Arg Arg Ser Phe Glu Val Cys Val Pro Lys Thr Pro Lys
1 5 10 15

Thr

<210> SEQ ID NO 475
<211> LENGTH: 6
<212> TYPE: PRT
<213> ORGANISM: Artificial Sequence
<220> FEATURE:
<223> OTHER INFORMATION: toxin sequence element

<400> SEQUENCE: 475

Leu Gly Val Cys Met Trp
1 5

<210> SEQ ID NO 476
<211> LENGTH: 5
<212> TYPE: PRT
<213> ORGANISM: Artificial Sequence
<220> FEATURE:
<223> OTHER INFORMATION: toxin sequence element

<400> SEQUENCE: 476

Phe Phe Ala Cys Ala
1 5

<210> SEQ ID NO 477
<211> LENGTH: 5
<212> TYPE: PRT
<213> ORGANISM: Artificial Sequence
<220> FEATURE:
<223> OTHER INFORMATION: toxin sequence element

<400> SEQUENCE: 477

Val Leu Phe Cys Val
1 5

<210> SEQ ID NO 478
<211> LENGTH: 6
<212> TYPE: PRT
<213> ORGANISM: Artificial Sequence
<220> FEATURE:
<223> OTHER INFORMATION: toxin sequence element

<400> SEQUENCE: 478

Ile Val Phe Val Cys Thr
1 5

<210> SEQ ID NO 479
<211> LENGTH: 6
<212> TYPE: PRT
<213> ORGANISM: Artificial Sequence
<220> FEATURE:
<223> OTHER INFORMATION: toxin sequence element

<400> SEQUENCE: 479

Ile Leu Leu Phe Cys Ser
1 5

-continued

```
<210> SEQ ID NO 480
<211> LENGTH: 5
<212> TYPE: PRT
<213> ORGANISM: Artificial Sequence
<220> FEATURE:
<223> OTHER INFORMATION: toxin sequence element

<400> SEQUENCE: 480

Val Phe Val Cys Ile
1               5

<210> SEQ ID NO 481
<211> LENGTH: 6
<212> TYPE: PRT
<213> ORGANISM: Artificial Sequence
<220> FEATURE:
<223> OTHER INFORMATION: toxin sequence element

<400> SEQUENCE: 481

Ala Gln Phe Ile Cys Leu
1               5

<210> SEQ ID NO 482
<211> LENGTH: 6
<212> TYPE: PRT
<213> ORGANISM: Artificial Sequence
<220> FEATURE:
<223> OTHER INFORMATION: toxin sequence element

<400> SEQUENCE: 482

Gly Pro Phe Val Cys Val
1               5

<210> SEQ ID NO 483
<211> LENGTH: 30
<212> TYPE: DNA
<213> ORGANISM: Artificial Sequence
<220> FEATURE:
<223> OTHER INFORMATION: toxin sequence element

<400> SEQUENCE: 483
gcggcgtgcc tgggcatgtt tgaaagctgt                                      30

<210> SEQ ID NO 484
<211> LENGTH: 27
<212> TYPE: DNA
<213> ORGANISM: Artificial Sequence
<220> FEATURE:
<223> OTHER INFORMATION: toxin sequence element

<400> SEQUENCE: 484
gcgtgcggcc agttttggtg gaaatgt                                         27

<210> SEQ ID NO 485
<211> LENGTH: 27
<212> TYPE: DNA
<213> ORGANISM: Artificial Sequence
<220> FEATURE:
<223> OTHER INFORMATION: toxin sequence element

<400> SEQUENCE: 485
gcgtgcaaag gcgtgtttga tgcgtgt                                         27

<210> SEQ ID NO 486
<211> LENGTH: 27
<212> TYPE: DNA
<213> ORGANISM: Artificial Sequence
```

```
<220> FEATURE:
<223> OTHER INFORMATION: toxin sequence element

<400> SEQUENCE: 486
gcgtgccgcg aatggctggg cggctgt                                          27

<210> SEQ ID NO 487
<211> LENGTH: 30
<212> TYPE: DNA
<213> ORGANISM: Artificial Sequence
<220> FEATURE:
<223> OTHER INFORMATION: toxin sequence element

<400> SEQUENCE: 487
gcggattgcg gctggctgtt tcatagctgt                                       30

<210> SEQ ID NO 488
<211> LENGTH: 24
<212> TYPE: DNA
<213> ORGANISM: Artificial Sequence
<220> FEATURE:
<223> OTHER INFORMATION: toxin sequence element

<400> SEQUENCE: 488
tgcgcggcgg aaggcattcc gtgt                                             24

<210> SEQ ID NO 489
<211> LENGTH: 24
<212> TYPE: DNA
<213> ORGANISM: Artificial Sequence
<220> FEATURE:
<223> OTHER INFORMATION: toxin sequence element

<400> SEQUENCE: 489
tgcggcggct ggatggcgaa atgt                                             24

<210> SEQ ID NO 490
<211> LENGTH: 24
<212> TYPE: DNA
<213> ORGANISM: Artificial Sequence
<220> FEATURE:
<223> OTHER INFORMATION: toxin sequence element

<400> SEQUENCE: 490
tgcattggcg aaggcgtgcc gtgt                                             24

<210> SEQ ID NO 491
<211> LENGTH: 24
<212> TYPE: DNA
<213> ORGANISM: Artificial Sequence
<220> FEATURE:
<223> OTHER INFORMATION: toxin sequence element

<400> SEQUENCE: 491
tgcatgggct atgatattca ttgt                                             24

<210> SEQ ID NO 492
<211> LENGTH: 27
<212> TYPE: DNA
<213> ORGANISM: Artificial Sequence
<220> FEATURE:
<223> OTHER INFORMATION: toxin sequence element

<400> SEQUENCE: 492
gattgcgcgg gctatatgcg cgaatgt                                          27
```

<210> SEQ ID NO 493
<211> LENGTH: 27
<212> TYPE: DNA
<213> ORGANISM: Artificial Sequence
<220> FEATURE:
<223> OTHER INFORMATION: toxin sequence element

<400> SEQUENCE: 493
gattgcggca ccatttggca ttattgt                                      27

<210> SEQ ID NO 494
<211> LENGTH: 27
<212> TYPE: DNA
<213> ORGANISM: Artificial Sequence
<220> FEATURE:
<223> OTHER INFORMATION: toxin sequence element

<400> SEQUENCE: 494
gattgcctgg gctttctgtg gaaatgt                                      27

<210> SEQ ID NO 495
<211> LENGTH: 26
<212> TYPE: DNA
<213> ORGANISM: Artificial Sequence
<220> FEATURE:
<223> OTHER INFORMATION: toxin sequence element

<400> SEQUENCE: 495
gattgcctgg gcctgttttg gattgt                                       26

<210> SEQ ID NO 496
<211> LENGTH: 27
<212> TYPE: DNA
<213> ORGANISM: Artificial Sequence
<220> FEATURE:
<223> OTHER INFORMATION: toxin sequence element

<400> SEQUENCE: 496
gattgcctgg gctggtttaa aggctgt                                      27

<210> SEQ ID NO 497
<211> LENGTH: 27
<212> TYPE: DNA
<213> ORGANISM: Artificial Sequence
<220> FEATURE:
<223> OTHER INFORMATION: toxin sequence element

<400> SEQUENCE: 497
gattgcctgg gctggtttaa aagctgt                                      27

<210> SEQ ID NO 498
<211> LENGTH: 27
<212> TYPE: DNA
<213> ORGANISM: Artificial Sequence
<220> FEATURE:
<223> OTHER INFORMATION: toxin sequence element

<400> SEQUENCE: 498
gattgccgcg cgctgtatgg cggctgt                                      27

<210> SEQ ID NO 499
<211> LENGTH: 27
<212> TYPE: DNA
<213> ORGANISM: Artificial Sequence
<220> FEATURE:
<223> OTHER INFORMATION: toxin sequence element

<400> SEQUENCE: 499
gattgccgca aaatgtttgg cggctgt                                               27

<210> SEQ ID NO 500
<211> LENGTH: 27
<212> TYPE: DNA
<213> ORGANISM: Artificial Sequence
<220> FEATURE:
<223> OTHER INFORMATION: toxin sequence element

<400> SEQUENCE: 500
gattgcaccc gcatgtttgg cgcgtgt                                               27

<210> SEQ ID NO 501
<211> LENGTH: 27
<212> TYPE: DNA
<213> ORGANISM: Artificial Sequence
<220> FEATURE:
<223> OTHER INFORMATION: toxin sequence element

<400> SEQUENCE: 501
gattgcgtgc gcttttgggg caaatgt                                               27

<210> SEQ ID NO 502
<211> LENGTH: 30
<212> TYPE: DNA
<213> ORGANISM: Artificial Sequence
<220> FEATURE:
<223> OTHER INFORMATION: toxin sequence element

<400> SEQUENCE: 502
gatgattgcg gcggcctgtt tagcggctgt                                            30

<210> SEQ ID NO 503
<211> LENGTH: 30
<212> TYPE: DNA
<213> ORGANISM: Artificial Sequence
<220> FEATURE:
<223> OTHER INFORMATION: toxin sequence element

<400> SEQUENCE: 503
gatgattgcg gcaaactgtt tagcggctgt                                            30

<210> SEQ ID NO 504
<211> LENGTH: 30
<212> TYPE: DNA
<213> ORGANISM: Artificial Sequence
<220> FEATURE:
<223> OTHER INFORMATION: toxin sequence element

<400> SEQUENCE: 504
gatgattgcg gcaccctgtt tagcggctgt                                            30

<210> SEQ ID NO 505
<211> LENGTH: 30
<212> TYPE: DNA
<213> ORGANISM: Artificial Sequence
<220> FEATURE:
<223> OTHER INFORMATION: toxin sequence element

<400> SEQUENCE: 505
gatgattgcc tgggcatgtt tagcagctgt                                            30

<210> SEQ ID NO 506

```
<211> LENGTH: 33
<212> TYPE: DNA
<213> ORGANISM: Artificial Sequence
<220> FEATURE:
<223> OTHER INFORMATION: toxin sequence element

<400> SEQUENCE: 506
gatgatgatt gcggctggat tatggatgat tgt                              33

<210> SEQ ID NO 507
<211> LENGTH: 33
<212> TYPE: DNA
<213> ORGANISM: Artificial Sequence
<220> FEATURE:
<223> OTHER INFORMATION: toxin sequence element

<400> SEQUENCE: 507
gatggcgaat gcggcggctt ttggtggaaa tgt                              33

<210> SEQ ID NO 508
<211> LENGTH: 27
<212> TYPE: DNA
<213> ORGANISM: Artificial Sequence
<220> FEATURE:
<223> OTHER INFORMATION: toxin sequence element

<400> SEQUENCE: 508
gaatgcggca aatttatgtg gaaatgt                                     27

<210> SEQ ID NO 509
<211> LENGTH: 27
<212> TYPE: DNA
<213> ORGANISM: Artificial Sequence
<220> FEATURE:
<223> OTHER INFORMATION: toxin sequence element

<400> SEQUENCE: 509
gaatgcggca ccctgtttag cggctgt                                     27

<210> SEQ ID NO 510
<211> LENGTH: 27
<212> TYPE: DNA
<213> ORGANISM: Artificial Sequence
<220> FEATURE:
<223> OTHER INFORMATION: toxin sequence element

<400> SEQUENCE: 510
gaatgcaaag gctttggcaa aagctgt                                     27

<210> SEQ ID NO 511
<211> LENGTH: 27
<212> TYPE: DNA
<213> ORGANISM: Artificial Sequence
<220> FEATURE:
<223> OTHER INFORMATION: toxin sequence element

<400> SEQUENCE: 511
gaatgcaaaa aactgtttgg cggctgt                                     27

<210> SEQ ID NO 512
<211> LENGTH: 27
<212> TYPE: DNA
<213> ORGANISM: Artificial Sequence
<220> FEATURE:
<223> OTHER INFORMATION: toxin sequence element

<400> SEQUENCE: 512
```
gaatgcaaat ggtatctggg cgattgt                                    27

<210> SEQ ID NO 513
<211> LENGTH: 27
<212> TYPE: DNA
<213> ORGANISM: Artificial Sequence
<220> FEATURE:
<223> OTHER INFORMATION: toxin sequence element

<400> SEQUENCE: 513
gaatgcaaat atctgtgggg cacctgt                                    27

<210> SEQ ID NO 514
<211> LENGTH: 27
<212> TYPE: DNA
<213> ORGANISM: Artificial Sequence
<220> FEATURE:
<223> OTHER INFORMATION: toxin sequence element

<400> SEQUENCE: 514
gaatgcctgg aaattttaa agcgtgt                                     27

<210> SEQ ID NO 515
<211> LENGTH: 27
<212> TYPE: DNA
<213> ORGANISM: Artificial Sequence
<220> FEATURE:
<223> OTHER INFORMATION: toxin sequence element

<400> SEQUENCE: 515
gaatgcctgg gctttggcaa aggctgt                                    27

<210> SEQ ID NO 516
<211> LENGTH: 27
<212> TYPE: DNA
<213> ORGANISM: Artificial Sequence
<220> FEATURE:
<223> OTHER INFORMATION: toxin sequence element

<400> SEQUENCE: 516
gaatgccgca aaatgtttgg cggctgt                                    27

<210> SEQ ID NO 517
<211> LENGTH: 26
<212> TYPE: DNA
<213> ORGANISM: Artificial Sequence
<220> FEATURE:
<223> OTHER INFORMATION: toxin sequence element

<400> SEQUENCE: 517
gaatgccgct ggctgtttgg cggtgt                                     26

<210> SEQ ID NO 518
<211> LENGTH: 27
<212> TYPE: DNA
<213> ORGANISM: Artificial Sequence
<220> FEATURE:
<223> OTHER INFORMATION: toxin sequence element

<400> SEQUENCE: 518
gaatgccgct ggtatctggg cggctgt                                    27

<210> SEQ ID NO 519
<211> LENGTH: 27
<212> TYPE: DNA

```
<213> ORGANISM: Artificial Sequence
<220> FEATURE:
<223> OTHER INFORMATION: toxin sequence element

<400> SEQUENCE: 519
gaatgccgct atttttgggg cgaatgt                                          27

<210> SEQ ID NO 520
<211> LENGTH: 27
<212> TYPE: DNA
<213> ORGANISM: Artificial Sequence
<220> FEATURE:
<223> OTHER INFORMATION: toxin sequence element

<400> SEQUENCE: 520
gaatgccgct atctgtttgg cggctgt                                          27

<210> SEQ ID NO 521
<211> LENGTH: 27
<212> TYPE: DNA
<213> ORGANISM: Artificial Sequence
<220> FEATURE:
<223> OTHER INFORMATION: toxin sequence element

<400> SEQUENCE: 521
gaatgccgct attggctggg cggctgt                                          27

<210> SEQ ID NO 522
<211> LENGTH: 27
<212> TYPE: DNA
<213> ORGANISM: Artificial Sequence
<220> FEATURE:
<223> OTHER INFORMATION: toxin sequence element

<400> SEQUENCE: 522
gaatgccgct attggctggg cacctgt                                          27

<210> SEQ ID NO 523
<211> LENGTH: 27
<212> TYPE: DNA
<213> ORGANISM: Artificial Sequence
<220> FEATURE:
<223> OTHER INFORMATION: toxin sequence element

<400> SEQUENCE: 523
gaatgcacca aatttctggg cggctgt                                          27

<210> SEQ ID NO 524
<211> LENGTH: 27
<212> TYPE: DNA
<213> ORGANISM: Artificial Sequence
<220> FEATURE:
<223> OTHER INFORMATION: toxin sequence element

<400> SEQUENCE: 524
gaatgcacca aactgctggg cggctgt                                          27

<210> SEQ ID NO 525
<211> LENGTH: 30
<212> TYPE: DNA
<213> ORGANISM: Artificial Sequence
<220> FEATURE:
<223> OTHER INFORMATION: toxin sequence element

<400> SEQUENCE: 525
gaagattgca ttccgaaatg gaaaggctgt                                       30
```

<210> SEQ ID NO 526
<211> LENGTH: 33
<212> TYPE: DNA
<213> ORGANISM: Artificial Sequence
<220> FEATURE:
<223> OTHER INFORMATION: toxin sequence element

<400> SEQUENCE: 526
gaaggcgaat gcggcggctt ttggtggaaa tgt    33

<210> SEQ ID NO 527
<211> LENGTH: 30
<212> TYPE: DNA
<213> ORGANISM: Artificial Sequence
<220> FEATURE:
<223> OTHER INFORMATION: toxin sequence element

<400> SEQUENCE: 527
ggcgcgtgcc gctggtttct gggcggctgt    30

<210> SEQ ID NO 528
<211> LENGTH: 27
<212> TYPE: DNA
<213> ORGANISM: Artificial Sequence
<220> FEATURE:
<223> OTHER INFORMATION: toxin sequence element

<400> SEQUENCE: 528
ggctgcgcga acgcgtataa aagctgt    27

<210> SEQ ID NO 529
<211> LENGTH: 27
<212> TYPE: DNA
<213> ORGANISM: Artificial Sequence
<220> FEATURE:
<223> OTHER INFORMATION: toxin sequence element

<400> SEQUENCE: 529
ggctgcggcg gcctgatggc gggctgt    27

<210> SEQ ID NO 530
<211> LENGTH: 27
<212> TYPE: DNA
<213> ORGANISM: Artificial Sequence
<220> FEATURE:
<223> OTHER INFORMATION: toxin sequence element

<400> SEQUENCE: 530
ggctgcggcg gcctgatgga tggctgt    27

<210> SEQ ID NO 531
<211> LENGTH: 27
<212> TYPE: DNA
<213> ORGANISM: Artificial Sequence
<220> FEATURE:
<223> OTHER INFORMATION: toxin sequence element

<400> SEQUENCE: 531
ggctgcggca ccatgtggag cccgtgt    27

<210> SEQ ID NO 532
<211> LENGTH: 27
<212> TYPE: DNA
<213> ORGANISM: Artificial Sequence
<220> FEATURE:

<223> OTHER INFORMATION: toxin sequence element

<400> SEQUENCE: 532
ggctgcattc cgagctttgg cgaatgt                                27

<210> SEQ ID NO 533
<211> LENGTH: 27
<212> TYPE: DNA
<213> ORGANISM: Artificial Sequence
<220> FEATURE:
<223> OTHER INFORMATION: toxin sequence element

<400> SEQUENCE: 533
ggctgcaaag gctttggcga tagctgt                                27

<210> SEQ ID NO 534
<211> LENGTH: 27
<212> TYPE: DNA
<213> ORGANISM: Artificial Sequence
<220> FEATURE:
<223> OTHER INFORMATION: toxin sequence element

<400> SEQUENCE: 534
ggctgcaaac tgaccttttg gaaatgt                                27

<210> SEQ ID NO 535
<211> LENGTH: 27
<212> TYPE: DNA
<213> ORGANISM: Artificial Sequence
<220> FEATURE:
<223> OTHER INFORMATION: toxin sequence element

<400> SEQUENCE: 535
ggctgcctgg aattttggtg gaaatgt                                27

<210> SEQ ID NO 536
<211> LENGTH: 21
<212> TYPE: DNA
<213> ORGANISM: Artificial Sequence
<220> FEATURE:
<223> OTHER INFORMATION: toxin sequence element

<400> SEQUENCE: 536
ggctgcctgg gcgataaatg t                                      21

<210> SEQ ID NO 537
<211> LENGTH: 27
<212> TYPE: DNA
<213> ORGANISM: Artificial Sequence
<220> FEATURE:
<223> OTHER INFORMATION: toxin sequence element

<400> SEQUENCE: 537
ggctgcaacc gcaaaaacaa aaaatgt                                27

<210> SEQ ID NO 538
<211> LENGTH: 27
<212> TYPE: DNA
<213> ORGANISM: Artificial Sequence
<220> FEATURE:
<223> OTHER INFORMATION: toxin sequence element

<400> SEQUENCE: 538
ggctgccaga aatttttttg gacctgt                                27

```
<210> SEQ ID NO 539
<211> LENGTH: 30
<212> TYPE: DNA
<213> ORGANISM: Artificial Sequence
<220> FEATURE:
<223> OTHER INFORMATION: toxin sequence element

<400> SEQUENCE: 539
ggcgattgcc tgccgcatct gaaactgtgt                              30

<210> SEQ ID NO 540
<211> LENGTH: 30
<212> TYPE: DNA
<213> ORGANISM: Artificial Sequence
<220> FEATURE:
<223> OTHER INFORMATION: toxin sequence element

<400> SEQUENCE: 540
ggcgattgcc tgccgcatct gaaacgctgt                              30

<210> SEQ ID NO 541
<211> LENGTH: 30
<212> TYPE: DNA
<213> ORGANISM: Artificial Sequence
<220> FEATURE:
<223> OTHER INFORMATION: toxin sequence element

<400> SEQUENCE: 541
ggcggctgcc tgccgcataa ccgcttttgt                              30

<210> SEQ ID NO 542
<211> LENGTH: 42
<212> TYPE: DNA
<213> ORGANISM: Artificial Sequence
<220> FEATURE:
<223> OTHER INFORMATION: toxin sequence element

<400> SEQUENCE: 542
ggcgtggata aagcgggctg ccgctatatg tttggcggct gt                42

<210> SEQ ID NO 543
<211> LENGTH: 42
<212> TYPE: DNA
<213> ORGANISM: Artificial Sequence
<220> FEATURE:
<223> OTHER INFORMATION: toxin sequence element

<400> SEQUENCE: 543
ggcgtggata aagaaggctg ccgcaaactg ctgggcggct gt                42

<210> SEQ ID NO 544
<211> LENGTH: 30
<212> TYPE: DNA
<213> ORGANISM: Artificial Sequence
<220> FEATURE:
<223> OTHER INFORMATION: toxin sequence element

<400> SEQUENCE: 544
attgcgtgcg cgccgcgctt tagcatttgt                              30

<210> SEQ ID NO 545
<211> LENGTH: 30
<212> TYPE: DNA
<213> ORGANISM: Artificial Sequence
<220> FEATURE:
<223> OTHER INFORMATION: toxin sequence element
```

-continued

```
<400> SEQUENCE: 545
attgcgtgcg cgccgcgctt tagcctgtgt                                           30

<210> SEQ ID NO 546
<211> LENGTH: 30
<212> TYPE: DNA
<213> ORGANISM: Artificial Sequence
<220> FEATURE:
<223> OTHER INFORMATION: toxin sequence element

<400> SEQUENCE: 546
attgcgtgcg cgccgcgcgg cctgctgtgt                                           30

<210> SEQ ID NO 547
<211> LENGTH: 27
<212> TYPE: DNA
<213> ORGANISM: Artificial Sequence
<220> FEATURE:
<223> OTHER INFORMATION: toxin sequence element

<400> SEQUENCE: 547
aaatgcctgc cgccgggcaa accgtgt                                              27

<210> SEQ ID NO 548
<211> LENGTH: 24
<212> TYPE: DNA
<213> ORGANISM: Artificial Sequence
<220> FEATURE:
<223> OTHER INFORMATION: toxin sequence element

<400> SEQUENCE: 548
ctgtgcagcc gcgaaggcga attt                                                 24

<210> SEQ ID NO 549
<211> LENGTH: 27
<212> TYPE: DNA
<213> ORGANISM: Artificial Sequence
<220> FEATURE:
<223> OTHER INFORMATION: toxin sequence element

<400> SEQUENCE: 549
cagtgcggcg aatttatgtg gaaatgt                                              27

<210> SEQ ID NO 550
<211> LENGTH: 27
<212> TYPE: DNA
<213> ORGANISM: Artificial Sequence
<220> FEATURE:
<223> OTHER INFORMATION: toxin sequence element

<400> SEQUENCE: 550
cgctgcattg aagaaggcaa atggtgt                                              27

<210> SEQ ID NO 551
<211> LENGTH: 33
<212> TYPE: DNA
<213> ORGANISM: Artificial Sequence
<220> FEATURE:
<223> OTHER INFORMATION: toxin sequence element

<400> SEQUENCE: 551
agcgcggtgt gcattccgag cggccagccg tgt                                       33

<210> SEQ ID NO 552
<211> LENGTH: 27
```

```
<212> TYPE: DNA
<213> ORGANISM: Artificial Sequence
<220> FEATURE:
<223> OTHER INFORMATION: toxin sequence element

<400> SEQUENCE: 552
agctgcaaac tgaccttttg gcgctgt                                              27

<210> SEQ ID NO 553
<211> LENGTH: 30
<212> TYPE: DNA
<213> ORGANISM: Artificial Sequence
<220> FEATURE:
<223> OTHER INFORMATION: toxin sequence element

<400> SEQUENCE: 553
agcgaatgcc gctggtttat gggcggctgt                                           30

<210> SEQ ID NO 554
<211> LENGTH: 36
<212> TYPE: DNA
<213> ORGANISM: Artificial Sequence
<220> FEATURE:
<223> OTHER INFORMATION: toxin sequence element

<400> SEQUENCE: 554
agcgaaaaag attgcattaa acatctgcag cgctgt                                    36

<210> SEQ ID NO 555
<211> LENGTH: 27
<212> TYPE: DNA
<213> ORGANISM: Artificial Sequence
<220> FEATURE:
<223> OTHER INFORMATION: toxin sequence element

<400> SEQUENCE: 555
agcttttgca ttccgtttaa accgtgt                                              27

<210> SEQ ID NO 556
<211> LENGTH: 33
<212> TYPE: DNA
<213> ORGANISM: Artificial Sequence
<220> FEATURE:
<223> OTHER INFORMATION: toxin sequence element

<400> SEQUENCE: 556
agcccgacct gcattccgag cggccagccg tgt                                       33

<210> SEQ ID NO 557
<211> LENGTH: 33
<212> TYPE: DNA
<213> ORGANISM: Artificial Sequence
<220> FEATURE:
<223> OTHER INFORMATION: toxin sequence element

<400> SEQUENCE: 557
agcccgacct gcattccgac cggccagccg tgt                                       33

<210> SEQ ID NO 558
<211> LENGTH: 33
<212> TYPE: DNA
<213> ORGANISM: Artificial Sequence
<220> FEATURE:
<223> OTHER INFORMATION: toxin sequence element

<400> SEQUENCE: 558
```
agcccgacct gcattcgcag cggccagccg tgt            33

<210> SEQ ID NO 559
<211> LENGTH: 33
<212> TYPE: DNA
<213> ORGANISM: Artificial Sequence
<220> FEATURE:
<223> OTHER INFORMATION: toxin sequence element

<400> SEQUENCE: 559
agcccggtgt gcaccccgag cggccagccg tgt            33

<210> SEQ ID NO 560
<211> LENGTH: 33
<212> TYPE: DNA
<213> ORGANISM: Artificial Sequence
<220> FEATURE:
<223> OTHER INFORMATION: toxin sequence element

<400> SEQUENCE: 560
agcagcacct gcattccgag cggccagccg tgt            33

<210> SEQ ID NO 561
<211> LENGTH: 33
<212> TYPE: DNA
<213> ORGANISM: Artificial Sequence
<220> FEATURE:
<223> OTHER INFORMATION: toxin sequence element

<400> SEQUENCE: 561
cggctggccg ctcggaatgc aggtgctgct tgt            33

<210> SEQ ID NO 562
<211> LENGTH: 30
<212> TYPE: DNA
<213> ORGANISM: Artificial Sequence
<220> FEATURE:
<223> OTHER INFORMATION: toxin sequence element

<400> SEQUENCE: 562
agcacctgca ccccgaccga tcagccgtgt               30

<210> SEQ ID NO 563
<211> LENGTH: 30
<212> TYPE: DNA
<213> ORGANISM: Artificial Sequence
<220> FEATURE:
<223> OTHER INFORMATION: toxin sequence element

<400> SEQUENCE: 563
agcgtgtgca ttccgagcgg ccagccgtgt               30

<210> SEQ ID NO 564
<211> LENGTH: 27
<212> TYPE: DNA
<213> ORGANISM: Artificial Sequence
<220> FEATURE:
<223> OTHER INFORMATION: toxin sequence element

<400> SEQUENCE: 564
acctgccgct atctgtttgg cggctgt                  27

<210> SEQ ID NO 565
<211> LENGTH: 27
<212> TYPE: DNA
<213> ORGANISM: Artificial Sequence
<220> FEATURE:
<223> OTHER INFORMATION: toxin sequence element

<400> SEQUENCE: 565
acctgctatg atattggcga actgtgt						27

<210> SEQ ID NO 566
<211> LENGTH: 27
<212> TYPE: DNA
<213> ORGANISM: Artificial Sequence
<220> FEATURE:
<223> OTHER INFORMATION: toxin sequence element

<400> SEQUENCE: 566
gtgtgccgcg gctatggcct gccgtgt						27

<210> SEQ ID NO 567
<211> LENGTH: 27
<212> TYPE: DNA
<213> ORGANISM: Artificial Sequence
<220> FEATURE:
<223> OTHER INFORMATION: toxin sequence element

<400> SEQUENCE: 567
tattgccaga aatggctgtg gacctgt						27

<210> SEQ ID NO 568
<211> LENGTH: 27
<212> TYPE: DNA
<213> ORGANISM: Artificial Sequence
<220> FEATURE:
<223> OTHER INFORMATION: toxin sequence element

<400> SEQUENCE: 568
tattgccaga aatggatgtg gacctgt						27

<210> SEQ ID NO 569
<211> LENGTH: 24
<212> TYPE: DNA
<213> ORGANISM: Artificial Sequence
<220> FEATURE:
<223> OTHER INFORMATION: toxin sequence element

<400> SEQUENCE: 569
tgcaaacagg cggatgaacc gtgt						24

<210> SEQ ID NO 570
<211> LENGTH: 27
<212> TYPE: DNA
<213> ORGANISM: Artificial Sequence
<220> FEATURE:
<223> OTHER INFORMATION: toxin sequence element

<400> SEQUENCE: 570
gcgtgccgca aaaatggga atattgt						27

<210> SEQ ID NO 571
<211> LENGTH: 33
<212> TYPE: DNA
<213> ORGANISM: Artificial Sequence
<220> FEATURE:
<223> OTHER INFORMATION: toxin sequence element

<400> SEQUENCE: 571
gatgatgatt gcgaaccgcc gggcaactt tgt						33

<210> SEQ ID NO 572
<211> LENGTH: 33
<212> TYPE: DNA
<213> ORGANISM: Artificial Sequence
<220> FEATURE:
<223> OTHER INFORMATION: toxin sequence element

<400> SEQUENCE: 572
gtgaaaccgt gccgcaaaga aggccagctg tgt         33

<210> SEQ ID NO 573
<211> LENGTH: 27
<212> TYPE: DNA
<213> ORGANISM: Artificial Sequence
<220> FEATURE:
<223> OTHER INFORMATION: toxin sequence element

<400> SEQUENCE: 573
tggtgcaaac agagcggcga aatgtgt         27

<210> SEQ ID NO 574
<211> LENGTH: 24
<212> TYPE: DNA
<213> ORGANISM: Artificial Sequence
<220> FEATURE:
<223> OTHER INFORMATION: toxin sequence element

<400> SEQUENCE: 574
tgcctgagcg gcggcgaagt gtgt         24

<210> SEQ ID NO 575
<211> LENGTH: 33
<212> TYPE: DNA
<213> ORGANISM: Artificial Sequence
<220> FEATURE:
<223> OTHER INFORMATION: toxin sequence element

<400> SEQUENCE: 575
ggcaaaccgt gccatgaaga aggccagctg tgt         33

<210> SEQ ID NO 576
<211> LENGTH: 24
<212> TYPE: DNA
<213> ORGANISM: Artificial Sequence
<220> FEATURE:
<223> OTHER INFORMATION: toxin sequence element

<400> SEQUENCE: 576
tgcattccgt ttctgcatcc gtgt         24

<210> SEQ ID NO 577
<211> LENGTH: 27
<212> TYPE: DNA
<213> ORGANISM: Artificial Sequence
<220> FEATURE:
<223> OTHER INFORMATION: toxin sequence element

<400> SEQUENCE: 577
gcgtgcagca aaaatggga atattgt         27

<210> SEQ ID NO 578
<211> LENGTH: 36
<212> TYPE: DNA
<213> ORGANISM: Artificial Sequence
<220> FEATURE:
<223> OTHER INFORMATION: toxin sequence element

<400> SEQUENCE: 578
gcggatagcg atgattgctg cgaaacctttt cattgc				36

<210> SEQ ID NO 579
<211> LENGTH: 39
<212> TYPE: DNA
<213> ORGANISM: Artificial Sequence
<220> FEATURE:
<223> OTHER INFORMATION: toxin sequence element

<400> SEQUENCE: 579
gcgtggttta gcggcgaaag ctgctgcacc ggcatttgc				39

<210> SEQ ID NO 580
<211> LENGTH: 36
<212> TYPE: DNA
<213> ORGANISM: Artificial Sequence
<220> FEATURE:
<223> OTHER INFORMATION: toxin sequence element

<400> SEQUENCE: 580
gatgaagaac gcaaatgctg cgaaggcctg gtgtgc				36

<210> SEQ ID NO 581
<211> LENGTH: 39
<212> TYPE: DNA
<213> ORGANISM: Artificial Sequence
<220> FEATURE:
<223> OTHER INFORMATION: toxin sequence element

<400> SEQUENCE: 581
gatgaaaacg atccgcgctg ctgcagcggc ctggtgtgc				39

<210> SEQ ID NO 582
<211> LENGTH: 39
<212> TYPE: DNA
<213> ORGANISM: Artificial Sequence
<220> FEATURE:
<223> OTHER INFORMATION: toxin sequence element

<400> SEQUENCE: 582
gatggcaaaa gcaccttttg ctgcagcggc tttaactgc				39

<210> SEQ ID NO 583
<211> LENGTH: 39
<212> TYPE: DNA
<213> ORGANISM: Artificial Sequence
<220> FEATURE:
<223> OTHER INFORMATION: toxin sequence element

<400> SEQUENCE: 583
gatggcaaaa gcaccttttg ctgcagcggc tataactgc				39

<210> SEQ ID NO 584
<211> LENGTH: 39
<212> TYPE: DNA
<213> ORGANISM: Artificial Sequence
<220> FEATURE:
<223> OTHER INFORMATION: toxin sequence element

<400> SEQUENCE: 584
gatccggata acgataaatg ctgcgaaggc tataaatgc				39

<210> SEQ ID NO 585

```
<211> LENGTH: 39
<212> TYPE: DNA
<213> ORGANISM: Artificial Sequence
<220> FEATURE:
<223> OTHER INFORMATION: toxin sequence element

<400> SEQUENCE: 585
gatccgaaaa acgataaatg ctgcaaaaac tatacctgc                    39

<210> SEQ ID NO 586
<211> LENGTH: 39
<212> TYPE: DNA
<213> ORGANISM: Artificial Sequence
<220> FEATURE:
<223> OTHER INFORMATION: toxin sequence element

<400> SEQUENCE: 586
gatccgaaaa acgataaatg ctgcccgaac cgcgtgtgc                    39

<210> SEQ ID NO 587
<211> LENGTH: 39
<212> TYPE: DNA
<213> ORGANISM: Artificial Sequence
<220> FEATURE:
<223> OTHER INFORMATION: toxin sequence element

<400> SEQUENCE: 587
gatccgaaca acgataaatg ctgcccgaac cgcgaatgc                    39

<210> SEQ ID NO 588
<211> LENGTH: 39
<212> TYPE: DNA
<213> ORGANISM: Artificial Sequence
<220> FEATURE:
<223> OTHER INFORMATION: toxin sequence element

<400> SEQUENCE: 588
gatccgaaca acgataaatg ctgcccgaac cgcgtgtgc                    39

<210> SEQ ID NO 589
<211> LENGTH: 48
<212> TYPE: DNA
<213> ORGANISM: Artificial Sequence
<220> FEATURE:
<223> OTHER INFORMATION: toxin sequence element

<400> SEQUENCE: 589
gatccgaacc cggtgaaaga tctgccgtgc tgcagcggcc tggcgtgc          48

<210> SEQ ID NO 590
<211> LENGTH: 36
<212> TYPE: DNA
<213> ORGANISM: Artificial Sequence
<220> FEATURE:
<223> OTHER INFORMATION: toxin sequence element

<400> SEQUENCE: 590
gatagcgcgc gcaaatgctg cgaaggcctg gtgtgc                       36

<210> SEQ ID NO 591
<211> LENGTH: 36
<212> TYPE: DNA
<213> ORGANISM: Artificial Sequence
<220> FEATURE:
<223> OTHER INFORMATION: toxin sequence element

<400> SEQUENCE: 591
```
gatagcgaac gcaaatgctg cgaagatatg gtgtgc 36

<210> SEQ ID NO 592
<211> LENGTH: 36
<212> TYPE: DNA
<213> ORGANISM: Artificial Sequence
<220> FEATURE:
<223> OTHER INFORMATION: toxin sequence element

<400> SEQUENCE: 592
gatagcgaac gcaaatgctg cgaaggcatg gtgtgc 36

<210> SEQ ID NO 593
<211> LENGTH: 36
<212> TYPE: DNA
<213> ORGANISM: Artificial Sequence
<220> FEATURE:
<223> OTHER INFORMATION: toxin sequence element

<400> SEQUENCE: 593
gatagcgaac gcaaatgctg cgaaggctat gtgtgc 36

<210> SEQ ID NO 594
<211> LENGTH: 36
<212> TYPE: DNA
<213> ORGANISM: Artificial Sequence
<220> FEATURE:
<223> OTHER INFORMATION: toxin sequence element

<400> SEQUENCE: 594
gatagcaaac gcgcgtgctg cgaaggcctg cgctgc 36

<210> SEQ ID NO 595
<211> LENGTH: 36
<212> TYPE: DNA
<213> ORGANISM: Artificial Sequence
<220> FEATURE:
<223> OTHER INFORMATION: toxin sequence element

<400> SEQUENCE: 595
gatagcaaac gcaaatgctg cgaagatatg gtgtgc 36

<210> SEQ ID NO 596
<211> LENGTH: 36
<212> TYPE: DNA
<213> ORGANISM: Artificial Sequence
<220> FEATURE:
<223> OTHER INFORMATION: toxin sequence element

<400> SEQUENCE: 596
gatagcaacg cggattgctg cgaaggctat gtgtgc 36

<210> SEQ ID NO 597
<211> LENGTH: 36
<212> TYPE: DNA
<213> ORGANISM: Artificial Sequence
<220> FEATURE:
<223> OTHER INFORMATION: toxin sequence element

<400> SEQUENCE: 597
gatagcaccc tggattgctg caaacatctg agctgc 36

<210> SEQ ID NO 598
<211> LENGTH: 36
<212> TYPE: DNA

```
<213> ORGANISM: Artificial Sequence
<220> FEATURE:
<223> OTHER INFORMATION: toxin sequence element

<400> SEQUENCE: 598
gataccaacg cggattgctg cgaaggctat gtgtgc                                36

<210> SEQ ID NO 599
<211> LENGTH: 36
<212> TYPE: DNA
<213> ORGANISM: Artificial Sequence
<220> FEATURE:
<223> OTHER INFORMATION: toxin sequence element

<400> SEQUENCE: 599
gataccagca aagattgctg cgaaggctat gtgtgc                                36

<210> SEQ ID NO 600
<211> LENGTH: 36
<212> TYPE: DNA
<213> ORGANISM: Artificial Sequence
<220> FEATURE:
<223> OTHER INFORMATION: toxin sequence element

<400> SEQUENCE: 600
gattataaca acggctgctg cagcggctat gtgtgc                                36

<210> SEQ ID NO 601
<211> LENGTH: 36
<212> TYPE: DNA
<213> ORGANISM: Artificial Sequence
<220> FEATURE:
<223> OTHER INFORMATION: toxin sequence element

<400> SEQUENCE: 601
gaaaaagatg aacattgctg cgaacatctg ggctgc                                36

<210> SEQ ID NO 602
<211> LENGTH: 36
<212> TYPE: DNA
<213> ORGANISM: Artificial Sequence
<220> FEATURE:
<223> OTHER INFORMATION: toxin sequence element

<400> SEQUENCE: 602
gaaaaagata gcgattgctg cgaacatctg ggctgc                                36

<210> SEQ ID NO 603
<211> LENGTH: 36
<212> TYPE: DNA
<213> ORGANISM: Artificial Sequence
<220> FEATURE:
<223> OTHER INFORMATION: toxin sequence element

<400> SEQUENCE: 603
gaaagcaacg cggattgctg cgaaaactgg gcgtgc                                36

<210> SEQ ID NO 604
<211> LENGTH: 36
<212> TYPE: DNA
<213> ORGANISM: Artificial Sequence
<220> FEATURE:
<223> OTHER INFORMATION: toxin sequence element

<400> SEQUENCE: 604
tttcgcgata aagaatgctg caaaggcctg acctgc                                36
```

<210> SEQ ID NO 605
<211> LENGTH: 39
<212> TYPE: DNA
<213> ORGANISM: Artificial Sequence
<220> FEATURE:
<223> OTHER INFORMATION: toxin sequence element

<400> SEQUENCE: 605
ggcgcgggca aaccgacctg ctgcagcggc tatgattgc                                 39

<210> SEQ ID NO 606
<211> LENGTH: 39
<212> TYPE: DNA
<213> ORGANISM: Artificial Sequence
<220> FEATURE:
<223> OTHER INFORMATION: toxin sequence element

<400> SEQUENCE: 606
ggcgaaggca aaccgccgtg ctgcgcgaac tttgcgtgc 39

<210> SEQ ID NO 607
<211> LENGTH: 39
<212> TYPE: DNA
<213> ORGANISM: Artificial Sequence
<220> FEATURE:
<223> OTHER INFORMATION: toxin sequence element

<400> SEQUENCE: 607
ggccgcggca aaccgccgtg ctgcaaaggc tatgcgtgc 39

<210> SEQ ID NO 608
<211> LENGTH: 39
<212> TYPE: DNA
<213> ORGANISM: Artificial Sequence
<220> FEATURE:
<223> OTHER INFORMATION: toxin sequence element

<400> SEQUENCE: 608
ggcagcggca aaccggcgtg ctgcccgaaa tatgtgtgc 39

<210> SEQ ID NO 609
<211> LENGTH: 39
<212> TYPE: DNA
<213> ORGANISM: Artificial Sequence
<220> FEATURE:
<223> OTHER INFORMATION: toxin sequence element

<400> SEQUENCE: 609
ggcaccgatc agagcgaatg ctgcgaaggc tggaaatgc 39

<210> SEQ ID NO 610
<211> LENGTH: 39
<212> TYPE: DNA
<213> ORGANISM: Artificial Sequence
<220> FEATURE:
<223> OTHER INFORMATION: toxin sequence element

<400> SEQUENCE: 610
catccgggcc agccgccgtg ctgcagcggc ctggcgtgc 39

<210> SEQ ID NO 611
<211> LENGTH: 33
<212> TYPE: DNA
<213> ORGANISM: Artificial Sequence
<220> FEATURE:

<223> OTHER INFORMATION: toxin sequence element

<400> SEQUENCE: 611
aaagcggata acgattgctg cggcaaaaaa tgc                      33

<210> SEQ ID NO 612
<211> LENGTH: 36
<212> TYPE: DNA
<213> ORGANISM: Artificial Sequence
<220> FEATURE:
<223> OTHER INFORMATION: toxin sequence element

<400> SEQUENCE: 612
aaagcgcatg aagattgctg cgaacatctg cgctgc                   36

<210> SEQ ID NO 613
<211> LENGTH: 36
<212> TYPE: DNA
<213> ORGANISM: Artificial Sequence
<220> FEATURE:
<223> OTHER INFORMATION: toxin sequence element

<400> SEQUENCE: 613
aaagaagata gcgaatgctg cgaacatctg cagtgc                   36

<210> SEQ ID NO 614
<211> LENGTH: 33
<212> TYPE: DNA
<213> ORGANISM: Artificial Sequence
<220> FEATURE:
<223> OTHER INFORMATION: toxin sequence element

<400> SEQUENCE: 614
aaagaaaaac tgtgctgcag cggctatgtg tgc                      33

<210> SEQ ID NO 615
<211> LENGTH: 33
<212> TYPE: DNA
<213> ORGANISM: Artificial Sequence
<220> FEATURE:
<223> OTHER INFORMATION: toxin sequence element

<400> SEQUENCE: 615
aaagaaaaca aagattgctg cagcaaaaaa tgc                      33

<210> SEQ ID NO 616
<211> LENGTH: 36
<212> TYPE: DNA
<213> ORGANISM: Artificial Sequence
<220> FEATURE:
<223> OTHER INFORMATION: toxin sequence element

<400> SEQUENCE: 616
aaaaaagata aagaatgctg cggctggaac atttgc                   36

<210> SEQ ID NO 617
<211> LENGTH: 36
<212> TYPE: DNA
<213> ORGANISM: Artificial Sequence
<220> FEATURE:
<223> OTHER INFORMATION: toxin sequence element

<400> SEQUENCE: 617
aaaaacaaaa aagaatgctg cggctggaac gcgtgc                   36

```
<210> SEQ ID NO 618
<211> LENGTH: 36
<212> TYPE: DNA
<213> ORGANISM: Artificial Sequence
<220> FEATURE:
<223> OTHER INFORMATION: toxin sequence element

<400> SEQUENCE: 618
aaaaacagca acgattgctg caaagatctg gtgtgc                            36

<210> SEQ ID NO 619
<211> LENGTH: 36
<212> TYPE: DNA
<213> ORGANISM: Artificial Sequence
<220> FEATURE:
<223> OTHER INFORMATION: toxin sequence element

<400> SEQUENCE: 619
aaaagcgatg aaaactgctg caaaaatttt aaatgc                            36

<210> SEQ ID NO 620
<211> LENGTH: 36
<212> TYPE: DNA
<213> ORGANISM: Artificial Sequence
<220> FEATURE:
<223> OTHER INFORMATION: toxin sequence element

<400> SEQUENCE: 620
aaaagcacca gcgattgctg cgaacatctg agctgc                            36

<210> SEQ ID NO 621
<211> LENGTH: 36
<212> TYPE: DNA
<213> ORGANISM: Artificial Sequence
<220> FEATURE:
<223> OTHER INFORMATION: toxin sequence element

<400> SEQUENCE: 621
aaaaccaccg cggattgctg caaacatctg gcgtgc                            36

<210> SEQ ID NO 622
<211> LENGTH: 36
<212> TYPE: DNA
<213> ORGANISM: Artificial Sequence
<220> FEATURE:
<223> OTHER INFORMATION: toxin sequence element

<400> SEQUENCE: 622
aaaaccaccg cggattgctg caaacatctg ggctgc                            36

<210> SEQ ID NO 623
<211> LENGTH: 36
<212> TYPE: DNA
<213> ORGANISM: Artificial Sequence
<220> FEATURE:
<223> OTHER INFORMATION: toxin sequence element

<400> SEQUENCE: 623
aaaaccacca gcgattgctg caaacatctg ggctgc                            36

<210> SEQ ID NO 624
<211> LENGTH: 42
<212> TYPE: DNA
<213> ORGANISM: Artificial Sequence
<220> FEATURE:
<223> OTHER INFORMATION: toxin sequence element
```

<400> SEQUENCE: 624
aacgcgctga gcggcccgcg ctgctgcagc ggcctgaaat gc					42

<210> SEQ ID NO 625
<211> LENGTH: 36
<212> TYPE: DNA
<213> ORGANISM: Artificial Sequence
<220> FEATURE:
<223> OTHER INFORMATION: toxin sequence element

<400> SEQUENCE: 625
aacgatgaaa tggtgtgctg cgaacatctg gtgtgc					36

<210> SEQ ID NO 626
<211> LENGTH: 51
<212> TYPE: DNA
<213> ORGANISM: Artificial Sequence
<220> FEATURE:
<223> OTHER INFORMATION: toxin sequence element

<400> SEQUENCE: 626
aacggcccgc atacctgctg ctggggctat aacggctata aaaaagcgtg c					51

<210> SEQ ID NO 627
<211> LENGTH: 39
<212> TYPE: DNA
<213> ORGANISM: Artificial Sequence
<220> FEATURE:
<223> OTHER INFORMATION: toxin sequence element

<400> SEQUENCE: 627
aacccggata acgataaatg ctgcgaaggc cgcaaatgc					39

<210> SEQ ID NO 628
<211> LENGTH: 42
<212> TYPE: DNA
<213> ORGANISM: Artificial Sequence
<220> FEATURE:
<223> OTHER INFORMATION: toxin sequence element

<400> SEQUENCE: 628
aacccgaacg atgataaatg ctgccgcccg aaactgaaat gc					42

<210> SEQ ID NO 629
<211> LENGTH: 42
<212> TYPE: DNA
<213> ORGANISM: Artificial Sequence
<220> FEATURE:
<223> OTHER INFORMATION: toxin sequence element

<400> SEQUENCE: 629
aacccgagca acgataaatg ctgccgcccg aacctggtgt gc					42

<210> SEQ ID NO 630
<211> LENGTH: 45
<212> TYPE: DNA
<213> ORGANISM: Artificial Sequence
<220> FEATURE:
<223> OTHER INFORMATION: toxin sequence element

<400> SEQUENCE: 630
aacccgagca acgatcagtg ctgcaaaagc gcgaacctgg tgtgc					45

<210> SEQ ID NO 631
<211> LENGTH: 45

<212> TYPE: DNA
<213> ORGANISM: Artificial Sequence
<220> FEATURE:
<223> OTHER INFORMATION: toxin sequence element

<400> SEQUENCE: 631
aacccgagca acgatcagtg ctgcaaaagc agcaaactgg tgtgc 45

<210> SEQ ID NO 632
<211> LENGTH: 45
<212> TYPE: DNA
<213> ORGANISM: Artificial Sequence
<220> FEATURE:
<223> OTHER INFORMATION: toxin sequence element

<400> SEQUENCE: 632
aacccgagca acgatcagtg ctgcaaaagc agcaacctgg tgtgc 45

<210> SEQ ID NO 633
<211> LENGTH: 39
<212> TYPE: DNA
<213> ORGANISM: Artificial Sequence
<220> FEATURE:
<223> OTHER INFORMATION: toxin sequence element

<400> SEQUENCE: 633
aacagcgatg cggattgctg ccgctatggc gaacgctgc 39

<210> SEQ ID NO 634
<211> LENGTH: 36
<212> TYPE: DNA
<213> ORGANISM: Artificial Sequence
<220> FEATURE:
<223> OTHER INFORMATION: toxin sequence element

<400> SEQUENCE: 634
aacagcgata aagaatgctg caaaggcctg cgctgc 36

<210> SEQ ID NO 635
<211> LENGTH: 39
<212> TYPE: DNA
<213> ORGANISM: Artificial Sequence
<220> FEATURE:
<223> OTHER INFORMATION: toxin sequence element

<400> SEQUENCE: 635
aactatatgg atgataaatg ctgcccgggc tataaatgc 39

<210> SEQ ID NO 636
<211> LENGTH: 36
<212> TYPE: DNA
<213> ORGANISM: Artificial Sequence
<220> FEATURE:
<223> OTHER INFORMATION: toxin sequence element

<400> SEQUENCE: 636
ccgaaaaaag cgccgtgctg cggccgcctg gaatgc 36

<210> SEQ ID NO 637
<211> LENGTH: 33
<212> TYPE: DNA
<213> ORGANISM: Artificial Sequence
<220> FEATURE:
<223> OTHER INFORMATION: toxin sequence element

<400> SEQUENCE: 637

```
ccgtatcatg aaagctgctg cagcggcagc tgc                                    33
```

<210> SEQ ID NO 638
<211> LENGTH: 33
<212> TYPE: DNA
<213> ORGANISM: Artificial Sequence
<220> FEATURE:
<223> OTHER INFORMATION: toxin sequence element

<400> SEQUENCE: 638

```
ccgtataacg aacattgctg cagcggcagc tgc                                    33
```

<210> SEQ ID NO 639
<211> LENGTH: 33
<212> TYPE: DNA
<213> ORGANISM: Artificial Sequence
<220> FEATURE:
<223> OTHER INFORMATION: toxin sequence element

<400> SEQUENCE: 639
ccgtataacg aaaactgctg cagcaaaagc tgc 33

<210> SEQ ID NO 640
<211> LENGTH: 33
<212> TYPE: DNA
<213> ORGANISM: Artificial Sequence
<220> FEATURE:
<223> OTHER INFORMATION: toxin sequence element

<400> SEQUENCE: 640
ccgtataacg aaaactgctg cagccagagc tgc 33

<210> SEQ ID NO 641
<211> LENGTH: 33
<212> TYPE: DNA
<213> ORGANISM: Artificial Sequence
<220> FEATURE:
<223> OTHER INFORMATION: toxin sequence element

<400> SEQUENCE: 641
ccgtataacg aaagctgctg cagcggcagc tgc 33

<210> SEQ ID NO 642
<211> LENGTH: 33
<212> TYPE: DNA
<213> ORGANISM: Artificial Sequence
<220> FEATURE:
<223> OTHER INFORMATION: toxin sequence element

<400> SEQUENCE: 642
ccgtatagca aatattgctg cagcggcagc tgc 33

<210> SEQ ID NO 643
<211> LENGTH: 57
<212> TYPE: DNA
<213> ORGANISM: Artificial Sequence
<220> FEATURE:
<223> OTHER INFORMATION: toxin sequence element

<400> SEQUENCE: 643
cagccgaaca cccagccgtg ctgcaacaac gcggaagaag aacagaccat taactgc 57

<210> SEQ ID NO 644
<211> LENGTH: 33
<212> TYPE: DNA
<213> ORGANISM: Artificial Sequence -continued

```
<220> FEATURE:
<223> OTHER INFORMATION: toxin sequence element

<400> SEQUENCE: 644
cgcgaaaaca aagattgctg cagcaaaaaa tgc                                    33

<210> SEQ ID NO 645
<211> LENGTH: 36
<212> TYPE: DNA
<213> ORGANISM: Artificial Sequence
<220> FEATURE:
<223> OTHER INFORMATION: toxin sequence element

<400> SEQUENCE: 645
cgccgcgata gcgattgctg cccgcatctg ggctgc                                 36

<210> SEQ ID NO 646
<211> LENGTH: 36
<212> TYPE: DNA
<213> ORGANISM: Artificial Sequence
<220> FEATURE:
<223> OTHER INFORMATION: toxin sequence element

<400> SEQUENCE: 646
agcgcgggcc agacctgctg caaacatctg gtgtgc                                 36

<210> SEQ ID NO 647
<211> LENGTH: 36
<212> TYPE: DNA
<213> ORGANISM: Artificial Sequence
<220> FEATURE:
<223> OTHER INFORMATION: toxin sequence element

<400> SEQUENCE: 647
agcgaagata gcgaatgctg cccgcatctg ggctgc                                 36

<210> SEQ ID NO 648
<211> LENGTH: 36
<212> TYPE: DNA
<213> ORGANISM: Artificial Sequence
<220> FEATURE:
<223> OTHER INFORMATION: toxin sequence element

<400> SEQUENCE: 648
agcaaagatg cggattgctg cgcgcatctg gaatgc                                 36

<210> SEQ ID NO 649
<211> LENGTH: 36
<212> TYPE: DNA
<213> ORGANISM: Artificial Sequence
<220> FEATURE:
<223> OTHER INFORMATION: toxin sequence element

<400> SEQUENCE: 649
agcaaacatg aagattgctg cgcgcatctg gcgtgc                                 36

<210> SEQ ID NO 650
<211> LENGTH: 36
<212> TYPE: DNA
<213> ORGANISM: Artificial Sequence
<220> FEATURE:
<223> OTHER INFORMATION: toxin sequence element

<400> SEQUENCE: 650
agcaaaaccg gcgattgctg cagccatctg agctgc                                 36
```

<210> SEQ ID NO 651
<211> LENGTH: 36
<212> TYPE: DNA
<213> ORGANISM: Artificial Sequence
<220> FEATURE:
<223> OTHER INFORMATION: toxin sequence element

<400> SEQUENCE: 651
agccaggatg gcgattgctg caaacatctg cagtgc                                    36

<210> SEQ ID NO 652
<211> LENGTH: 36
<212> TYPE: DNA
<213> ORGANISM: Artificial Sequence
<220> FEATURE:
<223> OTHER INFORMATION: toxin sequence element

<400> SEQUENCE: 652
agccagacca gcgattgctg cccgcatctg gcgtgc 36

<210> SEQ ID NO 653
<211> LENGTH: 36
<212> TYPE: DNA
<213> ORGANISM: Artificial Sequence
<220> FEATURE:
<223> OTHER INFORMATION: toxin sequence element

<400> SEQUENCE: 653
agcagcgata aaccgtgctg cagcggctat tattgc 36

<210> SEQ ID NO 654
<211> LENGTH: 36
<212> TYPE: DNA
<213> ORGANISM: Artificial Sequence
<220> FEATURE:
<223> OTHER INFORMATION: toxin sequence element

<400> SEQUENCE: 654
agcagcacca gcgattgctg caaacatctg agctgc 36

<210> SEQ ID NO 655
<211> LENGTH: 36
<212> TYPE: DNA
<213> ORGANISM: Artificial Sequence
<220> FEATURE:
<223> OTHER INFORMATION: toxin sequence element

<400> SEQUENCE: 655
agcaccgaaa aaccgtgctg cgataacttt agctgc 36

<210> SEQ ID NO 656
<211> LENGTH: 36
<212> TYPE: DNA
<213> ORGANISM: Artificial Sequence
<220> FEATURE:
<223> OTHER INFORMATION: toxin sequence element

<400> SEQUENCE: 656
agcacccatg cggattgctg cgaaggcttt atttgc 36

<210> SEQ ID NO 657
<211> LENGTH: 36
<212> TYPE: DNA
<213> ORGANISM: Artificial Sequence
<220> FEATURE:
<223> OTHER INFORMATION: toxin sequence element

```
<400> SEQUENCE: 657
agcgtggata gcgattgctg cgcgcatctg ggctgc                           36

<210> SEQ ID NO 658
<211> LENGTH: 36
<212> TYPE: DNA
<213> ORGANISM: Artificial Sequence
<220> FEATURE:
<223> OTHER INFORMATION: toxin sequence element

<400> SEQUENCE: 658
agcgtgcata gcgattgctg cgcgcatctg ggctgc                           36

<210> SEQ ID NO 659
<211> LENGTH: 36
<212> TYPE: DNA
<213> ORGANISM: Artificial Sequence
<220> FEATURE:
<223> OTHER INFORMATION: toxin sequence element

<400> SEQUENCE: 659
agcgtgaacg atgattgctg cccgcgcctg ggctgc                           36

<210> SEQ ID NO 660
<211> LENGTH: 36
<212> TYPE: DNA
<213> ORGANISM: Artificial Sequence
<220> FEATURE:
<223> OTHER INFORMATION: toxin sequence element

<400> SEQUENCE: 660
accgatcgcc tgccgtgctg ctttggcctg gaatgc                           36

<210> SEQ ID NO 661
<211> LENGTH: 36
<212> TYPE: DNA
<213> ORGANISM: Artificial Sequence
<220> FEATURE:
<223> OTHER INFORMATION: toxin sequence element

<400> SEQUENCE: 661
accattgatg atgattgctg cccgcatctg ggctgc                           36

<210> SEQ ID NO 662
<211> LENGTH: 36
<212> TYPE: DNA
<213> ORGANISM: Artificial Sequence
<220> FEATURE:
<223> OTHER INFORMATION: toxin sequence element

<400> SEQUENCE: 662
accaaagatg aagattgctg caaacatctg gcgtgc                           36

<210> SEQ ID NO 663
<211> LENGTH: 36
<212> TYPE: DNA
<213> ORGANISM: Artificial Sequence
<220> FEATURE:
<223> OTHER INFORMATION: toxin sequence element

<400> SEQUENCE: 663
accaaagata gcgaatgctg cccgcatctg ggctgc                           36

<210> SEQ ID NO 664
```

```
<211> LENGTH: 39
<212> TYPE: DNA
<213> ORGANISM: Artificial Sequence
<220> FEATURE:
<223> OTHER INFORMATION: toxin sequence element

<400> SEQUENCE: 664
accccggaaa aaaacgattg ctgccagcgc ctgtattgc                          39

<210> SEQ ID NO 665
<211> LENGTH: 39
<212> TYPE: DNA
<213> ORGANISM: Artificial Sequence
<220> FEATURE:
<223> OTHER INFORMATION: toxin sequence element

<400> SEQUENCE: 665
accccgggca aaacgaatg ctgcccgaac cgcgtgtgc                           39

<210> SEQ ID NO 666
<211> LENGTH: 39
<212> TYPE: DNA
<213> ORGANISM: Artificial Sequence
<220> FEATURE:
<223> OTHER INFORMATION: toxin sequence element

<400> SEQUENCE: 666
accccgggca aaacgaatg ctgcccgaac tatgcgtgc                           39

<210> SEQ ID NO 667
<211> LENGTH: 36
<212> TYPE: DNA
<213> ORGANISM: Artificial Sequence
<220> FEATURE:
<223> OTHER INFORMATION: toxin sequence element

<400> SEQUENCE: 667
accagcgata gcgattgctg cccgaactgg gtgtgc                             36

<210> SEQ ID NO 668
<211> LENGTH: 36
<212> TYPE: DNA
<213> ORGANISM: Artificial Sequence
<220> FEATURE:
<223> OTHER INFORMATION: toxin sequence element

<400> SEQUENCE: 668
accaccagca gcgaatgctg cgcgcatctg ggctgc                             36

<210> SEQ ID NO 669
<211> LENGTH: 39
<212> TYPE: DNA
<213> ORGANISM: Artificial Sequence
<220> FEATURE:
<223> OTHER INFORMATION: toxin sequence element

<400> SEQUENCE: 669
gtgaaccgcc atggcgattg ctgcgaaggc ctggaatgc                          39

<210> SEQ ID NO 670
<211> LENGTH: 39
<212> TYPE: DNA
<213> ORGANISM: Artificial Sequence
<220> FEATURE:
<223> OTHER INFORMATION: toxin sequence element

<400> SEQUENCE: 670
```
gtgccgggca aaaacgaatg ctgcagcggc tatgcgtgc                               39

<210> SEQ ID NO 671
<211> LENGTH: 39
<212> TYPE: DNA
<213> ORGANISM: Artificial Sequence
<220> FEATURE:
<223> OTHER INFORMATION: toxin sequence element

<400> SEQUENCE: 671
tatggcgcga cccagaaaat tccgtgctgc ggcgtgtgc                               39

<210> SEQ ID NO 672
<211> LENGTH: 36
<212> TYPE: DNA
<213> ORGANISM: Artificial Sequence
<220> FEATURE:
<223> OTHER INFORMATION: toxin sequence element

<400> SEQUENCE: 672
tataaactgc gcaaatgctg cgcgggcttt tattgc                                  36

<210> SEQ ID NO 673
<211> LENGTH: 36
<212> TYPE: DNA
<213> ORGANISM: Artificial Sequence
<220> FEATURE:
<223> OTHER INFORMATION: toxin sequence element

<400> SEQUENCE: 673
gatgtgttta gcctggattg ctgcaccggc atttgc                                  36

<210> SEQ ID NO 674
<211> LENGTH: 48
<212> TYPE: DNA
<213> ORGANISM: Artificial Sequence
<220> FEATURE:
<223> OTHER INFORMATION: toxin sequence element

<400> SEQUENCE: 674
attgtgccga ttattggctt tatttattgc tgcccgggcc tgatttgc                     48

<210> SEQ ID NO 675
<211> LENGTH: 42
<212> TYPE: DNA
<213> ORGANISM: Artificial Sequence
<220> FEATURE:
<223> OTHER INFORMATION: toxin sequence element

<400> SEQUENCE: 675
ggcatgatta aaattggccc gccgtgctgc agcggctggt gc                           42

<210> SEQ ID NO 676
<211> LENGTH: 39
<212> TYPE: DNA
<213> ORGANISM: Artificial Sequence
<220> FEATURE:
<223> OTHER INFORMATION: toxin sequence element

<400> SEQUENCE: 676
gatccgattt ttcagaactg ctgccgcggc tggaactgc                               39

<210> SEQ ID NO 677
<211> LENGTH: 36
<212> TYPE: DNA

```
<213> ORGANISM: Artificial Sequence
<220> FEATURE:
<223> OTHER INFORMATION: toxin sequence element

<400> SEQUENCE: 677
aacgtgctgg atcagaactg ctgcgatggc tattgc                                36

<210> SEQ ID NO 678
<211> LENGTH: 33
<212> TYPE: DNA
<213> ORGANISM: Artificial Sequence
<220> FEATURE:
<223> OTHER INFORMATION: toxin sequence element

<400> SEQUENCE: 678
gattttctgt ttccgaaatg ctgcaactat tgc                                   33

<210> SEQ ID NO 679
<211> LENGTH: 39
<212> TYPE: DNA
<213> ORGANISM: Artificial Sequence
<220> FEATURE:
<223> OTHER INFORMATION: toxin sequence element

<400> SEQUENCE: 679
gatccgtttc tgcagaactg ctgcctgggc tggaactgc                             39

<210> SEQ ID NO 680
<211> LENGTH: 36
<212> TYPE: DNA
<213> ORGANISM: Artificial Sequence
<220> FEATURE:
<223> OTHER INFORMATION: toxin sequence element

<400> SEQUENCE: 680 acctttttt ttccggattg ctgcaacagc atttgc                                 36

<210> SEQ ID NO 681
<211> LENGTH: 48
<212> TYPE: DNA
<213> ORGANISM: Artificial Sequence
<220> FEATURE:
<223> OTHER INFORMATION: toxin sequence element

<400> SEQUENCE: 681
attgtgccga ttctgggctt tgtgtattgc tgcccgggcc tgatttgc                   48

<210> SEQ ID NO 682
<211> LENGTH: 24
<212> TYPE: DNA
<213> ORGANISM: Artificial Sequence
<220> FEATURE:
<223> OTHER INFORMATION: toxin sequence element

<400> SEQUENCE: 682
gcgctgggca tttgcatgcc gcgc                                             24

<210> SEQ ID NO 683
<211> LENGTH: 42
<212> TYPE: DNA
<213> ORGANISM: Artificial Sequence
<220> FEATURE:
<223> OTHER INFORMATION: toxin sequence element

<400> SEQUENCE: 683
gcgaccaccg gccgctttcg ctatctgtgc aaatatcaga tt                         42
```

<210> SEQ ID NO 684
<211> LENGTH: 36
<212> TYPE: DNA
<213> ORGANISM: Artificial Sequence
<220> FEATURE:
<223> OTHER INFORMATION: toxin sequence element

<400> SEQUENCE: 684
gatcgccgcg atcagtggtg caaatggaac ccgtgg            36

<210> SEQ ID NO 685
<211> LENGTH: 24
<212> TYPE: DNA
<213> ORGANISM: Artificial Sequence
<220> FEATURE:
<223> OTHER INFORMATION: toxin sequence element

<400> SEQUENCE: 685
gaactgtggt gcaaatataa cctg            24

<210> SEQ ID NO 686
<211> LENGTH: 36
<212> TYPE: DNA
<213> ORGANISM: Artificial Sequence
<220> FEATURE:
<223> OTHER INFORMATION: toxin sequence element

<400> SEQUENCE: 686
gaacgcagca gcccgtggtg caaaattgat atttgg            36

<210> SEQ ID NO 687
<211> LENGTH: 21
<212> TYPE: DNA
<213> ORGANISM: Artificial Sequence
<220> FEATURE:
<223> OTHER INFORMATION: toxin sequence element

<400> SEQUENCE: 687
catctgtggt gcaaatataa a            21

<210> SEQ ID NO 688
<211> LENGTH: 45
<212> TYPE: DNA
<213> ORGANISM: Artificial Sequence
<220> FEATURE:
<223> OTHER INFORMATION: toxin sequence element

<400> SEQUENCE: 688
catagcctgt ttagctattg cgcgtgggat ctgaccttta gcgat            45

<210> SEQ ID NO 689
<211> LENGTH: 45
<212> TYPE: DNA
<213> ORGANISM: Artificial Sequence
<220> FEATURE:
<223> OTHER INFORMATION: toxin sequence element

<400> SEQUENCE: 689
catagcaact atgaatggtg catttgggat ggcacctttta gcaaa            45

<210> SEQ ID NO 690
<211> LENGTH: 36
<212> TYPE: DNA
<213> ORGANISM: Artificial Sequence
<220> FEATURE:

<223> OTHER INFORMATION: toxin sequence element

<400> SEQUENCE: 690
catagcaact atgaatggtg cgtgtgggat ggcacc                                36

<210> SEQ ID NO 691
<211> LENGTH: 39
<212> TYPE: DNA
<213> ORGANISM: Artificial Sequence
<220> FEATURE:
<223> OTHER INFORMATION: toxin sequence element

<400> SEQUENCE: 691
catagccgct gggattggtg catttgggat ggcacctttt                            39

<210> SEQ ID NO 692
<211> LENGTH: 39
<212> TYPE: DNA
<213> ORGANISM: Artificial Sequence
<220> FEATURE:
<223> OTHER INFORMATION: toxin sequence element

<400> SEQUENCE: 692
catagctatt gggaatggtg cctgtgggat ggcagcttt                             39

<210> SEQ ID NO 693
<211> LENGTH: 21
<212> TYPE: DNA
<213> ORGANISM: Artificial Sequence
<220> FEATURE:
<223> OTHER INFORMATION: toxin sequence element

<400> SEQUENCE: 693
atttgcagcg gcaactggaa a                                                21

<210> SEQ ID NO 694
<211> LENGTH: 42
<212> TYPE: DNA
<213> ORGANISM: Artificial Sequence
<220> FEATURE:
<223> OTHER INFORMATION: toxin sequence element

<400> SEQUENCE: 694
attagcacca aagtgaacta ttatcgcccg gatcgcggcc cg                         42

<210> SEQ ID NO 695
<211> LENGTH: 30
<212> TYPE: DNA
<213> ORGANISM: Artificial Sequence
<220> FEATURE:
<223> OTHER INFORMATION: toxin sequence element

<400> SEQUENCE: 695
aaagcgtttg tgctgcattg ctatcgcaac                                       30

<210> SEQ ID NO 696
<211> LENGTH: 39
<212> TYPE: DNA
<213> ORGANISM: Artificial Sequence
<220> FEATURE:
<223> OTHER INFORMATION: toxin sequence element

<400> SEQUENCE: 696
aaagatgtgc tgtattattg cgcgtgggat ggcacctttt                            39

```
<210> SEQ ID NO 697
<211> LENGTH: 51
<212> TYPE: DNA
<213> ORGANISM: Artificial Sequence
<220> FEATURE:
<223> OTHER INFORMATION: toxin sequence element

<400> SEQUENCE: 697
aaagaaaaat ggccgattac ctataaaatt tgcgtgtggg atcgcacctt t          51

<210> SEQ ID NO 698
<211> LENGTH: 33
<212> TYPE: DNA
<213> ORGANISM: Artificial Sequence
<220> FEATURE:
<223> OTHER INFORMATION: toxin sequence element

<400> SEQUENCE: 698
aaagaactga gcatttggga tagccgctgc ctg                              33

<210> SEQ ID NO 699
<211> LENGTH: 42
<212> TYPE: DNA
<213> ORGANISM: Artificial Sequence
<220> FEATURE:
<223> OTHER INFORMATION: toxin sequence element

<400> SEQUENCE: 699
aaatttcgcg ataaatattg cgcgtgggat tttaccttta gc                    42

<210> SEQ ID NO 700
<211> LENGTH: 39
<212> TYPE: DNA
<213> ORGANISM: Artificial Sequence
<220> FEATURE:
<223> OTHER INFORMATION: toxin sequence element

<400> SEQUENCE: 700
aaaggcccga gcccgaaaca gaaaaaatgc acccgcccg                        39

<210> SEQ ID NO 701
<211> LENGTH: 42
<212> TYPE: DNA
<213> ORGANISM: Artificial Sequence
<220> FEATURE:
<223> OTHER INFORMATION: toxin sequence element

<400> SEQUENCE: 701
aaaggccgct tgtgaacac ctggccgacc ttttgcctgg tg                     42

<210> SEQ ID NO 702
<211> LENGTH: 33
<212> TYPE: DNA
<213> ORGANISM: Artificial Sequence
<220> FEATURE:
<223> OTHER INFORMATION: toxin sequence element

<400> SEQUENCE: 702
aaaattggcc tgtatctgtg catttggagc ccg                              33

<210> SEQ ID NO 703
<211> LENGTH: 27
<212> TYPE: DNA
<213> ORGANISM: Artificial Sequence
<220> FEATURE:
<223> OTHER INFORMATION: toxin sequence element
```

```
<400> SEQUENCE: 703
aaactgtggt gccgcaaaat tattggc                                        27

<210> SEQ ID NO 704
<211> LENGTH: 30
<212> TYPE: DNA
<213> ORGANISM: Artificial Sequence
<220> FEATURE:
<223> OTHER INFORMATION: toxin sequence element

<400> SEQUENCE: 704
aaactgtggt gccgctatga acgcacctgg                                     30

<210> SEQ ID NO 705
<211> LENGTH: 39
<212> TYPE: DNA
<213> ORGANISM: Artificial Sequence
<220> FEATURE:
<223> OTHER INFORMATION: toxin sequence element

<400> SEQUENCE: 705
aaaatgggcc tggattattg cgcgtgggat ggcacctttt                          39

<210> SEQ ID NO 706
<211> LENGTH: 39
<212> TYPE: DNA
<213> ORGANISM: Artificial Sequence
<220> FEATURE:
<223> OTHER INFORMATION: toxin sequence element

<400> SEQUENCE: 706
aaaatgggcc tgtattattg cgcgtgggat ggcacctttt                          39

<210> SEQ ID NO 707
<211> LENGTH: 36
<212> TYPE: DNA
<213> ORGANISM: Artificial Sequence
<220> FEATURE:
<223> OTHER INFORMATION: toxin sequence element

<400> SEQUENCE: 707
aaaccgaccc tgaaatattg cgcgtgggat ggcacc                              36

<210> SEQ ID NO 708
<211> LENGTH: 39
<212> TYPE: DNA
<213> ORGANISM: Artificial Sequence
<220> FEATURE:
<223> OTHER INFORMATION: toxin sequence element

<400> SEQUENCE: 708
aaaccgaccc tgaaatattg cgcgtgggat ggcaccttt                           39

<210> SEQ ID NO 709
<211> LENGTH: 39
<212> TYPE: DNA
<213> ORGANISM: Artificial Sequence
<220> FEATURE:
<223> OTHER INFORMATION: toxin sequence element

<400> SEQUENCE: 709
aaaccgacca gcaaatattg cgcgtgggat ggcaccatt                           39

<210> SEQ ID NO 710
<211> LENGTH: 42
```

```
<212> TYPE: DNA
<213> ORGANISM: Artificial Sequence
<220> FEATURE:
<223> OTHER INFORMATION: toxin sequence element

<400> SEQUENCE: 710
aaacagaaat ggccgtttta ttgcgcgtgg gattggagct tt                          42

<210> SEQ ID NO 711
<211> LENGTH: 36
<212> TYPE: DNA
<213> ORGANISM: Artificial Sequence
<220> FEATURE:
<223> OTHER INFORMATION: toxin sequence element

<400> SEQUENCE: 711
aaacgccgcg gcaccaacgc ggaaaaacgc tgccgc                                 36

<210> SEQ ID NO 712
<211> LENGTH: 36
<212> TYPE: DNA
<213> ORGANISM: Artificial Sequence
<220> FEATURE:
<223> OTHER INFORMATION: toxin sequence element

<400> SEQUENCE: 712
aaacgccgcg gcaccaacat tgaaaaacgc tgccgc                                 36

<210> SEQ ID NO 713
<211> LENGTH: 45
<212> TYPE: DNA
<213> ORGANISM: Artificial Sequence
<220> FEATURE:
<223> OTHER INFORMATION: toxin sequence element

<400> SEQUENCE: 713
aaacgcacct ttaactattg cgcgtgggat ggcagcttta gcaaa                       45

<210> SEQ ID NO 714
<211> LENGTH: 45
<212> TYPE: DNA
<213> ORGANISM: Artificial Sequence
<220> FEATURE:
<223> OTHER INFORMATION: toxin sequence element

<400> SEQUENCE: 714
aaaagcaaat ggccgcgcaa catttgcgtg tgggatggca gcgtg                       45

<210> SEQ ID NO 715
<211> LENGTH: 33
<212> TYPE: DNA
<213> ORGANISM: Artificial Sequence
<220> FEATURE:
<223> OTHER INFORMATION: toxin sequence element

<400> SEQUENCE: 715
aaaaccaccg gcattgtgaa actgtgccgc tgg                                    33

<210> SEQ ID NO 716
<211> LENGTH: 54
<212> TYPE: DNA
<213> ORGANISM: Artificial Sequence
<220> FEATURE:
<223> OTHER INFORMATION: toxin sequence element

<400> SEQUENCE: 716
```
aaatgggtgt tttttaccag caaatttatg tgccgccgcg tgtggggcaa agat    54

<210> SEQ ID NO 717
<211> LENGTH: 54
<212> TYPE: DNA
<213> ORGANISM: Artificial Sequence
<220> FEATURE:
<223> OTHER INFORMATION: toxin sequence element

<400> SEQUENCE: 717
ctgaaaccga ccctgcatgg catttggtat aaacatcatt attgctatac ccag    54

<210> SEQ ID NO 718
<211> LENGTH: 54
<212> TYPE: DNA
<213> ORGANISM: Artificial Sequence
<220> FEATURE:
<223> OTHER INFORMATION: toxin sequence element

<400> SEQUENCE: 718
ctgaaaccga ccctgcatgg catttggtat aaaagctatt attgctataa aaaa    54

<210> SEQ ID NO 719
<211> LENGTH: 27
<212> TYPE: DNA
<213> ORGANISM: Artificial Sequence
<220> FEATURE:
<223> OTHER INFORMATION: toxin sequence element

<400> SEQUENCE: 719
aacggcaaca ccgtgtatcg ctgcgcg    27

<210> SEQ ID NO 720
<211> LENGTH: 39
<212> TYPE: DNA
<213> ORGANISM: Artificial Sequence
<220> FEATURE:
<223> OTHER INFORMATION: toxin sequence element

<400> SEQUENCE: 720
aacaaaaaac atggctggtg cggctgggat ggcaccttt    39

<210> SEQ ID NO 721
<211> LENGTH: 39
<212> TYPE: DNA
<213> ORGANISM: Artificial Sequence
<220> FEATURE:
<223> OTHER INFORMATION: toxin sequence element

<400> SEQUENCE: 721
aacaaaaaat attggcattg cggctgggat ggcaccttt    39

<210> SEQ ID NO 722
<211> LENGTH: 36
<212> TYPE: DNA
<213> ORGANISM: Artificial Sequence
<220> FEATURE:
<223> OTHER INFORMATION: toxin sequence element

<400> SEQUENCE: 722
aaccgcaaac ataaatggtg caaatataaa ctgtgg    36

<210> SEQ ID NO 723
<211> LENGTH: 36
<212> TYPE: DNA
<213> ORGANISM: Artificial Sequence

```
<220> FEATURE:
<223> OTHER INFORMATION: toxin sequence element

<400> SEQUENCE: 723
aaccgccgcg ataaatggtg caaatataaa ctgtgg                              36

<210> SEQ ID NO 724
<211> LENGTH: 33
<212> TYPE: DNA
<213> ORGANISM: Artificial Sequence
<220> FEATURE:
<223> OTHER INFORMATION: toxin sequence element

<400> SEQUENCE: 724
aacagccgcg ataaatggtg caaagtgctg ctg                                 33

<210> SEQ ID NO 725
<211> LENGTH: 24
<212> TYPE: DNA
<213> ORGANISM: Artificial Sequence
<220> FEATURE:
<223> OTHER INFORMATION: toxin sequence element

<400> SEQUENCE: 725
cagctgtggt gcaaaaaacg cctg                                           24

<210> SEQ ID NO 726
<211> LENGTH: 33
<212> TYPE: DNA
<213> ORGANISM: Artificial Sequence
<220> FEATURE:
<223> OTHER INFORMATION: toxin sequence element

<400> SEQUENCE: 726
cagccggcga ttaaatggtg catttggagc ccg                                 33

<210> SEQ ID NO 727
<211> LENGTH: 42
<212> TYPE: DNA
<213> ORGANISM: Artificial Sequence
<220> FEATURE:
<223> OTHER INFORMATION: toxin sequence element

<400> SEQUENCE: 727
cagagccgca ttgcgaacat gtggccgacc ttttgcctgg tg                       42

<210> SEQ ID NO 728
<211> LENGTH: 42
<212> TYPE: DNA
<213> ORGANISM: Artificial Sequence
<220> FEATURE:
<223> OTHER INFORMATION: toxin sequence element

<400> SEQUENCE: 728
cagagccgca ttgcgaacat gtggccgacc ttttgcagcc ag                       42

<210> SEQ ID NO 729
<211> LENGTH: 42
<212> TYPE: DNA
<213> ORGANISM: Artificial Sequence
<220> FEATURE:
<223> OTHER INFORMATION: toxin sequence element

<400> SEQUENCE: 729
cgcaaaaaat ggccgtatca ttgcggctgg gatggcacct tt                       42
```

<210> SEQ ID NO 730
<211> LENGTH: 42
<212> TYPE: DNA
<213> ORGANISM: Artificial Sequence
<220> FEATURE:
<223> OTHER INFORMATION: toxin sequence element

<400> SEQUENCE: 730
cgcaaaaaat ggccgtatca ttgcgtgtgg gattggaccg tg        42

<210> SEQ ID NO 731
<211> LENGTH: 24
<212> TYPE: DNA
<213> ORGANISM: Artificial Sequence
<220> FEATURE:
<223> OTHER INFORMATION: toxin sequence element

<400> SEQUENCE: 731
cgcctgtggt gcaaaaaaat tatt        24

<210> SEQ ID NO 732
<211> LENGTH: 33
<212> TYPE: DNA
<213> ORGANISM: Artificial Sequence
<220> FEATURE:
<223> OTHER INFORMATION: toxin sequence element

<400> SEQUENCE: 732
cgcctgtggt gcaaaaaaaa aattgaagaa ggc        33

<210> SEQ ID NO 733
<211> LENGTH: 30
<212> TYPE: DNA
<213> ORGANISM: Artificial Sequence
<220> FEATURE:
<223> OTHER INFORMATION: toxin sequence element

<400> SEQUENCE: 733
cgcctgtggt gcaaaaaaaa aattgaatgg        30

<210> SEQ ID NO 734
<211> LENGTH: 27
<212> TYPE: DNA
<213> ORGANISM: Artificial Sequence
<220> FEATURE:
<223> OTHER INFORMATION: toxin sequence element

<400> SEQUENCE: 734
cgcctgtggt gcaaaaaaaa actgtgg        27

<210> SEQ ID NO 735
<211> LENGTH: 24
<212> TYPE: DNA
<213> ORGANISM: Artificial Sequence
<220> FEATURE:
<223> OTHER INFORMATION: toxin sequence element

<400> SEQUENCE: 735
cgcctgtggt gcaaaaaacg cctg        24

<210> SEQ ID NO 736
<211> LENGTH: 24
<212> TYPE: DNA
<213> ORGANISM: Artificial Sequence
<220> FEATURE:
<223> OTHER INFORMATION: toxin sequence element

```
<400> SEQUENCE: 736
cgcctgtggt gcaaactgga ttgg                                              24

<210> SEQ ID NO 737
<211> LENGTH: 30
<212> TYPE: DNA
<213> ORGANISM: Artificial Sequence
<220> FEATURE:
<223> OTHER INFORMATION: toxin sequence element

<400> SEQUENCE: 737
cgcctgtggt gcaaacgcat tattaacatg                                        30

<210> SEQ ID NO 738
<211> LENGTH: 24
<212> TYPE: DNA
<213> ORGANISM: Artificial Sequence
<220> FEATURE:
<223> OTHER INFORMATION: toxin sequence element

<400> SEQUENCE: 738
cgcctgtggt gcaaatataa actg                                              24

<210> SEQ ID NO 739
<211> LENGTH: 42
<212> TYPE: DNA
<213> ORGANISM: Artificial Sequence
<220> FEATURE:
<223> OTHER INFORMATION: toxin sequence element

<400> SEQUENCE: 739
cgccgcgcga aaccgagctg gtgcggctgg gattttacct tt                          42

<210> SEQ ID NO 740
<211> LENGTH: 42
<212> TYPE: DNA
<213> ORGANISM: Artificial Sequence
<220> FEATURE:
<223> OTHER INFORMATION: toxin sequence element

<400> SEQUENCE: 740
cgccgcgcga aaccgagctg gtgcggctgg gattttaccg tg                          42

<210> SEQ ID NO 741
<211> LENGTH: 45
<212> TYPE: DNA
<213> ORGANISM: Artificial Sequence
<220> FEATURE:
<223> OTHER INFORMATION: toxin sequence element

<400> SEQUENCE: 741
cgccgcaccc tgccgaccta ttgcgcgtgg gatctgacct ttccg                       45

<210> SEQ ID NO 742
<211> LENGTH: 39
<212> TYPE: DNA
<213> ORGANISM: Artificial Sequence
<220> FEATURE:
<223> OTHER INFORMATION: toxin sequence element

<400> SEQUENCE: 742
cgcagcgatg gcaaatattg cgcgtgggat ggcacctttt                             39

<210> SEQ ID NO 743
```

```
<211> LENGTH: 42
<212> TYPE: DNA
<213> ORGANISM: Artificial Sequence
<220> FEATURE:
<223> OTHER INFORMATION: toxin sequence element

<400> SEQUENCE: 743
cgcagcgatt ggaaatattg cgcgtgggat ggcaccttta gc                    42

<210> SEQ ID NO 744
<211> LENGTH: 36
<212> TYPE: DNA
<213> ORGANISM: Artificial Sequence
<220> FEATURE:
<223> OTHER INFORMATION: toxin sequence element

<400> SEQUENCE: 744
cgcagccgcg atcagtggtg caaatataaa ctgtgg                           36

<210> SEQ ID NO 745
<211> LENGTH: 36
<212> TYPE: DNA
<213> ORGANISM: Artificial Sequence
<220> FEATURE:
<223> OTHER INFORMATION: toxin sequence element

<400> SEQUENCE: 745
cgcgtgcgcg atcagtggtg caaatataaa ctgtgg                           36

<210> SEQ ID NO 746
<211> LENGTH: 33
<212> TYPE: DNA
<213> ORGANISM: Artificial Sequence
<220> FEATURE:
<223> OTHER INFORMATION: toxin sequence element

<400> SEQUENCE: 746
agcgataaac ataaatggtg caaatggaaa ctg                              33

<210> SEQ ID NO 747
<211> LENGTH: 18
<212> TYPE: DNA
<213> ORGANISM: Artificial Sequence
<220> FEATURE:
<223> OTHER INFORMATION: toxin sequence element

<400> SEQUENCE: 747
agccataaca aatgcacc                                               18

<210> SEQ ID NO 748
<211> LENGTH: 33
<212> TYPE: DNA
<213> ORGANISM: Artificial Sequence
<220> FEATURE:
<223> OTHER INFORMATION: toxin sequence element

<400> SEQUENCE: 748
agcaaactgt ttaaactgtg caactttagc ttt                              33

<210> SEQ ID NO 749
<211> LENGTH: 42
<212> TYPE: DNA
<213> ORGANISM: Artificial Sequence
<220> FEATURE:
<223> OTHER INFORMATION: toxin sequence element

<400> SEQUENCE: 749
```
agcaaaaccg ctttgtgaa aaacatttgc aaatatgaaa tg                42

<210> SEQ ID NO 750
<211> LENGTH: 36
<212> TYPE: DNA
<213> ORGANISM: Artificial Sequence
<220> FEATURE:
<223> OTHER INFORMATION: toxin sequence element

<400> SEQUENCE: 750
agcaaaacct ggggctggtg cgcggtggaa gcgccg                      36

<210> SEQ ID NO 751
<211> LENGTH: 45
<212> TYPE: DNA
<213> ORGANISM: Artificial Sequence
<220> FEATURE:
<223> OTHER INFORMATION: toxin sequence element

<400> SEQUENCE: 751
agcccgaaac atggctggtg cgtgtgggat tggacctttc gcaaa            45

<210> SEQ ID NO 752
<211> LENGTH: 36
<212> TYPE: DNA
<213> ORGANISM: Artificial Sequence
<220> FEATURE:
<223> OTHER INFORMATION: toxin sequence element

<400> SEQUENCE: 752
agcccgaaat ggggcctgtg caactttccg atgccg                      36

<210> SEQ ID NO 753
<211> LENGTH: 45
<212> TYPE: DNA
<213> ORGANISM: Artificial Sequence
<220> FEATURE:
<223> OTHER INFORMATION: toxin sequence element

<400> SEQUENCE: 753
agcccgcgct ggggctggtg catttatagc acccgcggcg gccgc            45

<210> SEQ ID NO 754
<211> LENGTH: 45
<212> TYPE: DNA
<213> ORGANISM: Artificial Sequence
<220> FEATURE:
<223> OTHER INFORMATION: toxin sequence element

<400> SEQUENCE: 754
agcccgacct ggaaatggtg cgtgctgaaa agcccgggcc gccgc            45

<210> SEQ ID NO 755
<211> LENGTH: 36
<212> TYPE: DNA
<213> ORGANISM: Artificial Sequence
<220> FEATURE:
<223> OTHER INFORMATION: toxin sequence element

<400> SEQUENCE: 755
agcccgacct ggaaatggtg cgtgtatgcg cgcccg                      36

<210> SEQ ID NO 756
<211> LENGTH: 30
<212> TYPE: DNA

```
<213> ORGANISM: Artificial Sequence
<220> FEATURE:
<223> OTHER INFORMATION: toxin sequence element

<400> SEQUENCE: 756
agccagcatc gcctgtgcag cgtgaaagcg                                    30

<210> SEQ ID NO 757
<211> LENGTH: 33
<212> TYPE: DNA
<213> ORGANISM: Artificial Sequence
<220> FEATURE:
<223> OTHER INFORMATION: toxin sequence element

<400> SEQUENCE: 757
agccgcaaag ataaatggtg caaatatcag att                                33

<210> SEQ ID NO 758
<211> LENGTH: 33
<212> TYPE: DNA
<213> ORGANISM: Artificial Sequence
<220> FEATURE:
<223> OTHER INFORMATION: toxin sequence element

<400> SEQUENCE: 758
agccgcaaac atcgctggtg caaatatgaa att                                33

<210> SEQ ID NO 759
<211> LENGTH: 33
<212> TYPE: DNA
<213> ORGANISM: Artificial Sequence
<220> FEATURE:
<223> OTHER INFORMATION: toxin sequence element

<400> SEQUENCE: 759
agccgcaaaa cccgctggtg caaatatcag att                                33

<210> SEQ ID NO 760
<211> LENGTH: 33
<212> TYPE: DNA
<213> ORGANISM: Artificial Sequence
<220> FEATURE:
<223> OTHER INFORMATION: toxin sequence element

<400> SEQUENCE: 760
agccgccagc tgtgcaaata tgtgattgat tgg                                33

<210> SEQ ID NO 761
<211> LENGTH: 33
<212> TYPE: DNA
<213> ORGANISM: Artificial Sequence
<220> FEATURE:
<223> OTHER INFORMATION: toxin sequence element

<400> SEQUENCE: 761
agccgccgcg atcgctggtg caaatatgat ctg                                33

<210> SEQ ID NO 762
<211> LENGTH: 33
<212> TYPE: DNA
<213> ORGANISM: Artificial Sequence
<220> FEATURE:
<223> OTHER INFORMATION: toxin sequence element

<400> SEQUENCE: 762
agccgccgcg atcgctggtg caaatattat ctg                                33
```

<210> SEQ ID NO 763
<211> LENGTH: 36
<212> TYPE: DNA
<213> ORGANISM: Artificial Sequence
<220> FEATURE:
<223> OTHER INFORMATION: toxin sequence element

<400> SEQUENCE: 763
agccgccgcg gcaccaaccc ggaaaaacgc tgccgc                     36

<210> SEQ ID NO 764
<211> LENGTH: 42
<212> TYPE: DNA
<213> ORGANISM: Artificial Sequence
<220> FEATURE:
<223> OTHER INFORMATION: toxin sequence element

<400> SEQUENCE: 764
agccgccgcc atggctggtg cgtgtgggat ggcacctta gc               42

<210> SEQ ID NO 765
<211> LENGTH: 39
<212> TYPE: DNA
<213> ORGANISM: Artificial Sequence
<220> FEATURE:
<223> OTHER INFORMATION: toxin sequence element

<400> SEQUENCE: 765
agccgcacct ggaaatggtg cgtgctggcg ggcccgtgg                  39

<210> SEQ ID NO 766
<211> LENGTH: 33
<212> TYPE: DNA
<213> ORGANISM: Artificial Sequence
<220> FEATURE:
<223> OTHER INFORMATION: toxin sequence element

<400> SEQUENCE: 766
agcagcaaac ataaatggtg caaagtgtat ctg                        33

<210> SEQ ID NO 767
<211> LENGTH: 39
<212> TYPE: DNA
<213> ORGANISM: Artificial Sequence
<220> FEATURE:
<223> OTHER INFORMATION: toxin sequence element

<400> SEQUENCE: 767
agcagccgct ggaaatggtg cgtgctggcg agcccgttt                  39

<210> SEQ ID NO 768
<211> LENGTH: 39
<212> TYPE: DNA
<213> ORGANISM: Artificial Sequence
<220> FEATURE:
<223> OTHER INFORMATION: toxin sequence element

<400> SEQUENCE: 768
agcagccgct ggaaatggtg cgtgctgccg gcgccgtgg                  39

<210> SEQ ID NO 769
<211> LENGTH: 45
<212> TYPE: DNA
<213> ORGANISM: Artificial Sequence
<220> FEATURE:

<223> OTHER INFORMATION: toxin sequence element

<400> SEQUENCE: 769
acctttaaag aaaacgaaaa cggcaacacc gtgaaacgct gcgat    45

<210> SEQ ID NO 770
<211> LENGTH: 45
<212> TYPE: DNA
<213> ORGANISM: Artificial Sequence
<220> FEATURE:
<223> OTHER INFORMATION: toxin sequence element

<400> SEQUENCE: 770
acctttaaaa ccaacgaaaa cggcaacacc gtgaaacgct gcgat    45

<210> SEQ ID NO 771
<211> LENGTH: 21
<212> TYPE: DNA
<213> ORGANISM: Artificial Sequence
<220> FEATURE:
<223> OTHER INFORMATION: toxin sequence element

<400> SEQUENCE: 771
accggcctgt gcattccgcc g    21

<210> SEQ ID NO 772
<211> LENGTH: 24
<212> TYPE: DNA
<213> ORGANISM: Artificial Sequence
<220> FEATURE:
<223> OTHER INFORMATION: toxin sequence element

<400> SEQUENCE: 772
acccgcttta acgtgtgcgg caaa    24

<210> SEQ ID NO 773
<211> LENGTH: 27
<212> TYPE: DNA
<213> ORGANISM: Artificial Sequence
<220> FEATURE:
<223> OTHER INFORMATION: toxin sequence element

<400> SEQUENCE: 773
acctggccga ccgaaatttg cattgat    27

<210> SEQ ID NO 774
<211> LENGTH: 45
<212> TYPE: DNA
<213> ORGANISM: Artificial Sequence
<220> FEATURE:
<223> OTHER INFORMATION: toxin sequence element

<400> SEQUENCE: 774
acctataaag cgaacgaaaa cggcaaccag gtgaaacgct gcgat    45

<210> SEQ ID NO 775
<211> LENGTH: 45
<212> TYPE: DNA
<213> ORGANISM: Artificial Sequence
<220> FEATURE:
<223> OTHER INFORMATION: toxin sequence element

<400> SEQUENCE: 775
acctataaag aaaacgaaaa cggcaacacc gtgaaacgct gcgat    45

```
<210> SEQ ID NO 776
<211> LENGTH: 45
<212> TYPE: DNA
<213> ORGANISM: Artificial Sequence
<220> FEATURE:
<223> OTHER INFORMATION: toxin sequence element

<400> SEQUENCE: 776
acctataaag aaaacgaaaa cggcaacacc gtgcagcgct gcgat          45

<210> SEQ ID NO 777
<211> LENGTH: 45
<212> TYPE: DNA
<213> ORGANISM: Artificial Sequence
<220> FEATURE:
<223> OTHER INFORMATION: toxin sequence element

<400> SEQUENCE: 777
acctataaaa ccaacgaaaa cggcaacagc gtgcagcgct gcgat          45

<210> SEQ ID NO 778
<211> LENGTH: 54
<212> TYPE: DNA
<213> ORGANISM: Artificial Sequence
<220> FEATURE:
<223> OTHER INFORMATION: toxin sequence element

<400> SEQUENCE: 778
gtgaaaacca gcggctattg gtggtataaa aaaacctatt gccgccgcaa aagc          54

<210> SEQ ID NO 779
<211> LENGTH: 51
<212> TYPE: DNA
<213> ORGANISM: Artificial Sequence
<220> FEATURE:
<223> OTHER INFORMATION: toxin sequence element

<400> SEQUENCE: 779
tggaaacgcc gccgcagctt tgaagtgtgc gtgccgaaaa ccccgaaaac c          51

<210> SEQ ID NO 780
<211> LENGTH: 18
<212> TYPE: DNA
<213> ORGANISM: Artificial Sequence
<220> FEATURE:
<223> OTHER INFORMATION: toxin sequence element

<400> SEQUENCE: 780
ctgggcgtgt gcatgtgg          18

<210> SEQ ID NO 781
<211> LENGTH: 15
<212> TYPE: DNA
<213> ORGANISM: Artificial Sequence
<220> FEATURE:
<223> OTHER INFORMATION: toxin sequence element

<400> SEQUENCE: 781
ttttttgcgt gcgcg          15

<210> SEQ ID NO 782
<211> LENGTH: 15
<212> TYPE: DNA
<213> ORGANISM: Artificial Sequence
<220> FEATURE:
<223> OTHER INFORMATION: toxin sequence element
```

```
<400> SEQUENCE: 782
gtgctgtttt gcgtg                                                      15

<210> SEQ ID NO 783
<211> LENGTH: 18
<212> TYPE: DNA
<213> ORGANISM: Artificial Sequence
<220> FEATURE:
<223> OTHER INFORMATION: toxin sequence element

<400> SEQUENCE: 783
attgtgtttg tgtgcacc                                                   18

<210> SEQ ID NO 784
<211> LENGTH: 18
<212> TYPE: DNA
<213> ORGANISM: Artificial Sequence
<220> FEATURE:
<223> OTHER INFORMATION: toxin sequence element

<400> SEQUENCE: 784
attctgctgt tttgcagc                                                   18

<210> SEQ ID NO 785
<211> LENGTH: 15
<212> TYPE: DNA
<213> ORGANISM: Artificial Sequence
<220> FEATURE:
<223> OTHER INFORMATION: toxin sequence element

<400> SEQUENCE: 785
gtgtttgtgt gcatt                                                      15

<210> SEQ ID NO 786
<211> LENGTH: 18
<212> TYPE: DNA
<213> ORGANISM: Artificial Sequence
<220> FEATURE:
<223> OTHER INFORMATION: toxin sequence element

<400> SEQUENCE: 786
gcgcagttta tttgcctg                                                   18

<210> SEQ ID NO 787
<211> LENGTH: 18
<212> TYPE: DNA
<213> ORGANISM: Artificial Sequence
<220> FEATURE:
<223> OTHER INFORMATION: toxin sequence element

<400> SEQUENCE: 787
ggcccgtttg tgtgcgtg                                                   18

<210> SEQ ID NO 788
<211> LENGTH: 83
<212> TYPE: PRT
<213> ORGANISM: Artificial Sequence
<220> FEATURE:
<223> OTHER INFORMATION: toxin sequence element

<400> SEQUENCE: 788

Glu Cys Arg Tyr Leu Phe Gly Gly Cys Lys Thr Thr Ser Asp Cys Cys
1               5                   10                  15

Lys His Leu Gly Cys Lys Phe Arg Asp Lys Tyr Cys Ala Trp Asp Phe
            20                  25                  30
```

```
Thr Phe Ser Gly Asn Gly Asn Gly Ser Ser Thr Cys Ile Pro
        35                  40                  45

Ser Gly Gln Pro Cys Ala Asp Ser Asp Cys Cys Glu Thr Phe His
    50                  55                  60

Cys Lys Trp Val Phe Phe Thr Ser Lys Phe Met Cys Arg Arg Val Trp
65                  70                  75                  80

Gly Lys Asp

<210> SEQ ID NO 789
<211> LENGTH: 92
<212> TYPE: PRT
<213> ORGANISM: Artificial Sequence
<220> FEATURE:
<223> OTHER INFORMATION: toxin sequence element

<400> SEQUENCE: 789

Ser Ser Thr Cys Ile Pro Ser Gly Gln Pro Cys Ala Asp Ser Asp Asp
1               5                   10                  15

Cys Cys Glu Thr Phe His Cys Lys Trp Val Phe Phe Thr Ser Lys Phe
                20                  25                  30

Met Cys Arg Arg Val Trp Gly Lys Asp Asp Ser Ser Pro Tyr Val Pro
            35                  40                  45

Val Thr Thr Ser Thr Cys Ile Pro Ser Gly Gln Pro Cys Ala Asp
        50                  55                  60

Ser Asp Asp Cys Cys Glu Thr Phe His Cys Lys Trp Val Phe Phe Thr
65                  70                  75                  80

Ser Lys Phe Met Cys Arg Arg Val Trp Gly Lys Asp
                85                  90

<210> SEQ ID NO 790
<211> LENGTH: 92
<212> TYPE: PRT
<213> ORGANISM: Artificial Sequence
<220> FEATURE:
<223> OTHER INFORMATION: toxin sequence element

<400> SEQUENCE: 790

Ser Ser Thr Cys Ile Pro Ser Gly Gln Pro Cys Ala Asp Ser Asp Asp
1               5                   10                  15

Cys Cys Glu Thr Phe His Cys Lys Trp Val Phe Phe Thr Ser Lys Phe
                20                  25                  30

Met Cys Arg Arg Val Trp Gly Lys Asp Asp Ser Ser Gly Asn Gly Asn
            35                  40                  45

Gly Asn Gly Ser Ser Thr Cys Ile Pro Ser Gly Gln Pro Cys Ala Asp
        50                  55                  60

Ser Asp Asp Cys Cys Glu Thr Phe His Cys Lys Trp Val Phe Phe Thr
65                  70                  75                  80

Ser Lys Phe Met Cys Arg Arg Val Trp Gly Lys Asp
                85                  90

<210> SEQ ID NO 791
<211> LENGTH: 120
<212> TYPE: PRT
<213> ORGANISM: Artificial Sequence
<220> FEATURE:
<223> OTHER INFORMATION: toxin sequence element

<400> SEQUENCE: 791

Ser Ser Thr Cys Ile Pro Ser Gly Gln Pro Cys Ala Asp Ser Asp Asp
```

```
                1               5                  10                 15
Cys Cys Glu Thr Phe His Cys Lys Trp Val Phe Phe Thr Ser Lys Phe
            20                  25                 30

Met Cys Arg Arg Val Trp Gly Lys Asp Asp Ser Ser Gly Gly Asn Gly
            35                  40                 45

Asn Gly Asn Gly Asn Gly Asn Gly Asn Gly Ala Ala Ala Gly
 50                  55                  60

Gly Asn Gly Asn Gly Asn Gly Asn Gly Asn Gly Asn Gly Ser
 65                  70                  75                 80

Ser Thr Cys Ile Pro Ser Gly Gln Pro Cys Ala Asp Ser Asp Cys
             85                  90                 95

Cys Glu Thr Phe His Cys Lys Trp Val Phe Phe Thr Ser Lys Phe Met
            100                 105                110

Cys Arg Arg Val Trp Gly Lys Asp
            115                 120

<210> SEQ ID NO 792
<211> LENGTH: 56
<212> TYPE: PRT
<213> ORGANISM: Artificial Sequence
<220> FEATURE:
<223> OTHER INFORMATION: toxin sequence element

<400> SEQUENCE: 792

Met Ser Ala Leu Leu Ile Leu Ala Leu Val Gly Ala Ala Val Ala Ser
 1               5                  10                 15

Ser Thr Cys Ile Pro Ser Gly Gln Pro Cys Ala Asp Ser Asp Asp Cys
            20                  25                 30

Cys Glu Thr Phe His Cys Lys Trp Val Phe Phe Thr Ser Lys Phe Met
            35                  40                 45

Cys Arg Arg Val Trp Gly Lys Asp
            50                  55

<210> SEQ ID NO 793
<211> LENGTH: 98
<212> TYPE: PRT
<213> ORGANISM: Artificial Sequence
<220> FEATURE:
<223> OTHER INFORMATION: toxin sequence element

<400> SEQUENCE: 793

Met Ser Ala Leu Leu Ile Leu Ala Leu Val Gly Ala Ala Val Ala Glu
 1               5                  10                 15

Cys Arg Tyr Leu Phe Gly Gly Cys Lys Thr Thr Ser Asp Cys Cys Lys
            20                  25                 30

His Leu Gly Cys Lys Phe Arg Asp Lys Tyr Cys Ala Trp Asp Phe Thr
            35                  40                 45

Phe Ser Gly Asn Gly Asn Gly Asn Gly Ser Ser Thr Cys Ile Pro Ser
 50                  55                  60

Gly Gln Pro Cys Ala Asp Ser Asp Asp Cys Cys Glu Thr Phe His Cys
 65                  70                  75                 80

Lys Trp Val Phe Phe Thr Ser Lys Phe Met Cys Arg Arg Val Trp Gly
             85                  90                 95

Lys Asp

<210> SEQ ID NO 794
<211> LENGTH: 107
<212> TYPE: PRT
```

<213> ORGANISM: Artificial Sequence
<220> FEATURE:
<223> OTHER INFORMATION: toxin sequence element

<400> SEQUENCE: 794

Met Ser Ala Leu Leu Ile Leu Ala Leu Val Gly Ala Ala Val Ala Ser
1               5                   10                  15

Ser Thr Cys Ile Pro Ser Gly Gln Pro Cys Ala Asp Ser Asp Asp Cys
                20                  25                  30

Cys Glu Thr Phe His Cys Lys Trp Val Phe Phe Thr Ser Lys Phe Met
            35                  40                  45

Cys Arg Arg Val Trp Gly Lys Asp Asp Ser Ser Pro Tyr Val Pro Val
        50                  55                  60

Thr Thr Ser Ser Thr Cys Ile Pro Ser Gly Gln Pro Cys Ala Asp Ser
65                  70                  75                  80

Asp Asp Cys Cys Glu Thr Phe His Cys Lys Trp Val Phe Phe Thr Ser
                85                  90                  95

Lys Phe Met Cys Arg Arg Val Trp Gly Lys Asp
                100                 105

<210> SEQ ID NO 795
<211> LENGTH: 107
<212> TYPE: PRT
<213> ORGANISM: Artificial Sequence
<220> FEATURE:
<223> OTHER INFORMATION: toxin sequence element

<400> SEQUENCE: 795

Met Ser Ala Leu Leu Ile Leu Ala Leu Val Gly Ala Ala Val Ala Ser
1               5                   10                  15

Ser Thr Cys Ile Pro Ser Gly Gln Pro Cys Ala Asp Ser Asp Asp Cys
                20                  25                  30

Cys Glu Thr Phe His Cys Lys Trp Val Phe Phe Thr Ser Lys Phe Met
            35                  40                  45

Cys Arg Arg Val Trp Gly Lys Asp Asp Ser Ser Gly Asn Gly Asn Gly
        50                  55                  60

Asn Gly Ser Ser Thr Cys Ile Pro Ser Gly Gln Pro

```
Gly Asn Gly Asn Gly Asn Gly Asn Gly Ala Ala Ala Gly Gly
 65                  70                  75                  80

Asn Gly Asn Gly Asn Gly Asn Gly Asn Gly Asn Gly Ser Ser
                 85                  90                  95

Thr Cys Ile Pro Ser Gly Gln Pro Cys Ala Asp Ser Asp Cys Cys
            100                 105                 110

Glu Thr Phe His Cys Lys Trp Val Phe Phe Thr Ser Lys Phe Met Cys
        115                 120                 125

Arg Arg Val Trp Gly Lys Asp
130                 135

<210> SEQ ID NO 797
<211> LENGTH: 67
<212> TYPE: PRT
<213> ORGANISM: Artificial Sequence
<220> FEATURE:
<223> OTHER INFORMATION: toxin sequence element

<400> SEQUENCE: 797

Met Ser Ala Leu Leu Ile Leu Ala Leu Val Gly Ala Ala Val Ala Ser
 1               5                  10                  15

Ser Thr Cys Ile Pro Ser Gly Gln Pro Cys Ala Asp Ser Asp Asp Cys
            20                  25                  30

Cys Glu Thr Phe His Cys Lys Trp Val Phe Phe Thr Ser Lys Phe Met
         35                 40                  45

Cys Arg Arg Val Trp Gly Lys Asp Gly Glu Gln Lys Leu Ile Ser Glu
     50                  55                  60

Glu Asp Leu
 65

<210> SEQ ID NO 798
<211> LENGTH: 109
<212> TYPE: PRT
<213> ORGANISM: Artificial Sequence
<220> FEATURE:
<223> OTHER INFORMATION: toxin sequence element

<400> SEQUENCE: 798

Met Ser Ala Leu Leu Ile Leu Ala Leu Val Gly Ala Ala Val Ala Glu
 1               5                  10                  15

Cys Arg Tyr Leu Phe Gly Gly Cys Lys Thr Thr Ser Asp Cys Cys Lys
            20                  25                  30

His Leu Gly Cys Lys Phe Arg Asp Lys Tyr Cys Ala Trp Asp Phe Thr
         35                 40                  45

Phe Ser Gly Asn Gly Asn Gly Asn Gly Ser Ser Thr Cys Ile Pro Ser
     50                  55                  60

Gly Gln Pro Cys Ala Asp Ser Asp Asp Cys Cys Glu Thr Phe His Cys
 65                  70                  75                  80

Lys Trp Val Phe Phe Thr Ser Lys Phe Met Cys Arg Arg Val Trp Gly
                 85                  90                  95

Lys Asp Gly Glu Gln Lys Leu Ile Ser Glu Glu Asp Leu
            100                 105

<210> SEQ ID NO 799
<211> LENGTH: 118
<212> TYPE: PRT
<213> ORGANISM: Artificial Sequence
<220> FEATURE:
<223> OTHER INFORMATION: toxin sequence element
```

```
<400> SEQUENCE: 799

Met Ser Ala Leu Leu Ile Leu Ala Leu Val Gly Ala Val Ala Ser
1               5                   10                  15

Ser Thr Cys Ile Pro Ser Gly Gln Pro Cys Ala Asp Ser Asp Cys
            20                  25                  30

Cys Glu Thr Phe His Cys Lys Trp Val Phe Phe Thr Ser Lys Phe Met
        35                  40                  45

Cys Arg Arg Val Trp Gly Lys Asp Asp Ser Ser Pro Tyr Val Pro Val
    50                  55                  60

Thr Thr Ser Ser Thr Cys Ile Pro Ser Gly Gln Pro Cys Ala Asp Ser
65                  70                  75                  80

Asp Asp Cys Cys Glu Thr Phe His Cys Lys Trp Val Phe Phe Thr Ser
                85                  90                  95

Lys Phe Met Cys Arg Arg Val Trp Gly Lys Asp Gly Glu Gln Lys Leu
                100                 105                 110

Ile Ser Glu Glu Asp Leu
            115

<210> SEQ ID NO 800
<211> LENGTH: 118
<212> TYPE: PRT
<213> ORGANISM: Artificial Sequence
<220> FEATURE:
<223> OTHER INFORMATION: toxin sequence element

<400> SEQUENCE: 800

Met Ser Ala Leu Leu Ile Leu Ala Leu Val Gly Ala Val Ala Ser
1               5                   10                  15

Ser Thr Cys Ile Pro Ser Gly Gln Pro Cys Ala Asp Ser Asp Cys
            20                  25                  30

Cys Glu Thr Phe His Cys Lys Trp Val Phe Phe Thr Ser Lys Phe Met
        35                  40                  45

Cys Arg Arg Val Trp Gly Lys Asp Asp Ser Ser Gly Asn Gly Asn Gly
    50                  55                  60

Asn Gly Ser Ser Thr Cys Ile Pro Ser Gly Gln Pro Cys Ala Asp Ser
65                  70                  75                  80

Asp Asp Cys Cys Glu Thr Phe His Cys Lys Trp Val Phe Phe Thr Ser
                85                  90                  95

Lys Phe Met Cys Arg Arg Val Trp Gly Lys Asp Gly Glu Gln Lys Leu
                100                 105                 110

Ile Ser Glu Glu Asp Leu

```
Cys Arg Arg Val Trp Gly Lys Asp Asp Ser Ser Gly Asn Gly Asn
        50                  55                  60

Gly Asn Gly Asn Gly Asn G

```
                    100                 105                 110
Cys Asn Gly Ala Gly Phe Ala Thr Pro Val Thr Leu Ala Leu Val Pro
            115                 120                 125

Ala Leu Leu Ala Thr Phe Trp Ser Leu Leu
            130                 135

<210> SEQ ID NO 804
<211> LENGTH: 147
<212> TYPE: PRT
<213> ORGANISM: Artificial Sequence
<220> FEATURE:
<223> OTHER INFORMATION: toxin sequence element

<400> SEQUENCE: 804

Met Ser Ala Leu Leu Ile Leu Ala Leu Val Gly Ala Ala Val Ala Ser
1               5                   10                  15

Ser Thr Cys Ile Pro Ser Gly Gln Pro Cys Ala Asp Ser Asp Asp Cys
            20                  25                  30

Cys Glu Thr Phe His Cys Lys Trp Val Phe Phe Thr Ser Lys Phe Met
        35                  40                  45

Cys Arg Arg Val Trp Gly Lys Asp Asp Ser Ser Pro Tyr Val Pro Val
    50                  55                  60

Thr Thr Ser Ser Thr Cys Ile Pro Ser Gly Gln Pro Cys Ala Asp Ser
65                  70                  75                  80

Asp Asp Cys Cys Glu Thr Phe His Cys Lys Trp Val Phe Phe Thr Ser
                85                  90                  95

Lys Phe Met Cys Arg Arg Val Trp Gly Lys Asp Gly Glu Gln Lys Leu
            100                 105                 110

Ile Ser Glu Glu Asp Leu Gly Ala Leu Cys Asn Gly Ala Gly Phe Ala
            115                 120                 125

Thr Pro Val Thr Leu Ala Leu Val Pro Ala Leu Leu Ala Thr Phe Trp
        130                 135                 140

Ser Leu Leu
145

<210> SEQ ID NO 805
<211> LENGTH: 147
<212> TYPE: PRT
<213> ORGANISM: Artificial Sequence
<220> FEATURE:
<223> OTHER INFORMATION: toxin sequence element

<400> SEQUENCE: 805

Met Ser Ala Leu Leu Ile Leu Ala Leu Val Gly Ala Ala Val Ala Ser
1               5                   10

```
Ile Ser Glu Glu Asp Leu Gly Ala Leu Cys Asn Gly Ala Gly Phe Ala
        115                 120                 125

Thr Pro Val Thr Leu Ala Leu Val Pro Ala Leu Leu Ala Thr Phe Trp
    130                 135                 140

Ser Leu Leu
145

<210> SEQ ID NO 806
<211> LENGTH: 175
<212> TYPE: PRT
<213> ORGANISM: Artificial Sequence
<220> FEATURE:
<223> OTHER INFORMATION: toxin sequence element

<400> SEQUENCE: 806

Met Ser Ala Leu Leu Ile Leu Ala Leu Val Gly Ala Ala Val Ala Ser
1               5                   10                  15

Ser Thr Cys Ile Pro Ser Gly Gln Pro Cys Ala Asp Ser Asp Asp Cys
            20                  25                  30

Cys Glu Thr Phe His Cys Lys Trp Val Phe Phe Thr Ser Lys Phe Met
        35                  40                  45

Cys Arg Arg Val Trp Gly Lys Asp Asp Ser Ser Gly Gly Asn Gly Asn
    50                  55                  60

Gly Asn Gly Asn Gly Asn Gly Asn Gly Asn Gly Ala Ala Ala Gly Gly
65                  70                  75                  80

Asn Gly Asn Gly Asn Gly Asn Gly Asn Gly Asn Gly Asn Gly Ser Ser
                85                  90                  95

Thr Cys Ile Pro Ser Gly Gln Pro Cys Ala Asp Ser Asp Cys Cys
            100                 105                 110

Glu Thr Phe His Cys Lys Trp Val Phe Phe Thr Ser Lys Phe Met Cys
        115                 120                 125

Arg Arg Val Trp Gly Lys Asp Gly Glu Gln Lys Leu Ile Ser Glu Glu
    130                 135                 140

Asp Leu Gly Ala Leu Cys Asn Gly Ala Gly Phe Ala Thr Pro Val Thr
145                 150                 155                 160

Leu Ala Leu Val Pro Ala Leu Leu Ala Thr Phe Trp Ser Leu Leu
                165                 170                 175

<210> SEQ ID NO 807
<211> LENGTH: 1167
<212> TYPE: DNA
<213> ORGANISM: Artificial Sequence
<220> FEATURE:
<223> OTHER INFORMATION: Transmembrane T-toxin

<400> SEQUENCE: 807
atgtctgcac ttctgatcct agctcttgtt ggagctgcaa tgagcagcac ctgcattccg      60
agcggccagc cgtgtgcgga tagcgatgat tgctgcgaaa cctttcattg caaatgggtg     120
ttttttacca gcaaatttat gtgccgccgc gtgtggggca agataccgg tgttgctatc      180 gattacaaag acgatgacga caagcttgcg gccgctggta acggaaatgg caacgggaat     240
ggcaacggta acgaaacgg ggatggtact cgagttgctg tgggccagga cacgcaggag      300
gtcatcgtgg tgccacactc cttgcccttt aaggtggtgg tgatctcagc catcctggcc     360
ctggtggtgc tcaccatcat ctcccttatc atcctcatca tgctttggca gaagaaacca     420
cgtaggatcc accggccggt cgccaccatg gtgagcaagg gcgaggagct gttcaccggg     480
gtggtgccca tcctggtcga gctggacggc gacgtaaacg gccacaagtt cagcgtgtcc     540
```

```
ggcgagggcg agggcgatgc cacctacggc aagctgaccc tgaagctgat ctgcaccacc    600
ggcaagctgc ccgtgccctg cccaccctc gtgaccaccc tgggctacgg ccttcagtgc     660
ttcgcccgct accccgacca catgaagcag cacgacttct tcaagtccgc catgcccgaa    720
ggctacgtcc aggagcgcac catcttcttc aaggacgacg gcaactacaa gacccgcgcc    780
gaggtgaagt tcgagggcga caccctggtg aaccgcatcg agctgaaggg catcgacttc    840
aaggaggacg gcaacatcct ggggcacaag ctggagtaca actacaacag ccacaacgtc    900
tatatcaccg ccgacaagca gaagaacggc atcaaggcca acttcaagat ccgccacaac    960
atcgaggacg gcgccgtgca gctcgccgac cactaccagc agaacacccc catcggcgac   1020
ggccccgtgc tgctgcccga caaccactac ctgagctacc agtccaaact gagcaaagac   1080
cccaacgaga gcgccgatca catggtcctg ctggagttcg tgaccgccgc cgggatcact   1140
ctcggcatgg acgagctgta caagtaa                                      1167
```

<210> SEQ ID NO 808
<211> LENGTH: 388
<212> TYPE: PRT
<213> ORGANISM: Artificial Sequence
<220> FEATURE:
<223> OTHER INFORMATION: Transmembrane T-toxin

<400> SEQUENCE: 808

```
Met Ser Ala Leu Leu Ile Leu Ala Leu Val Gly Ala Ala Met Ser Ser
1               5                   10                  15

Thr Cys Ile Pro Ser Gly Gln Pro Cys Ala Asp Ser Asp Cys Cys
            20                  25                  30

Glu Thr Phe His Cys Lys Trp Val Phe Phe Thr Ser Lys Phe Met Cys
        35                  40                  45

Arg Arg Val Trp Gly Lys Asp Thr Gly Val Ala Ile Asp Tyr Lys Asp
    50                  55                  60

Asp Asp Asp Lys Leu Ala Ala Ala Gly Asn Gly Asn Gly Asn Gly Asn
65                  70                  75                  80

Gly Asn Gly Asn Gly Asn Gly Asp Gly Thr Arg Val Ala Val Gly Gln
                85                  90                  95

Asp Thr Gln Glu Val Ile Val Val Pro His Ser Leu Pro Phe Lys Val
            100                 105                 110

Val Val Ile Ser Ala Ile Leu Ala Leu Val Val Leu Thr Ile Ile Ser
        115                 120                 125

Leu Ile Ile Leu Ile Met Leu Trp Gln Lys Lys Pro Arg Arg Ile His
    130                 135                 140

Arg Pro Val Ala Thr Met Val Ser Lys Gly Glu Glu Leu Phe Thr Gly
145                 150                 155                 160

Val Val Pro Ile Leu Val Glu Leu Asp Gly Asp Val Asn Gly His Lys
                165                 170                 175

Phe Ser Val Ser Gly Glu Gly Glu Gly Asp Ala Thr Tyr Gly Lys Leu
            180                 185                 190

Thr Leu Lys Leu Ile Cys Thr Thr Gly Lys Leu Pro Val Pro Trp Pro
        195                 200                 205

Thr Leu Val Thr Thr Leu Gly Tyr Gly Leu Gln Cys Phe Ala Arg Tyr
    210                 215                 220

Pro Asp His Met Lys Gln His Asp Phe Phe Lys Ser Ala Met Pro Glu
225                 230                 235                 240

Gly Tyr Val Gln Glu Arg Thr Ile Phe Phe Lys Asp Asp Gly Asn Tyr
```

-continued

```
                 245                 250                 255
Lys Thr Arg Ala Glu Val Lys Phe Glu Gly Asp Thr Leu Val Asn Arg
            260                 265                 270

Ile Glu Leu Lys Gly Ile Asp Phe Lys Glu Asp Gly Asn Ile Leu Gly
        275                 280                 285

His Lys Leu Glu Tyr Asn Tyr Asn Ser His Asn Val Tyr Ile Thr Ala
    290                 295                 300

Asp Lys Gln Lys Asn Gly Ile Lys Ala Asn Phe Lys Ile Arg His Asn
305                 310                 315                 320

Ile Glu Asp Gly Gly Val Gln Leu Ala Asp His Tyr Gln Gln Asn Thr
                325                 330                 335

Pro Ile Gly Asp Gly Pro Val Leu Leu Pro Asp Asn His Tyr Leu Ser
            340                 345                 350

Tyr Gln Ser Lys Leu Ser Lys Asp Pro Asn Glu Lys Arg Asp His Met
        355                 360                 365

Val Leu Leu Glu Phe Val Thr Ala Ala Gly Ile Thr Leu Gly Met Asp
    370                 375                 380

Glu Leu Tyr Lys
385
```

<210> SEQ ID NO 809
<211> LENGTH: 9
<212> TYPE: PRT
<213> ORGANISM: Artificial Sequence
<220> FEATURE:
<223> OTHER INFORMATION: toxin sequence element

<400> SEQUENCE: 809

```
Gly Cys Lys Trp Tyr Leu Gly Asp Cys
1               5
```

<210> SEQ ID NO 810
<211> LENGTH: 38
<212> TYPE: PRT
<213> ORGANISM: Artificial Sequence
<220> FEATURE:
<223> OTHER INFORMATION: toxin sequence element

<400> SEQUENCE: 810

```

<210> SEQ ID NO 812
<211> LENGTH: 38
<212> TYPE: PRT
<213> ORGANISM: Artificial Sequence
<220> FEATURE:
<223> OTHER INFORMATION: chimeric Hv1

<400> SEQUENCE: 812

Val Val Val Val Ser Phe Gly Val Asp Ile Ala Leu Ile Phe Val
1               5                   10                  15

Gly Glu Ser Glu Ala Leu Ala Ala Ile Gly Leu Leu Val Ile Leu Arg
            20                  25                  30

Leu Trp Arg Val Ala Arg
        35

<210> SEQ ID NO 813
<211> LENGTH: 36
<212> TYPE: PRT
<213> ORGANISM: Artificial Sequence
<220> FEATURE:
<223> OTHER INFORMATION: chimeric Hv1

<400> SEQUENCE: 813

Val Val Val Val Ile Ser Phe Gly Val Asp Ile Ala Leu Leu Phe Gln
1               5                   10                  15

Glu His Gln Phe Glu Ala Leu Gly Leu Leu Ile Leu Leu Arg Leu Trp
            20                  25                  30

Arg Val Phe Arg
        35

<210> SEQ ID NO 814
<211> LENGTH: 36
<212> TYPE: PRT
<213> ORGANISM: Artificial Sequence
<220> FEATURE:
<223> OTHER INFORMATION: chimeric Hv1

<400> SEQUENCE: 814

Val Val Val Val Ile Ser Phe Gly Val Asp Ile Ala Leu Leu Phe Gln
1               5                   10                  15

Glu His Gln Phe Ala Ala Ile Gly Leu Leu Val Ile Leu Arg Leu Trp
            20                  25                  30

Arg Val Phe Arg
        35

<210> SEQ ID NO 815
<211> LENGTH: 36
<212> TYPE: PRT
<213> ORGANISM: Artificial Sequence
<220> FEATURE:
<223> OTHER INFORMATION: chimeric Hv1

<400> SEQUENCE: 815

Val Val Val Val Ile Ser Phe Ile Leu Asp Ile Val Leu Leu Phe Gln
1               5                   10                  15

Glu His Gln Phe Ala Ala Ile Gly Leu Leu Val Ile Leu Arg Leu Trp
            20                  25                  30

Arg Val Phe Arg
        35

<210> SEQ ID NO 816

```
<211> LENGTH: 38
<212> TYPE: PRT
<213> ORGANISM: Artificial Sequence
<220> FEATURE:
<223> OTHER INFORMATION: chimeric Hv1

<400> SEQUENCE: 816

Val Val Val Val Ser Phe Ile Leu Asp Ile Val Leu Phe Val
 1               5                  10                  15

Gly Glu Ser Glu Ala Leu Ala Ala Ile Gly Leu Leu Val Ile Leu Arg
            20                  25                  30

Leu Trp Arg Val Ala Arg
        35

<210> SEQ ID NO 817
<211> LENGTH: 36
<212> TYPE: PRT
<213> ORGANISM: Artificial Sequence
<220> FEATURE:
<223> OTHER INFORMATION: chimeric Hv1

<400> SEQUENCE: 817

Val Val Val Val Ile Ser Phe Gly Val Asp Ile Ala Leu Ile Phe Gln
 1               5                  10                  15

Glu His Gln Phe Glu Ala Leu Gly Leu Leu Ile Leu Leu Arg Leu Trp
            20                  25                  30

Arg Val Phe Arg
        35

<210> SEQ ID NO 818
<211> LENGTH: 36
<212> TYPE: PRT
<213> ORGANISM: Artificial Sequence
<220> FEATURE:
<223> OTHER INFORMATION: chimeric Hv1

<400> SEQUENCE: 818

Val Val Val Val Ile Ser Phe Gly Val Asp Ile Ala Leu Ile Phe Gln
 1               5                  10                  15

Glu His Gln Phe Glu Ala Leu Gly Leu Leu Ile Leu Leu Arg Leu Trp
            20                  25                  30

Arg Val Phe Arg
        35

<210> SEQ ID NO 819
<211> LENGTH: 36
<212> TYPE: PRT
<213> ORGANISM: Artificial Sequence
<220> FEATURE:
<223> OTHER INFORMATION: chimeric Hv1

<400> SEQUENCE: 819

Val Val Val Val Ile Ser Phe Ile Leu Asp Val Leu Leu Phe Gln
 1               5                  10                  15

Glu His Gln Phe Glu Ala Leu Gly Leu Leu Ile Leu Leu Arg Leu Trp
            20                  25                  30

Arg Val Phe Arg
        35

<210> SEQ ID NO 820
<211> LENGTH: 36
<212> TYPE: PRT
<213> ORGANISM: Artificial Sequence
```

```
<220> FEATURE:
<223> OTHER INFORMATION: chimeric Hv1

<400> SEQUENCE: 820

Val Val Val Val Ile Ser Phe Gly Val Asp Ile Ala Leu Leu Phe Gln
1               5                   10                  15

Glu His Gln Phe Glu Ala Leu Gly Leu Leu Val Ile Leu Arg Leu Trp
            20                  25                  30

Arg Val Phe Arg
            35

<210> SEQ ID NO 821
<211> LENGTH: 36
<212> TYPE: PRT
<213> ORGANISM: Artificial Sequence
<220> FEATURE:
<223> OTHER INFORMATION: chimeric Hv1

<400> SEQUENCE: 821

Val Val Val Val Ile Ser Phe Ile Leu Asp Ile Val Leu Leu Phe Gln
1               5                   10                  15

Glu His Gln Phe Glu Ala Leu Gly Leu Leu Val Ile Leu Arg Leu Trp
            20                  25                  30

Arg Val Phe Arg
            35
```

HV1 MODULATORS AND USES

CROSS REFERENCE TO RELATED APPLICATIONS

This application is a national phase application claiming benefit of priority under 35 U.S.C. § 371 to International (PCT) Patent Application serial number PCT/US2017/068896, filed Dec. 29, 2017, now pending, which claims priority from provisional patent application U.S. Ser. No. 62/441,097, filed Dec. 30, 2016, and provisional patent application U.S. Ser. No. 62/447,433, filed Jan. 17, 2017, the contents of which are incorporated herein in entirety. The aforementioned applications are expressly incorporated herein by reference in their entirety and for all purposes.

SEQUENCE LISTING

The instant application contains a Sequence Listing which has been submitted electronically in ASCII format and is hereby incorporated by reference in its entirety.

BACKGROUND

Voltage-gated ion channels facilitate the transfer of ions across cell membranes and function as key components of essential cellular processes. One particular type of voltage-gated ion channel is the voltage-gated proton channel (Hv1). Hv1 is a transmembrane protein that regulates the transfer of protons across cell membranes. When the Hv1 channel is open, protons permeate the channel and cross the cellular membrane.

The Hv1 channel is expressed in many different tissues and is associated with a wide variety of physiological and pathological processes. For example, Hv1 channels may play a role in immune defense, sperm activity, and cancer progression. For these and other reasons, Hv1 may be an attractive drug target (Seredenina, T., et al. "Voltage-gated proton channels as novel drug targets: from NADPH oxidase regulation to sperm biology." *Antioxid Redox Signal.* 10; 23(5): 490-513 (2015)). However, clinically compatible Hv1 activators or inhibitors are not known. For these reasons, there is a need for the development of activators and inhibitors of Hv1 channels.

SUMMARY

The present disclosure provides technologies relating to modulation of Hv1 channels. Among other things, the present disclosure provides Hv1 modulating agents, and various compositions and methods relating thereto.

In some embodiments, an Hv1 modulating agent is or comprises an engineered polypeptide component having an inhibitor cysteine knot (ICK)-like structural motif.

In some embodiments, an Hv1 modulating agent is or comprises an engineered polypeptide component that includes one or more toxin sequence elements, each of which has an amino acid sequence that is substantially identical to, but differs from, that of a corresponding element found in a wild-type toxin.

In some embodiments, an Hv1 modulating agent shares one or more cysteines with a wild-type toxin sequence. In some embodiments, an Hv1 modulating agent shares the same approximate relative position of cysteines with a wild-type toxin.

In some embodiments, an Hv1 modulating agent is or comprises a polypeptide sequence set forth in Tables 2A, 3A, and 4.

In some embodiments, an Hv1 modulating agent is encoded by a nucleotide sequence that is or comprises a sequence set forth in Tables 2C and 3B.

In some embodiments, an Hv1 modulating agent can be expressed from a vector including a nucleic acid sequence encoding the Hv1 modulating agent.

In some embodiments, an Hv1 modulating agent binds to the external surface of human Hv1. In some embodiments, an Hv1 modulating agent binds to the S3-S4 external loop region of human Hv1.

In some embodiments, an Hv1 modulating agent inhibits human Hv1 function. For example, in some embodiments, an Hv1 modulating agent may decrease or block proton current. In some embodiments, an Hv1 modulating agent may reduce the number or likelihood of Hv1 channel opening. In some embodiments, an Hv1 modulating agent may increase the rate of Hv1 channel closing.

In some embodiments, an Hv1 modulating agent activates human Hv1 function. For example, in some embodiments, an Hv1 modulating agent increases proton current. In some embodiments, an Hv1 modulating agent increase the rate of Hv1 channel opening. In some embodiments, an Hv1 modulating agent slows the rate of Hv1 channel closing.

In some embodiments, an Hv1 modulating agent inhibits sperm capacitation.

In some embodiments, an Hv1 modulating agent decreases reactive oxygen species (ROS) production in white blood cells.

The present invention further provides various reagents and methods associated with Hv1 modulating agents including, for example, systems for identifying and characterizing them, strategies for preparing them, and various therapeutic compositions and methods relating to them. Further description of certain embodiments of these aspects, and others, of the present invention is presented below.

BRIEF DESCRIPTION OF THE DRAWING

FIG. 2 Presents the amino acid sequences of exemplary Hv1 modulating agents C5 and C6 and the amino acid sequence of hanatoxin (HaTx1). Sequence elements corresponding to sequences in Table 3A are labeled. Conserved cysteine residues are highlighted. NT, N-terminus. CT, C-terminus.

FIG. 3 Presents exemplary T-toxin amino acid sequences and effects of T-toxins on hHv1 function. (FIG. 3A) depicts an exemplary T-toxin comprising the amino acid sequence of Hv1 modulating agent C6 linked to a trypsin secretory signal sequence at the N-terminus, a 16 amino acid linker with embedded C-Myc epitope tag at the C-terminus, and a hydrophobic sequence for GPI attachment from the mammalian Lynx1 peptide. (FIG. 3B) depicts an exemplary T-toxin comprising an N-terminal trypsin secretory signal sequence, the amino acid sequence of HaTx1 linked by a flexible 7 amino acid linker to C6, a C-Myc epitope embedded into a 6 amino acid linker at the C-terminus, and a hydrophobic sequence for GPI attachment. (FIG. 3C) depicts an exemplary T-toxin comprising an N-terminal trypsin secretory signal sequence, C6 dimers linked by a rigid 10 amino acid linker, a C-Myc epitope embedded into a 6 amino acid linker at the C-terminus, and a hydrophobic sequence for GPI attachment. (FIG. 3D) depicts an exemplary T-toxin comprising an N-terminal trypsin secretory signal sequence, C6 dimers linked by a flexible 10 amino acid linker, a C-Myc epitope embedded into a 6 amino acid linker at the C-terminus, and a hydrophobic sequence for GPI attachment. (FIG. 3E) depicts an exemplary T-toxin comprising an N-terminal trypsin secretory signal sequence, C6 dimers linked by long flexible 38 amino acid linker, a C-Myc epitope embedded into a 6 amino acid linker at the C-terminus, and a hydrophobic sequence for GPI attachment. (FIG. 3F) shows inhibition of wild-type hHv1 measured as unblocked fractional current in oocytes expressing only hHv1 or both hHv1 and T-toxin.

FIG. 4 Illustrates activating and inhibiting effects of exemplary Hv1 modulators C5 and C6 on hHv1. Whole-cell patch clamp recordings were performed on HEK-293T cells over-expressing hHv1. Proton currents are shown with C5 (FIG. 4A) and C6 (FIG. 4B) versus current without any peptide or modifications (black traces).

FIG. 5 Illustrates that Hv1 modulating agent C6 affects response of sperm to progesterone, but not other changes related to sperm capacitation. C6 did not affect the vitality (FIG. 5A), the protein tyrosine phosphorylation (FIG. 5F and FIG. 5G), or the cholesterol content of the membranes (FIG. 5H). C6 did not significantly alter the mobility of sperm (FIGS. 5B-5E). C6 did affect the response of sperm to progesterone. The increase of cytosolic calcium triggered by progesterone is diminished in the presence of the Hv1 modulating agent and the acrosome reaction induced by the hormone is inhibited (FIGS. 5I-5K). All responses with C6 were compared to control peptide. VSL, velocity straight line; PROG, progression; VAP, velocity average path; Capac, capacitating medium (Human tubal fluid (HTF) media supplemented with 5 mg/mL BSA; as described, for example, in Pocognoni, C. A., et al., "PerfringolysinO as a useful tool to study human sperm physiology," *Fertility & Sterility* 99(1): 99-106(2013)).

FIG. 6 Demonstrates that Hv1 modulating agent C6 blocks production of ROS in human blood cells in a dose-dependent manner. Phorbol myristate acetate (PMA) was used to stimulate ROS production as shown by the increase of fluorescence over baseline (blood). The known inhibitor of Hv1, zinc (Zn), blocks to background levels. Various concentrations of C6 also blocked fluorescence intensity in a dose-dependent manner. Two other toxins that block potassium channels with nM affinity (Moka and KTX) had no effect. FIG. 6A shows relative fluorescence intensity, measured at 590 nM (excited at 530 nM) using Amplex Red, which reacts with ROS to give a fluorescent product, for whole blood alone, PMA-stimulated whole blood, and PMA-stimulated whole blood with various inhibitors. 10 μM of MOKA toxin was used as a control. FIG. 6B shows dose response curve plotted as the percentage of fluorescence from PMA-stimulated whole blood blocked versus concentration of C6 present. MOKA toxin and KTX were used as controls and showed no effect at 10 μM.

FIG. 7 Presents an exemplary T-toxin nucleotide (FIG. 7A; SEQ ID NO: 807) and amino acid (FIG. 7B; SEQ ID NO: 808) sequence comprising a PDGFR transmembrane helix which links an internal mVenus fluorescent protein to an external C6.

FIG. 8 Illustrates effects of Hv1 modulating agent C6 tethered to HEK-293T cell surfaces via a PDGFR transmembrane link. (FIG. 8A) shows current recordings for WT Hv1 without any tether or peptide (top), expressed with the transmembrane mVenus without a peptide sequence (middle), or expressed with tethered mVenus-C6 (bottom). (FIG. 8B) shows WT Hv1 current with various amounts of tethered toxin plasmid normalized to current with the transmembrane tether without peptide (I(C6)/I(notox)) or to WT Hv1 with no tether expressed (I(C6)/I(Hv1)). (FIG. 8C) demonstrates small shifts observed in g-V normalized to the maximum seen for each condition. Black line is WT Hv1, Green line is WT Hv1 with transmembrane without tether, Red line is WT-Hv1 with tethered C6. (FIG. 8D) demonstrates current-voltage (I-V) showing the decrease in current in WT (black), WT with tether without toxin (green) or WT with tethered C6 (red). (FIG. 8E) shows amount of current blocked by 1 μg of expressed tethered C6 in peak (end of pulse) or tail current. Current is normalized to the maximum of either WT alone (I(C6)/I(Hv1)) or the WT co-expressed with a tether without toxin (I(C6)/I(notox)). (FIG. 8F) shows FRET measurements between Hv1-TFP and mVenus transmembrane without toxin or with C6. Normalized fluorescence versus time is fit with a single exponential decay to determine the time constants for fluorescence decay with or without toxin. (FIG. 8G) shows average taus measured with the tether without toxin and with the tether with C6 from the fit in FIG. 8F. Increase in decay rate indicates FRET and indicates an interaction between C6 and Hv1.

FIG. 9 Demonstrates that Hv1 modulating agent C6 targets an S3-S4 external loop region of hHv1. (FIG. 9A) illustrates sequence alignments of *Ciona intestinalis* Hv1 (CiHv1, yellow), human Hv1 (hHv1, cyan), a chimeric Hv1 where an S3-S4 external loop region from hHv1 replaces a corresponding region from CiHv1 (hS3S4CiHv1), a chimeric Hv1 where an S3-S4 external loop region from CiHv1 replaces an hHv1 loop region, as well as other examples of chimeric sequences. If C6 blocks (YES) or does not (NO) block the channel is indicated. X indicates that proton currents were not measurable. (FIG. 9B) demonstrates a representative trace (left) for CiHv1 with 1 μM C6 (red trace) or without (black trace), a representative trace (middle) for hS3S4CiHv1 which is sensitive to C6 (red trace, 1 μM C6), and a representative trace (right) for CiS3S4hHv1 which is insensitive to C6 (red trace, 1 μM C6). Black traces are current without any applied peptide. (FIG. 9C) demonstrates results from a cysteine scan of part of the transferred epitope. Bars are the amount of current with 1 μM C6 normalized to current without toxin (Itox/Ictr). Many residues show decreased affinity but only G199 and E192 show dramatically different effects to the WT (first bar).

DEFINITIONS

Component: The term "component" as used herein refers to a relevant part, portion, or moiety of an entity of interest. For example, in some embodiments, an entity of interest may be a polypeptide component.

Comprising: A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Figure 1:
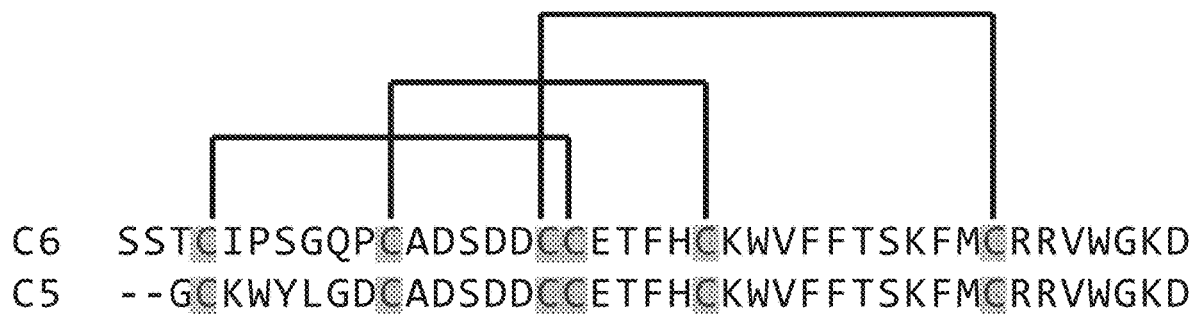
FIG. 1 Presents an amino acid sequence alignment of exemplary Hv1 modulating agents C5 and C6. Six conserved cysteine residues and three disulfide bridges of an inhibitor cysteine knot (ICK)-like structural motif are indicated.
Figure 4:
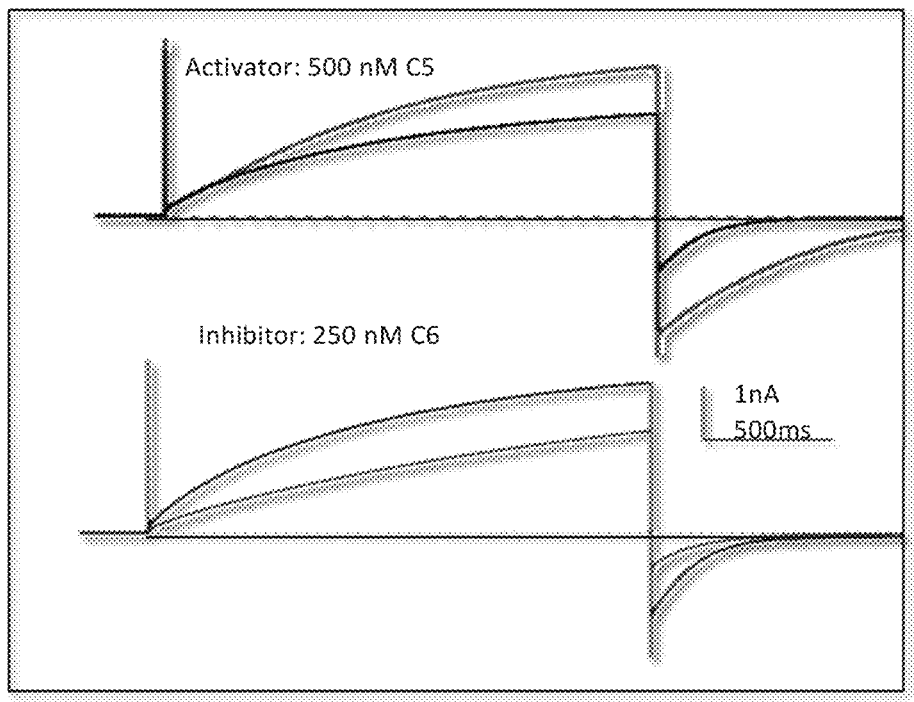
Figure 5:
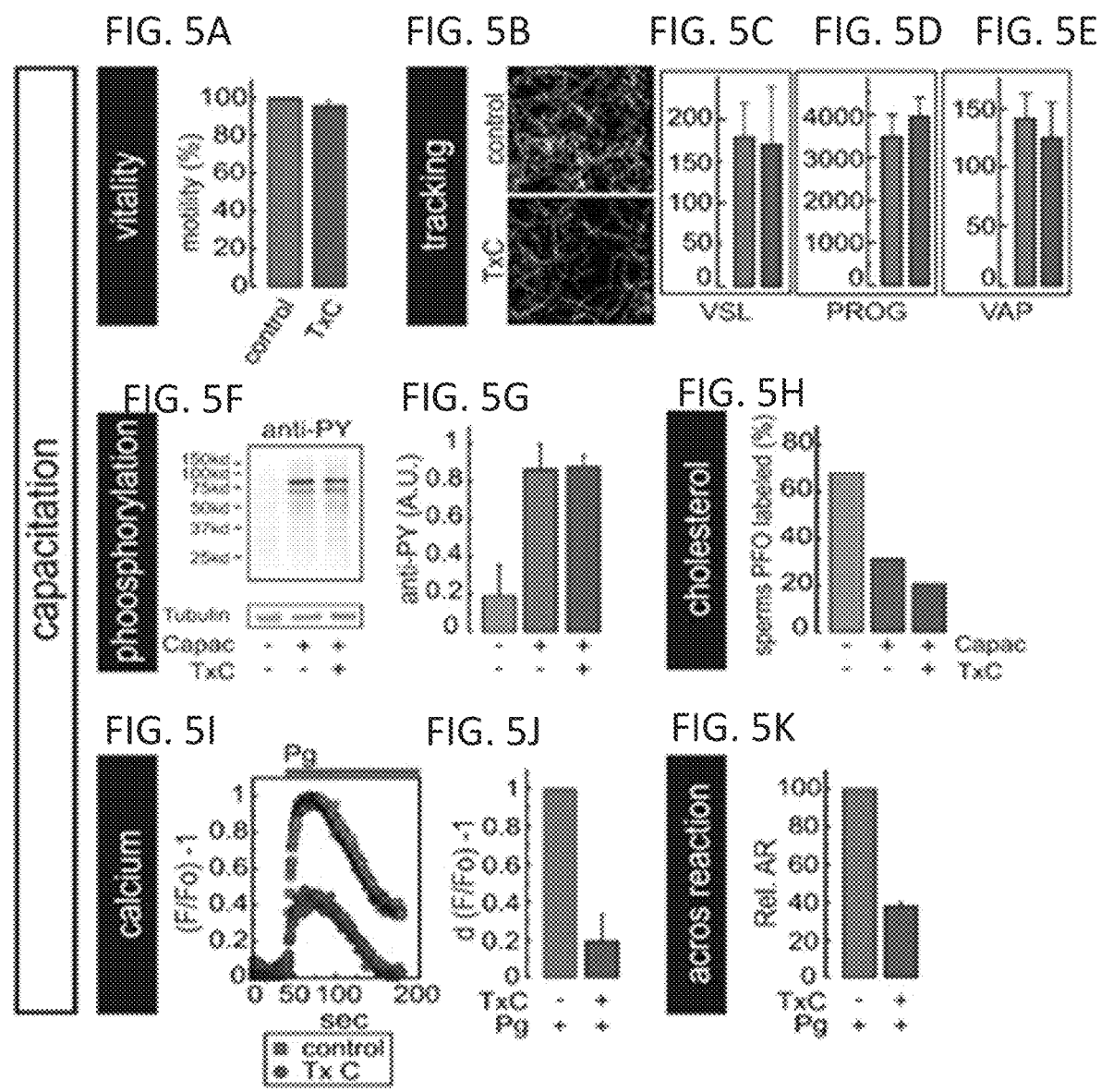
Figure 8D:
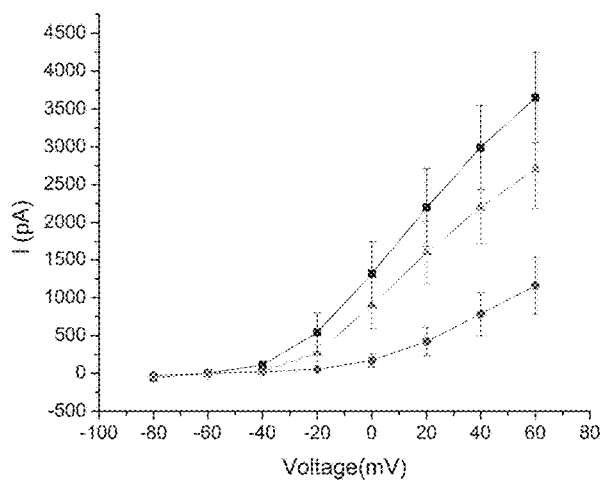
Figure 8E:
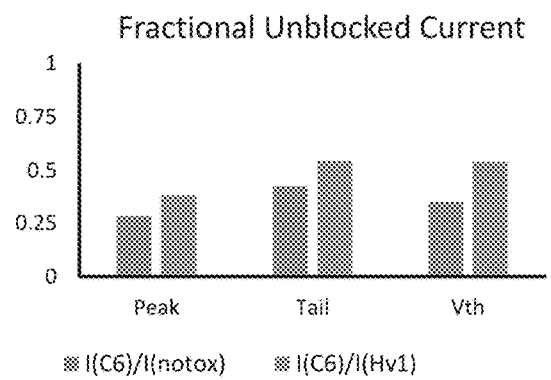
Figure 8F:
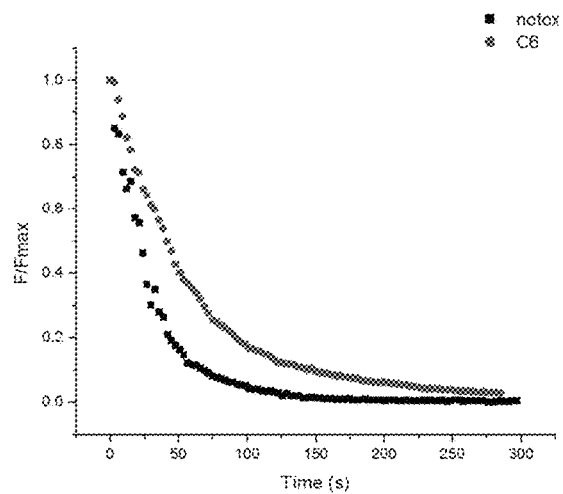
Figure 8G:
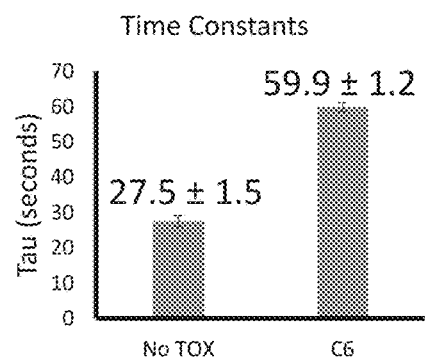

Corresponding to: As used herein, the term "corresponding to" designates the position/identity of a structural element in a compound or composition through comparison with an appropriate reference compound or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids.

Engineered: In general, the term "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. For example, in some embodiments of the present invention, an engineered polynucleotide comprises a regulatory sequence that is found in nature in operative association with a first coding sequence but not in operative association with a second coding sequence, is linked by the hand of man so that it is operatively associated with the second coding sequence. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, progeny of an engineered polynucleotide or cell are typically still referred to as "engineered" even though the actual manipulation was performed on a prior entity.

Inhibitor Cysteine Knot (ICK)-like structural motif: As used herein, the term "inhibitor cysteine knot (ICK)-like structural motif" designates a peptide structure that has substantial structural similarity to an ICK structural motif. In some embodiments, an ICK-like structural motif has three disulfide bridges. In some embodiments, an ICK-like structural motif has two, one, or zero disulfide bridges. In some embodiments, an ICK-like structural motif has three beta strands. In some embodiments, an ICK-like structural motif has two, one, or zero beta strands. In some embodiments, an ICK-like structural motif has an amino acid sequence with six conserved cysteine residues of an ICK structural motif. In some embodiments, an ICK-like structural motif has an amino acid sequence with 5, 4, 3, 2, 1, or 0 conserved cysteine residues of an ICK structural motif.

Hv1 associated disease or condition: As used herein, the phrase "Hv1 associated disease or condition" refers to a disease, disorder, or condition in which cells exhibit relatively abnormal, uncontrolled, or undesired Hv1 channel function. Abnormal or uncontrolled Hv1 function may arise from, among other mechanisms, dysregulatd phosphorylation, differential isoform expression, or single nucleotide polymorphisms (SNPs) that alter Hv1 properties. In some embodiments, abnormal or uncontrolled Hv1 function includes abnormal activation or opening of Hv1 channels. In some embodiments, abnormal or uncontrolled Hv1 function includes abnormal closing of Hv1 channels. In some embodiments, cells that exhibit abnormal or uncontrolled Hv1 function display an abnormal level or regulation of transmembrane proton flux, transmembrane voltage and/or transmembrane pH gradient ($\Delta$pH, defined as $pH_o$-$pH_i$). In some embodiments, such cells display an abnormal level or regulation of NOX enzyme activity and/or reactive oxygen species (ROS) production. A variety of types of Hv1 associated diseases or conditions may exist, for example, inflammation, autoimmunity, cancer, asthma, brain damage in ischemic stroke, Alzheimer's disease, infertility, and numerous other conditions. In some embodiments, an Hv1 associated disease or condition refers to a condition in which Hv1 channel function is within normal, but undesired range. For example, an Hv1 associated disease or condition may refer to a condition in which changing Hv1 function would achieve a more preferred physiological outcome than not changing Hv1 function. For example, suppression of Hv1 function in human sperm may be used as a form of birth control to block fertilization.

Library: As used herein, the term "library" refers to a collection of members. A library may be comprised of any type of members. For example, in some embodiments, a library comprises a collection of phage particles. In some embodiments, a library comprises a collection of peptides. In some embodiments, a library comprises a collection of cells. A library typically includes diverse members (i.e., members of a library differ from each other by virtue of variability in an element, such as a peptide sequence, between members). For example, a library of phage particles can include phage particles that express unique peptides. A library of peptides can include peptides having diverse sequences. A library can include, for example, at least $10^1$, $10^2$, $10^3$, $10^4$, $10^5$, $10^6$, $10^7$, $10^8$, $10^9$, or more unique members.

Modulate: The term "modulate" is used to refer to the characteristic of changing the state and/or nature of an entity of interest. For example, a particular agent is considered to modulate an entity of interest if the presence, level, and/or form of the agent correlates with a change in the presence, level, and/or form of the entity of interest. In some embodiments, to modulate means to increase activity. In some embodiments, to modulate means to antagonize, inhibit, or reduce activity. In some embodiments, modulation involves binding or direct interaction between a modulator and the entity of interest. In some embodiments, to modulate means to affect level of a target entity of interest; alternatively or additionally, in some embodiments, to modulate means to affect activity of a target entity without affecting level of the target entity. In some embodiments, to modulate means to affect both level and activity of a target entity of interest. In some embodiments, effects of a modulator are apparent at the level of the whole-cell, tissue, system (e.g. immune system), or whole organism.

Pharmaceutical Composition: As used herein, the term "pharmaceutical composition" refers to a composition that is suitable for administration to a human or animal subject. In some embodiments, a pharmaceutical composition comprises an active agent formulated together with one or more pharmaceutically acceptable carriers. In some embodiments, the active agent is present in a unit dose amount appropriate for administration in a therapeutic regimen. In some embodiments, a therapeutic regimen comprises one or more doses administered according to a schedule that has been determined to show a statistically significant probability of achieving a desired therapeutic effect when administered to a subject or population in need thereof. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces. In some embodiments, a pharmaceutical composition is intended and suitable for administration to a human subject. In some embodiments, a pharmaceutical composition is sterile and substantially pyrogen-free.

Polypeptide: As used herein, the term "polypeptide" refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide is referred to as a "peptide."

Substantial identity: As used herein, the term "substantial identity" refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., Basic local alignment search tool, J. Mol. Biol., 215(3): 403-410, 1990; Altschul et al., Methods in Enzymology; Altschul et al., Nucleic Acids Res. 25:3389-3402, 1997; Baxevanis et al., Bioinformatics: A Practical Guide to the Analysis of Genes and Proteins, Wiley, 1998; and Misener, et al, (eds.), Bioinformatics Methods and Protocols (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial structural similarity: As used herein, the term "substantial structural similarity" refers to presence of shared structural features such as presence and/or identity of particular amino acids at particular positions. In some embodiments the term "substantial structural similarity" refers to presence and/or identity of structural elements (for example: loops, sheets, helices, H-bond donors, H-bond acceptors, glycosylation patterns, salt bridges, and disulfide bonds). In some embodiments, the term "substantial structural similarity" refers to three dimensional arrangement and/or orientation of atoms or moieties relative to one another (for example: distance and/or angles between or among them between an agent of interest and a reference agent).

Toxin: As used herein, the term "toxin" refers to all peptides and/or proteins, of any amino acid length and sequence, in either monomeric or multimeric forms, naturally present in animal venoms or poisons and their non-venom homologues. Non-venom homologues include any molecule present outside of a venom gland or not used as a venom component but similar in sequence, structure and/or function to toxins. Animal toxins include all molecules identified or inferred by any means (e.g., physical, chemical, biochemical, genetic, genomic, proteomic) from animal venoms or poisons, including but not limited to isolation from crude venoms, isolation from venom gland tissues or extracts, identification based on venom gland proteome/proteomics, venome/venomics, transcriptome, and/or EST analysis. In some embodiments, a toxin is a toxin from a venom or poison of a centipede, lizard, scorpion, sea anemone, snail, snake, spider, or toad. In some embodiments, the amino acid sequence of a toxin can be a sequence that encodes an expressed and/or active toxin, or a sequence showing substantial identity thereto. In some embodiments, the amino acid sequence of a toxin is substantially identical to that of a wild-type toxin. In some embodiments, the amino acid sequence of a toxin is less than 100, 90, 80, 70, 60, 50, 40, 30, 20 or fewer amino acids long. In some embodiments, the amino acid sequence of a toxin is more than 5, 6, 7, 8 9, 10, 11, 12, 13, 14, 15, 16, 17, 18, 19, 20, 21, 22, 23, 24, 25, 26, 27, 28, 29, 30 or more amino acids long. Representative toxins, and their amino acid sequences and source designations are presented in Table 1.

Toxin Sequence Element: The phrase "toxin sequence element" is used herein to refer to a stretch of amino acid sequence, typically at least 5 amino acids in length, that corresponds to an element found in a wild-type toxin. In some embodiments, a toxin sequence element has a length within a range of about 5 to about 100 amino acids. In some embodiments, a toxin sequence has a length of about 5, 6, 7, 8, 9, 10, 11, 12, 13, 14, 15, 16, 17, 18, 19, 20, 21, 22, 23, 24, 25, or more amino acids. In some embodiments, a toxin sequence element has a length within a range of about 5 to about 25 amino acids. In some embodiments, a toxin sequence element differs from a corresponding sequence element found in the wild-type toxin; for example, in some embodiments, a toxin sequence element differs from its corresponding wild-type sequence element, by a sequence variation that includes an addition, substitution, or deletion of at least one amino acid residue. In some embodiments, the variation alters (e.g., adds, substitutes or deletes) 1, 2, 3, 4, 5 or more residues. In some embodiments, the variation alters exactly 1 residue. In some embodiments, the variation alters exactly 2 residues. In some embodiments, the variation alters exactly 3 residues. In some embodiments, the variation alters not more than 5, 4, 3, 2, or 1 residues. In some embodiments, the variation alters fewer than 15%, 14%, 13%, 12%, 11%, 10%, 9%, 8%, 7%, 6%, 5%, 4%, 3%, 2%, or 1% of the relevant residues. In some embodiments, a toxin sequence element corresponds to a full-length toxin. In some embodiments, a toxin sequence element corresponds to a full-length reference wild-type toxin. In some embodiments, a toxin sequence element corresponds to a portion of a reference wild-type toxin. In some embodiments, a toxin sequence element corresponds to a portion of a wild-type reference toxin, which portion is bounded on at least one end by a cysteine residue (e.g., a cysteine residue that, in the wild-type toxin, may participate in a disulfide bond).

Wild-type: As used herein, the term "wild-type" refers to a form of an entity (e.g., a polypeptide or nucleic acid) that has a structure and/or activity as found in nature in a "normal" (as contrasted with mutant, diseased, altered) state or context. In some embodiments, more than one "wild type" form of a particular polypeptide or nucleic acid may exist in nature, for example as "alleles" of a particular gene or normal variants of a particular polypeptide. In some embodiments, that form (or those forms) of a particular polypeptide or nucleic acid that is most commonly observed in a population (e.g., in a human population) is the "wild-type" form.

DETAILED DESCRIPTION OF CERTAIN EMBODIMENTS

Hv1 Channel

The voltage-gated proton channel (Hv1), also known as the hydrogen voltage-gated channel 1 (HVCN1), is a protein that in humans is encoded by the HVCN1 gene. There are at least ten species with functionally confirmed Hv1 genes, including human (hHv1) and mouse (mHv1), in addition to several species with predicted Hv1 genes that have not yet been confirmed by expression and electrophysiology studies. Among its functions, Hv1 transports protons (mHv1) across cell membranes (DeCoursey, T. E. "The voltage-gated proton channel: a riddle, wrapped in a mystery, inside an enigma." *Biochemistry* 54(21): 3250-68 (2015)). In humans, the Hv1 protein is expressed in a variety of tissues and body systems, including the immune system, the circulatory system, and the reproductive system. In these and other areas, Hv1 plays important physiological functions, such as regulation of cell charge and pH. In the present disclosure the terms Hv1 channel and Hv1 are equivalent.

Hv1 belongs to a superfamily of voltage-gated ion channels. Similar to other voltage-gated ion channels, Hv1 is a transmembrane protein that facilitates the transfer of ions (e.g. $H^+$) across cell membranes. Also like other voltage-gated ion channels, Hv1 has a voltage sensor domain (VSD). However, Hv1 channels also have several unique features that distinguish them from other voltage-gated ion channels. For example, Hv1 channels are exquisitely selective for protons, whereas other ion channels such as potassium channels have some permeability to other ions besides $K^+$.

According to the National Center for Biotechnology Information (NCBI) Gene database, there are three transcript variants for human HVCN1. Variant 1 (NM_001040107.1) represents the longest transcript. Variant 2 (NM_032369.3) differs in the 5' untranslated region (UTR) compared to variant 1. Variants 1 and 2 encode the same protein (isoform 1), which is 273 amino acids. Variant 3 (NM_001256413.1) differs in the 5' UTR, lacks a portion of the 5' coding region, and initiates translation at a downstream start codon compared with variant 1. The resulting protein (isoform 2) is shorter (253 amino acids) and has a distinct N-terminus compared to isoform 1. The longer isoform (isoform 1) is considered to be most widely expressed, while the shorter isoform (isoform 2) has been found only in B-lymphocytes and exhibits functionally important differences compared to the full-length protein. Recently, another Hv1 isoform (Hv1Sper, post-translationally cleaved) was reported in human sperm. At least seven validated, nonsynonymous single-nucleotide polymorphisms (SNPs) for human HVCN1 have been identified. Only two of these seven have a frequencies above 1%.

Hv1 Channel Structure

The structure of the Hv1 channel differs from other voltage-gated ion channels. Other voltage-gated ion channels consist of six transmembrane segments, with segments S1-S4 constituting the VSD that detects changes in membrane potential and S5-S6 forming the pore domain responsible for selective ion permeation. In contrast, Hv1 channels lack the pore domain (S5-S6). Instead, Hv1 channels have the first four transmembrane segments (S1-S4) and assemble as a dimer with each subunit containing its own permeation pathway. The N-terminus and C-terminus of Hv1 are on the cytoplasmic side. The main region of attachment of the Hv1 channel dimer is in the intracellular C-terminus.

Hv1 from several multicellular species (human, mouse, and the sea squirt *Ciona intestinalis*) exist as dimers, whereas Hv1 in several unicellular species are predicted to exist as monomers. When Hv1 from species with dimeric channels are forced to express as monomers, the channels open (activate) several-fold faster than dimeric forms and their $g_H$-V relationship is somewhat (10-15 mV) more positive. The promoters of each monomer in an Hv1 channel dimer gate cooperatively, such that both promoters must undergo voltage-induced conformational change before either conduction pathway is open. Consequently, the probability that dimeric Hv1 will open is more dependent on voltage compared to the monomeric form.

Certain amino acids may be important for Hv1 selectivity for protons. The acidic amino acid aspartate at position 112 (Asp112), which is located in the middle of the S1 transmembrane helix, is one such amino acid important for Hv1 proton selectivity. Mutating Asp112 to any other amino acid except Glu (another acidic amino acid) converts hHv1 channel into an anion channel. Asp112 interacts with arginine (Arg208) in the S4 segment via two hydrogen bonds, with Asp or Arg protonated. Introducing a hydronium ion, $H3O^+$, into either configuration results in protonation of Asp, breaking of the hydrogen bonds, and resulting in a neutral water molecule that mediates interactions in $AspH^0$—$H_2O^0$-$Arg^+$. From this protonated selectivity filter configuration, reprotonation of the water molecule results in net H$^+$ permeation. Therefore, the unique abilities of protons to travel with a water molecule and to transfer readily and reversibly with other groups is exploited by Hv1 in achieving proton selectivity. Proton selectivity can also be preserved when Asp is replaced with Glu, or when Arg is replaced with Lys.

Besides the selectivity filter, there is another hydrophobic region in hHv1 predicted by molecular dynamic simulations. This second region is a highly conserved Phe150. The proton may inject its own water wire through this hydrophobic region. Thus, protons are uniquely able to open the selectivity filter and to hydrate dry regions of the pore.

Hv1 Channel Mechanism

Hv1 channels are uniquely selective for protons, with detectably no other ion permeation. The requirement of such selectivity is crucial because the concentration of protons in mammalian cells or bodily fluids is orders of magnitude lower than that of other major cations like Na$^+$ and K$^+$. As already discussed above, Hv1 channel selectivity is dependent on specific amino acids, including Asp112 and Arg208.

The primary determinants of Hv1 channel activation are transmembrane voltage and transmembrane pH gradient ($\Delta$pH, defined as pH$_o$-pH$_i$). Hv1 opens at relatively positive transmembrane voltages (i.e. depolarization), but voltage-dependence is strongly modulated by pH. When the cytosol becomes more acidic relative to the extracellular or intraluminal space, the entire conductance-voltage relationship of the channel shifts by 40 mV to more negative voltages for each unit increase in $\Delta$pH. Conversely, when the extracellular or intraluminal side becomes more acidic than the cytosol, the conductance-voltage relationship shifts by 40 mV to more positive voltages for each unitary change in $\Delta$pH. Parameters that are useful in determining Hv1 channel activation include: (1) the membrane voltage (measured on the cytosolic side, relative to the extracellular or luminal side); (2) the cytosolic pH (whereby acidification favors activation at any given voltage); and (3) the extracellular or intra-luminal pH (whereby acidification opposes activation at any given voltage). Three charged Arg residues in the S4 transmembrane segment of Hv1 confer voltage dependency, while the structural basis for pH sensing is not fully understood.

Besides voltage and $\Delta$pH, other parameters can also influence Hv1 channel activation. For example, phosphorylation of the channel by PKC can produce an enhanced responsiveness mode, allowing for more channels to open more quickly. PKC phosphorylates Hv1 at Thr29 located in the intracellular N-terminus. A situational example of enhanced gating of Hv1 is phagocyte exposure to pathogenic stimuli, such as bacteria. A diversity of stimuli can induce enhanced gating, including chemotactic peptides such as fMLF in neutrophils, lipopolysaccharide (LPS) in dendritic cells, IgE in basophils, IL-5 in eosinophils, and arachidonic acid in neutrophils and eosinophils. Such enhanced Hv1 gating is only functional in certain cells. The intensity of enhanced gating response may be associated with the presence of an active NADPH oxidase complex. Additionally, slower tail current decay (channel closing), is temporally correlated with NADPH oxidase activity. Enhanced gating makes Hv1 channels more likely to open or remain open, thereby requiring a smaller stimulus to activate H$^+$ flux. Hv1 proton currents are also sensitive to temperature, and have a small (15 fF) unitary conductance.

Hv1 Channel Expression

Hv1 channels have been identified directly by voltage-clamp recordings in many primary tissue cell types, including neutrophils, basophils, eosinophils, cardiac fibroblasts, cultured myotubes, tracheal epithelium, and monocytes. Neutrophil and eosinophil granulocytes express the highest levels of Hv1.

In most cells, Hv1 is expressed in plasma membranes, though there is evidence that Hv1 can also be expressed on intracellular membranes such as Golgi membranes in some cells. Full-length Hv1 can be detected in human granulocytes by western blot as a 30 kDa monomer or 70 kDa dimer. Based on immunocytochemistry, Hv1 partially colocalizes with NOX2 in the membrane of intracellular granules and in the plasma membrane.

Hv1 Channel Functions

Functions of Hv1 channels differ depending on the cells in which they are expressed. Cells in which high activity and a physiological function for Hv1 channels have been documented include immune cells, central nervous system cells, airway epithelia, spermatozoa, and cardiac fibroblasts. Under normal circumstances, when Hv1 channels open, H$^+$ efflux occurs and thereby increases pH$_i$, decreases pH$_o$ and hyperpolarizes the membrane potential. These changes can have different consequences in different cells.

In some cells, Hv1 channel expression and function is closely linked to expression and function of the enzyme NADPH oxidase (NOX), of which there are four isoforms: NOX1, NOX2, NOX3 and NOX4. NOX is a membrane-bound enzyme that transfers electrons from NADPH across cell membranes and couples these electrons to molecular oxygen to produce superoxide anion. In some locations, superoxide can undergo further reactions to generate reactive oxygen species (ROS). One of the functions of Hv1 linked to NOX activity is the extrusion of protons to compensate for the loss of electrons, as discussed in more detail below.

Hv1 expression and/or function has been detected in both innate and adaptive immune cells. A major role of Hv1 channels is in the phagosome, an intracellular organelle in white blood cells where pathogens such as bacteria are engulfed and destroyed. The primary role for Hv1 channels in the phagosome is to allow NOX2 (the NADPH oxidase enzyme complex) to produce large quantities of reactive oxygen species (ROS) to kill pathogens, in a process called "respiratory burst". During the respiratory burst, NOX enzymes catalyze the transfer of electrons from NADPH across the plasma membrane to reduce molecular oxygen to $O^{2-}$, generating two protons in the cytoplasm. The resulting depolarization and cytoplasmic acidification inhibits NOX2 activity. Depolarization opens Hv1 channels to sustain NOX2 activity by extruding protons from the cytoplasm, thereby maintaining physiological membrane potential and re-establishing normal pH. Such contributions of Hv1 channels to NOX2-dependent ROS release are characterized in granulocytes and in particular neutrophils. H$^+$ current has also been detected in basophils. In these cells, IgE stimulates Hv1 channels, which facilitate release of histamine. Hv1 may also participate in ROS production and/or histamine release by mast cells.

B lymphocytes of the adaptive immune system, which are responsible for antibody production, express Hv1 protein. It has been suggested that Hv1 mediates signaling in the antibody maturation process upon B-cell receptor activation by antigen binding. For example, Hv1 channels may be required for ROS production by NOX2 in mature B lymphocytes upon antigen stimulation. Given the involvement of Hv1 in B cell receptor signaling, inhibitors of Hv1 may be useful for treating autoimmune diseases and B cell malignancies.

Hv1 channels are also expressed in T lymphocytes, which are cells of the adaptive immune system that recognize antigens presented by major histocompatibility complex I or II. Here, Hv1 may function to facilitate ROS production and help regulate the number of activated T lymphocytes, thereby opposing an autoimmune phenotype.

Expression and activity of Hv1 has been confirmed in human sperm. Functional data indicate that Hv1 activity may be necessary for sperm activation and mobility of human sperm to achieve fertilization. The process that prepares sperm to fertilize an oocyte is called capacitation, a kind of maturation process that is triggered by an increase in intracellular pH and ROS. Changes related to capacitation include: changes in sperm motility, decrease of cholesterol in the membranes, increase of tyrosine phosphorylation in several proteins, and maturation of the sperm response to progesterone. Interestingly, seminal fluid has an unusually high concentration of $Zn^{2+}$ (which is known to inhibit Hv1), whereas the female reproductive tract has low $Zn^{2+}$ concentrations. It is hypothesized that on arrival of sperm in the female reproductive tract, Hv1 becomes activated and cooperates with the sperm-specific $Ca^{2+}$ channel CatSper and NOX5 to activate sperm effector functions such as sperm movement, capacitation, sperm-zona pellucida interaction, acrosome reaction, and sperm-oocyte fusion.

There is evidence to suggest the presence of Hv1 channels in mammalian brain tissue. Without wishing to be bound by any particular theory, the present disclosure proposes that Hv1 channels may play a neuroprotective role by extruding protons from metabolically active neurons and regulating neuronal pH homeostasis. Hv1 expression has been detected in human microglia, the macrophage-like cells of the central nervous system. Hv1 in microglia may contribute to CNS disease by supporting NOX function. Microglia can become activated in acute and chronic brain disorders including brain injury, ischemia, and neurodegeneration. The expression and function of Hv1 is correlated with the expression and function of NOX2. Hv1 channels may support the activity of NOX2 in microglia by extruding excess protons from the cytoplasm. Oxidative stress, at least in part due to ROS generation by NOX, can contribute to the development of CNS disease. Hv1 inhibition could be beneficial for the treatment of neurodegenerative processes accompanied by excessive production of ROS by microglia, such as stroke, Alzheimer's disease, Parkinson's disease, and amyotrophic lateral sclerosis, among others.

The present disclosure proposes that NOX-independent Hv1 channel functions may also exist, given that certain cell types (e.g., basophil granulocytes) that exhibit Hv1 channel activity are not known to express NOX.

Evidence indicates that Hv1 also functions in airway epithelia (e.g. tracheal epithelia) in functions such as providing a protective mechanism through acidification of the airway surface liquid. Hv1 may also function in cardiac fibroblasts, though its function in these cells is not fully known. Some experimental data also suggests Hv1 function in monocytes and macrophages. Hv1 channels may promote osteoclast cell function, for instance by promoting bone resorption by osteoclast cells. Hv1 channels may also mediate antigen presentation by dendritic cells.

Many other tissues and cells not mentioned here also express Hv1 channels, some at relatively low levels. For most of the cell types and tissues that have been reported to express low levels of Hv1 channels, a specific function has not been assigned.

Given the widespread expression and function of Hv1 channels, it may not be surprising that channel dysfunction can cause or enhance pathologic states. Moreover, genomic studies have identified the HVCN1 gene as being relevant to multiple diseases. For example, HVCN1 has been associated with Crohn's disease activity and cystic fibrosis. A study in HVCN1 knockout rats indicated that Hv1 may contribute to the development of hypertension and renal disease with a high-salt diet. The link between Hv1 function and ROS production provides some insight on the mechanism of some Hv1-associated disorders. Excessive ROS production is thought to cause local tissue damage and contribute to several pathological conditions, including atherosclerosis, ischemic stroke, Parkinson's disease, ischemic liver disease, Alzheimer's disease, and aging. A study on ischemic stroke has confirmed that Hv1 can exacerbate brain damage by facilitating production of ROS by NOX in microglia. Moreover, it was recently shown that Hv1-deficient mice are protected in models of stroke, suggesting that pharmacological inhibition of Hv1 channels may have neuroprotective benefits (see Seredenina, T., et al. "Voltage-gated proton channels as novel drug targets: from NADPH oxidase regulation to sperm biology." *Antioxid Redox Signal.* 10; 23(5): 490-513 (2015) and references cited therein).

Hv1 channels may contribute to the malignancy of several cancers, including breast cancer, colorectal cancer and leukemia. For example, higher levels of Hv1 expression occur in breast cancer cell lines with greater metastatic likelihood and knockdown of Hv1 in breast cancer cell lines reduced proliferation and invasiveness. In human patients, a high level of Hv1 expression was correlated with poor prognosis. One mechanism by which Hv1 contributes to cancer cell malignancy is related to the abnormal metabolism of cancer cells, which use glycolysis in preference to oxidative phosphorylation even in the presence of adequate oxygen. This altered metabolism creates a buildup of lactic acid that acidifies the cells, thus requiring enhanced activity of $H^+$ extrusion to prevent cell death.

The particular isoform of Hv1 that is expressed may contribute to certain malignancies. The levels of the short isoform of Hv1 are higher in malignant B cell lines as compared to normal B lymphocytes. Moreover, the short isoform comprises approximately one-third of the Hv1 protein in malignant B cells from patients with chronic lymphocytic leukemia. The enhanced gating response is substantially more pronounced in the short compared to the long isoform of Hv1. Hv1 channel activity, proliferation and cell migration are all promoted by the expression of the short isoform.

Hv1 Channel Modulators

Modulation of Hv1 channel activity is an attractive strategy for treating Hv1-related pathologies, including the ones described above. For example, agents that modulate Hv1 may be expected to ameliorate inflammation, allergies, autoimmunity, cancer, asthma, brain damage from ischemic stroke, Alzheimer's disease, infertility, and numerous other conditions. Depending on the disease and affected tissue, either Hv1 activation or inhibition could prove useful. However, clinically compatible Hv1 modulators are not known. Therefore, there is an unmet need in identifying potent and selective modulators of Hv1.

One of the challenges in creating modulators of Hv1 channels stems from the channel structure. The extracellular loops of hHv1 are fewer than a dozen amino acids, resulting in a relatively small extracellular portion of the Hv1 molecule to which drugs can bind. For example, this limits the epitope possibilities for antibodies to bind externally. Additionally, inhibition of Hv1 by physical occlusion is also a challenge, since the channel is structured to be closely packed and prevent other ions from permeating.

In some instances, such as autoimmune disease and male infertility, Hv1 activation may be an attractive pharmacological strategy. Unsaturated long-chain fatty acids such as oleic acid and arachidonic acid have been shown to enhance Hv1 proton currents. This appears to be a direct pharmacological activation of Hv1. Arachidonic acid has been observed to activate a proton conductance in phagocytes. However, arachidonic acid can also activate multiple signaling pathways, which in certain cases can lead to activation of NOX enzymes and therefore indirectly activate H$^+$ currents. Activators of enhanced gating can also enhance Hv1 function. In general, ion channel activators are more difficult to identify than inhibitors since binding to the channel usually produces inhibition.

$Zn^{2+}$ and other polyvalent cations are known to inhibit Hv1 channels. Hv1 channels can be blocked by $Zn^{2+}$ at concentrations ranging from 100 nM to 1 mM depending on the extracellular pH and on the presence of other polyvalent cations. The mechanism by which $Zn^{2+}$ inhibits Hv1 involves $Zn^{2+}$ competing with H$^+$ for binding to the external surface of Hv1 channels. Two His residues (His140 and His193) located at the interface between the channel monomers coordinate $Zn^{2+}$ in the closed channel and thereby oppose channel opening. This mechanism changes the membrane potential perceived by the channel, and therefore requires stronger voltage to elicit proton current. $Zn^{2+}$ shifts the current-voltage relationship positively and slows the kinetics of Hv1 channel activation. However, $Zn^{2+}$ ions are implicated in many other physiological processes, and therefore the usefulness of $Zn^{2+}$ as a specific H$^+$ channel blocker is limited.

There are no documented high-affinity blockers of Hv1 channels that originate in venom or toxin. Tarantula toxins, including hanatoxin, can inhibit Hv1 at low micromolar concentrations by interacting with the S3 and S4 helices from the membrane interior and shifting the $g_H$-V relationship in the positive direction. However, hanatoxin is not specific for Hv1. Different voltage-sensing proteins, including Hv1 and other ion channels, contain the highly conserved voltage sensor regions composed of S3 and S4 helices, termed the paddle motif. Binding of hanatoxin to the paddle motif inhibits ion fluxes through various voltage-dependent ion channels besides Hv1.

Guanidine derivatives have been shown to inhibit depolarization-induced H$^+$ current (see Seredenina, T., et al. "Voltage-gated proton channels as novel drug targets: from NADPH oxidase regulation to sperm biology." *Antioxid Redox Signal*. 10; 23(5): 490-513 (2015); DeCoursey, T. E. "The voltage-gated proton channel: a riddle, wrapped in a mystery, inside an enigma." *Biochemistry* 54(21): 3250-68 (2015); and references cited therein). The derivative 2GBI [2-guanidinobenzimidazole ($IC_{50}$=38 μM)] was found to have an intracellular site of action and to only bind when the channel was open. Other identified derivatives include 1-(1, 3-benzothiasol-2-yl)guanidine and 5-chloro-2-guanidinobenzimidazole. Guanidine derivatives have shown neuroprotective potential in an in vitro model of ischemia. The biggest challenge for pharmaceutical application of guanidine derivatives is their intracellular site of action.

Several other compounds have been observed to block H$^+$ currents. Examples of such other compounds include weak bases (e.g. 4-aminopyridine, amiloride, verapamil or D600), tricyclic antidepressants (imipramine, amitryptiline, and desipramine), the selective serotonin reuptake inhibitor fluoxetine, the morphine-derivative dextromethorphan (DM), and a tea catechin flavonoid EGCG. These other potential inhibitors have several drawbacks, including mechanisms of action that do not directly involve Hv1 channels, multiple other targets, and effective concentrations that are too high to be of pharmaceutical interest.

To-date, there are no selective inhibitors of Hv1 channels. There is an unmet need to develop such inhibitors, especially ones that are compatible with clinical use.

Hv1 Modulating Agents

Hv1 Modulating Agent Activities

The present disclosure provides agents that modulate Hv1. Among other things, the present disclosure provides agents that, for example, modulate one or more Hv1 activities when contacted with an Hv1 channel, for example, in vitro and/or in vivo. In some embodiments, Hv1 modulating agents modulate Hv1 activities of Hv1 monomers and dimers with similar $IC_{50}$. In some embodiments, Hv1 modulating agents specifically bind Hv1. In some embodiments, Hv1 modulating agents inhibit Hv1. In some embodiments, Hv1 modulating agents activate Hv1.

In some embodiments, Hv1 modulating agents do not physically occlude Hv1 channels. In some embodiments, Hv1 modulating agents bind to Hv1 but do not bind to other voltage-gated channels or other ion channels.

In some embodiments, Hv1 modulating agents bind to the external surface of Hv1. In some embodiments, Hv1 modulating agents target or bind to the S3-S4 external loop region of hHv1. For example, Hv1 modulating agents may bind to hHv1 at amino acid residues I183 to L204. In some embodiments, Hv1 modulating agents bind to regions of hHv1 comprising an amino acid sequence corresponding to (SEQ ID NO: 111)
ILDIVLLFQEHQFEALGLLILL.

In some embodiments, Hv1 modulating agent binding to Hv1 is reversible. In some embodiments, Hv1 modulating agent binding to Hv1 may be irreversible. In some embodiments, Hv1 modulating agent binding to Hv1 is strong but not irreversible.

In some embodiments Hv1 modulating agents bind to open Hv1 channels. In some embodiments, Hv1 modulating agents bind to closed channels. In some embodiments, affinity of Hv1 modulating agents for closed states of Hv1 is about 1 nM. In some embodiments, affinity of Hv1 modulating agents is lower for open states of the channel (e.g. about 200 nM) as compared to closed states of the channel. In some embodiments, Hv1 modulating agents slow opening of closed states of Hv1 even as they unbind.

In some embodiments, provided Hv1 modulating agents may change transmembrane voltage of a cell. Hv1 modulating agents may hyperpolarize the membrane potential. Hv1 modulating agents may depolarize the membrane potential. Effects of Hv1 modulating agents may be measured by, for example, direct electrophysiological recordings of voltage-gated proton currents, such as patch-clamp recordings.

In some embodiments, provided Hv1 modulating agents are characterized in that, for example, they decrease or block proton current. In some embodiments, Hv1 modulating agents may reduce the number or likelihood of Hv1 channel opening. In some embodiments, Hv1 modulating agents may speed up the rate of Hv1 channel closing. In some embodiments, Hv1 modulating agents may cause an Hv1 channel to require stronger voltage to elicit proton current.

In some embodiments, provided Hv1 modulating agents are characterized in that, for example, they increase proton currents and/or slow the closing of Hv1 channels. In some embodiments, Hv1 modulating agents may provide an enhanced responsiveness mode, allowing more channels to open more quickly, increasing likelihood that Hv1 channels will open or remain open, and/or reducing the stimulus required to activate H⁺ flux.

In some embodiments, Hv1 modulating agents may increase or decrease proton (H⁺) current but do not directly alter current of other ions (e.g. $Na^+$, $K^{2+}$, $Ca^{2+}$).

In some embodiments, Hv1 modulating agents may change the transmembrane pH gradient ($\Delta pH$, defined as $pH_o$-$pH_i$). In some embodiments, provided Hv1 modulating agents may increase or decrease intracellular or cytosolic pH ($pH_i$). Thus, Hv1 modulating agents may decrease or increase the cytoplasmic acidity. In some embodiments, provided Hv1 modulating agents may increase or decrease the extracellular, intraluminal, or organelle pH ($pH_o$). Thus, Hv1 modulating agents may decrease or increase the extracellular, intraluminal, or organelle acidity.

In some embodiments, Hv1 modulating agents may increase or decrease cellular ROS production.

In some embodiments, Hv1 modulating agents may increase or decrease the function and/or activity of NOX enzymes, including NOX1, NOX2, NOX3, and/or NOX4. In some such embodiments, Hv1 modulating agents may enhance or reduce the ability of NOX enzymes to transfer electrons. In some such embodiments, Hv1 modulating agents may increase or decrease the production of superoxide anion by a cell. In some such embodiments, Hv1 modulating agents may increase or decrease the quantity of ROS production mediated by NOX enzymes. In some embodiments, Hv1 modulating agents may sustain NOX activity by extruding protons from the cytoplasm.

In some embodiments, Hv1 modulating agents may alter signaling pathways that can be affected by Hv1 activity. In some embodiments, Hv1 modulating agents may affect cellular, physiological, or pathological processes that can be affected by Hv1 activity. In some such embodiments, Hv1 modulating agents may influence inflammation, allergies, autoimmunity, cancer, asthma, brain damage from ischemic stroke, Alzheimer's disease, and fertility.

In some embodiments, Hv1 modulating agents may alter sperm activity or fertilization. Hv1 modulating agents may affect sperm mobility, capacitation, sperm-zona pellucida interaction, acrosome reaction, and sperm-oocyte fusion. In a particular example, Hv1 modulating agents inhibit properties associated with sperm capacitation.

In another example, Hv1 modulating agents may alter the ability of white blood cells to fight infections. Hv1 modulating agents may alter the activity of phagosomes, NOX enzymes, or ROS production. In a particular example, Hv1 modulating agents may decrease ROS production in white blood cells.

Hv1 Modulating Agent Structure

In some embodiments, an Hv1 modulating agent is or comprises a polypeptide. In some embodiments, a polypeptide component of an Hv1 modulating agent is 10-100 amino acids in length.

In many embodiments in which a provided Hv1 modulating agent includes a polypeptide component, the polypeptide component of the agent has an amino acid tertiary structure that is characterized as an inhibitor cysteine knot (ICK)-like structural motif. In some embodiments, a polypeptide component has a structure that has substantial structural similarity to an ICK structural motif. In some embodiments, a polypeptide component has three disulfide bridges. In some embodiments, a polypeptide component has three beta strands. In some embodiments, a polypeptide component has an amino acid sequence with six conserved cysteine residues of an ICK motif (FIG. 1).

In many embodiments in which a provided Hv1 modulating agent includes a polypeptide component, the polypeptide component of the agent has an amino acid sequence that includes one or more elements that is substantially identical to, but different from, that of wild-type toxin sequences (e.g., of a wild-type voltage sensor toxin). In some embodiments, such a sequence element has a length of about 5 to about 20 amino acids. In some embodiments, such a sequence element shows at least 40%, 50%, 60%, 70%, 80%, 90%, 91%, 92%, 93%, 94%, 95%, 96%, 97%, 98%, 99%, or 100% sequence identity with a corresponding element of a wild-type toxin. In some embodiments, a polypeptide component of a provided Hv1 modulating agent may show significant (e.g., at least 40%, 50%, 60%, 70%, 80%, 90%, 91%, 92%, 93%, 94%, 95%, 96%, 97%, or higher) overall sequence identity with, while differing from, a wild-type toxin. In some embodiments, a polypeptide component has an amino acid sequence that includes a plurality of toxin sequence elements, each of which is substantially identical to a sequence element that is found in the same, or a different, reference wild-type toxin. In some such embodiments, the plurality of toxin sequence elements are assembled in linear order so that the amino acid sequence shows overall correspondence with (e.g., shares one or more certain structural features, such as number and/or [relative] location of one or more cysteine residues) a full-length toxin. In some embodiments, a polypeptide component has an amino acid sequence that includes one or more residues found in a wild-type toxin that participates in binding by that wild-type toxin to a voltage-sensing protein.

Exemplary wild-type toxin sequences are presented in Table 1. In some embodiments, a wild-type toxin is a venom toxin. In some embodiments, a venom toxin is a toxin found in venom of organisms such as scorpion (e.g., *Pandinus imperator*), sea anemone, snails (e.g. *Conus marmoreus*), snakes, and spiders (e.g., *Grammostola rosea*).

TABLE 1

| SEQ ID NO: | Toxin Name | Sequence | NCBI Accession NO: | Animal Species |
|---|---|---|---|---|
| 1 | HwTx-IV | ECLEIFKACNPSNDQCCKSSKLVCSRKTRWCKYQI | P83303.2 | *Haplopelma schmidti* (Chinese bird spider) |
| 2 | HnTx-IV | ECLGFGKGCNPSNDQCCKSSNLVCSRKHRWCKYEI | D2Y232.1 | *Haplopelma hainanum* (Chinese bird spider) |

TABLE 1-continued

| SEQ ID NO: | Toxin Name | Sequence | NCBI Accession NO: | Animal Species |
|---|---|---|---|---|
| 3 | HnTx-V | ECLGFGKGCNPSNDQCCKSANLVCSRKHRWCKYEI | P60975.1 | Haplopelma hainanum (Chinese bird spider) |
| 4 | PaurTx3 | DCLGFLWKCNPSNDKCCRPNLVCSRKDKWCKYQI | P84510.1 | Paraphysa scrofa (Chilean copper tarantula) |
| 5 | CcoTx1 | DCLGWFKSCDPKNDKCCKNYTCSRRDRWCKYDL | P84507.1 | Ceratogyrus marshalli (Straighthorned baboon tarantula) |
| 6 | CcoTx2 | DCLGWFKSCDPKNDKCCKNYTCSRRDRWCKYYL | P84508.1 | Ceratogyrus marshalli (Straighthorned baboon tarantula) |
| 7 | VSTX3 | DCLGWFKGCDPDNDKCCEGYKCNRRDKWCKYKLW | P0C2P5.1 | Grammostola rosea (Chilean rose tarantula) |
| 8 | T1Tx1 | AACLGMFESCDPNNDKCCPNRECNRKHKWCKYKLW | P83745.1 | Theraphosa blondi (Goliath birdeating spider) |
| 9 | JZTX-25 | DDCLGMFSSCNPDNDKCCEGRKCDRRDQWCKWNPW | B1P1F1.1 | Chilobrachys guangxiensis (Chinese earth tiger tarantula) |
| 10 | JZTX-27 | DCLGLFWICNYMDDKCCPGYKCERSSPWCKIDI | B1P1H2.1 | Chilobrachys guangxiensis (Chinese earth tiger tarantula) |
| 11 | T1Tx3 | DDCLGMFSSCDPNNDKCCPNRVCRVRDQWCKYKLW | P83747.1 | Theraphosa blondi (Goliath birdeating spider) |
| 12 | T1Tx2 | DDCLGMFSSCDPKNDKCCPNRVCRSRDQWCKYKLW | P83746.1 | Theraphosa blondi (Goliath birdeating spider) |
| 13 | HwTx-I | ACKGVFDACTPGKNECCPNRVCSDKHKWCKWKL | P56676.2 | Haplopelma schmidti (Chinese bird spider) |
| 14 | GsMTx4 | GCLEFWWKCNPNDDKCCRPKLKCSKLFKLCNFSFGK | Q7Y139.1 | Grammostola rosea (Chilean rose tarantula) |
| 15 | Omega-AcTx-Hv1b | ADCGWLFHSCESNADCCENWACATTGRFRYLCKYQI | P81595.1 | Hadronyche versuta (Blue mountains funnel-web spider) |
| 16 | IpTxa | GDCLPHLKRCKADNDCCGKKCKRRGTNAEKRCR | P59868.1 | Pandinus imperator (Emperor scorpion) |
| 17 | VSTX1 | ECGKFMWKCKNSNDCCKDLVCSSRWKWCVLASPF | P60980.2 | Grammostola rosea (Chilean rose tarantula) |
| 18 | HnTx-I | ECKGFGKSCVPGKNECCSGYACNSRDKWCKVLL | D2Y1X6.1 | Haplopelma hainanum (Chinese bird spider) |
| 19 | Maurocalcine | GDCLPHLKLCKENKDCCSKKCKRRGTNIEKRCR | P60254.1 | Scorpio maurus palmatus (Chactoid scorpion) |
| 20 | HpTX3 | ECGTLFSGCSTHADCCEGFICKLWCRYERTW | P58427.1 | Heteropoda venatoria (Brown huntsman spider) |

TABLE 1-continued

| SEQ ID NO | Toxin Name | Sequence | NCBI Accession NO: | Animal Species |
|---|---|---|---|---|
| 21 | HNTX-VII | ECRYWLGTCSKTGDCCSHLSCSPKHGWCVWDWTFRK | D2Y2C3.1 | Haplopelma hainanum (Chinese bird spider) |
| 22 | JZTX F4-32.60 | GCQKFFWTCHPGQPPCCSGLACTWPTEICIDG | P0CH50.1 | Chilobrachys guangxiensis (Chinese earth tiger tarantula) |
| 23 | HnTx-III | GCKGFGDSCTPGKNECCPNYACSSKHKWCKVYL | D2Y1X9.1 | Haplopelma hainanum (Chinese bird spider) |
| 24 | Toxin_KJ1 | DDCGTLFSGCDTSKDCCEGYVCHLWCKYK | P61791.1 | Heteropoda venatoria (Brown huntsman spider) |
| 25 | ScTx1 | DCTRMFGACRRDSDCCPHLGCKPTSKYCAWDGTI | P60991.1 | Stromatopelma calceatum (Featherleg baboon tarantula) |
| 26 | JZTX-50 | RCIEEGKWCPKKAPCCGRLECKGPSPKQKKCTRP | B1P1130.1 | Chilobrachys guangxiensis (Chinese earth tiger tarantula) |
| 27 | ProTx-1 | ECRYWLGGCSAGQTCCKHLVCSRRHGWCVWDGTFS | P83480.1 | Thrixopelma pruriens (Peruvian green velvet tarantula) |
| 28 | HmTx1 | ECRYLFGGCSSTSDCCKHLSCRSDWKYCAWDGTFS | P60992.1 | Heteroscodra maculata (Togo starburst tarantula) |
| 29 | GxTx1E | EGECGGFWWKCGSGKPACCPKYVCSPKWGLCNFPMP | P84835.1 | Chilobrachys guangxiensis (Chinese earth tiger tarantula) |
| 30 | GxTX-1D | DGECGGFWWKCGSGKPACCPKYVCSPKWGLCNFPMP | P84836.1 | Chilobrachys guangxiensis (Chinese earth tiger tarantula) |
| 31 | Omega-AcTx-Hv1a | DDDCGWIMDDCTSDSDCCPNWVCSKTGFVKNICKYEM | P56207.1 | Hadronyche versuta (Blue mountains funnel-web spider) |
| 32 | JZTX F7-15.33 | LCSREGEFCYKLRKCCAGFYCKAFVLHCYRN | P0CH55.1 | Chilobrachys guangxiensis (Chinese earth tiger tarantula) |
| 33 | Tx2-9 | SFCIPFKPCKSDENCCKKFKCKTTGIVKLCRW | AAB32862.1 | Brachypelma smithii (Mexican red knee tarantula) |
| 34 | GxTX-2 | ECRKMFGGCSVDSDCCAHLGCKPTLKYCAWDGT | P84837.1 | Chilobrachys guangxiensis (Chinese earth tiger tarantula) |
| 35 | HpTX1 | DCGTIWHYCGTDQSECCEGWKCSRQLCKYVIDW | P58425.1 | Heteropoda venatoria (Brown huntsman spider) |
| 36 | SHLP-I | GCLGDKCDYNNGCCSGYVCSRTWKWCVLAGPWRR | Q86C51.1 | Haplopelma schmidti (Chinese bird spider) |

TABLE 1-continued

| SEQ ID NO: | Toxin Name | Sequence | NCBI Accession NO: | Animal Species |
|---|---|---|---|---|
| 37 | JZTX-VII | GCGGLMAGCDGKSTFCCSGYNCSPTWKWCVYARP | P0C2X7.2 | *Chilobrachys guangxiensis* (Chinese earth tiger tarantula) |
| 38 | JZTX-29 | ECRKMFGGCSVHSDCCAHLGCKPTLKYCAWDGTF | B1P1E4.1 | *Chilobrachys guangxiensis* (Chinese earth tiger tarantula) |
| 39 | JZTX-12.1 | GCGGLMDGCDGKSTFCCSGFNCSPTWKWCVYARP | B1P1C4.1 | *Chilobrachys guangxiensis* (Chinese earth tiger tarantula) |
| 40 | Toxin_AU2 | DDCGGLFSGCDSNADCCEGYVCRLWCKYKL | P61792.1 | *Heteropoda venatoria* (Brown huntsman spider) |
| 41 | HaTx1 | ECRYLFGGCKTTSDCCKHLGCKFRDKYCAWDFTFS | P56852.1 | *Grammostola rosea* (Chilean rose tarantula) |
| 42 | HaTx2 | ECRYLFGGCKTTADCCKHLGCKFRDKYCAWDFTFS | P56853.1 | *Grammostola rosea* (Chilean rose tarantula) |
| 43 | VaTx1 | SECRWFMGGCDSTLDCCKHLSCKMGLYYCAWDGTF | P0C244.1 | *Psalmopoeus cambridgei* (Trinidad chevron tarantula) |
| 44 | JzTx-XI | ECRKMFGGCSVDSDCCAHLGCKPTLKYCAWDGTFGK | P0C247.2 | *Chilobrachys guangxiensis* (Chinese earth tiger tarantula) |
| 45 | HmTx2 | ECRYFWGECNDEMVCCEHLVCKEKWPITYKICVWDRTF | P60993.1 | *Heteroscodra maculata* (Togo starburst tarantula) |
| 46 | JzTx-III | DGECGGFWWKCGRGKPPCCKGYACSKTWGWCAVEAP | P62520.1 | *Chilobrachys guangxiensis* (Chinese earth tiger tarantula) (Chilobrachys jingzhao) |
| 47 | PcTx1 | EDCIPKWKGCVNRHGDCCEGLECWKRRRSFEVCVPKTPKT | P60514.1 | *Psalmopoeus cambridgei* (Trinidad chevron tarantula) |
| 48 | Agelenin | GGCLPHNRFCNALSGPRCCSGLKCKELSIWDSRCL | P31328.1 | *Allagelena opulenta* (Funnel weaving spider) |
| 49 | JZTX-13 | QCGEFMWKCGAGKPTCCSGYDCSPTWKWCVLKSPGRR | B1P1C9.1 | *Chilobrachys guangxiensis* (Chinese earth tiger tarantula) |
| 50 | JZTX-15 | TCYDIGELCSSDKPCCSGYYCSPRWGWCIYSTRGGR | B1P1D4.1 | *Chilobrachys guangxiensis* (Chinese earth tiger tarantula) |
| 51 | Omega-AcTx-Hv1f | SAVCIPSGQPCPYSKYCCSGSCTYKTNENGNSVQRCD | P81599.1 | *Hadronyche versuta* (Blue mountains funnel-web spider) |
| 52 | HNTX-XIX | CAAEGIPCDPNPVKDLPCCSGLACLKPTLHGIWYKHHYCYTQ | D2Y299.1 | *Haplopelma hainanum* (Chinese bird spider) |

TABLE 1-continued

| SEQ ID NO: | Toxin Name | Sequence | NCBI Accession NO: | Animal Species |
|---|---|---|---|---|
| 53 | lamda-MeuTx | GCNRKNKKCNSDADCCRYGERCISTKVNYYCRPDRGP | P86399.2 | *Mesobuthus eupeus* (Lesser Asian scorpion) |
| 54 | JZTX-24 | VCRGYGLPCTPEKNDCCQRLYCSQHRLCSVKA | B1P1F0.1 | *Chilobrachys guangxiensis* (Chinese earth tiger tarantula) |
| 55 | HwTx-X | KCLPPGKPCYGATQKIPCCGVCSHNKCT | P68424.2 | *Haplopelma schmidti* (Chinese bird spider) |
| 56 | JZTX-21 | CGGWMAKCADSDDCCETFHCTRFNVCGK | B1P1E6.1 | *Chilobrachys guangxiensis* (Chinese earth tiger tarantula) |
| 57 | magi-11 | SCKLTFWRCKKDKECCGWNICTGLCIPP | Q75WH2.1 | *Macrothele gigas* (Spider) |
| 58 | SGTx1 | TCRYLFGGCKTTADCCKHLACRSDGKYCAWDGTF | P56855.1 | *Stromatopelma calceatum griseipes* (Feather leg baboon tarantula) |
| 59 | JZTX-44 | ECKWYLGDCKAHEDCCEHLRCHSRWDWCIWDGTF | B1P1G8.1 | *Chilobrachys guangxiensis* (Chinese earth tiger tarantula) |
| 60 | HNTX-VI | ECKYLWGTCEKDEHCCEHLGCNKKHGWCGWDGTF | P0CH70 | *Haplopelma hainanum* (Chinese bird spider) |
| 61 | GsAF_I | YCQKWLWTCDSERKCCEDMVCRLWCKKRL | P61408.1 | *Grammostola rosea* (Chilean rose tarantula) |
| 62 | GrTx1 | YCQKWMWTCDSKRKCCEDMVCQLWCKKRL | P85117.1 | *Grammostola rosea* (Chilean rose tarantula) |
| 63 | PaTX1 | YCQKWMWTCDSARKCCEGLVCRLWCKKII | P61230.1 | *Paraphysa scrofa* (Chilean copper tarantula) |
| 64 | Magi-5 | GCKLTFWKCKNKKECCGWNACALGICMPR | P83561.2 | *Macrothele gigas* (Spider) |
| 65 | HwTx-V | ECRWYLGGCSQDGDCCKHLQCHSNYEWCVWDGTFSK | P61104.2 | *Haplopelma schmidti* (Chinese bird spider) |
| 66 | VaTx2 | GACRWFLGGCKSTSDCCEHLSCKMGLDYCAWDGTF | P0C245.1 | *Psalmopoeus cambridgei* (Trinidad chevron tarantula) |
| 67 | 5NX482 | GVDKAGCRYMFGGCSVNDDCCPRLGCHSLFSYCAWDL TFSD | P56854.1 | *Hysterocrates gigas* (African tarantula) |
| 68 | PnVIIA | DCTSWFGRCTVNSECCSNSCDQTYCELYAFPSFGA | P56711.2 | *Conus pennaceus* (Feathered cone) |
| 69 | PNTx27C4 | IACAPRFSLCNSDKECCKGLRCQSRIANMWPTFCSQ | P83996.2 | *Phoneutria nigriventer* (Brazilian armed spider) |
| 70 | PRTx27C3 | IACAPRGLLCFRDKECCKGLTCKGRFVNTWPTFCLV | P83892.1 | *Phoneutria reidyi* (Brazilian Amazonian armed spider) |

TABLE 1-continued

| SEQ ID NO | Toxin Name | Sequence | NCBI Accession NO: | Animal Species |
|---|---|---|---|---|
| 71 | JZTX-36 | DCRKMFGGCSKHEDCCAHLACKRTFNYCAWDGSFSK | B1P1D7.1 | Chilobrachys guangxiensis (Chinese earth tiger tarantula) |
| 72 | JZTX-38 | ECRWLFGGCEKDSDCCEHLGCRRAKPSWCGWDFTV | B1P1G2.1 | Chilobrachys guangxiensis (Chinese earth tiger tarantula) |
| 73 | JZTX-39 | ECRWLFGGCEKDSDCCEHLGCRRAKPSWCGWDFTF | B1P1G4.1 | Chilobrachys guangxiensis (Chinese earth tiger tarantula) |
| 74 | PRTx26AnOC3 | IACAPRFSICNSDKECCKGLRCQSRIANMWPTFCLV | P86418.1 | Phoneutria nigriventer (Brazilian armed spider) |
| 75 | HNTX-XVI | CIGEGVPCDENDPRCCSGLVCLKPTLHGIWYKSYYCYKK | D2Y253.1 | Haplopelma hainanum (Chinese bird spider) |
| 76 | HNTX-VIII | DCAGYMRECKEKLCCSGYVCSSRWKWCVLPAPWRR | D2Y240.1 | Haplopelma hainanum (Chinese bird spider) |
| 77 | HNTX-IX | ECRWYLGGCSQDGDCCKHLQCHSNYEWCIWDGTFSK | D2Y236.1 | Haplopelma hainanum (Chinese bird spider) |
| 78 | F5-21.66 | ECKKLFGGCTTSSECCAHLGCKQKWPFYCAWDWSF | P0CH51.1 | Chilobrachys guangxiensis (Chinese earth tiger tarantula) |
| 79 | Hm-2 | GCIPSFGECAWFSGESCCTGICKWVFFTSKFMCRRVWGKD | P85506.1 | Heriaeus melloteei (Crab spider) |
| 80 | HdCa | SEKDCIKHLQRCRENKDCCSKKCSRRGTNPEKRCR | B8QG00.1 | Hadrurus gertschi (Scorpion) |
| 81 | ProTx-2 | YCQKWMWTCDSERKCCEGMVCRLWCKKKLW | P83476.1 | Thrixopelma pruriens (Peruvian green velvet tarantula) |
| 82 | JzTx-V | YCQKWMWTCDSKRACCEGLRCKLWCRKIIG | Q2PAY4.1 | Chilobrachys guangxiensis (Chinese earth tiger tarantula) |
| 83 | HpTX2 | DDCGKLFSGCDTNADCCEGYVCRLWCKLDW | P58426.1 | Heteropoda venatoria (Brown huntsman spider) |
| 84 | GsAF_II | YCQKWMWTCDEERKCCEGLVCRLWCKKKIEW | P61409.2 | Grammostola rosea (Chilean rose tarantula) (Grammostola spatulata) |
| 85 | MrvIB | ACSKKWEYCIVPILGFVYCCPGLICGPFVCV | AAB34194.1 | Conus marmoreus (Marble cone) |
| 86 | GsMTx-2 | YCQKWMWTCDEERKCCEGLVCRLWCKRIINM | P60273.1 | Grammostola rosea (Chilean rose tarantula) |
| 87 | VSTX2 | YCQKWMWTCDEERKCCEGLVCRLWCKKKIEEG | P0C2P4.1 | Grammostola rosea (Chilean rose tarantula) |

TABLE 1-continued

| SEQ ID NO: | Toxin Name | Sequence | NCBI Accession NO: | Animal Species |
|---|---|---|---|---|
| 88 | JZTX-2 | GCGTMWSPCSTEKPCCDNFSCQPAIKWCIWSP | B1P1B9.1 | *Chilobrachys guangxiensis* (Chinese earth tiger tarantula) |
| 89 | VaTx3 | ECRWYLGGCKEDSECCEHLQCHSYWEWCLWDGSF | P0C246.1 | *Psalmopoeus cambridgei* (Trinidad chevron tarantula) |
| 90 | CcoTx3 | GVDKEGCRKLLGGCTIDDDCCPHLGCNKKYWHCGWDGTF | P84509.1 | *Ceratogyrus marshalli* (Straighthorned baboon tarantula) |
| 91 | JZTX-IV | ECTKFLGGCSEDSECCPHLGCKDVLYYCAWDGTFGK | P0CH56.1 | *Chilobrachys guangxiensis* (Chinese earth tiger tarantula) |
| 92 | JzTx-IX | ECTKLLGGCTKDSECCPHLGCRKKWPYHCGWDGTF | B1P1F5.2 | *Chilobrachys guangxiensis* (Chinese earth tiger tarantula) |
| 93 | AcTx-Hv1 | SPTCIPSGQPCPYNENCCSQSCTFKENENGNTVKRCD | P56207.1 | *Hadronyche versuta* (Blue mountains funnel-web spider) (Atrax versutus) |
| 94 | JZTX-34 | ACREWLGGCSKDADCCAHLECRKKWPYHCVWDWTV | B1P1F7.1 | *Chilobrachys guangxiensis* (Chinese earth tiger tarantula) |
| 95 | Omega-AcTx-Ar1a | SVCIPSGQPCPYNEHCCSGSCTYKENENGNTVQRCD | P83580.2 | *Atrax robustus* |
| 96 | Omega-hexatoxin-Hv1b | SSTCIPSGQPCPYNENCCSQSCTYKENENGNTVKRCD | P81595 | *Hadronyche versuta* (Blue mountains funnel-web spider) |
| 97 | Omega-AcTx-Hi1a | STCTPTDQPCPYHESCCSGSCTYKANENGNQVKRCD | P0C2L4.1 | *Hadronyche formidabilis* (Northern tree funnel-web spider) |
| 98 | Omega-AcTx-Hf1a | SPTCIRSGQPCPYNENCCSQSCTFKTNENGNTVKRCD | P0C2L4.1 | *Hadronyche formidabilis* (Northern tree funnel-web spider) |
| 99 | Omega-AcTx-Hi1b | SPTCIPTGQPCPYNENCCSQSCTYKANENGNQVKRCD | P0C2L6.1 | *Hadronyche infensa* (Fraser island funnel-web spider) |
| 100 | Omega-AcTx-Hi1c | SSTCIRTDQPCPYNESCCSGSCTYKANENGNQVKRCD | P0C2L7.1 | *Hadronyche infensa* (Fraser island funnel-web spider) |
| 101 | Omega-AcTx-Hv1c | SSTCIPSGQPCPYNENCCSQSCTFKENENGNTVKRCD | P81596.1 | *Hadronyche versuta* (Blue mountains funnel-web spider) |
| 102 | Omega-AcTx-Hv1d | SPTCIPSGQPCPYNENCCSKSCTYKENENGNTVQRCD | P81597.1 | *Hadronyche versuta* (Blue mountains funnel-web spider) |
| 103 | Omega-AcTx-Hv1e | SPTCIPSGQPCPYNENCCSQSCTYKENENGNTVKRCD | P81598.1 | *Hadronyche versuta* (Blue mountains funnel-web spider) |
| 104 | magi-1 | CMGYDIFICTDRLPCCFGLECVKTSGYWWYKKTYCRRKS | P83557.1 | *Macrothele gigas* (Spider) |

TABLE 1-continued

| SEQ ID NO: | Toxin Name | Sequence | NCBI Accession NO: | Animal Species |
|---|---|---|---|---|
| 105 | Omega-MSTX-Mb1a | SPVCTPSGQPCQPNTQPCCNNAEEEQTINCNGNTVYRCA | P83588.1 | *Missulena bradleyi* (Eastern mouse spider) |
| 106 | F3-24.71 | SPVCTPSGQPCQPNTQPCCNNAEEEQTINCNGNTVYRCA | P0CH70.1 | *Haplopelma hainanum* (Chinese bird spider) |
| 107 | JzTx-XII | YCQKWMWTCDSERKCCEGYVCELWCKYNL | P0C5X7.2 | *Chilobrachys guangxiensis* (Chinese earth tiger tarantula) |
| 108 | JZTX-1.2 | ACGQFWWKCGEGKPPCCANFACKIGLYLCIWSP | B1P1B7.1 | *Chilobrachys guangxiensis* (Chinese earth tiger tarantula) |
| 109 | GrTx-SIA | DCVRFWGKCSQTSDCCPHLACKSKWPRNICVWDGSV | P60590.2 | *Grammostola rosea* (Chilean rose tarantula) |
| 110 | JZTX-35 | DCRALYGGCTKDEDCCKHLACRRTLPTYCAWDLTFP | B1P1F9.1 | *Chilobrachys guangxiensis* (Chinese earth tiger tarantula) |

In some embodiments, a wild-type toxin sequence can be a predicted wild-type toxin sequence. In some embodiments, a predicted wild-type toxin sequence is identified in public protein databases. In some embodiments, a sequence element found in a wild-type toxin sequence is identified by isolating an amino acid sequence delineated by six conserved cysteine residues that form disulfide bridges in an ICK motif of a wild-type toxin sequence. In some embodiments, a known amino acid sequence of a wild-type toxin sequence can be used as a template to align amino acid sequences from public protein databases and identify predicted wild type-toxin sequences. In one example, the amino acid sequence of the Peruvian green velvet tarantula (*Thrixopelma pruriens*) is used as a template to identify predicted wild-type toxin sequences using basic local alignment search tools in public protein databases.

In some embodiments, a polypeptide component has an amino acid sequence that is substantially identical to a sequence set forth in Table 2. In some embodiments, a polypeptide component has an amino acid sequence that is substantially identical to a sequence set forth in Table 2 and an activating or inhibiting effect on Hv1 as set forth in Table 2B. In some embodiments, a polypeptide component has an amino acid sequence that is encoded by a nucleotide sequence that is substantially identical to a sequence set forth in Table 2C.

TABLE 2A

| SEQ ID NO: | Name | Sequence |
|---|---|---|
| 115 | A1 | DCAGYMRECKKDKECCGWNICNRKHKWCKYKLW |
| 116 | A2 | GCQMTFWKCNALDHNCCHGYAACGCKKIIVSARIA |
| 117 | A4 | GGCLPHNRFCNPSNDQCCKSANLVCRLWCKKKIEGDP |
| 118 | A6, G2 | GCKGFGDSCADSDDCCETFHCKWVFFTSKFMCRRVWGKD |
| 119 | B1 | GCLGDKCADSDDCCETFHCKWVFFTSKFMCRRVWGKD |
| 120 | B2 | SPTCIPSGQPCADSDDCCETFHCKWVFFTSKFMCRRVWGKD |
| 121 | B3 | DEDCQPPGNFCXNTSDCCEHLXCPTTPRFPYLCQYXMG |
| 122 | B4 | GACRWFLGGCTPEKNDCCQRLYCGPFVCV |
| 123 | B5 | SPVCTPSGQPCRENKDCCSKKCKTTGIVKLCRW |
| 124 | B6 | ACSKKWEYCTKDSECCPHLGCWKRRRSFEVCVPKTPKT |
| 125 | C1 | RCIEEGKWCTKDEDCCKHLACNRKHKWCKYKLW |
| 126 | C2, F2 | SPTCIRSGQPCADSDDCCETFHCKWVFFTSKFMCRRVWGKD |
| 127 | C3 | STCTPTDQPCADSDDCCETFHCKWVFFTSKFMCRRVWGKD |

TABLE 2A-continued

| SEQ ID NO: | Name | Sequence |
|---|---|---|
| 128 | C5 | GCKWYLGDCADSDDCCETFHCKWVFFTSKFMCRRVWGKD |
| 129 | C6, D5 | SSTCIPSGQPCADSDDCCETFHCKWVFFTSKFMCRRVWGKD |
| 130 | D3 | ACSKKWEYCKEKLCCSGYVCKRRGTNIEKRCRG |
| 131 | D4 | ACGQFWWKCTSDSDCCPNWVCRLWCKYKL |
| 132 | D6, E2 | CRYWLGGCSQDGDCCKHLQCSPRWGWCIYSTRGGR |
| 133 | E1 | DCGTIWHYCTPEKNDCCQRLYCSPRWRLVHL |
| 134 | E3 | IACAPRFSICDPKNDKCCPNRVCSDKHKWCKWKL |
| 135 | E4 | SSTCIPSGQPCRENKDCCSKKCSDKHKWCKWKLG |
| 136 | E5 | DGECGGFWWKCKNSNDCCKDLVCKEKWPITYKICVWDRTF |
| 137 | E6 | IACAPRFSLCDTSKDCCEGYVCNRKHKWCKYKLW |
| 138 | F4 | ECKGFGKSCADSDDCCETFHCKWVFFTSKFMCRRVWGKD |
| 139 | F5 | SPVCTPSGQPCADSDDCCETFHCKWVFFTSKFMCRRVWGKD |
| 140 | F6 | DDCGGLFSGCTPGKNECCPNRVCKIGLYLCIWS |
| 141 | G1 | GCLGDKCADSDDCCETFHCKWVFFTSKFMCRRVWGKD |
| 142 | G3 | CRYLFGGCAWFSGESCCTGICSPRWGWCIYSTRGGR |
| 143 | G4 | GDCLPHLKLCNPNDDKCCRPKLKCSRRGTNPEKRCR |
| 144 | G6 | DDCGTLFSGCPYSKYCCSGSCKRRGTNIEKRCR |
| 145 | H4 | AAEGCLCDRCXHSGDCCEDFHCTCEFFNM |

TABLE 2B

| SEQ ID NO: | Name | Sequence | Activator/Inhibitor |
|---|---|---|---|
| 118 | A6 | GCKGFGDSCADSDDCCETFHCKWVFFTSKFMCRRVWGKD | ACTIVATOR |
| 119 | B1 | GCLGDKCADSDDCCETFHCKWVFFTSKFMCRRVWGKD | ACTIVATOR |
| 128 | C5 | GCKWYLGDCADSDDCCETFHCKWVFFTSKFMCRRVWGKD | ACTIVATOR |
| 129 | C6 | SSTCIPSGQPCADSDDCCETFIICKWVFFTSKFMCRRVWGKD | INHIBITOR |
| 129 | D5 | SSTCIPSGQPCADSDDCCETFHCKWVFFTSKFMCRRVWGKD | INHIBITOR |
| 126 | F2 | SPTCIRSGQPCADSDDCCETFHCKWVFFTSKFMCRRVWGKD | ACTIVATOR |
| 118 | G2 | GCKGFGDSCADSDDCCETFHCKWVFFTSKFMCRRVWGKD | ACTIVATOR |

TABLE 2C

| SEQ ID NO: | Name | Nucleotide Sequences |
|---|---|---|
| 146 | A1 | GATTGCGCGGGCTATATGCGCGAATGTAAAAAAGATAAAGAATGCTGCGGCTGGAACATTTGCAACCGCAAACATAAATGGTGCAAATATAAACTGTGG |
| 147 | A2 | GGCTGCCAAATGACCTTTTGGAAATGTAACGCGCTGGATCACAACTGCTGCCATGGCTATGCCGCCTGTGGATGCAAAAAAATTATTGTATCCGCGAGAATCGCG |
| 148 | A4 | GGCGGCTGCCTGCCGCATAACCGCTTTTGTAACCCGAGCAACGATCAGTGCTGCAAAAGCGCGAACCTGGTGTGCCGCCTGTGGTGCAAAAAAAAAATTGAAGGGGATCCG |

TABLE 2C-continued

| SEQ ID NO: | Name | Nucleotide Sequences |
|---|---|---|
| 149 | A6, G2 | GGCTGCAAAGGCTTTGGCGATAGCTGTGCGGATAGCGATGATTGCTGCGAAACCTTTCATTGCAAATGGGTG TTTTTTACCAGCAAATTTATGTGCCGCCGCGTGTGGGGCAAAGAT |
| 150 | B1 | GGCTGCCTGGGCGATAAATGTGCGGATAGCGATGATTGCTGCGAAACCTTTCATTGCAAATGGGTGTTTTTT ACCAGCAAATTTATGTGCCGCCGCGTGTGGGGCAAAGAT |
| 151 | B2 | AGCCCGACCTGCATTCCGAGCGGCCAGCCGTGTGCGGATAGCGATGATTGCTGCGAAACCTTTCATTGCAAA TGGGTGTTTTTTACCAGCAAATTTATGTGCCGCCGCGTGTGGGGCAAAGATGGAT |
| 152 | B3 | GACGAAGATTGCCAACCGCCGGGCAACTTTTGTANCAACACCAGCGATTGCTGCGAACATCTGNNCTGCCCG ACCACCCCCGCTTTCCCTATCTGTGCCAATACCNCATGGGA |
| 153 | B4 | AGGCGCGTGCCGCTGGTTTCTGGGCGGCTGTACCCCGGAAAAAAACGATTGCTGCCAGCGCCTGTATTGCGG CCCGTTTGTGTGCGTG |
| 154 | B5 | AGCCCGGTGTGCACCCCGAGCGGCCAGCCGTGTCGCGAAAACAAAGATTGCTGCAGCAAAAAATGCAAACC ACCGGCATTGTGAAACTGTGCCGCTGG |
| 155 | B6 | GCGTGCAGCAAAAAATGGGAATATTGTACCAAAGATAGCGAATGCTGCCCGCATCTGGGCTGCTGGAAACGC CGCCGCAGCTTTGAAGTGTGCGTGCCGAAAACCCCGAAAACC |
| 156 | C1 | CGCTGCATTGAAGAAGGCAAATGGTGTACCAAAGATGAAGATTGCTGCAAACATCTGGCGTGCAACCGCAAA CATAAATGGTGCAAATATAAACTGTGG |
| 157 | C2, F2 | AGCCCGACCTGCATTCGCAGCGGCCAGCCGTGTGCGGATAGCGATGATTGCTGCGAAACCTTTCATTGCAAA TGGGTGTTTTTTACCAGCAAATTTATGTGCCGCCGCGTGTGGGGCAAAGAT |
| 158 | C3 | AGCACCTGCACCCCGACCGATCAGCCGTGTGCGGATAGCGATGATTGCTGCGAAACCTTTCATTGCAAATGG GTGTTTTTTACCAGCAAATTTATGTGCCGCCGCGTGTGGGGCAAAGAT |
| 159 | C4 | AAATGCCGCTGGCTGTTTGGCGGGGTACCCCGGGCAAAAACGAATGCTGGCCGAACTATGCGTGCCATAGCT ATTGGGAATGGGGCCTGTGGGATGGCAGCTTTGGATCCG |
| 160 | C5 | GGCTGCAAATGGTATCTGGGCGATTGTGCGGATAGCGATGATTGCTGCGAAACCTTTCATTGCAAATGGGTG TTTTTTACCAGCAAATTTATGTGCCGCCGCGTGTGGGGCAAAGAT |
| 161 | C6, D5 | AGCAGCACCTGCATTCCGAGCGGCCAGCCGTGTGCGGATAGCGATGATTGCTGCGAAACCTTTCATTGCAAA TGGGTGTTTTTTACCAGCAAATTTATGTGCCGCCGCGTGTGGGGCAAAGAT |
| 162 | D3 | GCGTGCAGCAAAAAATGGGAATATTGTAAAGAAAAACTGTGCTGCAGCGGCTATGTGTGCAAACGCCGCGGC ACCAACATTGAAAAACGCTGCCGCGGA |
| 163 | D4 | GCGTGCGGCCAGTTTTGGTGGAAATGTACCAGCGATAGCGATTGCTGCCCGAACTGGGTGTGCCGCCTGTGG TGCAAATATAAACTG |
| 164 | D6, E2 | TGCCGCTATTGGCTGGGCGGCTGTAGCCAGGATGGCGATTGCTGCAAACATCTGCAGTGCAGCCCGCGCTGG GGCTGGTGCATTTATAGCACCCGCGGCGGCCGC |
| 165 | E1 | GATTGCGGCACCATTTGGCATTATTGTACCCCGGAAAAAAACGATTGCTGCCAGCGCCTGTATTGCAGCCCG CGCTGGAGGCTGGTGCATTTA |
| 166 | E3 | ATTGCGTGCGCGCCGCGCTTTAGCATTTGTGATCCGAAAAACGATAAATGCTGCCCCGAACCGCGTGTGCAGC GATAAACATAAATGGTGCAAATGGAAACTG |
| 167 | E4 | AGCAGCACCTGCATTCCGAGCGGCCAGCCGTGTCGCGAAAACAAAGATTGCTGCAGCAAAAAATGCAGCGAT AAACATAAATGGTGCAAATGGAAACTGGGA |
| 168 | E5 | GATGGCGAATGCGGCGGCTTTTGGTGGAAATGTAAAAACAGCAACGATTGCTGCAAAGATCTGGTGTGCAAA GAAAAATGGCCGATTACCTATAAAATTTGCGTGTGGGATCGCACCTTT |
| 169 | E6 | ATTGCGTGCGCGCCGCGCTTTAGCCTGTGTGATACCAGCAAAGATTGCTGCGAAGGCTATGTGTGCAACCGC AAACATAAATGGTGCAAATATAAACTGTGG |
| 170 | F4 | GAATGCAAAGGCTTTGGCAAAAGCTGTGCGGATAGCGATGATTGCTGCGAAACCTTTCATTGCAAATGGGTG TTTTTTACCAGCAAATTTATGTGCCGCCGCGTGTGGGGCAAAGAT |
| 171 | F5 | AGCCCGGTGTGCACCCCGAGCGGCCAGCCGTGTGCGGATAGCGATGATTGCTGCGAAACCTTTCATTGCAAA TGGGTGTTTTTTACCAGCAAATTTATGTGCCGCCGCGTGTGGGGCAAAGAT |
| 172 | F6 | GATGATTGCGGCGGCCTGTTAGCGGCTGTACCCCGGGCAAAAACGAATGCTGCCCCGAACCGCGTGTGCAAA ATTGGCCTGTATCTGTGCCATTTGGAGCCCG |
| 173 | G1 | GGCTGCCTGGGCGATAAATGTGCGGATAGCGATGATTGCTGCGAAACCTTTCATTGCAAATGGGTGTTTTTT ACCAGCAAATTTATGTGCCGCCGCGTGTGGGGCAAAGAT |
| 174 | G3 | TGCCGCTATCTGTTTGGCGGCTGTGCGTGGTTTAGCGGCGAAAGCTGCTGCACCGGCATTTGCAGCCCGCGC TGGGGCTGGTGCATTTATAGCACCCGCGGCGGCCGC |

TABLE 2C-continued

| SEQ ID NO: | Name | Nucleotide Sequences |
|---|---|---|
| 175 | G4 | GGCGATTGCCTGCCGCATCTGAAACTGTGTAACCCGAACGATGATAAATGCTGCCGCCCGAAACTGAAATGC AGCCGCCGCGGCACCAACCCGGAAAAACGCTGCCGC |
| 176 | G6 | GATGATTGCGGCACCCTGTTTAGCGGCTGTCCGTATAGCAAATATTGCTGCAGCGGCAGCTGCAAACGCCGC GGCACCAACATTGAAAAACGCTGCCGC |
| 177 | H4 | GCTGCCTGTGCGATAGATGTGTNCATAGCGGTGATTGTTGCGAAGACTTTCATTGCACCTGCGAGTTTTTTA ACATGTAATTTATG |

In some embodiments, a polypeptide component is composed of one or more polypeptide elements, each of which has an amino acid sequence that is substantially identical to a reference sequence element A, B, or C as set forth in Table 3A. In some embodiments, one or more A, B, C reference sequence elements is or comprises a wild type toxin sequence element. In some embodiments, a polypeptide component has an amino acid sequence that comprises or consists of a single sequence element corresponding to an A reference sequence element, a single sequence element corresponding to a B reference sequence element, and a single sequence element corresponding to a C reference sequence element. In some such embodiments, the single sequence elements are arranged in a linear order as follows: A-B-C. Examples of Hv1 modulating agents having A-B-C sequence elements are depicted in FIG. 2 and Table 2. Examples of nucleotide sequences encoding polypeptide sequence elements A, B, and C are set forth in Table 3B.

TABLE 3A

| SEQ ID NO: | Element A | SEQ ID NO: | Element B | SEQ ID NO: | Element C |
|---|---|---|---|---|---|
| 178 | AACLGMFESC | 273 | ADSDDCCETFHC | 377 | ALGICMPR |
| 179 | ACGQFWWKC | 274 | AWFSGESCCTGIC | 378 | ATTGRFRYLCKYQI |
| 180 | ACKGVFDAC | 275 | DEERKCCEGLVC | 379 | DRRDQWCKWNPW |
| 181 | ACREWLGGC | 276 | DENDPRCCSGLVC | 380 | ELWCKYNL |
| 182 | ADCGWLFHSC | 277 | DGKSTFCCSGFNC | 381 | ERSSPWCKIDIW |
| 183 | CAAEGIPC | 278 | DGKSTFCCSGYNC | 382 | HLWCKYK |
| 184 | CGGWMAKC | 279 | DPDNDKCCEGYKC | 383 | HSLFSYCAWDLTFSD |
| 185 | CIGEGVPC | 280 | DPKNDKCCKNYTC | 384 | HSNYEWCIWDGTFSK |
| 186 | CMGYDIHC | 281 | DPKNDKCCPNRVC | 385 | HSNYEWCVWDGT |
| 187 | DCAGYMREC | 282 | DPNNDKCCPNREC | 386 | HSRWDWCIWDGTF |
| 188 | DCGTIWHYC | 283 | DPNNDKCCPNRVC | 387 | HSYWEWCLWDGSF |
| 189 | DCLGFLWKC | 284 | DPNPVKDLPCCSGLAC | 388 | ICSGXNWK |
| 190 | DCLGLFWIC | 285 | DSARKCCEGLVC | 389 | ISTKVNYYCRPDRGP |
| 191 | DCLGWFKGC | 286 | DSERKCCEDMVC | 390 | KAFVLHCYRN |
| 192 | DCLGWFKSC | 287 | DSERKCCEGMVC | 391 | KDVLYYCAWDGTF |
| 193 | DCRALYGGC | 288 | DSERKCCEGYVC | 392 | KEKWPITYKICVWDRTF |
| 194 | DCRKMFGGC | 289 | DSKRACCEGLRC | 393 | KELSIWDSRCL |
| 195 | DCTRMFGAC | 290 | DSKRKCCEDMVC | 394 | KFRDKYCAWDFTFS |
| 196 | DCVRFWGKC | 291 | DSNADCCEGYVC | 395 | KGPSPKQKKCTRP |
| 197 | DDCGGLFSGC | 292 | DSTLDCCKHLSC | 396 | KGRFVNTWPTFCLV |
| 198 | DDCGKLFSGC | 293 | DTNADCCEGYVC | 397 | KIGLYLCIWSP |
| 199 | DDCGTLFSGC | 294 | DTSKDCCEGYVC | 398 | KLWCRKIIG |
| 200 | DDCLGMFSSC | 295 | DYNNGCCSGYVC | 399 | KLWCRYERTW |
| 201 | DDDCGWIMDDC | 296 | EKDEHCCEHLGC | 400 | KMGLDYCAWDGTF |

TABLE 3A-continued

| SEQ ID NO: | Element A | SEQ ID NO: | Element B | SEQ ID NO: | Element C |
|---|---|---|---|---|---|
| 202 | DGECGGFWWKC | 297 | EKDSDCCEHLGC | 401 | KMGLYYCAWDGTF |
| 203 | ECGKFMWKC | 298 | ESNADCCENWAC | 402 | KPTLKYCAWDGT |
| 204 | ECGTLFSGC | 299 | FRDKECCKGLTC | 403 | KPTLKYCAWDGTF |
| 205 | ECKGFGKSC | 300 | GAGKPTCCSGYDC | 404 | KPTSKYCAWDGTI |
| 206 | ECKKLFGGC | 301 | GEGKPPCCANFAC | 405 | KQKWPFYCAWDWSF |
| 207 | ECKWYLGDC | 302 | GRGKPPCCKGYAC | 406 | KRRGTNAEKRCR |
| 208 | ECKYLWGTC | 303 | GSGKPACCPKYVC | 407 | KRRGTNIEKRCR |
| 209 | ECLEIFKAC | 304 | GTDQSECCEGWKC | 408 | KRTFNYCAWDGSFSK |
| 210 | ECLGFGKGC | 305 | HPGQPPCCSGLAC | 409 | KSKWPRNICVWDGSV |
| 211 | ECRKMFGGC | 306 | KADNDCCGKKC | 410 | KTTGIVKLCRW |
| 212 | ECRWLFGGC | 307 | KAHEDCCEHLRC | 411 | KWVFFTSKFMCRRVWGKD |
| 213 | ECRWYLGGC | 308 | KEDSECCEHLQC | 412 | LKPTLHGIWYKHHYCYTQ |
| 214 | ECRYFWGEC | 309 | KEKLCCSGYVC | 413 | LKPTLHGIWYKSYYCYKK |
| 215 | ECRYLFGGC | 310 | KENKDCCSKKC | 414 | NGNTVYRCA |
| 216 | ECRYWLGGC | 311 | KKDKECCGWNIC | 415 | NKKHGWCGWDGTF |
| 217 | ECRYWLGTC | 312 | KNKKECCGWNAC | 416 | NKKYWHCGWDGTF |
| 218 | ECTKFLGGC | 313 | KNSNDCCKDLVC | 417 | NRKHKWCKYKLW |
| 219 | ECTKLLGGC | 314 | KSDENCCKKFKC | 418 | NRRDKWCKYKLW |
| 220 | EDCIPKWKGC | 315 | KSTSDCCEHLSC | 419 | NSRDKWCKVLL |
| 221 | EGECGGFWWKC | 316 | KTTADCCKHLAC | 420 | QLWCKKRL |
| 222 | GACRWFLGGC | 317 | KTTADCCKHLGC | 421 | QPAIKWCIWSP |
| 223 | GCANAYKSC | 318 | KTTSDCCKHLGC | 422 | QSRIANMWPTFCLV |
| 224 | GCGGLMAGC | 319 | NALSGPRCCSGLKC | 423 | QSRIANMWPTFCSQ |
| 225 | GCGGLMDGC | 320 | NDEMVCCEHLVC | 424 | RKKWPYHCGWDGTF |
| 226 | GCGTMWSPC | 321 | NGPHTCCWGYNGYKKAC | 425 | RKKWPYHCVWDWTV |
| 227 | GCIPSFGEC | 322 | NPDNDKCCEGRKC | 426 | RLWCKKII |
| 228 | GCKGFGDSC | 323 | NPNDDKCCRPKLKC | 427 | RLWCKKKIEEG |
| 229 | GCKLTFWKC | 324 | NPSNDKCCRPNLVC | 428 | RLWCKKKIEW |
| 230 | GCLEFWWKC | 325 | NPSNDQCCKSANLVC | 429 | RLWCKKKLW |
| 231 | GCLGDKC | 326 | NPSNDQCCKSSKLVC | 430 | RLWCKKRL |
| 232 | GCNRKNKKC | 327 | NPSNDQCCKSSNLVC | 431 | RLWCKLDW |
| 233 | GCQKFFWTC | 328 | NSDADCCRYGERC | 432 | RLWCKRIINM |
| 234 | GDCLPHLKLC | 329 | NSDKECCKGLRC | 433 | RLWCKYKL |
| 235 | GDCLPHLKRC | 330 | NYMDDKCCPGYKC | 434 | RRAKPSWCGWDFTF |
| 236 | GGCLPHNRFC | 331 | PKKAPCCGRLEC | 435 | RRAKPSWCGWDFTV |
| 237 | GVDKAGCRYMFGGC | 332 | PYHESCCSGSC | 436 | RRTLPTYCAWDLTFP |
| 238 | GVDKEGCRKLLGGC | 333 | PYNEHCCSGSC | 437 | RSDGKYCAWDGTF |
| 239 | IACAPRFSIC | 334 | PYNENCCSKSC | 438 | RSDWKYCAWDGTFS |
| 240 | IACAPRFSLC | 335 | PYNENCCSQSC | 439 | RSRDQWCKYKLW |

TABLE 3A-continued

| SEQ ID NO: | Element A | SEQ ID NO: | Element B | SEQ ID NO: | Element C |
|---|---|---|---|---|---|
| 241 | IACAPRGLLC | 336 | PYNESCCSGSC | 440 | RVRDQWCKYKLW |
| 242 | KCLPPGKPC | 337 | PYSKYCCSGSC | 441 | SDKHKWCKWKL |
| 243 | LCSREGEFC | 338 | QPNTQPCCNNAEEEQTINC | 442 | SHNKCT |
| 244 | QCGEFMWKC | 339 | RENKDCCSKKC | 443 | SKLFKLCNFSF |
| 245 | RCIEEGKWC | 340 | RRDSDCCPHLGC | 444 | SKTGFVKNICKYEM |
| 246 | SAVCIPSGQPC | 341 | SAGQTCCKHLVC | 445 | SKTWGWCAVEAP |
| 247 | SCKLTFWRC | 342 | SEDSECCPHLGC | 446 | SPKHGWCVWDWTFRK |
| 248 | SECRWFMGGC | 343 | SKDADCCAHLEC | 447 | SPKWGLCNFPMP |
| 249 | SEKDCIKHLQRC | 344 | SKHEDCCAHLAC | 448 | SPRWGWCIYSTRGGR |
| 250 | SFCIPFKPC | 345 | SKTGDCCSHLSC | 449 | SPTWKWCVLKSPGRR |
| 251 | SPTCIPSGQPC | 346 | SQDGDCCKHLQC | 450 | SPTWKWCWARP |
| 252 | SPTCIPTGQPC | 347 | SQTSDCCPHLAC | 451 | SQHRLCSVKA |
| 253 | SPTCIRSGQPC | 348 | SSDKPCCSGYYC | 452 | SRKDKWCKYQI |
| 254 | SPVCTPSGQPC | 349 | SSTSDCCKHLSC | 453 | SRKHRWCKYEI |
| 255 | SSTCIPSGQPC | 350 | STEKPCCDNFSC | 454 | SRKTRWCKYQI |
| 256 | SSTCIRTDQPC | 351 | STHADCCEGFIC | 455 | SRQLCKYVIDW |
| 257 | STCTPTDQPC | 352 | SVDSDCCAHLGC | 456 | SRRDRWCKYDL |
| 258 | SVCIPSGQPC | 353 | SVHSDCCAHLGC | 457 | SRRDRWCKYYL |
| 259 | TCRYLFGGC | 354 | SVNDDCCPRLGC | 458 | SRRGTNPEKRCR |
| 260 | TCYDIGELC | 355 | TDRLPCCFGLEC | 459 | SRRHGWCVWDGTFS |
| 261 | VCRGYGLPC | 356 | TIDDDCCPHLGC | 460 | SRTWKWCVLAGPW |
| 262 | YfQKWLWTC | 357 | TKDEDCCKHLAC | 461 | SSKHKWCKVYL |
| 263 | YCQKWMWTC | 358 | TKDSECCPHLGC | 462 | SSRWKWCVLASPF |
| 264 | CKQADEPC | 359 | TPEKNDCCQRLYC | 463 | SSRWKWCVLPAPW |
| 265 | ACRKKWEYC | 360 | TPGKNECCPNRVC | 464 | TFKENENGNTVKRCD |
| 266 | DDDCEPPGNFC | 361 | TPGKNECCPNYAC | 465 | TFKTNENGNTVKRCD |
| 267 | VKPCRKEGQLC | 362 | TSDSDCCPNWVC | 466 | TGLCIPP |
| 268 | WCKQSGEMC | 363 | TTSSECCAHLGC | 467 | TRFNVCGK |
| 269 | CLSGGEVC | 364 | VNRHGDCCEGLEC | 468 | TWPTEICID |
| 270 | GKPCHEEGCQL | 365 | VPGKNECCSGYAC | 469 | TYKANENGNQVKRCD |
| 271 | CIPFLHPC | 366 | YGATQKIPCCGVC | 470 | TYKENENGNTVKRCD |
| 272 | ACSKKWEYC | 367 | YKLRKCCAGFYC | 471 | TYKENENGNTVQRCD |
|  |  | 368 | DVFSLDCCTGIC | 472 | TYKTNENGNSVQRCD |
|  |  | 369 | IVPIIGFIYCCPGLIC | 473 | VKTSGYWWYKKTYCRRKS |
|  |  | 370 | GMIKIGPPCCSGWC | 474 | WKRRRSFEVCVPKTPKT |
|  |  | 371 | DPIFQNCCRGWNC | 475 | LGVCMW |
|  |  | 372 | NVLDQNCCDGYC | 476 | FFACA |
|  |  | 373 | DFLFPKCCNYC | 477 | VLFCV |

TABLE 3A-continued

| SEQ ID NO: | Element A | SEQ ID NO: | Element B | SEQ ID NO: | Element C |
|---|---|---|---|---|---|
| | | 374 | DPFLQNCCLGWNC | 478 | IVFVCT |
| | | 375 | TFFFPDCCNSIC | 479 | ILLFCS |
| | | 376 | IVPILGFWCCPGLIC | 480 | VFVCI |
| | | | | 481 | AQFICL |
| | | | | 482 | GPFVCV |

TABLE 3B

| SEQ ID NO. | Element A | SEQ ID NO. | Element B | SEQ ID NO. | Element C |
|---|---|---|---|---|---|
| 483 | GCGGCGTGCCTGGGCATGTTTGAAAGCTGT | 578 | GCGGATAGCGATGATTGCTGCGAAACCTTTCATTGC | 682 | GCGCTGGGCATTTGCATGCCGCGC |
| 484 | GCGTGCGGCCAGTTTTGGTGGAAATGT | 579 | GCGTGGTTTAGCGGCGAAAGCTGCTGCACCGGCATTTGC | 683 | GCGACCACCGGCCGCTTTCGCTATCTGTGCAAATATCAGATT |
| 485 | GCGTGCAAAGGCGTGTTTGATGCGTGT | 580 | GATGAAGAACGCAAATGCTGCGAAGGCCTGGTGTGC | 684 | GATCGCCGCGATCAGTGGTGCAAATGGAACCCGTGG |
| 486 | GCGTGCCGCGAATGGCTGGGCGGCTGT | 581 | GATGAAAACGATCCGCGCTGCTGCAGCGGCCTGGTGTGC | 685 | GAACTGTGGTGCAAATATAACCTG |
| 487 | GCGGATTGCGGCTGGCTGTTTCATAGCTGT | 582 | GATGGCAAAAGCACCTTTTGCTGCAGCGGCTTTAACTGC | 686 | GAACGCAGCAGCCCGTGGTGCAAAATTGATATTTGG |
| 488 | TGCGCGGCGGAAGGCATTCCGTGT | 583 | GATGGCAAAAGCACCTTTTGCTGCAGCGGCTATAACTGC | 687 | CATCTGTGGTGCAAATATAAA |
| 489 | TGCGGCGGCTGGATGGCGAAATGT | 584 | GATCCGGATAACGATAAATGCTGCGAAGGCTATAAATGC | 688 | CATAGCCTGTTTAGCTATTGCGCGTGGGATCTGACCTTTAGCGAT |
| 490 | TGCATTGGCGAAGGCGTGCCGTGT | 585 | GATCCGAAAAACGATAAATGCTGCAAAAACTATACCTGC | 689 | CATAGCAACTATGAATGGTGCATTTGGGATGGCACCTTTAGCAAA |
| 491 | TGCATGGGCTATGATATTCATTGT | 586 | GATCCGAAAAACGATAAATGCTGCCCGAACCGCGTGTGC | 690 | CATAGCAACTATGAATGGTGCGTGTGGGATGGCACC |
| 492 | GATTGCGCGGGCTATATGCGCGAATGT | 587 | GATCCGAACAACGATAAATGCTGCCCGAACCGCGAATGC | 691 | CATAGCCGCTGGGATTGGTGCATTTGGGATGGCACCTTT |
| 493 | GATTGCGGCACCATTTGGCATTATTGT | 588 | GATCCGAACAACGATAAATGCTGCCCGAACCGCGTGTGC | 692 | CATAGCTATTGGGAATGGTGCCTGTGGGATGGCAGCTTT |
| 494 | GATTGCCTGGGCTTTCTGTGGAAATGT | 589 | GATCCGAACCCGGTGAAAGATCTGCCGTGCTGCAGCGGCCTGGCGTGC | 693 | ATTTGCAGCGGCAACTGGAAA |
| 495 | GATTGCCTGGGCCTGTTTTGGATTGT | 590 | GATAGCGCGCGCAAATGCTGCGAAGGCCTGGTGTGC | 694 | ATTAGCACCAAAGTGAACTATTATCGCCCGGATCGCGGCCCG |
| 496 | GATTGCCTGGGCTGGTTTAAAGGCTGT | 591 | GATAGCGAACGCAAATGCTGCGAAGATATGGTGTGC | 695 | AAAGCGTTTGTGCTGCATTGCTATCGCAAC |
| 497 | GATTGCCTGGGCTGGTTTAAAAGCTGT | 592 | GATAGCGAACGCAAATGCTGCGAAGGCATGGTGTGC | 696 | AAAGATGTGCTGTATTATTGCGCGTGGGATGGCACCTTT |

TABLE 3B-continued

| SEQ ID NO. | Element A | SEQ ID NO. | Element B | SEQ ID NO. | Element C |
|---|---|---|---|---|---|
| 498 | GATTGCCGCGCGCTGTATGGCGGCTGT | 593 | GATAGCGAACGCAAATGCTGCGAAGGCTATGTGTGC | 697 | AAAGAAAAATGGCCGATTACCTATAAAATTTGCGTGTGGGATCGCACCTTT |
| 499 | GATTGCCGCAAAATGTTTGGCGGCTGT | 594 | GATAGCAAACGCGTGCTGCGAAGGCCTGCGCTGC | 698 | AAAGAACTGAGCATTTGGGATAGCCGCTGCCTG |
| 500 | GATTGCACCCGCATGTTTGGCGCGTGT | 595 | GATAGCAAACGCAAATGCTGCGAAGATATGGTGTGC | 699 | AAATTTCGCGATAAATATTGCGCGTGGGATTTTACCTTTAGC |
| 501 | GATTGCGTGCGCTTTTGGGGCAAATGT | 596 | GATAGCAACGCGGATTGCTGCGAAGGCTATGTGTGC | 700 | AAAGGCCCGAGCCCGAAACAGAAAAAATGCACCCGCCCG |
| 502 | GATGATTGCGGCGGCCTGTTTAGCGGCTGT | 597 | GATAGCACCCTGGATTGCTGCAAACATCTGAGCTGC | 701 | AAAGGCCGCTTTGTGAACACCTGGCCGACCTTTTGCCTGGTG |
| 503 | GATGATTGCGGCAAACTGTTTAGCGGCTGT | 598 | GATACCAACGCGGATTGCTGCGAAGGCTATGTGTGC | 702 | AAAATTGGCCTGTATCTGTGCATTTGGAGCCCG |
| 504 | GATGATTGCGGCACCCTGTTTAGCGGCTGT | 599 | GATACCAGCAAAGATTGCTGCGAAGGCTATGTGTGC | 703 | AAACTGTGGTGCCGCAAAATTATTGG |
| 505 | GATGATTGCCTGGGCATGTTTAGCAGCTGT | 600 | GATTATAACAACGGCTGCTGCAGCGGCTATGTGTGC | 704 | AAACTGTGGTGCCGCTATGAACGCACCTGG |
| 506 | GATGATGATTGCGGCTGGATTATGGATGATTGT | 601 | GAAAAAGATGAACATTGCTGCGAACATCTGGGCTGC | 705 | AAAATGGGCCTGGATTATTGCGCGTGGGATGGCACCTTT |
| 507 | GATGGCGAATGCGGCGGCTTTTGGTGGAAATGT | 602 | GAAAAAGATAGCGATTGCTGCGAACATCTGGGCTGC | 706 | AAAATGGGCCTGTATTATTGCGCGTGGGATGGCACCTTT |
| 508 | GAATGCGGCAAATTTATGTGGAAATGT | 603 | GAAAGCAACGCGGATTGCTGCGAAAACTGGGCGTGC | 707 | AAACCGACCCTGAAATATTGCGCGTGGGATGGCACC |
| 509 | GAATGCGGCACCCTGTTTAGCGGCTGT | 604 | TTTCGCGATAAAGAATGCTGCAAAGGCCTGACCTGC | 708 | AAACCGACCCTGAAATATTGCGCGTGGGATGGCACCTTT |
| 510 | GAATGCAAAGGCTTTGGCAAAAGCTGT | 605 | GGCGCGGGCAAACCGACCTGCTGCAGCGGCTATGATTGC | 709 | AAACCGACCAGCAAATATTGCGCGTGGGATGGCACCATT |
| 511 | GAATGCAAAAAACTGTTTGGCGGCTGT | 606 | GGCGAAGGCAAACCGCCGTGCTGCGCGAACTTTGCGTGC | 710 | AAACAGAAATGGCCGTTTTATTGCGCGTGGGATTGGAGCTTT |
| 512 | GAATGCAAATGGTATCTGGGCGATTGT | 607 | GGCCGCGGCAAACCGCCGTGCTGCAAAGGCTATGCGTGC | 711 | AAACGCCGCGGCACCAACGCGGAAAAACGCTGCCGC |
| 513 | GAATGCAAATATCTGTGGGGCACCTGT | 608 | GGCAGCGGCAAACCGGCGTGCTGCCCGAAATATGTGTGC | 712 | AAACGCCGCGGCACCAACATTGAAAAACGCTGCCGC |
| 514 | GAATGCCTGGAAATTTTTAAAGCGTGT | 609 | GGCACCGATCAGAGCGAATGCTGCGAAGGCTGGAAATGC | 713 | AAACGCACCTTTAACTATTGCGCGTGGGATGGCAGCTTTAGCAAA |
| 515 | GAATGCCTGGGCTTTGGCAAAGGCTGT | 610 | CATCCGGGCCAGCCGCCGTGCTGCAGCGGCCTGGCGTGC | 714 | AAAAGCAAATGGCCGCGCAACATTTGCGTGTGGGATGGCAGCGTG |
| 516 | GAATGCCGCAAAATGTTTGGCGGCTGT | 611 | AAAGCGGATAACGATTGCTGCGGCAAAAAATGC | 715 | AAAACCACCGGCATTGTGAAACTGTGCCGCTGG |

TABLE 3B-continued

| SEQ ID NO. | Element A | SEQ ID NO. | Element B | SEQ ID NO. | Element C |
|---|---|---|---|---|---|
| 517 | GAATGCCGCTGGCTGTTTGGCGGTGT | 612 | AAAGCGCATGAAGATTGCTGCGAACATCTGCGCTGC | 716 | AAATGGGTGTTTTTTACCAGCAAATTTATGTGCCGCCGCGTGTGGGGCAAAGAT |
| 518 | GAATGCCGCTGGTATCTGGGCGGCTGT | 613 | AAAGAAGATAGCGAATGCTGCGAACATCTGCAGTGC | 717 | CTGAAACCGACCCTGCATGGCATTTGGTATAAACATCATTATTGCTATACCCAG |
| 519 | GAATGCCGCTATTTTTGGGGCGAATGT | 614 | AAAGAAAAACTGTGCTGCAGCGGCTATGTGTGC | 718 | CTGAAACCGACCCTGCATGGCATTTGGTATAAAGCTATTATTGCTATAAAAA |
| 520 | GAATGCCGCTATCTGTTTGGCGGCTGT | 615 | AAAGAAAACAAAGATTGCTGCAGCAAAAAATGC | 719 | AACGGCAACACCGTGTATCGCTGCGCG |
| 521 | GAATGCCGCTATTGGCTGGGCGGCTGT | 616 | AAAAAAGATAAAGAATGCTGCGGCTGGAACATTTGC | 720 | AACAAAAAACATGGCTGGTGCGGCTGGGATGGCACCTTT |
| 522 | GAATGCCGCTATTGGCTGGGCACCTGT | 617 | AAAAACAAAAAGAATGCTGCGGCTGGAACGCGTGC | 721 | AACAAAAAATATTGGCATTGCGGCTGGGATGGCACCTTT |
| 523 | GAATGCACCAAATTTCTGGGCGGCTGT | 618 | AAAAACAGCAACGATTGCTGCAAAGATCTGGTGTGC | 722 | AACCGCAAACATAAATGGTGCAAATATAAACTGTGG |
| 524 | GAATGCACCAAACTGCTGGGCGGCTGT | 619 | AAAAGCGATGAAAACTGCTGCAAAAATTTAAATGC | 723 | AACCGCCGCGATAAATGGTGCAAATATAAACTGTGG |
| 525 | GAAGATTGCATTCCGAAATGGAAAGGCTGT | 620 | AAAAGCACCAGCGATTGCTGCGAACATCTGAGCTGC | 724 | AACAGCCGCGATAAATGGTGCAAAGTGCTGCTG |
| 526 | GAAGGCGAATGCGGCGGCTTTTGGTGGAAATGT | 621 | AAAACCACCGCGGATTGCTGCAAACATCTGGCGTGC | 725 | CAGCTGTGGTGCAAAAAACGCCTG |
| 527 | GGCGCGTGCCGCTGGTTTCTGGGCGGCTGT | 622 | AAAACCACCGCGGATTGCTGCAAACATCTGGGCTGC | 726 | CAGCCGGCGATTAAATGGTGCATTTGGAGCCCG |
| 528 | GGCTGCGCGAACGCGTATAAAAGCTGT | 623 | AAAACCACCAGCGATTGCTGCAAACATCTGGGCTGC | 727 | CAGAGCCGCATTGCGAACATGTGGCCGACCTTTTGCCTGGTG |
| 529 | GGCTGCGGCGGCCTGATGGCGGGCTGT | 624 | AACGCGCTGAGCGGCCCGCGCTGCTGCAGCGGCCTGAAATGC | 728 | CAGAGCCGCATTGCGAACATGTGGCCGACCTTTTGCAGCCAG |
| 530 | GGCTGCGGCGGCCTGATGGATGGCTGT | 625 | AACGATGAAATGGTGTGCTGCGAACATCTGGTGTGC | 729 | CGCAAAAAATGGCCGTATCATTGCGGCTGGGATGGCACCTTT |
| 531 | GGCTGCGGCACCATGTGGAGCCCGTGT | 626 | AACGGCCCGCATACCTGCTGCTGGGGCTATAACGGCTATAAAAAGCGTGC | 730 | CGCAAAAAATGGCCGTATCATTGCGTGTGGGATTGGACCGTG |
| 532 | GGCTGCATTCCGAGCTTTGGCGAATGT | 627 | AACCCGGATAACGATAAATGCTGCGAAGGCCGCAAATGC | 731 | CGCCTGTGGTGCAAAAAAATTATT |
| 533 | GGCTGCAAAGGCTTTGGCGATAGCTGT | 628 | AACCCGAACGATGATAAATGCTGCCGCCCGAAACTGAAATGC | 732 | CGCCTGTGGTGCAAAAAAAAAATTGAAGAAGGC |
| 534 | GGCTGCAAACTGACCTTTTGGAAATGT | 629 | AACCCGAGCAACGATAAATGCTGCCGCCCGAACCTGGTGTGC | 733 | CGCCTGTGGTGCAAAAAAAAAATTGAATGG |
| 535 | GGCTGCCTGGAATTTTGGTGGAAATGT | 630 | AACCCGAGCAACGATCAGTGCTGCAAAAGCGCGAACCTGGTGTGC | 734 | CGCCTGTGGTGCAAAAAAAAACTGTGG |

TABLE 3B-continued

| SEQ ID NO. | Element A | SEQ ID NO. | Element B | SEQ ID NO. | Element C |
|---|---|---|---|---|---|
| 536 | GGCTGCCTGGGCGATAAATGT | 631 | AACCCGAGCAACGATCAGTGCTGCAAAAGCAGCAAACTGGTGTGC | 735 | CGCCTGTGGTGCAAAAAACGCCTG |
| 537 | GGCTGCAACCGCAAAAACAAAAAATGT | 632 | AACCCGAGCAACGATCAGTGCTGCAAAAGCAGCAACCTGGTGTGC | 736 | CGCCTGTGGTGCAAACTGGATTGG |
| 538 | GGCTGCCAGAAATTTTTTTGGACCTGT | 633 | AACAGCGATGCGGATTGCTGCCGCTATGGCGAACGCTGC | 737 | CGCCTGTGGTGCAAACGCATTATTAACATG |
| 539 | GGCGATTGCCTGCCGCATCTGAAACTGTGT | 634 | AACAGCGATAAAGAATGCTGCAAAGGCCTGCGCTGC | 738 | CGCCTGTGGTGCAAATATAAACTG |
| 540 | GGCGATTGCCTGCCGCATCTGAAACGCTGT | 635 | AACTATATGGATGATAAATGCTGCCCGGGCTATAAATGC | 739 | CGCCGCGCGAAACCGAGCTGGTGCGGCTGGGATTTTACCTTT |
| 541 | GGCGGCTGCCTGCCGCATAACCGCTTTTGT | 636 | CCGAAAAAAGCGCCGTGCTGCGGCCGCCTGGAATGC | 740 | CGCCGCGCGAAACCGAGCTGGTGCGGCTGGGATTTTACCGTG |
| 542 | GGCGTGGATAAAGCGGGCTGCCGCTATATGTTTGGCGGCTGT | 637 | CCGTATCATGAAAGCTGCTGCAGCGGCAGCTGC | 741 | CGCCGCACCCTGCCGACCTATTGCGCGTGGGATCTGACCTTTCCG |
| 543 | GGCGTGGATAAAGAAGGCTGCCGCAAACTGCTGGGCGGCTGT | 638 | CCGTATAACGAACATTGCTGCAGCGGCAGCTGC | 742 | CGCAGCGATGGCAAATATTGCGCGTGGGATGGCACCTTT |
| 544 | ATTGCGTGCGCGCCGCGCTTTAGCATTTGT | 639 | CCGTATAACGAAAACTGCTGCAGCAAAAGCTGC | 743 | CGCAGCGATTGGAAATATTGCGCGTGGGATGGCACCTTTAGC |
| 545 | ATTGCGTGCGCGCCGCGCTTTAGCCTGTGT | 640 | CCGTATAACGAAAACTGCTGCAGCCAGAGCTGC | 744 | CGCAGCCGCGATCAGTGGTGCAAATATAAACTGTGG |
| 546 | ATTGCGTGCGCGCCGCGCGGCCTGCTGTGT | 641 | CCGTATAACGAAAGCTGCTGCAGCGGCAGCTGC | 745 | CGCGTGCGCGATCAGTGGTGCAAATATAAACTGTGG |
| 547 | AAATGCCTGCCGCCGGGCAAACCGTGT | 642 | CCGTATAGCAAATATTGCTGCAGCGGCAGCTGC | 746 | AGCGATAAACATAAATGGTGCAAATGGAAACTG |
| 548 | CTGTGCAGCCGCGAAGGCGAATTT | 643 | CAGCCGAACACCCAGCCGTGCTGCAACAACGCGGAAGAAGAACAGACCATTAACTGC | 747 | AGCCATAACAAATGCACC |
| 549 | CAGTGCGGCGAATTTATGTGGAAATGT | 644 | CGCGAAAACAAAGATTGCTGCAGCAAAAAATGC | 748 | AGCAAACTGTTTAAACTGTGCAACTTTAGCTTT |
| 550 | CGCTGCATTGAAGAAGGCAAATGGTGT | 645 | CGCCGCGATAGCGATTGCTGCCCGCATCTGGGCTGC | 749 | AGCAAAACCGGCTTTGTGAAAAACATTTGCAAATATGAAATG |
| 551 | AGCGCGGTGTGCATTCCGAGCGGCCAGCCGTGT | 646 | AGCGCGGGCCAGACCTGCTGCAAACATCTGGTGTGC | 750 | AGCAAAACCTGGGGCTGGTGCGCGGTGGAAGCGCCG |
| 552 | AGCTGCAAACTGACCTTTTGGCGCTGT | 647 | AGCGAAGATAGCGAATGCTGCCCGCATCTGGGCTGC | 751 | AGCCCGAAACATGGCTGGTGCGTGTGGGATTGGACCTTTCGCAAA |
| 553 | AGCGAATGCCGCTGGTTTATGGGCGGCTGT | 648 | AGCAAGATGCGGATTGCTGCGCGCATCTGGAATGC | 752 | AGCCCGAAATGGGGCCTGTGCAACTTTCCGATGCCG |
| 554 | AGCGAAAAAGATTGCATTAAACATCTGCAGCGCTGT | 649 | AGCAAACATGAAGATTGCTGCGCGCATCTGGCGTGC | 753 | AGCCCGCGCTGGGGCTGGTGCATTTATAGCACCCGCGGCGGCCGC |

TABLE 3B-continued

| SEQ ID NO. | Element A | SEQ ID NO. | Element B | SEQ ID NO. | Element C |
|---|---|---|---|---|---|
| 555 | AGCTTTTGCATTCCGTTTAAACCGTGT | 650 | AGCAAAACCGGCGATTGCTGCAGCCATCTGAGCTGC | 754 | AGCCCGACCTGGAAATGGTGCGTGCTGAAAAGCCCGGGCCGCCGC |
| 556 | AGCCCGACCTGCATTCCGAGCGGCCAGCCGTGT | 651 | AGCCAGGATGGCGATTGCTGCAAACATCTGCAGTGC | 755 | AGCCCGACCTGGAAATGGTGCGTGTATGCGCGCCCG |
| 557 | AGCCCGACCTGCATTCCGACCGGCCAGCCGTGT | 652 | AGCCAGACCAGCGATTGCTGCCCGCATCTGGCGTGC | 756 | AGCCAGCATCGCCTGTGCAGCGTGAAAGCG |
| 558 | AGCCCGACCTGCATTCGCAGCGGCCAGCCGTGT | 653 | AGCAGCGATAAACCGTGCTGCAGCGGCTATTATTGC | 757 | AGCCGCAAAGATAAATGGTGCAAATATCAGATT |
| 559 | AGCCCGGTGTGCACCCCGAGCGGCCAGCCGTGT | 654 | AGCAGCACCAGCGATTGCTGCAAACATCTGAGCTGC | 758 | AGCCGCAAACATCGCTGGTGCAAATATGAAATT |
| 560 | AGCAGCACCTGCATTCCGAGCGGCCAGCCGTGT | 655 | AGCACCGAAAAACCGTGCTGCGATAACTTTAGCTGC | 759 | AGCCGCAAACCCGCTGGTGCAAATATCAGATT |
| 561 | CGGCTGGCCGCTCGGAATGCAGGTGCTGCTTGT | 656 | AGCACCCATGCGGATTGCTGCGAAGGCTTTATTTGC | 760 | AGCCGCCAGCTGTGCAAATATGTGATTGATTGG |
| 562 | AGCACCTGCACCCCGACCGATCAGCCGTGT | 657 | AGCGTGGATAGCGATTGCTGCGCGCATCTGGGCTGC | 761 | AGCCGCCGCGATCGCTGGTGCAAATATGATCTG |
| 563 | AGCGTGTGCATTCCGAGCGGCCAGCCGTGT | 658 | AGCGTGCATAGCGATTGCTGCGCGCATCTGGGCTGC | 762 | AGCCGCCGCGATCGCTGGTGCAAATATTATCTG |
| 564 | ACCTGCCGCTATCTGTTTGGCGGCTGT | 659 | AGCGTGAACGATGATTGCTGCCCGCGCCTGGGCTGC | 763 | AGCCGCCGCGGCACCAACCCGGAAAAACGCTGCCGC |
| 565 | ACCTGCTATGATATTGGCGAACTGTGT | 660 | ACCGATCGCCTGCCGTGCTGCTTTGGCCTGGAATGC | 764 | AGCCGCCGCCATGGCTGGTGCGTGTGGGATGGCACCTTTAGC |
| 566 | GTGTGCCGCGGCTATGGCCTGCCGTGT | 661 | ACCATTGATGATGATTGCTGCCCGCATCTGGGCTGC | 765 | AGCCGCACCTGGAAATGGTGCGTGCTGGCGGGCCCGTGG |
| 567 | TATTGCCAGAAATGGCTGTGGACCTGT | 662 | ACCAAAGATGAAGATTGCTGCAAACATCTGGCGTGC | 766 | AGCAGCAAACATAAATGGTGCAAAGTGTATCTG |
| 568 | TATTGCCAGAAATGGATGTGGACCTGT | 663 | ACCAAAGATAGCGAATGCTGCCCGCATCTGGGCTGC | 767 | AGCAGCCGCTGGAAATGGTGCGTGCTGGCGAGCCCGTTT |
| 569 | TGCAAACAGGCGGATGAACCGTGT | 664 | ACCCCGGAAAAAACGATTGCTGCCAGCGCCTGTATTGC | 768 | AGCAGCCGCTGGAAATGGTGCGTGCTGCCGGCGCCGTGG |
| 570 | GCGTGCCGCAAAAAATGGGAATATTGT | 665 | ACCCCGGGCAAAAACGAATGCTGCCCGAACCGCGTGTGC | 769 | ACCTTTAAAGAAAACGAAAACGGCAACACCGTGAAACGCTGCGAT |
| 571 | GATGATGATTGCGAACCGCCGGGCAACTTTTGT | 666 | ACCCCGGGCAAAAACGAATGCTGCCCGAACTATGCGTGC | 770 | ACCTTTAAAACCAACGAAAACGGCAACACCGTGAAACGCTGCGAT |
| 572 | GTGAAACCGTGCCGCAAAGAAGGCCAGCTGTGT | 667 | ACCAGCGATAGCGATTGCTGCCCGAACTGGGTGTGC | 771 | ACCGGCCTGTGCATTCCGCCG |
| 573 | TGGTGCAAACAGAGCGGCGAAATGTGT | 668 | ACCACCAGCAGCGAATGCTGCGCGCATCTGGGCTGC | 772 | ACCCGCTTTAACGTGTGCGGCAAA |
| 574 | TGCCTGAGCGGCGGCGAAGTGTGT | 669 | GTGAACCGCCATGGCGATTGCTGCGAAGGCCTGGAATGC | 773 | ACCTGGCCGACCGAAATTTGCATTGAT |

TABLE 3B-continued

| SEQ ID NO. | Element A | SEQ ID NO. | Element B | SEQ ID NO. | Element C |
|---|---|---|---|---|---|
| 575 | GGCAAACCGTGCCATGAAGAAGGCCAGCTGTGT | 670 | GTGCCGGGCAAAAACGAATGCTGCAGCGGCTATGCGTGC | 774 | ACCTATAAAGCGAACGAAAACGGCAACCAGGTGAAACGCTGCGAT |
| 576 | TGCATTCCGTTTCTGCATCCGTGT | 671 | TATGGCGCGACCCAGAAAATTCCGTGCTGCGGCGTGTGC | 775 | ACCTATAAAGAAAACGAAAACGGCAACACCGTGAAACGCTGCGAT |
| 577 | GCGTGCAGCAAAAAATGGGAATATTGT | 672 | TATAAACTGCGCAAATGCTGCGCGGGCTTTTATTGC | 776 | ACCTATAAAGAAAACGAAAACGGCAACACCGTGCAGCGCTGCGAT |
|  |  | 673 | GATGTGTTTAGCCTGGATTGCTGCACCGGCATTTGC | 777 | ACCTATAAAACCAACGAAAACGGCAACAGCGTGCAGCGCTGCGAT |
|  |  | 674 | ATTGTGCCGATTATTGGCTTTATTTATTGCTGCCCGGGCCTGATTTGC | 778 | GTGAAAACCAGCGGCTATTGGTGGTATAAAAAAACCTATTGCCGCCGCAAAAGC |
|  |  | 675 | GGCATGATTAAAATTGGCCCGCCGTGCTGCAGCGGCTGGTGC | 779 | TGGAAACGCCGCCGCAGCTTTGAAGTGTGCGTGCCGAAAACCCCGAAAACC |
|  |  | 676 | GATCCGATTTTTCAGAACTGCTGCCGCGGCTGGAACTGC | 780 | CTGGGCGTGTGCATGTGG |
|  |  | 677 | AACGTGCTGGATCAGAACTGCTGCGATGGCTATTGC | 781 | TTTTTTGCGTGCGCG |
|  |  | 678 | GATTTTCTGTTTCCGAAATGCTGCAACTATTGC | 782 | GTGCTGTTTTGCGTG |
|  |  | 679 | GATCCGTTTCTGCAGAACTGCTGCCTGGGCTGGAACTGC | 783 | ATTGTGTTTGTGTGCACC |
|  |  | 680 | ACCTTTTTTTTTCCGGATTGCTGCAACAGCATTTGC | 784 | ATTCTGCTGTTTTGCAGC |
|  |  | 681 | ATTGTGCCGATTCTGGGCTTTGTGTATTGCTGCCCGGGCCTGATTTGC | 785 | GTGTTTGTGTGCATT |
|  |  |  |  | 786 | GCGCAGTTTATTTGCCTG |
|  |  |  |  | 787 | GGCCCGTTTGTGTGCGTG |

In some embodiments, reference sequence element A has an amino acid sequence GCKWYLGDC (SEQ ID NO: 809). In some embodiments, reference sequence element A has an amino acid sequence SSTCIPSGQPC (SEQ ID NO: 255). In some embodiments, reference sequence element B has an amino acid sequence ADSDDCCETFHC (SEQ ID NO: 273). In some embodiments, reference sequence element C has an amino acid sequence KWVFFTSKFMCRRVWGKD (SEQ ID NO: 411).

In some embodiments, a provided polypeptide component has an amino acid sequence that is or comprises GCKWYLGDCADSDDCCETFHCKWVFFTSKFMCRRVWGKD (SEQ ID NO: 128), as is found in the Hv1 modulating agent labeled as "C5" in Table 2A.

In some embodiments, a provided polypeptide component has an amino acid sequence that is or comprises SSTCIPSGQPCADSDDCCETFHCKWVFFTSKFMCRRVWGKD (SEQ ID NO: 129), as is found in the Hv1 modulating agent labeled as "C6" in Table 2A.

In some embodiments, a polypeptide component has an amino acid sequence that includes one or more cysteine residues at positions corresponding to those at which a cysteine residue is found in a relevant wild-type toxin (e.g., wild-type voltage sensor toxin) sequence or reference sequence element (e.g., as depicted in FIG. 2). In some embodiments, a polypeptide component has an amino acid sequence that includes all cysteine residues at positions corresponding to those at which cysteine residues are found in a relevant wild-type toxin sequence or reference sequence element. In some embodiments, a polypeptide component has an amino acid sequence that shares the same approximate relative position of cysteines (e.g., number of residues between them) with a relevant wild-type toxin sequence or reference sequence element.

In some embodiments, a polypeptide component has an amino acid sequence that includes one or more sequence elements that are identical to or includes not more than 1, 2, 3, 4, or 5 sequence differences relative to a wild-type toxin sequence element or reference sequence element.

In some embodiments, such sequence difference(s) are or comprise one or more insertions, deletions, substitutions, rearrangements (e.g., inversions) or combinations thereof. In some embodiments, such sequence difference(s) do not include any insertions. In some embodiments, such sequence difference(s) do not include any deletions. In some embodiments, such sequence differences do not include any rearrangements (e.g., inversions). In some embodiments, such sequence difference(s) may include one or more random sequence alterations.

In some embodiments, a polypeptide component has an amino acid sequence that includes one or more sequence elements that shares one or more cysteines with a sequence set forth in Table 1, Table 2, and/or Table 3. In some embodiments, such a sequence element has an amino acid sequence that shares all cysteines with a sequence set forth in Table 1, Table 2, and/or Table 3. In some embodiments, a sequence element shares the same approximate relative position of cysteines (e.g., number of residues between them) with a sequence set forth in Table 1, Table 2, and/or Table 3.

In some embodiments, a reference sequence element has an amino acid sequence of an element found in a wild-type voltage toxin sequence that differs at residues that undergo posttranslational modifications.

In some embodiments, a polypeptide component of an Hv1 modulating agent may include one or more pendant groups or other modifications, e.g., modifying or attached to one or more amino acid residues (e.g., to one or more amino acid side chains), at the polypeptide component's N-terminus, at the polypeptide component's C-terminus, or any combination thereof. In some embodiments, such pendant groups or modifications may be selected from the group consisting of acetylation, amidation, glycosylation, lipidation, methylation, pegylation, phosphorylation, etc., and combinations thereof.

In some embodiments, exemplary Hv1 modulating agents comprise a polypeptide component whose amino acid sequence further comprises one or more tag elements (e.g., a detectable tag, a localizing tag, etc).

In some embodiments, an Hv1 modulating agent may be a dimer or multimer of relevant entities (e.g., of a polypeptide component as described herein); in some embodiments, an Hv1 modulating agent may be or comprise heterodimer or heteromultimer. In some embodiments, an Hv1 modulating agent may be or comprise a homodimer or homomultimer. Exemplary Hv1 modulating agent dimers are presented in Table 4.

TABLE 4A

Dimer Sequences (with linkers)

| SEQ ID NO: | Name | Sequence |
| --- | --- | --- |
| 788 | HaTx-C6 | ECRYLFGGCKTTSDCCKHLGCKFRDKYCAWDFTFSGNGNGNGSSTCIPSGQPCADSDDCCETFHCKWVFFTSKFMCRRVWGKD |
| 789 | C6-C6 with DkTx linker | SSTCIPSGQPCADSDDCCETFHCKWVFFTSKFMCRRVWGKDDSSPYVPVTTSSTCIPSGQPCADSDDCCETFHCKWVFFTSKFMCRRVWGKD |
| 790 | C6-C6 with flexible linker | SSTCIPSGQPCADSDDCCETFHCKWVFFTSKFMCRRVWGKDDSSGNGNGNGSSTCIPSGQPCADSDDCCETFHCKWVFFTSKFMCRRVWGKD |
| 791 | C6-C6 with long flexible linker | SSTCIPSGQPCADSDDCCETFHCKWVFFTSKFMCRRVWGKDDSSGGNGNGNGNGNGNGAAAGGNGNGNGNGNGNGSSTCIPSGQPCADSDDCCETFHCKWVFFTSKFMCRRVWGKD |

TABLE 4B

Monomer C6 + signal AND dimer + signal

| SEQ ID NO: | Name | Sequence |
| --- | --- | --- |
| 792 | C6 with signal peptide (MSALLILALVGAAVA) | MSALLILALVGAAVASSTCIPSGQPCADSDDCCETFHCKWVFFTSKFMCRRVWGKD |
| 793 | HaTx-C6 | MSALLILALVGAAVAECRYLFGGCKTTSDCCKHLGCKFRDKYCAWDFTFSGNGNGNGSSTCIPSGQPCADSDDCCETFHCKWVFFTSKFMCRRVWGKD |
| 794 | C6-C6 with DkTx linker with signal peptide | MSALLILALVGAAVASSTCIPSGQPCADSDDCCETFHCKWVFFTSKFMCRRVWGKDDSSPYVPVTTSSTCIPSGQPCADSDDCCETFHCKWVFFTSKFMCRRVWGKD |
| 795 | C6-C6 with flexible linker with signal peptide | MSALLILALVGAAVASSTCIPSGQPCADSDDCCETFHCKWVFFTSKFMCRRVWGKDDSSGNGNGNGSSTCIPSGQPCADSDDCCETFHCKWVFFTSKFMCRRVWGKD |
| 796 | C6-C6 with long flexible linker with signal peptide | MSALLILALVGAAVASSTCIPSGQPCADSDDCCETFHCKWVFFTSKFMCRRVWGKDDSSGGNGNGNGNGNGNGAAAGGNGNGNGNGNGNGSSTCIPSGQPCADSDDCCETFHCKWVFFTSKFMCRRVWGKD |

TABLE 4C

| Monomer + Myc tag, dimer + Myc tag, either/both plus signal and tag | | |
|---|---|---|
| SEQ ID NO: | Name | Sequence |
| 797 | C6 with signal peptide and Myc tag | MSALLILALVGAAVASSTCIPSGQPCADSDDCCETFHCKWVFFTSKFMCRRVWGKDGEQKLISEEDL |
| 798 | HaTx-C6 with signal peptide and Myc tag | MSALLILALVGAAVAECRYLFGGCKTTSDCCKHLGCKFRDKYCAWDFTFSGNGNGNGSSTCIPSGQPCADSDDCCETFHCKWVFFTSKFMCRRVWGKDGEQKLISEEDL |
| 799 | C6-C6 with DkTx linker with signal peptide and Myc tag | MSALLILALVGAAVASSICIPSWPCADSDDCCETFHCKWVFFTSKFMCRRVWGKDDSSPYVPVITSSTCIPSGQPCADSDDCCETFHCKWVFFTSKFMCRRVWGKDGEQKLISEEDL |
| 800 | C6-C6 with flexible linker with signal peptide and Myc tag | MSALLILALVGAAVASSICIPSWPCADSDDCCETFHCKWVFFTSKFMCRRVWGKDDSSGNGNGNGSSTCIPSGQPCADSDDCCETFHCKWVFFTSKFMCRRVWGKDGEQKLISEEDL |
| 801 | C6-C6 with long flexible linker with signal peptide and Myc tag | MSALLILALVGAAVASSTCIPSGQPCADSDDCCETFHCKWVFFTSKFMCRRVWGKDDSSGGNGNGNGNGNGNGAAAGGNGNGNGNGNGNGSSTCIPSGQPCADSDDCCETFHCKWVFFTSKFMCRRVWGKDGEQKLISEEDL |

TABLE 4D

| Monomer + GPI targeting, dimer + GPI targeting, either/both plus signal, tag and linker | | |
|---|---|---|
| SEQ ID NO: | Name | Sequence |
| 802 | C6 with signal peptide and Myc tag and GPI anchor | MSALLILALVGAAVASSTCIPSGQPCADSDDCCETFHCKWVFFTSKFMCRRVWGKDGEQKLISEEDLGALCNGAGFATPVTLALVPALLATFWSLL |
| 803 | HaTx-C6 with signal peptide and Myc tag and GPI anchor | MSALLILALVGAAVAECRYLFGGCKITSDCCKHLGCKFRDKYCAWDFTTSGNGNGNGSSTCIPSWPCADSDDCCETFHCKWVFFTSKFMCRRVWGKDGEQKLISEEDLGALCNGAGFATPVTLALVPALLATFWSLL |
| 804 | C6-C6 with Max linker with signal peptide and Myc tag and GPI anchor | MSALLILALVGAAVASSTCIPSWPCADSDDCCETFHCKWVFFTSKFMCRRVWGKDDSSPYVPVITSSTCIPSWPCADSDDCCETFHCKWVFFTSKFMCRRVWGKDGEQKLISEEDLGALCNGAGFATPVTLALVPALLATFWSLL |
| 805 | C6-C6 with flexible linker with signal peptide and Myc tag and GPI anchor | MSALLILALVGAAVASSICIPSWPCADSDDCCETFHCKWVFFTSKFMCRRVWGKDDSSGNGNGNGSSTCIPSWPCADSIDDCCETFHCKWVFFTSKFMCRRVWGKDGEQKLISEEDLGALCNGAGFATPVTLALVPALLATFWSLL |
| 806 | C6-C6 with long flexible linker with signal peptide and Myc tag and GPI anchor | MSALLILALVGAAVASSICIPSWPCADSDDCCETFHCKWVFFTSKFMCRRVWGKDDSSGGNGNGNGNGNGNGAAAGGNGNGNGNGNGNGSSTCIPSGQPCADSDDCCETFHCKWVFFTSKFMCRRVWGKDGEQKLISEEDLGALCNGAGFATPVTLALVPALLATFWSLL |

Optionally, monomer components of a dimer or multimer agent may be or become covalently linked to one another. In some embodiments, such components may be or become covalently linked to one another via one or more disulfide bonds; in some embodiments, such components may be or become covalently linked to one another via one or more peptide bonds; in some embodiments, such components may be or become covalently linked to one another via a bond other than a peptide bond. In some embodiments, such components may be or become covalently linked to one another via a linker (e.g., via a polypeptide linker). Those skilled in the art will appreciate that a linker may be comprised of any of a variety of chemical entities. In those embodiments in which a linker comprises one or a plurality of amino acids, it may be of any desired length. In some embodiments, a linker has a size (e.g., a length) that is smaller than that of one or more of the monomer components.

In some embodiments, a polypeptide component of an Hv1 modulating agent may be connected directly or via a linker sequence to a signal peptide and/or a coat protein of a phage (for phage display methods) and/or to any other domain that may alter one or more of Hv1 modulating agent expression, binding, or function.

In some embodiments, an Hv1 modulating agent may have structural modification(s). For example, an Hv1 modulating agent may be or comprise a cyclic structure, and/or may comprise a cyclic portion. For example, a polypeptide component of an Hv1 modulating agent may be cyclized such that its N-terminus is not part of the cyclic structure. In some embodiments, an Hv1 modulating agent is not cyclic and/or does not comprise any cyclic portion. In some embodiments, an Hv1 modulating agent is linear (e.g., one or more, or all, polypeptide components of an Hv1 modulating agent is/are linear polypeptide(s)). In some embodiments, an Hv1 modulating agent may be or comprise a stapled polypeptide.

In some embodiments, a polypeptide component of an Hv1 modulating agent is incorporated into a framework or scaffold structure. For example, such a polypeptide component can be incorporated into an antibody framework. Alternatively or additionally, a polypeptide component may be incorporated into a beta-sheet framework. In some embodiments, an Hv1 modulating agent may be or comprise an antibody agent or fragment or component thereof (e.g., an antigen-binding fragment or component, such as a polypeptide including sufficient CDR sequences to bind antigen comparably to an antibody). In some embodiments, an Hv1 modulating agent may be or comprise a polypeptide component that includes one or more of an immunoglobulin domain or fragment thereof. In some embodiments, an Hv1 modulating agent may be or comprise a polypeptide component that includes a domain of an immunoglobulin heavy chain. Strategies for preparing such antibody fusions are known in the art (U.S. Ser. No. 14/152,441).

Alternatively or additionally, in some embodiments, an Hv1 modulating agent may be or comprise a nucleic acid, for example that may encode a polypeptide having Hv1 modulating agent activity and/or structure, as described herein. Exemplary nucleic acid sequences for Hv1 modulating agents are illustrated in Table 2C.

Production of Hv1 Modulating Agents

Hv1 modulating agents can be produced by many methods. In some embodiments, an Hv1 modulating agent is produced by recombinant expression in a cell. In some embodiments, an Hv1 modulating agent is produced by peptide synthesis. In some embodiments, an Hv1 modulating agent is produced by in vitro translation.

Exemplary methods of designing and producing Hv1 modulating agents are presented in Example 1.

In some embodiments, an Hv1 modulating agent is presented on a replicable genetic package, e.g., in the form of a phage, yeast, ribosome, or nucleic acid-protein fusion.

In some embodiments, an Hv1 modulating agent is provided and/or utilized in the context of an expression or display system.

In some embodiments, Hv1 modulating agents are first synthesized as nucleic acids that encode polypeptide elements (e.g. elements A, B, and C in Table 3) and then annealed to produce nucleic acid sequences encoding polypeptide components (e.g. as in Table 2).

In some embodiments, a nucleic acid sequence encoding an Hv1 modulating agent may be inserted into a phagemid or phage vector, in-frame, to form a leader-linker-Hv1 modulating agent-linker-coat protein construct (Clackson and Lowman, Phage display. Oxford University Press, 2004; Barbas et al., Phage display. A laboratory manual. Cold Spring Harbor Laboratory Press, 2001). Exemplary upstream leader and downstream amino acid sequences are MAAE and GSASSA, respectively. An exemplary phage vector is pAS62. An exemplary coat protein is protein III or its truncated version. Phages can be grown, prepared, titered and stored (Clackson and Lowman, Phage display. Oxford University Press, 2004; Barbas et al., Phage display. A laboratory manual. Cold Spring Harbor Laboratory Press, 2001).

In some embodiments, Hv1 modulating agents can be inserted into vectors for expression and/or library selection. In some embodiments, a library is presented in a polypeptide array. In some embodiments, a library is presented on a replicable genetic package, e.g., in the form of a phage display, yeast display, ribosome, or nucleic acid-protein fusion library. See, e.g., U.S. Pat. No. 5,223,409; Garrard et al. (1991) Bio/Technology 9:1373-1377; WO 03/029456; and U.S. Pat. No. 6,207,446. Binding members of such libraries can be obtained by selection and screened in a high throughput format. See, e.g., U.S. 2003-0129659.

Hv1 modulating agent libraries for phage display can be generated by standard methods (Clackson and Lowman, Phage display. Oxford University Press, 2004; Barbas et al., Phage display. A laboratory manual. Cold Spring Harbor Laboratory Press, 2001). For example, Hv1 modulating agent libraries for phage display with a combinatorial arrangement of sequence elements are generated by designing overlapping or non-overlapping oligonucleotides corresponding to each individual element. These oligonucleotides are phosphorylated, annealed, mixed in a desired combination and concentration and ligated into a phagemid vector with or without linker sequences to create a library by standard methods (Sambrook et al., Molecular Cloning: A Laboratory Manual. Vols 1-3. Cold Spring Harbor Laboratory Press, 1989). Combinatorial arrangement of sequence elements to yield phage particles expressing a library of Hv1 modulating agents is demonstrated in Example 1A.

Identification and/or Characterization of Hv1 Modulating Agents

Identification and/or characterization of Hv1 modulating agents can include determining effects of candidate agents on Hv1, including Hv1 that is naturally or recombinantly expressed. In some embodiments, Hv1 is expressed in cells. In some embodiments, Hv1 is immobilized (e.g., immobilized on a solid support, an artificial membrane, or a plasma membrane of a cell). In some embodiments, Hv1 is purified.

Identification and/or characterization of Hv1 modulating agents can include the use of libraries of candidate agents.

In some embodiments, an Hv1 modulating agent is identified from a candidate library incorporated into a phage display system. In phage display, candidate Hv1 modulating agents are functionally displayed on the surface of phage and nucleic acid sequences encoding candidate Hv1 modulating agents are enclosed inside phage particles. Functional display permits selection of Hv1 modulating agents that interact with a target or targets (e.g. Hv1 channels). Selection of Hv1 modulating agents from the library can be based on the Hv1 modulating agent type (e.g., toxin type) and/or target biochemistry, pharmacology, immunology and/or other physicochemical or biological property.

A phage library can be transfected into *Escherichia coli* (*E. coli*) or other suitable bacterial species, propagated, and the phages purified. At this stage, Hv1 modulating agents or candidate agents can be functionally expressed on the surface of the phage and physically linked to their respective genes inside of the phage particle. A library is brought into contact with a target, such as Hv1 channels. For example, a phage library can be brought into contact with Hv1 channels that are immobilized on magnetic beads, as described in Example 2. After incubation with the target, those phages that express candidate Hv1 modulating agents with no or weak recognition for the target are washed away. The remaining Hv1 modulating agents that interact with the target are dissociated and can be (i) genotyped to establish the Hv1 modulating agent identity, or (ii) processed for one or more rounds of panning, or (iii) otherwise quantified and/or identified (e.g., ELISA, microbiological titering, functional testing).

Panning may be performed by the binding of candidate modulating agents to Hv1, followed by washes and modulating agent recovery. Panning may be repeated until the desired enrichment is achieved. In addition, libraries can be pre-depleted on surfaces or cells that contain no Hv1 or on an Hv1 where the putative modulating agent binding domain may be directly or indirectly altered. Additionally, any and all conditions of panning may be varied, altered or changed to achieve optimal results, such as the isolation of a specific Hv1 modulating agent. Panning variations include, but are not limited to, the presence of competing polypeptide(s), presence of excess target(s), length and temperature of binding, pre-absorption of the library on one or more different receptor(s) or cells or surfaces, composition of binding solution (e.g., ionic strength), stringency of washing, and recovery procedures. Phages recovered from panning may be processed for further rounds of panning, functional analysis, and/or sequencing/genotyping to deduce the resulting Hv1 modulating agent's amino acid sequence or biological properties (Clackson and Lowman, Phage display. Oxford University Press, 2004; Barbas et al., Phage display. A laboratory manual. Cold Spring Harbor Laboratory Press, 2001).

Following recovery after panning, Hv1 modulating agents of interest may be produced in native form by standard methods of peptide/protein synthesis/production (Sambrook et al., Molecular Cloning: A Laboratory Manual. Vols 1-3. Cold Spring Harbor Laboratory Press, 1989; Albericio, Solid-Phase Synthesis: A Practical Guide. CRC, 2000; Howl, Peptide Synthesis and Applications. Humana Press, 2005).

In some embodiments, Hv1 modulating agents are tested for activity toward recombinant or functional Hv1. Samples that include functional channels (e.g., cells or artificial membranes) can be treated with an Hv1 modulating agent and compared to control samples (e.g., samples without the Hv1 modulating agent), to examine the extent of modulation. In some embodiments, Hv1 may be naturally expressed.

In some embodiments, cells may be stably or transiently transfected with functional Hv1. For example, HEK-293T (mammalian human embryonic kidney) cells may be transfected with Hv1 (e.g. human Hv1 or human Hv1 tagged with a fluorescent protein) for transient expression. In one example, HEK-293T cells transiently expressing hHv1 tagged with teal fluorescent protein are used in patch clamp electrophysiology to determine effects of the Hv1 modulating agents C5 or C6 on proton currents.

Changes in proton flux may be assessed by determining changes in polarization (i.e., electrical potential) of a cell or membrane expressing Hv1. In some embodiments, a change in cellular polarization is measured by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., New Engl. J. Med. 336: 1575-1595, 1997). Whole cell currents can be determined using standard methodology (see, e.g., Hamil et al., PFlugers. Archiv. 391:85, 1981). Other assays include radio-labeled rubidium flux assays and fluorescence assays using voltage sensitive dyes (see, e.g., Vestergarrd-Bogind et al., J. Membrane Biol. 88:67-75, 1988; Daniel et al., J. Pharmacol. Meth. 25:185-193, 1991; Holevinsky et al., J. Membrane Biology 137:59-70, 1994). In some embodiments, candidate Hv1 modulating agents are present in the range from 1 pM to 100 mM. Other methods for assessing Hv1 modulating agent effects on proton flux are described in the Examples herein.

Hv1 modulating agents can also be identified or characterized by evaluating processes at the cellular, tissue and/or organism level. For example, Hv1 modulating agents can be evaluated for effects downstream of Hv1 activity or signaling. Various effects of Hv1 modulating agents that may be determined using intact cells or animals include transcriptional changes, changes in cell metabolism, and changes in intracellular second messengers.

In some embodiments, Hv1 modulating agents can be evaluated for effects on human sperm. For example, Hv1 modulating agents can be evaluated for effects on sperm capacitation-related processes, including changes in sperm motility, decrease of cholesterol in the membranes, increase of tyrosine phosphorylation in several proteins, or maturation of the sperm response to progesterone. Capacitation of spermatozoa occurs along with an increase in the amplitude of voltage-gated proton current. Known Hv1 inhibitor, $Zn^{2+}$" reduces $H^+$ current in sperm cells. Accordingly, an Hv1 modulating agent can be evaluated for suppression of such sperm capacitation-related processes. Alternatively, an Hv1 modulating agent can be evaluated for enhancing sperm capacitation-related processes. Alternatively or additionally, an Hv1 modulating agent can be evaluated for non-capacitation-related processes that affect sperm activation, mobility, and/or fertilization.

In some embodiments, Hv1 modulating agents can be evaluated for effects on cells that function in the immune system. For example, Hv1 is expressed in white blood cells (WBCs). Hv1 in WBCs has been shown to compensate charge buildup on the cell membrane during production of ROS. Hv1 knockout or inhibition impairs ROS production in these cells. Accordingly, an Hv1 modulating agent can be evaluated for suppression of ROS production in WBCs.

Hv1 modulating agents can be selected for their potency and selectivity of modulation of Hv1. For example, an Hv1 modulating agent that demonstrates low $IC_{50}$ value for Hv1, and a higher $IC_{50}$ value for other ion channels within the test panel, is considered to be selective toward Hv1.

Compositions

The present disclosure also features compositions that include and/or deliver Hv1 modulating agents.

In some embodiments, a composition is a pharmaceutically acceptable composition that includes and/or delivers an Hv1 modulating agent described herein. For example, in some embodiments, a provided composition includes an Hv1 modulating agent polypeptide component. Alternatively or additionally, in some embodiments, a provided composition includes a nucleic acid that encodes an Hv1 modulating agent polypeptide component, a cell that expresses (or is adapted to express) an Hv1 modulating agent polypeptide component, etc. In some embodiments Hv1 modulating agents having any of the modifications of the present disclosure are included in pharmaceutical compositions.

General considerations in the formulation and manufacture of pharmaceutical agents may be found, for example, in *Remington's Pharmaceutical Sciences*, 19$^{th}$ ed., Mack Publishing Co., Easton, Pa., 1995.

Pharmaceutical compositions may be in a variety of forms. These include, for example, liquid, semi-solid and solid dosage forms, such as liquid solutions (e.g., injectable and infusible solutions), dispersions or suspensions, microemulsions, liposomes and suppositories. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin. The preferred form of pharmaceutical composition depends on the intended mode of administration and therapeutic application. Typical compositions are in the form of injectable or infusible solutions, such as compositions similar to those used for administration of antibodies to humans.

The pharmaceutical composition can include a pharmaceutically acceptable carrier. For example, pharmaceutical compositions can include a therapeutic agent in addition to one or more inactive agents such as a sterile, biocompatible carrier.

Exemplary carriers include any and all solvents, dispersion media, coatings, antibacterial and antifungal agents, isotonic and absorption delaying agents, and the like that are physiologically compatible. For example, carriers may include sterile water, saline, buffered saline, or dextrose solution. Alternatively or additionally, the composition can contain any of a variety of additives, such as stabilizers, buffers, excipients (e.g., sugars, amino acids, etc.), or preservatives. Preferably, the carrier is suitable for oral, intravenous, intramuscular, subcutaneous, parenteral, spinal or epidermal administration (e.g., by injection or infusion).

The pharmaceutical composition can include a pharmaceutically acceptable salt, e.g., a salt that retains the desired biological activity of the Hv1 modulating agent and does not impart any undesired toxicological effects (see e.g., Berge, S. M., et al., J. Pharm. Sci. 66:1-19, 1977).

Depending on the route of administration, the Hv1 modulating agent may be coated in a material to protect the compound from the action of acids and other natural conditions that may inactivate the compound.

In certain embodiments, a pharmaceutical composition can include a therapeutic agent that is encapsulated, trapped, or bound within a lipid vesicle, a bioavailable and/or biocompatible and/or biodegradable matrix, or other microparticles.

In certain embodiments, an Hv1 modulating agent is prepared with a carrier that protects against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and poly lactic acid. Many methods for the preparation of such formulations are patented or generally known. See, e.g., Sustained and Controlled Release Drug Delivery Systems, J. R. Robinson, ed., Marcel Dekker, Inc., New York, 1978. Pharmaceutical formulation is a well-established art, and is further described in Gennaro (ed.), Remington: The Science and Practice of Pharmacy, 20.sup.th ed., Lippincott, Williams & Wilkins, 2000 (ISBN: 0683306472); Ansel et al., Pharmaceutical Dosage Forms and Drug Delivery Systems, 7.sup.th Ed., Lippincott Williams & Wilkins Publishers, 1999 (ISBN: 0683305727); and Kibbe (ed.), Handbook of Pharmaceutical Excipients American Pharmaceutical Association, 3rd ed., 2000 (ISBN: 091733096X).

In some embodiments, a provided pharmaceutical composition will include an Hv1 modulating agent that is not aggregated. For example, in some embodiments, less than 1%, 2%, 5%, 10%, 20%, or 30%, by dry weight or number, of Hv1 modulating agent is present in an aggregate.

In some embodiments, a provided pharmaceutical composition will include an Hv1 modulating agent that is not denatured. For example, less than 1%, 2%, 5%, 10%, 20%, or 30%, by dry weight or number, of Hv1 modulating agents administered is denatured.

In some embodiments, a provided pharmaceutical composition will include an Hv1 modulating agent that is not inactive. For example, less than 1%, 2%, 5%, 10%, 20%, or 30%, by dry weight or number, of Hv1 modulating agents administered is inactive.

In some embodiments, pharmaceutical compositions are formulated to reduce immunogenicity of provided Hv1 modulating agents. For example, in some embodiments, a provided Hv1 modulating agent is associated with (e.g., bound to) an agent, such as polyethylene glycol and/or carboxymethyl cellulose, that masks its immunogenicity. In some embodiments, a provided binding agent has additional glycosylating that reduces immunogenicity.

Kits

Also provided by the present disclosure are kits that include an Hv1 modulating agent described herein and instructions for use, e.g., treatment, prophylactic, or diagnostic use.

In addition to the Hv1 modulating agent, the composition of the kit can include other ingredients, such as a solvent or buffer, a stabilizer or a preservative, and/or a second agent for treating a condition or disorder described herein. Alternatively, other ingredients can be included in the kit, but in different compositions or containers than the Hv1 modulating agent. In such embodiments, the kit can include instructions for admixing the Hv1 modulating agent and the other ingredients, or for using the Hv1 modulating agent together with the other ingredients.

Alternatively or additionally, contents of kits may include, but are not limited to, expression plasmids containing nucleotides (or characteristic or biologically active portions) encoding Hv1 modulating agents of interest (or characteristic or biologically active portions). Alternatively or additionally, kits may contain expression plasmids that express Hv1 modulating agents of interest (or characteristic or biologically active portions). Alternatively or additionally, kits may contain isolated and stored Hv1 modulating agents.

In certain embodiments, kits for use in accordance with the present invention may include, a reference sample, instructions for processing samples, performing tests on samples, instructions for interpreting the results, buffers and/or other reagents necessary for performing tests. In certain embodiments the kit can comprise a panel of antibodies.

The present invention provides kits for administration of pharmaceutical compositions. For example, in some embodiments, the invention provides a kit comprising at least one dose of an Hv1 modulating agent. In some embodiments, the invention provides a kit comprising an initial unit dose and one or more subsequent unit doses of an Hv1 modulating agent. In some such embodiments, the initial unit dose is greater than the subsequent unit doses or wherein the all of the doses are equal.

Methods of Administration

Pharmaceutical compositions may be administered in any dose appropriate to achieve a desired outcome. In some embodiments, the desired outcome is reduction in intensity, severity, and/or frequency, and/or delay of onset of one or more symptoms of an Hv1 associated disease or condition.

A therapeutically effective amount of an Hv1 modulating agent composition can be administered, typically an amount which is effective, upon single or multiple dose administration to a subject, in treating a subject, e.g., curing, alleviating, relieving or improving at least one symptom of a disease or condition in a subject to a degree beyond that expected in the absence of such treatment. A therapeutically effective amount of the composition may vary according to factors such as the disease state, age, sex, and weight of the individual, and the ability of the compound to elicit a desired response in the individual. A therapeutically effective amount is also one in which any toxic or detrimental effects of the composition is outweighed by the therapeutically beneficial effects. A therapeutically effective dosage preferably modulates a measurable parameter, favorably, relative to untreated subjects. The ability of an Hv1 modulating agent to inhibit a measurable parameter can be evaluated in an animal model system predictive of efficacy in a human disorder.

In some embodiments, pharmaceutical compositions are administered in multiple doses. In some embodiments, pharmaceutical compositions are administered in multiple doses/day. In some embodiments, pharmaceutical compositions are administered according to a continuous dosing regimen, such that the subject does not undergo periods of less than therapeutic dosing interposed between periods of therapeutic dosing. In some embodiments, pharmaceutical compositions are administered according to an intermittent dosing regimen, such that the subject undergoes at least one period of less than therapeutic dosing interposed between two periods of therapeutic dosing.

Dosage regimens can be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of ligand calculated to produce the desired therapeutic effect in association with the required pharmaceutical carrier.

An exemplary, non-limiting range for a therapeutically or prophylactically effective amount of an Hv1 modulating agent described herein is 0.1-20 mg/Kg, more preferably 1-10 mg/Kg. In some embodiments, an agent can be administered by parenteral (e.g., intravenous or subcutaneous) infusion at a rate of less than 20, 10, 5, or 1 mg/min to reach a dose of about 1 to 50 mg/m$^2$ or about 5 to 20 mg/m$^2$. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions (e.g., the supervising physician), and that dosage ranges set forth herein are only exemplary.

Pharmaceutical compositions of the present invention can be administered by a variety of routes, including oral, intravenous, intramuscular, intra-arterial, subcutaneous, intraventricular, transdermal, interdermal, rectal, intravaginal, intraperitoneal, topical (as by powders, ointments, creams, or drops), mucosal, nasal, buccal, enteral, sublingual; by intratracheal instillation, bronchial instillation, and/or inhalation; and/or as an oral spray, nasal spray, and/or aerosol. For example, for therapeutic applications, an Hv1 modulating agent composition can be administered by intravenous infusion at a rate of less than 30, 20, 10, 5, or 1 mg/min to reach a dose of about 1 to 100 mg/m$^2$ or 7 to 25 mg/m$^2$. Alternatively, the dose could be 100 µg/Kg, 500 µg/Kg, 1 mg/Kg, 5 mg/Kg, 10 mg/Kg, or 50 mg/Kg. The route and/or mode of administration will vary depending upon the desired results. In general the most appropriate route of administration will depend upon a variety of factors including the nature of the agent (e.g., its stability in the environment of the gastrointestinal tract), the condition of the patient (e.g., whether the patient is able to tolerate oral administration), etc.

A common mode of administration is parenteral (e.g., intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion). In one embodiment, the Hv1 modulating agent composition is administered by intravenous infusion or injection. In another embodiment, the Hv1 modulating agent composition is administered by intramuscular or subcutaneous injection. In another embodiment, the Hv1 modulating agent composition is administered orally. In some embodiments, the Hv1 modulating agent composition is administered topically. In some embodiments, the Hv1 modulating agent composition is administered transdermally. Pharmaceutical compositions typically must be sterile and stable under the conditions of manufacture and storage.

Hv1 modulating agents or pharmaceutical compositions of the present disclosure may be administered either alone or in combination with one or more other agents. In some embodiments, Hv1 modulating agents or pharmaceutical compositions of the present disclosure may be administered with one or more other Hv1 modulating agents. In some embodiments, Hv1 modulating agents or pharmaceutical compositions of the present disclosure may be administered with one or more other pharmaceutical agent including, but not limited to, small molecules, vaccines and/or antibodies. In some embodiments, Hv1 modulating agents or pharmaceutical compositions may be administered in combination with an adjuvant.

Combinations of agents may be administered at the same time or formulated for delivery together. Alternatively, each agent may be administered at a dose and on a time schedule determined for that agent. Additionally, the invention encompasses the delivery of the pharmaceutical compositions in combination with agents that may improve their bioavailability, reduce or modify their metabolism, inhibit their excretion, or modify their distribution within the body. Although the pharmaceutical compositions of the present invention can be used for treatment of any subject (e.g., any animal) in need thereof, they are most preferably used in the treatment of humans.

Uses

As described herein, Hv1 channels have been reported to play a role in a variety of biological processes, and to impact various diseases, disorders, and conditions.

The present disclosure encompasses treatment of Hv1 associated diseases or conditions. Hv1 modulating agents and/or Hv1 modulating agent compositions described herein can be administered, alone or in combination with, another agent to a subject, e.g., a patient, e.g., a patient who has a disorder (e.g., an Hv1-associated disease or condition, e.g. immune deficiency), a symptom of a disorder or a predisposition toward a disorder, with the purpose to cure, heal, alleviate, relieve, alter, remedy, ameliorate, improve or affect the disorder, the symptoms of the disorder or the predisposition toward the disorder. The treatment may also delay onset, e.g., prevent onset, or prevent deterioration of a condition.

In some embodiments, Hv1 modulating agent pharmaceutical compositions are administered to a subject suffering from or susceptible to an Hv1 associated disease or condition. In some embodiments, a subject is considered to be suffering from an Hv1 associated disease or condition if the subject is displaying one or more symptoms commonly associated with said disease or condition. Hv1 modulating agents or Hv1 modulating agent compositions may be administered prior to or after development of one or more such symptoms.

For example Hv1 modulating agents may be used to ameliorate inflammation, allergies, autoimmunity, cancer, asthma, brain damage from ischemic stroke, Alzheimer's disease, infertility, and numerous other conditions. In some embodiments, the desired outcome is reduction in intensity, severity, and/or frequency, and/or delay of onset of one or more of these conditions. Additionally or alternatively, Hv1 modulating agents may be used as a form of birth control by blocking sperm function.

Additionally, Hv1 modulating agents may be used to change any of the functions of Hv1 channels described in the present disclosure to achieve a preferred or therapeutic outcome. As described herein, Hv1 channels transport protons across cell membranes and are expressed in a variety of cells and tissues. Functions of Hv1 channels differ depending on the cells in which they are expressed. Uses for Hv1 modulating agents can include increasing or decreasing proton current across cell membranes and/or increasing or decreasing pH in the cytosolic, extracellular, or intraluminal space of cells.

In some embodiments, uses for Hv1 modulating agents may include effects on Hv1-related processes. For example, in some embodiments, Hv1 modulating agents may be used to increase or decrease the expression and/or function of NOX enzymes, including NOX1, NOX2, NOX3, and/or NOX4. In some embodiments, Hv1 modulating agents may be used to increase or decrease production of ROS.

In some embodiments, uses for Hv1 modulating agents may include altering biological functions in specific cells. For example, the function of Hv1 channels in white blood cells includes extrusion of protons to facilitate ROS production via NOX activity in the phagosome. This process allows white blood cells to destroy bacteria and other pathogens. In some embodiments, uses of Hv1 modulating agents may include changing these functions in white blood cells. Alternatively, Hv1 channel function in human sperm has been associated with sperm capacitation, activation and mobility to achieve fertilization. In some embodiments, Hv1 modulating agent uses may include increasing or decreasing sperm function and/or fertilization ability.

While various aspects and examples have been described, it will be apparent to those of ordinary skill in the art that many more examples and implementations are possible within the scope of this disclosure. Accordingly, the disclosure is not to be restricted except in light of the attached claims and their equivalents.

EXEMPLIFICATION

Example 1: Designing Hv1 Modulating Agents

The present Example describes certain Hv1 modulating agents provided herein. Certain Hv1 modulating agents provided herein comprise a polypeptide component having an amino acid sequence including element(s) found in wild-type toxin polypeptides. In some embodiments, exemplary Hv1 modulating agents comprise a polypeptide component whose amino acid sequence further comprises one or more tag elements (e.g., a detectable tag, a localizing tag, etc). In some embodiments, exemplary Hv1 modulating agents have a structure that comprises both a polypeptide component and a non-polypeptide component (e.g., a modifying component such as a lipid-containing moiety, a saccharide-containing moiety, etc). Alternatively or additionally, in some embodiments, exemplary Hv1 modulating agents are multimeric in that their structure includes multiple (e.g., 2 or more) monomer components associated with one another. In some embodiments, all monomers in a multimer are structurally identical (or substantially identical) to one another. In some embodiments, a multimer may comprise 2 or more distinct monomers. In some embodiments, two or more monomers in a multimer may be covalently associated with one another (e.g., via a linker or cross-linker).

A. Toxin Sequences

As noted above, certain Hv1 modulating agents provided herein have an amino acid sequence including element(s) found in wild-type toxin polypeptides. Representative such agents were designed as described below.

The amino acid sequence of the Peruvian green velvet tarantula (*Thrixopelma pruriens*) was used as a template to identify predicted wild-type toxin sequences using the basic local alignment search tool (BLAST) in the UniProt and Pfam databases. A total of 110 predicted wild-type toxin sequences were identified (Table 1). All of these sequences encode a polypeptide characterized as having an inhibitor cysteine knot (ICK) structural motif. The amino acid sequences of these 110 predicted wild-type toxins were aligned around six conserved cysteine residues of the ICK motif. Three sequence elements, A, B, and C were delineated by the second and fifth of the six conserved cysteine residues in each predicted wild-type toxin sequence, resulting in 95 A, 104 B, and 106° C. sequence elements (Table 3). Nucleotides were synthesized corresponding to these A, B, and C elements.

Complementary nucleotide pairs for each unique element A, B, or C, were synthesized to produce nucleotide duplexes. These nucleotide duplexes were phosphorylated using T4 Polynucleotide Kinase and annealed unidirectionally to produce polynucleotide components having an A-B-C sequence element pattern linked at cysteine residues.

To achieve and monitor incorporation of the sequence elements, 104 separate reactions were performed to ligate the ABC inserts into the pAS62 phagemid vector in frame with phage particle coat protein pIII, resulting in phagemids having the ABC inserts (see, e.g., PCT/US2008/013385). Each reaction contained one B nucleotide duplex, 95 A nucleotide duplexes, and 106° C. nucleotide duplexes. Ligation mixtures were transformed in SS320 electrocompetent cells (Lucigen, Middleton, Wis.). To verify unbiased insert utilization, 416 plaques were sequenced. The processes yielded phage particles expressing the original 110 predicted wild-type toxins and approximately 1,047,170 novel peptides. Exemplary novel peptides are listed in Table 2A and FIG. 1. Exemplary A, B and C sequence elements are listed in Table 3.

B. Linkers and Dimerization

Certain exemplary Hv1 modulating agents were prepared by linking together two polypeptide components, each of which had an amino acid sequence comprising elements of wild-type toxin polypeptides as described above in Section A.

For example, two monomers of the agent labeled as "C6" in Table 2A were joined together via a peptide linker. Several different peptide linkers were utilized. For example, each of a rigid linker of 10 amino acid residues, a flexible linker of 10 amino acid residues, or a long flexible linker of 38 amino acid residues was used. Table 4A lists amino acid sequences of exemplary polypeptides created through such linkage.

C. Signal Peptides

In some embodiments, one or more signal peptides can be included in exemplary Hv1 modulating agents (Table 4B).

For example, Hv1 modulating agents with an N-terminal trypsin secretory signal sequence can be prepared.

D. Detectable Tags

In some embodiments, an Hv1 modulating agent may be modified with an epitope tag.

For example, a c-Myc epitope tag can be added near the C-terminus of a polypeptide component in an Hv1 modulating agent (Table 4C).

E. Tethering Moieties

In some embodiments, an Hv1 modulating agent may be modified with a tethering moiety that targets the Hv1 modulating agent to a specific surface.

For example, a hydrophobic sequence may be added to the C-terminus of an Hv1 modulating agent that targets the Hv1 modulating agent for covalent tethering to glycosylphosphatidylinositol (GPI) anchors inserted in the extracellular leaflet of the plasma membrane (Table 4D).

Annotated sequences of exemplary modified Hv1 modulating agents are presented in FIG. 3.

F. Generating Hv1 Modulating Agents with Linkers and Modifications

Representative Hv1 modulating agents having signal peptides, detectable tags, and tethering moieties were generated as follows. The sequence encoding mammalian Lynx1, a toxin-like nicotinic acetylcholine receptor modulator, was replaced by cDNA of the Hv1 modulating agent C6, in-frame between the secretion signal and the Lynx1 hydrophobic sequence for GPI attachment. A flexible linker containing a glycine-asparagine repeat was inserted between the C6 sequence and the hydrophobic sequence for GPI attachment, and a c-Myc epitope tag was introduced in the middle of the linker. Hv1 modulating agents having these modifications are also called "T-toxins." Exemplary T-toxin sequences are depicted in FIGS. 3A-3E. The present disclosure appreciates that methods analogous to those described in Gui, J. et al., "A tarantula-venom peptide antagonizes the TRPA1 nociceptor ion channel by binding to the S 1-S4 gating domain," Curr Biol. 24(5):473-83 (2014) can be employed to generate GPI-tethered toxins as described herein.

Example 2: Characterization of Hv1 Modulating Agents

The present Example demonstrates a high-throughput assay for characterization of Hv1 modulating agents. Specifically, this assay characterizes whether Hv1 modulating agents are capable of binding human Hv1 (hHv1) protein.

To characterize if an Hv1 modulating agent can bind to hHv1 channels, a phage display library expressing Hv1 modulating agents was generated. Phage particles from Example 1A were used to infect *Escherichia coli* (*E. coli*) XL1-Blue cells for 15 min at room temperature. The infected cells were grown overnight at 37° C. in 150 mL 2×YT in the presence of 1010/mL M13K07 helper phage, 100 g/mL ampicillin, and 0.1 mM isopropyl 13-D-1-thiogalactopyranoside (IPTG). Cultures were centrifuged and the supernatant was precipitated with PEG/NaCl solution. The phage pellet was collected by centrifugation and dissolved in TBS. Phage particle titer was determined by serial dilution in TBS and infection of *E. coli* XL1-Blue followed by plating on LB plates with antibiotic and determination of colony forming units (cfu).

hHv1 protein was biotinylated using sulfosuccinimidyl 2-(biotinamido)-ethyl-1,3-dithiopropionate (EZ-Link Sulfo-NHS-SS-Biotin, Thermo Scientific). Biotinylation was verified by a pull-down assay using streptavidin MagneSphere beads (Promega). Biotinylated hHv1 was adsorbed to 300 µl streptavidin MagneSphere paramagnetic particles, and free streptavidin-binding sites were blocked with biotin to prevent nonspecific binding.

After manual washing of the magnetic beads, library phage particles ($10^{11}$ cfu) were added in 300 µL TBSB (25 mM Tris-HCl, 140 mM NaCl, 3 mM KCl, 2 mM LPPG, 0.5% bovine serum albumin, pH 7.4) and incubated on a rocking shaker for 1 h. Poorly adherent phage particles were removed by washing 2-5 times with TBSTB (TBSB with 0.1% Tween 20). The captured phages on the magnetic beads were eluted with 100 mM DTT in 20 mM Tris, pH 8.0, for 10 min, and then used to infect *E. coli* XL1-Blue cells (Stratagene) for phage amplification. The phage particles captured in the first round were cycled through an additional five rounds of binding and selection using an automated magnetic bead manipulator (KingFisher, Thermo Scientific). Phage particles were quantified by titering before and after selective library sorting and genotyped by DNA sequencing after six rounds of panning. Phage enrichment was observed with immobilized hHv1 as the target compared with the control target streptavidin. Exemplary Hv1 modulating agents enriched by this method are listed in Table 2A. In some instances, repeats of Hv1 modulating agent sequences after several rounds of panning can be observed, as demonstrated by agents labeled as A6 and G2, C2 and F2, C6 and D5, and D6 and E2. Without wishing to be bound by any particular theory, any repeat may be considered significant (since the library had more than 1 million peptides initially) and may demonstrate selection and functional convergence.

Example 3: Characterization of Hv1 Modulating Agents by T-Toxin Assay

The present example demonstrates characterization of the effects of Hv1 modulating agents on hHv1 using T-toxins.

Specifically, the present example demonstrates inhibition of hHv1 function as measured by tail current from *Xenopus laevis* oocytes expressing only hHv1 or both hHv1 and Hv1 modulating agents tethered to the oocyte plasma membrane.

T-toxin cDNAs were cloned into the pCS2+ plasmid vector for in vitro transcription of T-toxin cRNA. Capped cRNAs were prepared by restriction enzyme linearization, followed by in vitro transcription reaction with SP6 (for T-toxins) and T7 (for hHv1) RNA polymerase (mMessenger mMachine kit, Ambion). Concentrations of cRNAs were measured using NanoDrop 2000 (Thermo Scientific).

cRNAs for T-toxins and hHv1 were mixed at 1:1 ratio (w/w) and injected into the *Xenopus laevis* oocytes. Currents were measured by Two Electrode Voltage Clamp (TEVC). Recording solution was (in mM): 90 NaCl, 1 $MgCl_2$, 2 $CaCl_2$, 120 HEPES, pH 7.3. Recordings were performed with constant gravity flow of solution at 2 ml/min yielding chamber exchange in ~5 s. Currents were recorded 2-3 days after cRNA injection using an oocyte clamp amplifier OC-725C (Warner Instruments, Hamden, Conn.), and electrodes filled with 3 M KCl with resistance of 0.3-1 MΩ. Data were filtered at 1 kHz and digitized at 20 kHz using pClamp software and assessed with Clampfit v9.0 and Origin 6.0. Inhibition was studied by comparing tail current from oocytes expressing only hHv1 and those with both hHv1 and T-toxins. Inhibition was calculated as unblocked fractional current (FIG. 3F).

Example 4: Characterization of Hv1 Modulating Agents with a Transmembrane Link The present example demonstrates characterization of Hv1 modulating agent effects on hHv1 using Hv1 modulating agents expressed from cells via a transmembrane link.

The Hv1 modulating agent C6 was tethered to cell surfaces using a transmembrane domain from the PDGF receptor, which links an internal mVenus fluorescent protein to an external C6 (FIG. 7). Unlike the tether in oocytes which attaches C6 to the outside of the cell (e.g. FIG. 3), this is a transmembrane link. To transiently express hHv1, 1 μg of hHv1 tagged with teal fluorescence protein (hHv1-TFP) was transfected into HEK-293T cells using Lipofectamine 2000. Changes in the single exponential fit of fluorescence decay were indicative of FRET (FIG. 8). Changes in current density and shifts in the $g_H$-V were indicative of blocking of hHv1.

Example 5: Hv1 Modulating Agents Activate or Inhibit Hv1 Proton Current

The present Example documents assessing activity of the voltage-gated proton channel Hv1 in response to Hv1 modulating agents. Activity of Hv1 was assessed by changes in proton currents.

To transiently express hHv1, 1 μg of hHv1 or hHv1 tagged with teal fluorescence protein (hHv1-TFP) was transfected into HEK-293T cells using Lipofectamine 2000. In some instances, green fluorescent protein was used as a transfection marker. Transfected cells were plated onto glass coverslips. Green or teal cells were selected for whole-cell patch clamp after 24 hours.

Patch clamp recordings were performed with an external solution of 100 mM HEPES, pH 7.5, 70 mM NaCl, and 10 mM glucose. The pipette solution was 100 mM Bis Tris buffer, pH 6.5, 70 mM NaCl and 10 mM glucose. Hv1 modulating agent was applied to these cells while pulsing to 40 mV every 10 seconds and proton currents were measured using whole-cell patch clamp electrophysiology.

FIG. 4 shows activation or inhibition of Hv1 proton currents by Hv1 modulating agent as compared to current without addition of modulating agent. Cells were incubated with either 500 nM C5 (FIG. 4A) or 250 nM C6 (FIG. 4B). Activation of Hv1 channels by C5 increased proton current and slowed channel closing. Block of Hv1 channels by C6 decreased proton currents.

Example 6: Hv1 Modulating Agent Inhibits Effects of Progesterone on Sperm Capacitation The present example demonstrates effectiveness of certain Hv1 modulating agents in suppressing maturation of the sperm response to progesterone. This example shows that activity of Hv1 channels during capacitation is necessary for calcium rise and acrosomal reaction stimulation by physiological inducers required for fertilization.

To test effects of Hv1 modulating agents on sperm capacitation in a blind study, human sperm was exposed to capacitating conditions in the presence or absence of Hv1 modulating agent C6 (Tx C) or a control peptide (Tx A) having the amino acid sequence GVEINVKCSGSPQCLKPCKDAGMDFGDCMNDKCHCTPK (SEQ ID NO: 810) (a mutant scorpion venom peptide; Takacs, Z., et al., "A designer ligand specific for Kv1.3 channels from a scorpion neurotoxin-based library," *Proc Natl Acad. Sci. USA.* 106(52): 22211-22216 (2009)). Sperm were incubated for 1 hour with the Tx C or Tx A (20 μM) in a medium that does not promote capacitation. Cells were transferred to a capacitating medium with Tx C or Tx A. After 4 hours of incubation, parameters related to capacitation were analyzed (FIG. 5). Known protocols for such analyses are described in Pocognoni, C. A., et al., "Perfringolysin O as a useful tool to study human sperm physiology," *Fertility and Sterility,* 99(1): p. 99-106.e2 (2013).

C6 did not affect the vitality (FIG. 5A), the protein tyrosine phosphorylation (FIG. 5F and FIG. 5G), or the cholesterol content of the membranes (FIG. 5H). C6 did not significantly alter the mobility of sperm (FIGS. 5B-5E). C6 did affect the response of sperm to progesterone. The increase of cytosolic calcium triggered by progesterone is diminished in the presence of the peptide modulator and the acrosome reaction induced by the hormone is inhibited (FIGS. 5I-5K). Moreover, when C6 was added after capacitation, both intracellular calcium and acrosomal reaction, triggered by progesterone, did not show any changes.

Example 7: Hv1 Modulating Agents Inhibit Production of Reactive Oxygen Species in Human Blood Cells The present example demonstrates effectiveness of certain Hv1 modulating agents in blocking ROS production by human blood cells.

Whole blood was purchased in 10 mL tubes from Innovative Research, Inc, in accordance with FDA guidelines. Blood was used within 24-48 hours after being drawn. Upon arrival, blood cells were counted using a hemocytometer and diluted in Tyrode's solution to approximately $5\times10^6$ cells/mL. Twenty μL of the dilute blood cells were added to each well of a 96-well plate with a total volume of 100 μL in Tyrode's solution. Reactive oxygen species (ROS) were detected by fluorescence readout using 100 μL Amplex Red with 2 units/mL horseradish peroxidase added to each well.

Blood was incubated with the following treatment conditions for 1 hour at 37° C.: control; 100 μL zinc; 100 pM-5 μM C6; and 10 μM MOKA toxin. Each treatment condition was added to wells in 5 repeats. After the incubation, 200 nM phorbol myristate acetate (PMA) was added to all wells except the control. PMA was used to stimulate ROS production. Fluorescence measurements were taken immediately after using excitation at 530 nM and emission at 590 nM. Measurements were repeated every 15 to 30 min for the next 2 hours. Relative fluorescence intensity was plotted versus time and used to calculate inhibition. FIG. 6 demonstrates that C6 blocks production of ROS in human blood cells in a dose-dependent manner. The known inhibitor of Hv1, zinc, blocks ROS production to background (control) levels. Two toxins that block potassium channels with nM affinity (Moka and KTX) had no effect.

Example 8: The Hv1 Modulating Agent C6 Targets an S3-S4 External Loop Region of hHv1

The present example demonstrates identification of regions in hHv1 that can bind and/or respond to modulation by the Hv1 modulating agent C6.

The Hv1 modulating agent C6 did not inhibit proton current of *Ciona intestinalis* (*C. intestinalis*) Hv1 channels (CiHv1). Chimeric forms of ciHv1 were generated in which amino acids from human Hv1 (hHv1) corresponding to the S3-S4 external loop replaced the same region of CiHv1 (hS3-S4-ciHv1). The resulting hS3-S4-ciHv1 chimera comprised hHv1 amino acids 1183 to L204: ILDIVLL-FQEHQFEALGLLILL (SEQ ID NO: 111) and maintained characteristics of Hv1 currents. C6 blocked current for hS3-S4-ciHv1 (FIGS. 9A and 9B).

Twelve residues in the S3-S4 external loop region of hHv1 (F190 to L201) were individually mutated to Cysteine. Current with 1 μM C6 normalized to current without toxin (Itox/Ictr) was measured (FIG. 9C). Mutating hHv1 E192C increased normalized current with C6 compared to WT hHv1. Mutating hHv1 G199C or G199L increased inhibitory effects of C6 compared to WT hHv1.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

I claim:

1. A voltage-gated proton channel (Hv1) activator consisting of the amino acid sequence set forth in SEQ ID NO:128.

2. A voltage-gated proton channel (Hv1) inhibitor consisting of the amino acid sequence set forth in SEQ ID NO:129.

* * * * *